US012747225B2

(12) United States Patent
Brognard et al.

(10) Patent No.: US 12,747,225 B2
(45) Date of Patent: Sep. 29, 2026

(54) LZK-TARGETING DEGRADERS AND METHODS OF USE

(71) Applicant: The United States of America, as represented by the Secretary, Department of Health and Human Services, Bethesda, MD (US)

(72) Inventors: John F. Brognard, Middletown, MD (US); Rolf E. Swenson, Silver Spring, MD (US); Amy L. Funk, Frederick, MD (US); Carolyn W. Hitko, Olney, MD (US); Katherine M. Nyswaner, Keedysville, MD (US); Eric Lindberg, Rockville, MD (US); Venkatareddy Sabbasani, Monrovia, MD (US); Knickole L. Bergman, Jefferson, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 662 days.

(21) Appl. No.: 18/176,849

(22) Filed: Mar. 1, 2023

(65) Prior Publication Data

US 2024/0190838 A1 Jun. 13, 2024

Related U.S. Application Data

(63) Continuation-in-part of application No. PCT/US2021/048600, filed on Sep. 1, 2021.

(60) Provisional application No. 63/073,835, filed on Sep. 2, 2020.

(51) Int. Cl.

| | |
|---|---|
| ***C07D 401/14*** | (2006.01) |
| ***A61K 31/4439*** | (2006.01) |
| ***A61P 35/00*** | (2006.01) |
| ***C07D 417/14*** | (2006.01) |

(52) U.S. Cl.

CPC ........ *C07D 401/14* (2013.01); *A61K 31/4439* (2013.01); *A61P 35/00* (2018.01); *C07D 417/14* (2013.01)

(58) Field of Classification Search

CPC .......................... A61K 31/4439; C07D 401/14

See application file for complete search history.

(56) References Cited

U.S. PATENT DOCUMENTS

| | | | |
|---|---|---|---|
| 9,399,636 | B2 | 7/2016 | Cohen et al. |
| 2014/0356322 | A1 | 12/2014 | Crews et al. |
| 2018/0125821 | A1 | 5/2018 | Crew et al. |
| 2018/0215731 | A1 | 8/2018 | Crew et al. |
| 2019/0210996 | A1 | 7/2019 | Harling et al. |
| 2019/0382381 | A1 | 12/2019 | Casillas et al. |
| 2020/0239430 | A1 | 7/2020 | Desantis et al. |
| 2020/0390894 | A1 | 12/2020 | Schiltz et al. |

FOREIGN PATENT DOCUMENTS

| | | | | |
|---|---|---|---|---|
| CN | 110143961 A | 8/2019 | | |
| CN | 111704648 A | 9/2020 | | |
| JP | 2019-528319 | 10/2019 | | |
| JP | 2020-502092 | 1/2020 | | |
| WO | WO 2016/169989 A1 | 10/2016 | | |
| WO | WO 2017/201449 A1 | 11/2017 | | |
| WO | WO 2018/107072 A1 | 6/2018 | | |
| WO | WO-2018118598 A1 * | 6/2018 | ........... | C07D 471/04 |
| WO | WO 2019/195609 A2 | 10/2019 | | |
| WO | WO 2020/041331 A1 | 2/2020 | | |
| WO | WO 2020/092662 A1 | 5/2020 | | |
| WO | WO 2020/172655 A1 | 8/2020 | | |
| WO | WO 2020/252397 A1 | 12/2020 | | |
| WO | WO-2021141662 A1 * | 7/2021 | ............ | C08G 65/00 |

OTHER PUBLICATIONS

Patel et al (Journal of Medicinal Chemistry, 2015, vol. 58 pp. 401-418) (Year: 2015).*

Bondeson et al., "Lessons in PROTAC Design from Selective Degradation with a Promiscuous Warhead," *Cell Chem. Biol.*, Jan. 18, 2018, vol. 25, pp. 78-87.

Buckley et al., "Targeting the von Hippel-Lindau E3 Ubiquitin Ligase Using Small Molecules to Disrupt the VHL/HIF-1α Interaction," *JACS*, Feb. 27, 2012, vol. 134, pp. 4465-4468.

Churcher, "Protac-Induced Protein Degradation in Drug Discovery: Breaking the Rules or Just Making New Ones?" *Journal of Medicinal Chemistry*, Jan. 25, 2018 (published online Dec. 19, 2017, first published Nov. 16, 2017), vol. 61, No. 2, 444-452.

Coll-Martinez et al., "The Potential of Proteolytic Chimeras as Pharmacological Tools and Therapeutic Agents," *Molecules*, Dec. 16, 2020, vol. 25, 5956, 31 pages.

International Search Report and Written Opinion for Application No. PCT/US2021/048600, mailed Dec. 9, 2021, 21 pages.

Ishida et al., "E3 Ligase Ligands for PROTACs: How They Were Found and How to Discover New Ones," *SLAS Discovery*, Sep. 21, 2020, vol. 26, No. 4, pp. 484-502.

Ito et al., "Molecular mechanisms of thalidomide and its derivatives," *Proc. Jpn. Acad., Ser. B*, Apr. 2, 2020, vol. 96, pp. 189-203.

Kounde et al., "A caged E3 ligase ligand for PROTAC-mediated protein degradation with light," *Chem. Commun.*, Mar. 31, 2020, 56:5532.

Krajčovičová et al., "Solid-phase Synthesis for Thalidomide-based Proteolysis-Targeting Chimeras (PROTAC)," Supplementary Material for *ChemComm*, Dec. 17, 2018, 21 pages.

Lai et al., "Induced protein degradation; an emerging drug discovery paradigm," *Nature Reviews Drug Discovery*, Nov. 25, 2016, vol. 16, No. 2, pp. 101-114.

(Continued)

*Primary Examiner* — Mark V Stevens

(74) *Attorney, Agent, or Firm* — Klarquist Sparkman, LLP

(57) ABSTRACT

Leucine zipper-bearing kinase (LZK) targeted degraders are disclosed. The compounds have a general formula Q-L-Z where Q is an LZK binding moiety, L is a linker, and Z is an E3-ligase binding moiety. The compounds inhibit LZK activity and/or degrade LZK. The compounds may be used to treat diseases or conditions characterized at least in part by LZK overexpression.

17 Claims, 46 Drawing Sheets

Specification includes a Sequence Listing.

(56) References Cited

OTHER PUBLICATIONS

Maple et al., "Developing degraders: principles and perspectives on design and chemical space," *MedChemComm*, Oct. 2019 (first published Aug. 12, 2019), vol. 10, pp. 1755-1764.
Mayor-Ruiz et al., "Identification and characterization of cancer vulnerabilities via targeted protein degradation," *Drug Discovery Today: Technologies*, Apr. 2019 (published online Jan. 2, 2019), vol. 31, pp. 81-90.
Momar et al., "Small-Molecule PROTACS: New Approaches to Protein Degradation," *Angewandte Chemie International Edition*, Jan. 12, 2016, vol. 55, No. 6, pp. 1966-1973.
Otto et al., "Targeting bromodomain-containing protein 4 (BRD4) inhibits MYC expression in colorectal cancer cells," *Neoplasia*, Nov. 14, 2019, vol. 21, No. 11, pp. 1110-1120.
Patel et al., "Discovery of Dual Leucine Zipper Kinase (DLK, MAP3K12) Inhibitors with Activity in Neurodegeneration Models," *Journal of Medicinal Chemistry*, Oct. 23, 2014, vol. 58, No. 1, pp. 401-418.
Patel et al., "Scaffold-Hopping and Structure-Based Discovery of Potent, Selective, and Brain Penetrant N-(1 H-Pyrazol-3-yl) pyridine-2-amine Inhibitors of Dual Leucine Zipper Kinase (DLK, MAP3K12)," *Journal of Medicinal Chemistry*, Oct. 2, 2015, vol. 58, No. 20, pp. 8182-8199.
Patel et al., "Selective Inhibitors of Dual Leucine Zipper Kinase (DLK, MAP3K12) with Activity in a Model of Alzheimer's Disease," *J Med Chem*, Sep. 20, 2017, vol. 60, pp. 8083-8102.
Robb et al., "Chemically induced degradation of CDK9 by a proteolysis targeting chimera (PROTAC)," *Chem Commun* (*Camb*), Jul. 4, 2017, vol. 53, No. 54, pp. 7577-7580.
Scheepstra et al., "Bivalent Ligands for Protein Degradation in Drug Discovery," *Comput Struct Biotechnol J.*, Jan. 25, 2019, vol. 17, pp. 160-176.
Siu et al., "Dual Leucine Zipper Kinase Inhibitors for the Treatment of Neurodegeneration: Miniperspective," *Journal of Medicinal Chemistry*, Jun. 4, 2018, vol. 61, No. 18, pp. 8078-8087.
Steinebach et al., "Systematic exploration of different E3 ubiquitin ligases: an approach towards potent and selective CDK6 degraders," *Chem. Sci.*, Feb. 28, 2020, vol. 11, No. 3474, 13 pages.
Steinebach et al., "A facile synthesis of ligands for the von Hippel-Lindau E3 ligase," Supplemental Information for DOI: 10.1055/s-0040-1707400, Sep. 2020, 64 pages.
VH 032, propargyl, Tocris Bioscience, https://www.tocris.com/products/vh-032-propargyl_6683, downloaded Apr. 26, 2021, 1 page.
VH 032, phenol, Tocris Bioscience, https://www.tocris.com/products/vh-032-phenol_6911, downloaded Apr. 26, 2021, 1 page.
VH 101, phenol, Tocris Bioscience, https://www.tocris.com/products/vh-101-phenol_6952, downloaded Apr. 26, 2021, 1 page.
Zengerle et al., "Selective Small Molecule Induced Degradation of the BET Bromodomain Protein BRD4," *ACS Chem Biol.*, Jun. 2, 2025, vol. 10, pp. 1770-1777.
Zhang et al., "The MAP3K13-TRIM25-FBXW7α axis affects c-Myc protein stability and tumor development," *Cell Death and Differentiation* 2020 (published online Jun. 11, 2019), vol. 27, pp. 420-433.
Zoppi et al., "Iterative Design and Optimization of Initially Inactive Proteolysis Targeting Chimeras (PROTACs) Identify VZ185 as a Potent, Fast, and Selective von Hippel-Lindau (VHL) Based Duel Degrader Probe of BRD9 and BRD7," *J Med Chem* 2019, (published online Dec. 12, 2018) vol. 62, pp. 699-726.
Zou et al., "The PROTAC technology in drug development," *Cell Biochem Funct.* Oct. 30, 2018, vol. 37, pp. 21-30.
Jin et al., "Multitasking: Dual Leucine Zipper-Bearing Kinases in Neuronal Development and Stress Management," *Annual Review of Cell and Developmental Biology*, 35:501-521 (Oct. 6, 2019).
Office Action for Japanese Patent Application No. 2023-513976, mailed Jul. 9, 2025.
Perry et al., "Arrestin-3 interaction with maternal embryonic leucine-zipper kinase," *Cellular Signalling*, 63:109366, 8 pages (Nov. 2019).
Amako, "PROTACs—Chimeric molecules that hijack ubiquitin ligases and break down proteins—," *Journal of the Society of Synthetic Organic Chemistry*, 76(4):358-359 (Mar. 4, 2018).
Office Action for Japanese Patent Application No. 2023-513976, mailed Mar. 17, 2026.
Ohoka et al., "PROTAC: A new drug discovery modality for small molecule drugs," *Farumashia*, 56(1):41-45 (Mar. 1, 2020).

* cited by examiner

GNE-3511

CAL33 TR LZK WT

CAL33 TR LZK WT

3

7

SEQUENCE LISTING

```
Sequence total quantity: 20
SEQ ID NO: 1          moltype = DNA  length = 26
FEATURE               Location/Qualifiers
misc_feature          1..26
                      note = Synthetic nucleic acid
source                1..26
                      mol_type = other DNA
                      organism = synthetic construct
```

```
SEQUENCE: 1
ctgtgcccat ggatcactct acgagg                                          26

SEQ ID NO: 2            moltype = DNA  length = 26
FEATURE                 Location/Qualifiers
misc_feature            1..26
                        note = Synthetic nucleic acid
source                  1..26
                        mol_type = other DNA
                        organism = synthetic construct
SEQUENCE: 2
cctcgtagag tgatccatgg gcacag                                          26

SEQ ID NO: 3            moltype = DNA  length = 25
FEATURE                 Location/Qualifiers
misc_feature            1..25
                        note = Synthetic nucleic acid
source                  1..25
                        mol_type = other DNA
                        organism = synthetic construct
SEQUENCE: 3
gaggtggcca tcaagaaagt gagag                                           25

SEQ ID NO: 4            moltype = DNA  length = 25
FEATURE                 Location/Qualifiers
misc_feature            1..25
                        note = Synthetic nucleic acid
source                  1..25
                        mol_type = other DNA
                        organism = synthetic construct
SEQUENCE: 4
ctctcacttt cttgatggcc acctc                                           25

SEQ ID NO: 5            moltype = DNA  length = 32
FEATURE                 Location/Qualifiers
misc_feature            1..32
                        note = Synthetic nucleic acid
source                  1..32
                        mol_type = other DNA
                        organism = synthetic construct
SEQUENCE: 5
taatctagaa tggccaactt tcaggagcac ct                                   32

SEQ ID NO: 6            moltype = DNA  length = 34
FEATURE                 Location/Qualifiers
misc_feature            1..34
                        note = Synthetic nucleic acid
source                  1..34
                        mol_type = other DNA
                        organism = synthetic construct
SEQUENCE: 6
ttagcggccg cttaccaggt agcagagctg tagt                                 34

SEQ ID NO: 7            moltype = DNA  length = 20
FEATURE                 Location/Qualifiers
misc_feature            1..20
                        note = Synthetic nucleic acid
source                  1..20
                        mol_type = other DNA
                        organism = synthetic construct
SEQUENCE: 7
taatacgact cactataggg                                                 20

SEQ ID NO: 8            moltype = DNA  length = 18
FEATURE                 Location/Qualifiers
misc_feature            1..18
                        note = Synthetic nucleic acid
source                  1..18
                        mol_type = other DNA
                        organism = synthetic construct
SEQUENCE: 8
tagaaggcac agtcgagg                                                   18

SEQ ID NO: 9            moltype = DNA  length = 32
FEATURE                 Location/Qualifiers
misc_feature            1..32
                        note = Synthetic nucleic acid
```

```
source                 1..32
                       mol_type = other DNA
                       organism = synthetic construct
SEQUENCE: 9
taatctagaa tgctgggtag tggagcccaa gg                                32

SEQ ID NO: 10          moltype = DNA  length = 34
FEATURE                Location/Qualifiers
misc_feature           1..34
                       note = Synthetic nucleic acid
source                 1..34
                       mol_type = other DNA
                       organism = synthetic construct
SEQUENCE: 10
ttagcggccg cttaggcaat gtctaaatgc atga                              34

SEQ ID NO: 11          moltype = DNA  length = 34
FEATURE                Location/Qualifiers
misc_feature           1..34
                       note = Synthetic nucleic acid
source                 1..34
                       mol_type = other DNA
                       organism = synthetic construct
SEQUENCE: 11
ttagcggccg cttacactgc ttgctcacgc ttaa                              34

SEQ ID NO: 12          moltype = DNA  length = 34
FEATURE                Location/Qualifiers
misc_feature           1..34
                       note = Synthetic nucleic acid
source                 1..34
                       mol_type = other DNA
                       organism = synthetic construct
SEQUENCE: 12
ttagcggccg cttaccaggt agcagagctg tagt                              34

SEQ ID NO: 13          moltype = DNA  length = 20
FEATURE                Location/Qualifiers
misc_feature           1..20
                       note = Synthetic nucleic acid
source                 1..20
                       mol_type = other DNA
                       organism = synthetic construct
SEQUENCE: 13
aactgattcg aaggcgcaga                                              20

SEQ ID NO: 14          moltype = DNA  length = 20
FEATURE                Location/Qualifiers
misc_feature           1..20
                       note = Synthetic nucleic acid
source                 1..20
                       mol_type = other DNA
                       organism = synthetic construct
SEQUENCE: 14
gggcgttttc caagagagga                                              20

SEQ ID NO: 15          moltype = DNA  length = 21
FEATURE                Location/Qualifiers
misc_feature           1..21
                       note = Synthetic nucleic acid
source                 1..21
                       mol_type = other DNA
                       organism = synthetic construct
SEQUENCE: 15
ggcaccacac cttctacaat g                                            21

SEQ ID NO: 16          moltype = DNA  length = 20
FEATURE                Location/Qualifiers
misc_feature           1..20
                       note = Synthetic nucleic acid
source                 1..20
                       mol_type = other DNA
                       organism = synthetic construct
```

-continued

```
SEQUENCE: 16
gtggtggtga agctgtagcc                                              20

SEQ ID NO: 17          moltype = DNA  length = 18
FEATURE                Location/Qualifiers
misc_feature           1..18
                       note = Synthetic nucleic acid
source                 1..18
                       mol_type = other DNA
                       organism = synthetic construct
SEQUENCE: 17
ccatggagaa ggctgggg                                                18

SEQ ID NO: 18          moltype = DNA  length = 21
FEATURE                Location/Qualifiers
misc_feature           1..21
                       note = Synthetic nucleic acid
source                 1..21
                       mol_type = other DNA
                       organism = synthetic construct
SEQUENCE: 18
gtccaccacc ctgttgctgt a                                            21

SEQ ID NO: 19          moltype = DNA  length = 21
FEATURE                Location/Qualifiers
misc_feature           1..21
                       note = Synthetic nucleic acid
source                 1..21
                       mol_type = other DNA
                       organism = synthetic construct
SEQUENCE: 19
cggaatgaac ctgtctctga a                                            21

SEQ ID NO: 20          moltype = DNA  length = 21
FEATURE                Location/Qualifiers
misc_feature           1..21
                       note = Synthetic nucleic acid
source                 1..21
                       mol_type = other DNA
                       organism = synthetic construct
SEQUENCE: 20
gatgtagatt cttcagccat t                                            21
```

LZK-TARGETING DEGRADERS AND METHODS OF USE

CROSS-REFERENCE TO RELATED APPLICATIONS

This application is a continuation-in-part of International Application No. PCT/US2021/048600, filed Sep. 1, 2021, which was published in English under PCT Article 21(2), which in turn claims the benefit of the earlier filing date of U.S. Provisional Application No. 63/073,835, filed Sep. 2, 2020, which is incorporated by reference in its entirety herein.

ACKNOWLEDGMENT OF GOVERNMENT SUPPORT

This invention was made with government support under Project No. Z01 600.129.15.01.024.001.0021.012 awarded by the National Institutes of Health. The government has certain rights in the invention.

FIELD

This invention concerns targeted degraders that target leucine zipper-bearing kinase, and methods for using the targeted degraders.

BACKGROUND

The worldwide frequency of head and neck squamous cell carcinoma (HNSCC) is approximately 800,000 new cases per year, with 430,000 deaths annually, statistics that have remained unchanged for several decades. Treatment options for HNSCC patients are primarily limited to surgery, radiotherapy, platinum-based chemotherapy, or combinations thereof. Cetuximab, a monoclonal antibody targeting EGFR, is the only approved targeted therapy for HNSCC (Bonner et al., *NEJM*2006, 364:567-578; Vermorken et al., *NEJM*2008, 359:1116-1127). However, only a subset (13%) of HNSCC patients respond to cetuximab (Vermorken et al., *J Clin Oncol* 2007, 25:2171-2177); therefore, there is an urgent need for new therapies.

Lung squamous cell carcinoma (LSCC) accounts for one-third of all lung cancer cases. Despite extensive genomic sequencing, the identification of oncogenic drivers in LSCC has remained challenging, and actionable alterations are unknown in the majority of LSCC patients (Gold et al., *Clin Cancer Res* 2012, 18(11):3002-7; Gandara et al., *Clin Cancer Res* 2015, 21(10):2236-43). As a result, no targeted therapies have been approved to treat LSCC, and treatment still relies on chemotherapy or radiotherapy. Genomic characterization of LSCC tumors shows that distal chromosome 3q amplification (3q26-29) is the most prevalent genomic alteration in LSCC, occurring in approximately 50% of LSCC patients (Cancer Genome Atlas Research Network, "Comprehensive genomic characterization of squamous cell lung cancers," Nature 2012, 489 (7417):519-25.).

SUMMARY

This disclosure concerns embodiments of targeted degraders that target leucine zipper-bearing kinase (LZK), and methods for using the targeted degraders. In some embodiments, the disclosed target degrader is a compound, or a stereoisomer, tautomer, or pharmaceutically acceptable salt thereof, having a general formula:

Q-L-Z where Q is a leucine zipper kinase (LZK) binding moiety; Z is an E3-ligase binding moiety; and L is a linker having a general formula

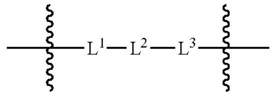

or L is absent.

$L^1$ is —C(O)—, —S(O)$_2$—, —CH$_2$—, —C(R$^b$)(R$^c$)—, —(CH$_2$)$_n$C(O)—, —C(O)—(CH$_2$)$_n$—, —N(R$^c$)—, —N(R$^c$)—(C(H)(R$^a$))$_s$—C(O)—, or —C(O)—(C(H)(R$^a$))$_s$—N(R$^c$)—, and $L^1$ binds to Q, or $L^1$ is absent and $L^2$ binds to Q. $L^3$ is —C(O)—, —S(O)$_2$—, —CH$_2$—, —C(R$^b$)(R$^c$)—, —C(O)—(CH$_2$)$_n$—, —(CH$_2$)$_n$—C(O)—, —N(R$^c$)—, —N(R$^c$)—(C(H)(R$^a$))$_s$—C(O)—, or —C(O)—(C(H)(R$^a$))$_s$—N(R$^c$)—, and -$L^3$ binds to Z, or $L^3$ is absent and $L^2$ binds to Z. $L^2$ is —(R$^d$)$_p$—, —N(R$^b$)—(R$^d$)$_p$—, —(R$^d$)$_p$—N(R$^b$)—, —N(R$^b$)—(R$^d$)$_p$—N(R$^b$)—, —(N(R$^b$)—(C(H)(R$^a$))$_s$—C(O))$_m$—N(R$^b$)—C(H)(R$^a$)—, or —C(H)(R$^a$)—N(R$^b$)—(C(O)—(C(H)(R$^a$))$_s$—N(R$^b$))$_m$—.

Each $R^a$ independently is an amino acid side chain. Each $R^b$ independently is H or $R^c$. Each $R^c$ independently is substituted or unsubstituted aliphatic, substituted or unsubstituted heteroaliphatic, substituted or unsubstituted aryl, substituted or unsubstituted heteroaryl, substituted or unsubstituted arylalkyl, or substituted or unsubstituted alkylaryl. Each $R^d$ independently is substituted or unsubstituted aliphatic, substituted or unsubstituted heteroaliphatic, substituted or unsubstituted aryl, substituted or unsubstituted heteroaryl, —(CH$_2$—CH$_2$—O)$_r$—, —(C(H)(R$^a$))$_s$—C(O)—, —C(O)N(R$^b$)—, or —N(R$^b$)C(O)—. Each $R^c$ independently is substituted or unsubstituted $C_1$-$C_3$ alkyl or H. In any of the foregoing or following embodiments, m is an integer from 0-11, n is an integer from 1-10, p is an integer from 0-5, r is an integer from 2-20, and s is an integer from 1-20. In some embodiments $L^2$ is not solely —C(O)N(R$^b$)— or —N(R$^b$)C(O)—. If $L^2$ terminates in —C(H)(R$^a$)—C(O)— or —N(R$^b$)C(O)—, then $L^3$ is not —C(O)— or —S(O)$_2$—. If $L^3$ is absent, $L^2$ is —(R$^d$)$_p$— and p is 0, then $L^1$ binds directly to Z.

In some embodiments, $L^2$ comprises:

one or more of

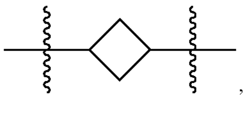, 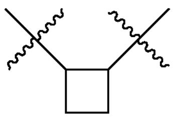,

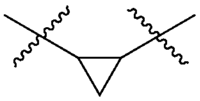, 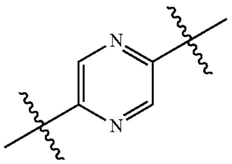,

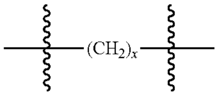, 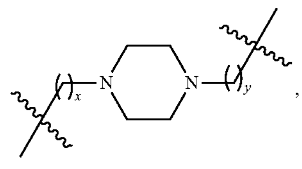,

-continued
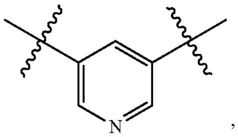,
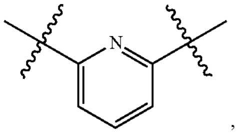,
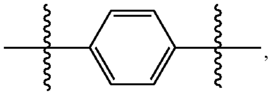,
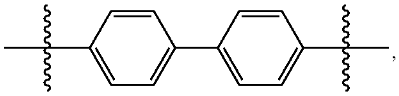,
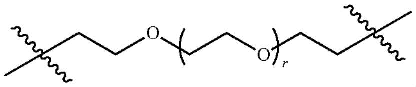,
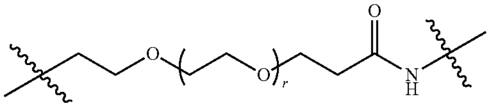,
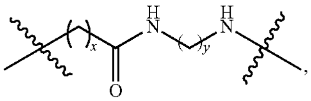,
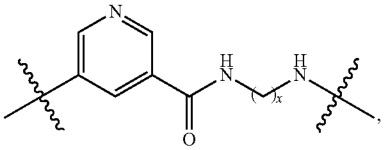,
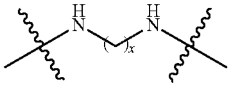,
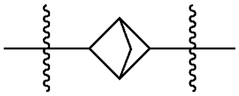,
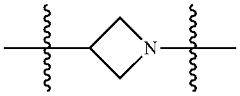,
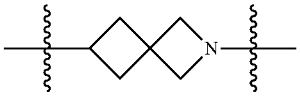,
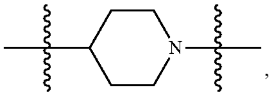, and
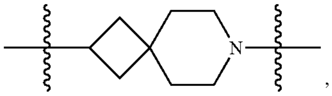,
where x and y independently are integers from 1-20, optionally in combination with one or more of —C(O)N(H)— and —N(H)C(O)—.
In any of the foregoing or following embodiments, Z may be:
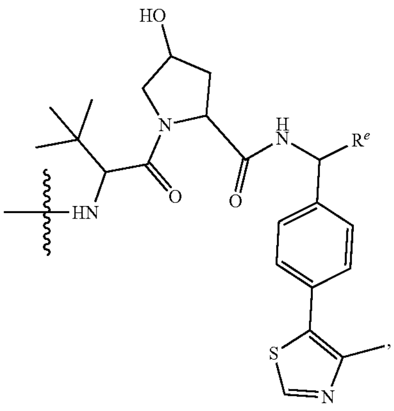
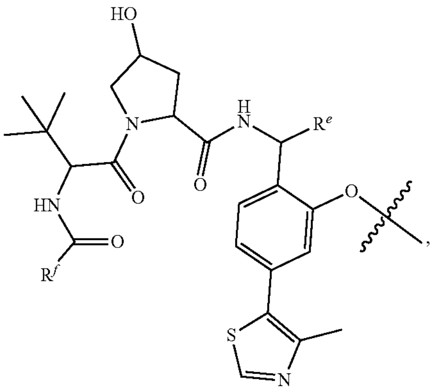
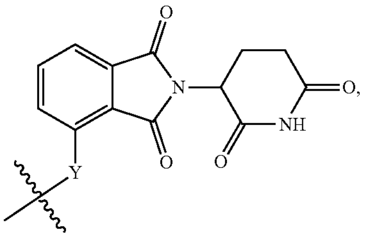
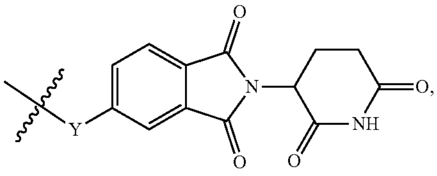
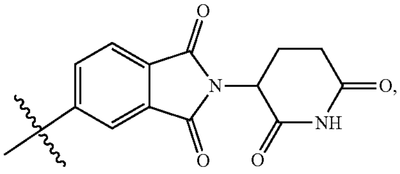

-continued

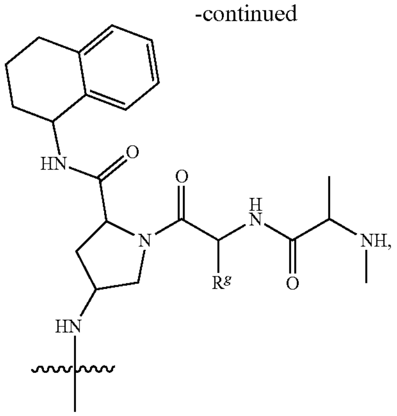

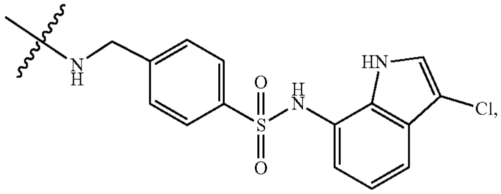

, or

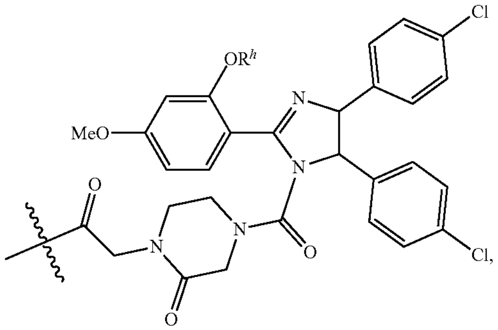

, where each $R^e$ independently is substituted or unsubstituted $C_1$-$C_3$ alkyl or H. $R^f$ is substituted or unsubstituted $C_1$-$C_3$ alkyl or —N($R^e$)$_2$. $R^g$ is substituted or unsubstituted $C_1$-$C_6$ alkyl. $R^h$ is substituted or unsubstituted $C_1$-$C_3$ alkyl. Y is O or N($R^e$), or Y is absent.

In any of the foregoing or following embodiments, Q may be:

(Q1)

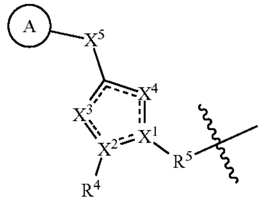

where each bond represented by ----- is a single or double bond as needed to satisfy valence requirements. The $-X^1$($R^5$)— moiety is —C($R^5$)—, —C($R^5$)—C(H)—, —C(H)—C($R^5$)—, —C($R^5$)—N—, —N—C($R^5$)—, or —N($R^5$)—. $X^2$ is N or C. $X^3$ is N or C(H). One or two of $X^1$—$X^3$ comprises N. $X^4$ is C(H) or S. $X^5$ is —N(H)— or absent. $Y^1$ is C($R^1$) or N. $Y^2$ is C($R^2$) or N. $Y^3$ is C($R^3$) or N. $Y^4$ is N or C($R^6$). $Y^5$ is C($R^7$) or N. $Y^6$ is C($R^8$) or N. One or two of $Y^1$-$Y^6$ are N, and at least one of $Y^1$-$Y^3$ or $Y^6$ is other than C(H). Two, three, or four of $Y^7$-$Y^{10}$ independently are N or N($R^9$), and the others of $Y^7$-$Y^{10}$ are C($R^{10}$). $R^1$ is cyano, perhaloalkyl, H, alkyl, or perhaloalkoxy. $R^2$ is H, alkoxy, perhaloalkyl, perhaloalkoxy, haloalkoxy, haloalkyl, cyanoalkyl, alkyl, cyano, amino, or heteroarylalkoxy or $R^1$ and $R^2$ together with the atoms to which they are attached form a 5- or 6-membered substituted or unsubstituted aryl or substituted or unsubstituted heteroaryl ring. $R^3$ is H, amino, alkylamino, aminoalkyl, alkoxy, or —N(H)C(O)R' where R' is alkyl, or $R^2$ and $R^3$ together with the atoms to which they are attached form a 5- or 6-membered substituted or unsubstituted aryl or substituted or unsubstituted heteroaryl ring. $R^4$ is substituted or unsubstituted aliphatic, substituted or unsubstituted azaalkyl, or aryl. $R^5$ is substituted or unsubstituted aliphatic, substituted or unsubstituted heteroaliphatic, or substituted or unsubstituted alkylamino. $R^6$-$R^8$ independently are H, alkyl, alkoxy, perhaloalkyl, perhaloalkoxy, or cyano. Each $R^9$ independently is H or alkyl. Each $R^{10}$ independently is H, alkyl, or cyano.

This disclosure further includes pharmaceutical compositions. A pharmaceutical composition includes at least one compound as disclosed herein, and at least one pharmaceutically acceptable carrier.

Methods of using the disclosed compounds are disclosed. In some embodiments, a method of inhibiting LZK activity includes contacting a cell expressing LZK with an effective amount of a compound disclosed herein, thereby inhibiting LZK activity. Inhibiting LZK activity may comprise degrading LZK. In some embodiments, inhibition, knockdown, or degradation of LZK results in cell cycle progression, reduces c-MYC expression, reduces gain-of-function (GOF) mutant p53 expression, inhibits c-Jun N-terminal kinase (JNK) pathway signaling, inhibits PI3K/AKT pathway signaling, inhibits cyclin dependent kinase 2 (CDK2) activity, or any combination thereof. In any of the foregoing or following embodiments, the cell may be characterized by amplification of chromosome 3q, overexpression of mitogen-activated protein kinase kinase kinase 13 (MAP3K13), or both. In some examples, the cell is a head and neck squamous cell carcinoma (HNSCC) cell, a lung squamous cell carcinoma (LSCC) cell, a hepatocellular carcinoma cell, an ovarian cancer cell, a small cell lung cancer cell, a neuroendocrine prostate cancer cell, or an esophageal cancer cell.

In some embodiments, contacting the cell with the compound comprises administering a therapeutically effective amount of the compound, or an amount of a pharmaceutical composition comprising the therapeutically effective amount of the compound, to a subject. The subject may have a disease or condition characterized at least in part by LZK overexpression. In some embodiments, the disease or condition is cancer, such as HNSCC, LSCC, hepatocellular carcinoma, ovarian cancer, small cell lung cancer, neuroendocrine prostate cancer, or esophageal cancer. Administering the therapeutically effective amount of the compound, or the amount of the pharmaceutical composition, may decrease viability of the cancer cells, inhibit tumor growth, or a combination thereof.

The foregoing and other objects, features, and advantages of the disclosure will become more apparent from the following detailed description, which proceeds with reference to the accompanying figures.

BRIEF DESCRIPTION OF THE DRAWINGS

FIG. 12A is a graph of mean tumor volume±SEM; FIG. 12B is a bar graph showing average tumor volume at the end of treatment, mean tumor volume±SEM, Student's t-test, *p<0.05; FIG. 12C is tumor images at the end of the study.

FIG. 55A is a graph of mean tumor volume SEM; FIG. 55B is a bar graph showing average tumor volume at the end of treatment, mean tumor volume±SEM, Student's t-test, *p<0.05; FIG. 55C is tumor images at the end of the study.

SEQUENCE LISTING

Figure 1:
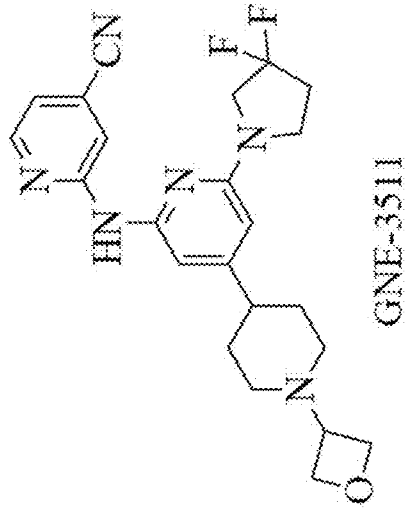
FIG. 1 is the structure of GNE-3511.
Figure 2A:
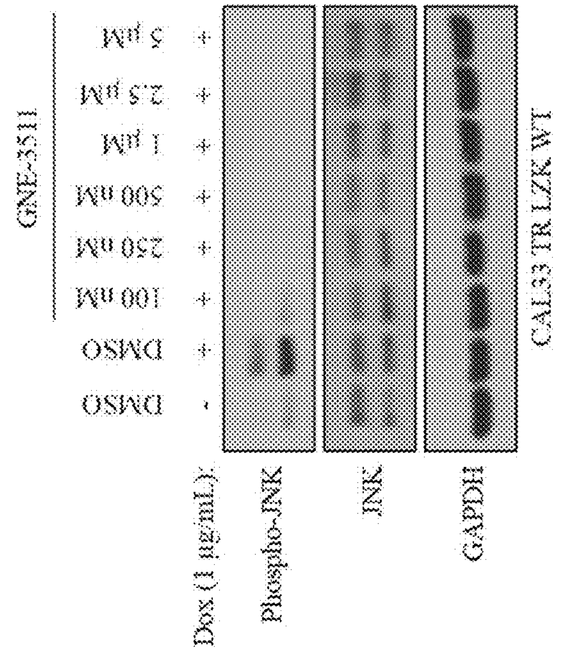
FIGS. 2A and 2B are images showing that GNE-3511 inhibited LZK activity, as monitored by downstream JNK phosphorylation from 100 nM to 5 μM at 1 hour (2A) and at 250 nM for up to 72 hours (2B).
Figure 2B:
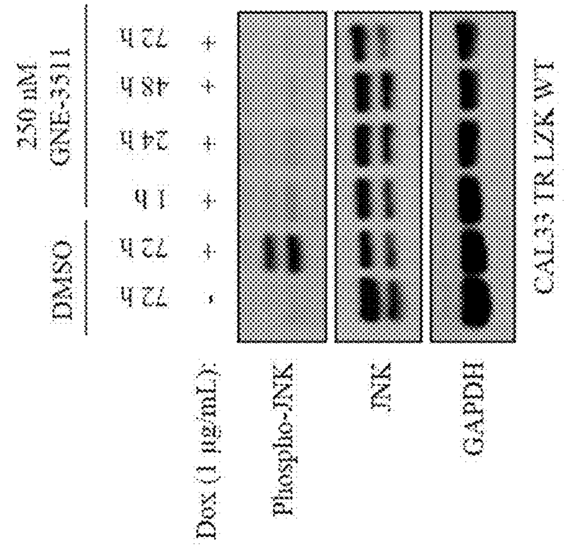
Figure 4:
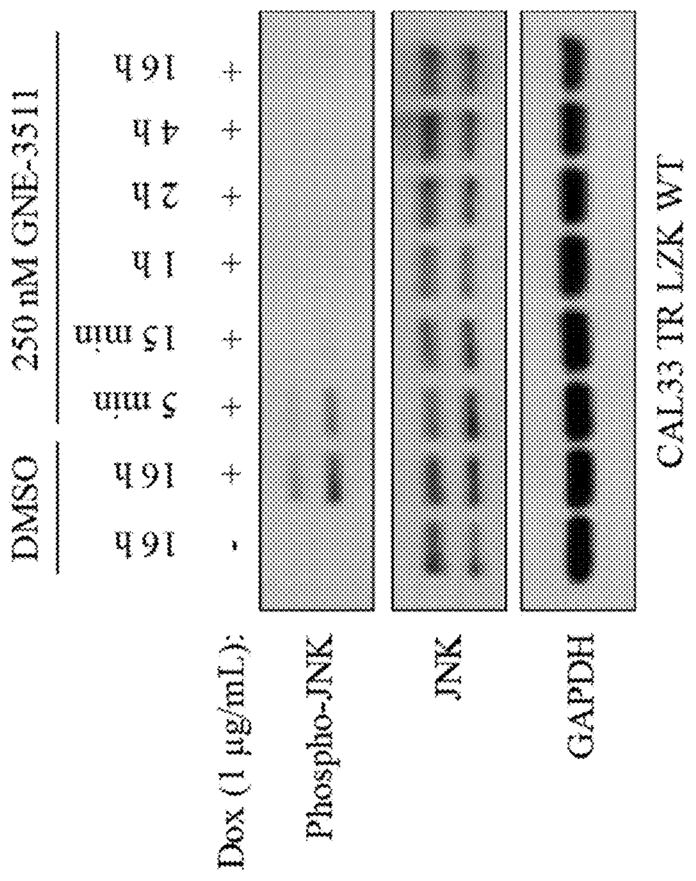
FIG. 4 shows that GNE-3511 250 nM, inhibited LZK activity toward JNK within 15 minutes.
Figure 3:
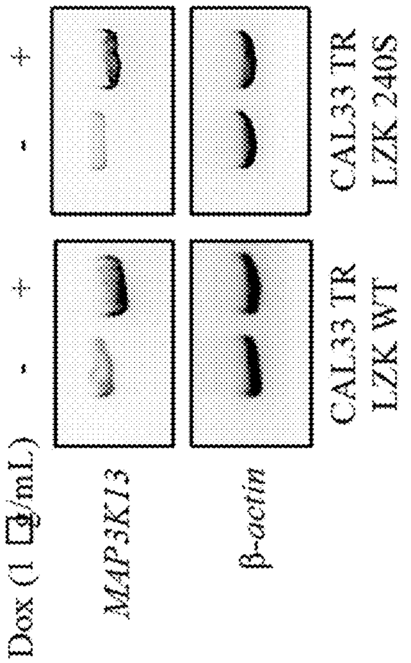
FIG. 3 shows RT-PCR analysis of CAL33 TR LZK WT or 240S cell lines with tetracycline-inducible expression of LZK.

The nucleic and amino acid sequences listed in the accompanying sequence listing are shown using standard letter abbreviations for nucleotide bases, and three letter code for amino acids, as defined in 37 C.F.R. § 1.822. Only one strand of each nucleic acid sequence is shown, but the complementary strand is understood as included by any reference to the displayed strand. The Sequence Listing is submitted as an ASCII text file, created on Aug. 17, 2021, 12 KB, which is incorporated by reference herein.

SEQ ID NO: 1 is the nucleotide sequence for an LZK Q240S forward primer.

SEQ ID NO: 2 is the nucleotide sequence for an LZK Q240S verse primer.

SEQ ID NO: 3 is the nucleotide sequence for an LZK K195M forward primer.

SEQ ID NO: 4 is the nucleotide sequence for an LZK K195M reverse primer.

SEQ ID NO: 5 is the nucleotide sequence for a Xbal to start of LZK forward primer.

SEQ ID NO: 6 is the nucleotide sequence for a Notl to end of LZK reverse primer.

SEQ ID NO: 7 is the nucleotide sequence for a T7 promoter primer.

SEQ ID NO: 8 is the nucleotide sequence for a BGH reverse primer.

SEQ ID NO: 9 is the nucleotide sequence for a Xbal to LZK kinase domain forward primer.

SEQ ID NO: 10 is the nucleotide sequence for a Xbal to LZK end kinase domain reverse primer.

SEQ ID NO: 11 is the nucleotide sequence for a Notl to LZK end zipper domain reverse primer.

SEQ ID NO: 12 is the nucleotide sequence for a Notl to LZK end stop codon reverse primer.

SEQ ID NO: 13 is the nucleotide sequence for aMAP3K13 forward primer.

SEQ ID NO: 14 is the nucleotide sequence for aMAP3K13 reverse primer.

SEQ ID NO: 15 is the nucleotide sequence for an ACTB forward primer.

SEQ ID NO: 16 is the nucleotide sequence for an ACTB reverse primer.

SEQ ID NO: 17 is the nucleotide sequence for a GAPDH forward primer.

SEQ ID NO: 18 is the nucleotide sequence for a GAPDH reverse primer.

SEQ ID NO: 19 is the nucleotide sequence for DNA corresponding to an shRNA.

SEQ ID NO: 20 is the nucleotide sequence for DNA corresponding to an shRNA.

DETAILED DESCRIPTION

This disclosure concerns embodiments of targeted degraders that target leucine zipper-bearing kinase (LZK), as well as methods of making and using the targeted degraders. LZK is implicated in both head and neck squamous cell carcinoma (HNSCC) and lung squamous cell carcinoma (LSCC). LZK has also been shown to regulate c-MYC protein stability in hepatocellular carcinoma and is required to maintain growth of hepatocellular carcinoma cells (Zhang et al., *Cell Death & Differentiation* 2020, 27:420-433). Furthermore, LZK is amplified in 20% of ovarian cancers, 25% of small cell lung cancers, 20% of neuroendocrine prostate cancer, and 20% of esophageal adenocarcinomas, implicating LZK as a driver in these additional cancers.

Kinase signaling pathways are integral to cell survival and proliferation, and kinase inhibition is an established approach to treating many forms of cancer. However, inhibition of kinase activity fails to account for additional scaffolding roles that can also affect downstream signaling;

thus, inhibition by itself may be an incomplete solution; this is especially true for kinases whose amplification and correlating high level of expression are driving tumorigenesis. Advantageously, degradation abolishes both kinase activity and scaffolding effects.

Leucine zipper-bearing kinase (LZK, MAPK3K13) is a serine/threonine kinase with high homology to MAPK3K12 (DLK) (Patel et al., *J Med Chem* 2015, 58:8182-8199). LZK has been shown to be amplified or to have copy-number gain in a majority of HNSCC tumors, making it an attractive target for therapy. LZK regulates c-MYC (Soth et al., US 2018/0057507 A1; Soth et al., U.S. Pat. No. 10,093,664 B2) and PI3K/AKT pathways in a kinase-dependent manner, and gain-of-function (GOF) mutant p53 in a kinase-independent manner. A targeted degradation approach would therefore be preferred over a kinase inhibition approach, in order to address all known downstream signaling pathways affected by LZK. Moreover, the c-MYC, p53 and PI3K/AKT pathways are implicated in a wide variety of cancers. Preventing the upregulation of these pathways by targeted LZK degradation could therefore be of potentially broad interest to cancer researchers.

LZK can directly phosphorylate the MAP2Ks (MAP kinase kinases) MKK7 and MKK4, leading to JNK (c-Jun N-terminal kinase) pathway activation (Ikeda et al., *J Biochem* 2001, 130:773-781). Amplified endogenous LZK does not activate the JNK pathway in HNSCC (Edwards et al., *Cancer Res* 2017, 77:4961-4972; Ikeda et al.). However, overexpressed LZK leads to JNK pathway activation, which can be used as a readout to assess catalytic inhibitors of LZK (Edwards et al.). Copy-number alterations are frequently observed in HNSCC, the most common being distal amplification of chromosome 3 (3q26-3q29, the 3q amplicon) (TCGA, *Nature* 2012, 489:519-525), which includes the protein LZK, encoded by MAP3K13. This amplification occurs in 20% of HNSCC patients, with another 50% presenting with gains of chromosome 3q (Edwards et al., *Cancer Res* 2017, 77:4961-4972).

Targeted degraders are tripartite molecules composed of a pharmacophore that binds the target protein of interest (POI), a ligase-binding moiety that attracts an E3 ligase, and a linker that combines the two into a single molecule (Churcher, *J Med Chem* 2018, 61:444-452; Lai et al., *Nat Rev Drug Discov* 2017, 16:101-114; Toure et al., *Angew Chem Int Ed Engl* 2016, 55:1966-1973). Upon entering the cell, the pharmacophore binds noncovalently to the POI and the ligase-binding moiety attracts an E3 ligase. Interaction between the POI and the E3 ligase complex results in ubiquitination of the POI, thereby marking it for proteasomal degradation. The targeted degrader can then dissociate from the tagged POI and seek another binding partner. Thus, targeted degrader activity is potentially catalytic, as a single targeted degrader molecule can induce ubiquitination of multiple POI molecules. Moreover, since the POI is degraded rather than inhibited, there is no need to maintain a steady concentration of targeted degrader as is the case in protein inhibition. Regeneration of protein is dependent on resynthesis by the ribosome. In the present disclosure, the POI is LZK.

Design and synthesis of a targeted degrader for a given target is not straightforward. First, the choice of pharmacophore is key as the targeted degrader advantageously binds the POI reversibly with reasonable on- and off-kinetics. Thus, a very tight-binding inhibitor with a slow off rate might be ideal for inhibition purposes, but would interfere with catalytic turnover for degradation. Secondly, the linker should not interfere with binding of targeted degrader pharmacophore to POI, but must also allow for binding of the E3 ligase to form a cooperative ternary complex—a POI-targeted degrader-E3 ligase complex. In many cases, the E3 ligase is a complex with other proteins including an E2 ligase, which further complicates the binding. Third, a number of E3 ligases exist, of which several have been used in targeted degradation applications. The complexity of the system does not lend itself readily to modeling. A successful targeted degrader possesses a degree of binding cooperativity in forming the putative ternary complex of POI, targeted degrader and E3 ligase complex. Targeted degraders are typically quite large molecules, often approaching or over 1000 Daltons, which is challenging in terms of balancing water solubility with membrane permeability.

Some embodiments of the disclosed targeted degraders inhibit LZK activity, thereby decreasing the viability of cancer cells with amplified MAP3K13 and/or suppressing tumor growth in vivo. The oncogene c-MYC identified as a downstream target that is regulated by catalytic activity of LZK, whereas gain-of-function (GOF) mutant p53 is regulated in a kinase-independent manner. In some embodiments, the disclosed targeted degraders specifically promote LZK degradation, thereby abolishing LZK expression and targeting both c-MYC and GOF-p53 leading to global inhibition of cell cycle progression and/or reduced expression of c-MYC and GOF-p53. Advantageously, some embodiments of the disclosed LZK-targeting degraders are catalytic, and sequentially bind to and degrade a plurality of LZK molecules.

I. Terms and Abbreviations

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

The disclosure of numerical ranges should be understood as referring to each discrete point within the range, inclusive of endpoints, unless otherwise noted. Unless otherwise indicated, all numbers expressing quantities of components, molecular weights, percentages, temperatures, times, and so forth, as used in the specification or claims are to be understood as being modified by the term "about." Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods as known to those of ordinary skill in the art. When directly and explicitly distinguishing embodiments from discussed prior art, the embodiment numbers are not approximates unless the word "about" is recited.

Although there are alternatives for various components, parameters, operating conditions, etc. set forth herein, that does not mean that those alternatives are necessarily equivalent and/or perform equally well. Nor does it mean that the alternatives are listed in a preferred order unless stated otherwise.

Definitions of common terms in chemistry may be found in Richard J. Lewis, Sr. (ed.), *Hawley's Condensed Chemical Dictionary*, published by John Wiley & Sons, Inc., 2016 (ISBN 978-1-118-13515-0).

In order to facilitate review of the various embodiments of the disclosure, the following explanations of specific terms are provided:

Administration: To provide or give a subject an agent, such as one or more compounds provided herein, by any effective route. Exemplary routes of administration include, but are not limited to, oral, injection (such as subcutaneous, intramuscular, intradermal, intraperitoneal, intravenous, intraosseous, intracerebroventricular, intrathecal, and intratumoral), sublingual, rectal, transdermal, intranasal, vaginal and inhalation routes.

Aliphatic: A substantially hydrocarbon-based compound, or a radical thereof (e.g., $C_6H_{13}$, for a hexane radical), including alkanes, alkenes, alkynes, including cyclic (monocyclic, bicyclic, and polycyclic) versions thereof, and further including straight- and branched-chain arrangements, and all stereo and position isomers as well. Unless expressly stated otherwise, an aliphatic group contains from one to twenty-five carbon atoms; for example, from one to fifteen, from one to ten, from one to six, or from one to four carbon atoms. An aliphatic chain may be substituted or unsubstituted. Unless expressly referred to as an "unsubstituted aliphatic," an aliphatic group can either be unsubstituted or substituted. An aliphatic group can be substituted with one or more substituents (up to two substituents for each methylene carbon in an aliphatic chain, or up to one substituent for each carbon of a —C═C— double bond in an aliphatic chain, or up to one substituent for a carbon of a terminal methine group). A substituted aliphatic group includes at least one $sp^3$-hybridized carbon or two $sp^2$-hybridized carbons bonded with a double bond or at least two sp-hybridized carbons bonded with a triple bond. Exemplary substituents include, but are not limited to, alkyl, alkenyl, alkynyl, alkoxy, alkylamino, alkylthio, acyl, aldehyde, amide, amino, aminoalkyl, aryl, arylalkyl, carboxyl, cyano, cycloalkyl, dialkylamino, halo, haloaliphatic, heteroaliphatic, heteroaryl, heterocycloaliphatic, hydroxyl, oxo, sulfonamide, sulfhydryl, thioalkoxy, or other functionality.

Alkoxy: A radical (or substituent) having the structure —OR, where R is a substituted or unsubstituted aliphatic group. Methoxy ($—OCH_3$) is an exemplary alkoxy group. In a substituted alkoxy, R is alkyl substituted with a non-interfering substituent. R may be linear, branched, cyclic, or a combination thereof (e.g., cyclopropylmethoxy).

Alkyl: A hydrocarbon radical or substituent having a saturated carbon chain. The chain may be cyclic, branched or unbranched. Examples, without limitation, of alkyl groups include methyl, ethyl, propyl, butyl, pentyl, hexyl, heptyl, octyl, nonyl and decyl. The term lower alkyl means the chain includes 1-10 carbon atoms. The terms alkenyl and alkynyl refer to hydrocarbon groups having carbon chains containing one or more double or triple bonds, respectively.

Alkylamino: A an amino group with an alkyl substituent, e.g., —N(H)R or —N(R)R', where R and R' are alkyl groups, and the bond to the remainder of the molecule is through the nitrogen atom.

Alkylaryl: An alkyl-substituted aryl group.

Amino: A chemical functional group —N(R)R' where R and R' are independently hydrogen, alkyl, heteroalkyl, haloalkyl, aliphatic, heteroaliphatic, aryl (such as optionally substituted phenyl or benzyl), heteroaryl, alkylsulfano, or other functionality. A "primary amino" group is $—NH_2$. "Mono-substituted amino" or "secondary amino" means a radical —N(H)R substituted as above and includes, e.g., methylamino, (1-methylethyl)amino, phenylamino, and the like. "Di-substituted amino" or "tertiary amino" means a radical —N(R)R' substituted as above and includes, e.g., dimethylamino, methylethylamino, di(1-methylethyl) amino, and the like.

Amino acid: An organic acid containing both a basic amino group ($—NH_2$) and an acidic carboxyl group (—COOH). The 25 amino acids that are protein constituents are α-amino acids, i.e., the $—NH_2$ group is attached to the carbon atom next to the —COOH group. As used herein, the term amino acid also encompasses D-amino acids and non-naturally occurring amino acids, e.g., amino acids such as ornithine and 2,4-diaminobutyric acid.

Aminoalkyl: A alkyl group including at least one amino substituent, wherein the bond to the remainder of the molecule is through a carbon atom of the alkyl group.

Aryl: A monovalent aromatic carbocyclic group of, unless specified otherwise, from 6 to 15 carbon atoms having a single ring (e.g., phenyl) or multiple fused rings in which at least one ring is aromatic (e.g., quinoline, indole, benzodioxole, pyridine, pyrimidine, pyrazole, benzopyrazole, thiazole, isoxazole, oxazole, triazole, and the like), provided that the point of attachment is through an atom of an aromatic portion of the aryl group and the aromatic portion at the point of attachment contains only carbons in the aromatic ring. If any aromatic ring portion contains a heteroatom, the group is a heteroaryl and not an aryl. Aryl groups are monocyclic, bicyclic, tricyclic or tetracyclic.

Arylalkyl: An aryl-substituted alkyl group, e.g., benzyl, wherein the bond to the remainder of the molecule is through a carbon atom of the alkyl group.

Azaalkyl: A heteroalkyl group including a nitrogen heteroatom.

Derivative: A compound that is derived from a similar compound or a compound that can be imagined to arise from another compound, for example, if one atom is replaced with another atom or group of atoms. The latter definition is common in organic chemistry. In biochemistry, the word is used for compounds that at least theoretically can be formed from the precursor compound.

Excipient: A physiologically inert substance that is used as an additive in a pharmaceutical composition. As used herein, an excipient may be incorporated within particles of a pharmaceutical composition, or it may be physically mixed with particles of a pharmaceutical composition. An excipient can be used, for example, to dilute an active agent and/or to modify properties of a pharmaceutical composition. Examples of excipients include but are not limited to polyvinylpyrrolidone (PVP), tocopheryl polyethylene glycol 1000 succinate (also known as vitamin E TPGS, or TPGS), dipalmitoyl phosphatidyl choline (DPPC), trehalose, sodium bicarbonate, glycine, sodium citrate, and lactose.

Heteroaliphatic: An aliphatic compound or group having at least one carbon atom in the chain and at least one heteroatom, i.e., one or more carbon atoms has been replaced with a non-carbon atom, typically nitrogen, oxygen, phosphorus, silicon, or sulfur. Heteroaliphatic compounds or groups may be substituted or unsubstituted, branched or unbranched, cyclic or acyclic, and include "heterocycle", "heterocyclyl", "heterocycloaliphatic", or "heterocyclic" groups. Heteroalkyl refers to an alkyl or cycloalkyl radical having at least one carbon atom in the chain and containing at least one heteroatom, such as N, O, S, or $S(O)_n$ (where n is 1 or 2).

Heteroaryl: An aromatic compound or group having at least one heteroatom, i.e., one or more carbon atoms in the ring has been replaced with a non-carbon atom, typically nitrogen, oxygen, phosphorus, silicon, or sulfur.

Heterocyclic: Refers to a closed-ring compound, or radical thereof as a substituent bonded to another group, particularly other organic groups, where at least one atom in the ring structure is other than carbon, and typically is oxygen, sulfur and/or nitrogen.

HNSCC: Head and neck squamous cell carcinoma.

IAP: Inhibitor of apoptosis protein. Includes cIAP—cellular IAP 1, and xIAP—X-linked IAP.

Linker: A molecule or group of atoms positioned between two moieties. Typically, linkers are bifunctional, i.e., the linker includes a functional group at each end, wherein the functional groups are used to couple the linker to the two moieties. The two functional groups may be the same, i.e., a homobifunctional linker, or different, i.e., a heterobifunctional linker.

LSCC: Lung squamous cell carcinoma.

LZK: Leucine zipper-bearing kinase, a regulator of neuronal degeneration, e.g., following neuronal injury and/or in neurodegenerative diseases.

MDM2: Mouse double minute 2 homolog

Pharmaceutically acceptable: A substance that can be taken into a subject without significant adverse toxicological effects on the subject. The term "pharmaceutically acceptable form" means any pharmaceutically acceptable derivative or variation, such as stereoisomers, stereoisomer mixtures, enantiomers, solvates, hydrates, isomorphs, polymorphs, pseudomorphs, neutral forms, salt forms, and prodrug agents.

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, PA, $21^{st}$ Edition (2005), describes compositions and formulations suitable for pharmaceutical delivery of one or more therapeutic compositions and additional pharmaceutical agents. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In some examples, the pharmaceutically acceptable carrier is a non-naturally occurring or synthetic carrier. The carrier also can be formulated in a unit-dosage form that carries a preselected therapeutic dosage of the active agent, for example in a pill, vial, bottle, or syringe.

Pharmaceutically acceptable salt: A biologically compatible salt of a compound that can be used as a drug, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. Pharmaceutically acceptable acid addition salts are those salts that retain the biological effectiveness of the free bases while formed by acid partners that are not biologically or otherwise undesirable, e.g., inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, benzene sulfonic acid (besylate), cinnamic acid, mandelic acid, methanesulfonic acid, ethanesulfonic acid, p-toluenesulfonic acid, salicylic acid and the like. Pharmaceutically acceptable base addition salts include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19, which is incorporated herein by reference.)

Stereoisomers: Isomers that have the same molecular formula and sequence of bonded atoms, but which differ only in the three-dimensional orientation of the atoms in space.

Subject: An animal (human or non-human) subjected to a treatment, observation or experiment. Includes both human and veterinary subjects, including human and non-human mammals, such as rats, mice, cats, dogs, pigs, horses, cows, and non-human primates. In some embodiments, the subject has cancer, such as head and neck squamous cell carcinoma or lung squamous cell carcinoma.

Substituent: An atom or group of atoms that replaces another atom in a molecule as the result of a reaction. The term "substituent" typically refers to an atom or group of atoms that replaces a hydrogen atom, or two hydrogen atoms if the substituent is attached via a double bond, on a parent hydrocarbon chain or ring. The term "substituent" may also cover groups of atoms having multiple points of attachment to the molecule, e.g., the substituent replaces two or more hydrogen atoms on a parent hydrocarbon chain or ring. In such instances, the substituent, unless otherwise specified, may be attached in any spatial orientation to the parent hydrocarbon chain or ring. Exemplary substituents include, for instance, alkyl, alkenyl, alkynyl, alkoxy, alkylamino, alkylthio, acyl, aldehyde, amido, amino, aminoalkyl, aryl, arylalkyl, arylamino, carbonate, carboxyl, cyano, cycloalkyl, dialkylamino, halo, haloaliphatic (e.g., haloalkyl), haloalkoxy, heteroaliphatic, heteroaryl, heterocycloaliphatic, hydroxyl, oxo, sulfonamide, sulfhydryl, thio, and thioalkoxy groups.

Substituted: A fundamental compound, such as an aryl or aliphatic compound, or a radical thereof, having coupled thereto one or more substituents, each substituent typically replacing a hydrogen atom on the fundamental compound. A person of ordinary skill in the art will recognize that compounds disclosed herein may be described with reference to particular structures and substituents coupled to such structures, and that such structures and/or substituents also can be further substituted, unless expressly stated otherwise or context dictates otherwise. Solely by way of example and without limitation, a substituted aryl compound may have an aliphatic group coupled to the closed ring of the aryl base, such as with toluene. Again solely by way of example and without limitation, a long-chain hydrocarbon may have a hydroxyl group bonded thereto.

Targeted degrader: A heterobifunctional molecular comprising two active domains and a linker. The disclosed targeted degraders include an E3-ligase binding moiety and a targeting molecule. Embodiments of the disclosed targeted degraders include a leucine zipper kinase inhibitor. The targeting molecule binds the targeted degrader to the target, LZK in the present disclosure, and the E3-ligase binding moiety recruits E3 ligase to the target, resulting in ubiquination and degradation of the target.

Tautomers: Constitutional isomers of organic compounds that differ only in the position of the protons and electrons, and are interconvertible by migration of a hydrogen atom. Tautomers ordinarily exist together in equilibrium.

Therapeutically effective amount or dose: An amount sufficient to provide a beneficial, or therapeutic, effect to a subject or a given percentage of subjects.

Treating or treatment: With respect to disease, either term includes (1) preventing the disease, e.g., causing the clinical symptoms of the disease not to develop in an animal that may be exposed to or predisposed to the disease but does not yet experience or display symptoms of the disease, (2) inhibiting the disease, e.g., arresting the development of the disease or its clinical symptoms, or (3) relieving the disease, e.g., causing regression of the disease or its clinical symptoms.

VHL: von Hippel-Lindau or von Hippel-Lindau ligase

II. LZK Proteolysis-Targeting Chimeras

Embodiments of the disclosed leucine zipper-bearing kinase (LZK) targeted degraders include compounds, or stereoisomers, tautomers, or pharmaceutically acceptable salts thereof, having a general formula Q-L-Z. Q is an LZK binding moiety, L is a linker or L is absent, and Z is an E3-ligase binding moiety. In some embodiments, Q binds to LZK and Z recruits E3 ligase to the LZK, whereby LZK is ubiquinated and degraded by the E3 ligase. Thus, some embodiments of the disclosed LZK-targeting degraders both inhibit and degrade LZK.

In any of the foregoing or following embodiments, the linker L may have a general formula:

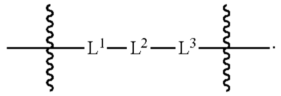

With respect to the above formula, $L^1$ is —C(O)—, —$S(O)_2$—, —$CH_2$—, —$C(R^b)(R^c)$—, —$(CH_2)_n C(O)$—, —C(O)—$(CH_2)_n$—, —$N(R^c)$—, —$N(R^c)$—$(C(H)(R^a))_s$—C(O)—, or —C(O)—$(C(H)(R^a))_s$—$N(R^c)$—, and $L^1$ binds to Q, or $L^1$ is absent and $L^2$ binds to Q. In one embodiment, $L^1$ binds to Q through a primary or secondary amino group on Q. In an independent embodiment $L^1$ binds to Q through a non-nitrogen attachment point. $L^3$ is —C(O)—, —$S(O)_2$—, —$CH_2$—, —$C(R^b)(R^c)$—, —C(O)—$(CH_2)_n$—, —$(CH_2)_n$—C(O)—, —$N(R^c)$—, —$N(R^c)$—$(C(H)(R^a))_s$—C(O)—, or —C(O)—$(C(H)(R^a))_s$—$N(R^c)$—, and -$L^3$ binds to Z, or $L^3$ is absent and $L^2$ binds to Z. In one embodiment, $L^3$ binds to Z through a primary or secondary amino group on Z. In an independent embodiment $L^3$ binds to Z through a non-nitrogen attachment point. Non-nitrogen attachment points may include, for example, carboxylates, ether linkages, thioether linkages, or even carbon atoms, such as aryl carbons. $L^2$ is —$(R^d)_p$—, —$N(R^b)$—$(R^d)_p$, —$(R^d)_p$—$N(R^b)$—, —$N(R^b)$—$(R^d)_p$—$N(R^b)$—, —$(N(R^b)$—$(C(H)(R^a))_s$—$C(O))_m$—$N(R^b)$—$C(H)(R^a)$—, or —$C(H)(R^a)$—$N(R^b)$—$(C(O)$—$(C(H)(R^a))_s$—$N(R^b))_m$—. Each $R^a$ independently is an amino acid side chain. Each $R^b$ independently is H or $R^c$. Each $R^c$ independently is substituted or unsubstituted aliphatic, substituted or unsubstituted heteroaliphatic, substituted or unsubstituted aryl, substituted or unsubstituted heteroaryl, substituted or unsubstituted arylalkyl, or substituted or unsubstituted alkylaryl. Each $R^d$ independently is substituted or unsubstituted aliphatic, substituted or unsubstituted heteroaliphatic, substituted or unsubstituted aryl, substituted or unsubstituted heteroaryl, —$(CH_2$—$CH_2$—$O)_r$—, —$(C(H)(R^a))_s$—C(O)—, —C(O)$N(R^b)$—, or —$N(R^b)C(O)$—. Each $R^c$ independently is substituted or unsubstituted $C_1$-$C_3$ alkyl or H. In any of the foregoing embodiments, m is an integer from 0-11; n is an integer from 1-10; p is an integer from 0-5; r is an integer from 2-20; and s is an integer from 1-20. $L^2$ is not solely —C(O)$N(R^b)$— or —$N(R^b)C(O)$—, and if $L^2$ terminates in —$C(H)(R^a)$—C(O)— or —$N(R^b)C(O)$—, then $L^3$ is not —C(O)— or —$S(O)_2$—. If $L^3$ is absent and $L^2$ is —$(R^d)_p$—, where p is 0, then $L^1$ binds to Z. In any of the foregoing or following embodiments, unless otherwise stated, suitable substituents on substituted moieties may include, but are not limited to, alkyl, alkoxy, halo, haloalkyl, perhaloalkyl, haloalkoxy, perhaloalkoxy, cyano, amino, aminoalkyl, alkylamino, imino, iminoalkyl, hydroxyl, thiol, —COOH, —COO-alkyl, and combinations thereof.

In any of the foregoing or following embodiments, $L^1$ and/or $L^3$ may be absent if $L^2$ begins or terminates with a moiety capable of binding to Q or Z, respectively. For example, $L^1$ and/or $L^3$ may be absent in some embodiments where $L^2$ begins or terminates with an amino or carbonyl group.

In any of the foregoing or following embodiments, $R^a$ is an amino acid side chain. In some embodiments, $R^a$ is a side chain of an alpha amino acid having a general formula $H_2N$—$C(H)(R^a)$—COOH. The amino acid may be a naturally occurring amino acid (e.g., an L-amino acid), a D-amino acid, or a non-naturally occurring amino acid, such as those typically used in peptide chemistry. Non-limiting examples of non-naturally occurring amino acids include ornithine and 2,4-diaminobutyric acid.

In any of the foregoing or following embodiments, each $R^b$ independently is H or $R^c$, and each $R^c$ independently is substituted or unsubstituted aliphatic, substituted or unsubstituted heteroaliphatic, substituted or unsubstituted aryl, substituted or unsubstituted heteroaryl, substituted or unsubstituted arylalkyl, or substituted or unsubstituted alkylaryl. In some embodiments, $R^b$ is H. In some embodiments, $R^c$ is substituted or unsubstituted alkyl, substituted or unsubstituted alkyl, substituted or unsubstituted aryl, substituted or unsubstituted heteroaryl, substituted or unsubstituted arylalkyl, or substituted or unsubstituted alkylaryl. In some examples, the alkyl portion of the arylalkyl or alkylaryl group includes from 1-3 carbon atoms. In certain embodiments, $R^c$ is unsubstituted alkyl or unsubstituted heteroalkyl. In some examples, $R^c$ is $C_1$-$C_6$ alkyl (e.g., methyl, ethyl, n-propyl, isopropyl, cyclopropyl, cyclobutyl, cyclopentyl, or cyclohexyl) or aryl (e.g., phenyl). In any of the foregoing or following embodiments, $N(R^b)$ may be NH or $N(R^c)$. In some embodiments, $N(R^b)$ is NH or $N(CH_3)$. In any of the foregoing or following embodiments, $—C(R^b)(R^c)—$ may be $—C(H)(R^c)$ or $—C(R^c)_2$. In some embodiments, $R^c$ is methyl and $—C(R^b)(R^c)—$ is $—C(H)(CH_3)—$ or $—C(CH_3)_2$.

In any of the foregoing or following embodiments, n is an integer from 1-10. In some embodiments, n is 1, 2, 3, 4, or 5. In certain embodiments, n is 1, 2, or 3. In some examples, $L^1$ is $—C(O)—$, $—(CH_2)_nC(O)—$, or $—C(O)—(CH_2)_n—$. In some examples, $L^3$ is $—C(O)—$, $—C(O)—(CH_2)_n—$, or $—(CH_2)_nC(O)—$. In any of the foregoing or following embodiments, $L^1$ and $L^3$ may have the same formula ($—(CH_2)_nC(O)—$ and $—C(O)—(CH_2)_n—$ are considered to have the same formula if n is the same). In some embodiments, $L^1$ and $L^3$ have different formulas. In some examples, $L^1$ and $L^3$ are both $—C(O)—$.

In any of the foregoing or following embodiments, $L^2$ is $—(R^d)_p—$, $—N(R^b)—(R^d)_p—$, $—(R^d)_p—N(R^b)—$, $—N(R^b)—(R^d)_p—N(R^b)—$, $—(N(R^b)—(C(H)(R^a))_s—C(O))_m—N(R^b)—C(H)(R^a)—$, or $—C(H)(R^a)—N(R^b)—(C(O)—(C(H)(R^a))_s—N(R^b))_m—$, where $R^a$, $R^b$, and $R^d$ are as previously defined, m is an integer from 0-11, n is an integer from 1-10, and p is an integer from 0-5. In some implementations, p is 1, 2, 3, 4, or 5. In some embodiments, $L^2$ is $—(R^d)_p—$, $—N(R^b)—(R^d)_p—$, $—(R^d)_p—N(R^b)—$, or $—N(R^b)—(R^d)_p—N(R^b)—$. In some embodiments, p is 1, 2, or 3. In any of the foregoing embodiments, $R^b$ may be H or $R^c$, where $R^c$ is $C_1$-$C_6$ alkyl (e.g., methyl, ethyl, n-propyl, isopropyl, cyclopropyl, cyclobutyl, cyclopentyl, or cyclohexyl) or aryl (e.g., phenyl). In certain embodiments, each $N(R^b)$ independently is NH or $N(CH_3)$.

In any of the foregoing or following embodiments, each $R^d$ independently is substituted or unsubstituted aliphatic, substituted or unsubstituted heteroaliphatic, substituted or unsubstituted aryl, substituted or unsubstituted heteroaryl, $—(CH_2—CH_2—O)_r—$, $C(H)(R^a)—C(O)—$, or $—C(O)N(R^b)—$, where r is an integer from 1-20. If $L^2$ terminates in $—C(H)(R^a)—C(O)—$, then $L^3$ is not $—C(O)—$ or $—S(O)_2—$. The aliphatic and heteroaliphatic groups may be linear, branched, cyclic, or a combination thereof. For instance, an aliphatic group may have a linear portion and a cyclic portion. The cyclic portion may be monocyclic, bicyclic, or polycyclic (e.g., cyclopropyl, cyclobutyl, bicyclo[1.1.1]pentyl). In some embodiments, each $R^d$ independently is substituted or unsubstituted alkyl, substituted or unsubstituted heteroalkyl, substituted or unsubstituted aryl, substituted or unsubstituted heteroaryl, $—(CH_2—CH_2—O)_r—$, $C(H)(R^a)—C(O)—$, or $—C(O)N(R^b)—$. In certain embodiments, each $R^d$ independently is alkyl, alkylamino, aminoalkyl, amino-alkyl-amino, piperazinyl, piperidinyl, phenyl, $—(CH_2—CH_2—O)_r—$, $—C(O)N(H)—$,

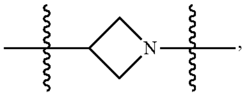,

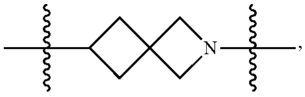, or

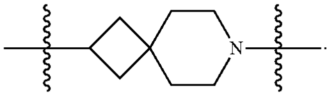.

Exemplary $L^2$ groups include but are not limited to, one or more of

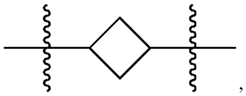, 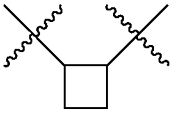,

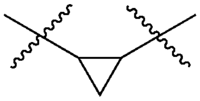, 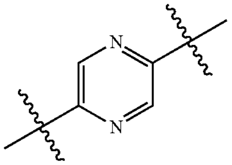,

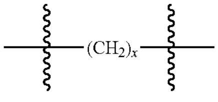, 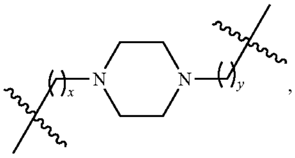,

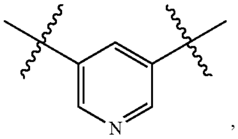, 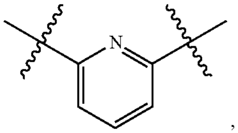,

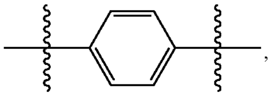,

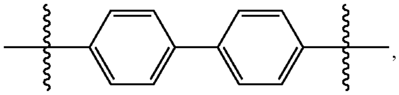,

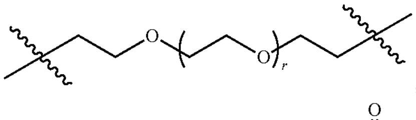,

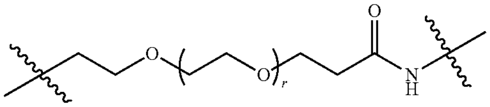,

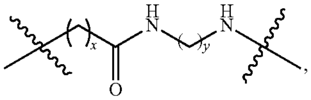,

-continued

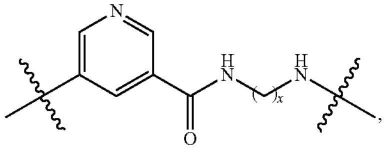,

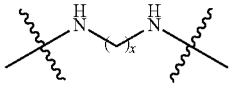, 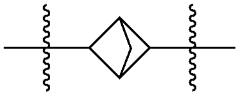,

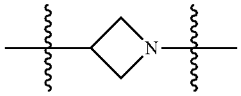,

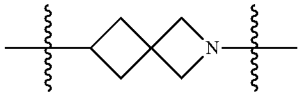,

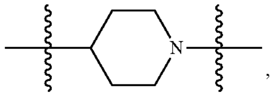, and

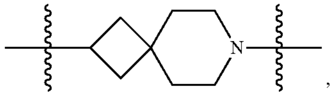, where r, x, and y independently are integers from 1-20, optionally in combination with one or more of —C(O)N(H)— and —N(H)C(O)—. Where $L^2$ is asymmetric, $L^2$ may be in the orientation shown above or in the reverse orientation. e.g.,

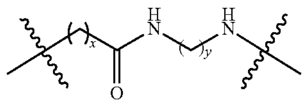 or

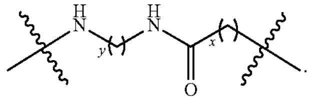.

In some embodiments, L comprises an amino acid-derived chain. For example, in one embodiment, L is —C(O)—(N($R^b$)—(C(H)($R^a$))$_s$—C(O))$_m$—N($R^b$)—C(H)($R^a$)—C(O)—. In another embodiment, L is —C(O)—C(H)($R^a$)—N($R^b$)—(C(O)—(C(H)($R^a$))$_s$—N($R^b$))$_m$—C(O)—, where s is an integer from 1-20. In some examples, s is an integer from 1-10 or 1-5. In certain examples, s is 1. In some embodiments, each $R^b$ independently is H or methyl. Other non-limiting examples of linkers L are shown in Table 1. Where the linker L is asymmetric, the linker L may be present in Q-L-Z in the orientation shown in Table 1 or in the reverse orientation.

TABLE 1

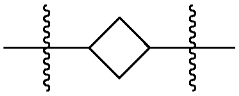 [SMILES: *C1CC(*)C1]

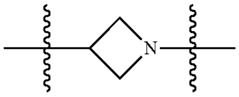

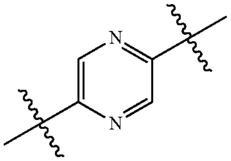 [SMILES: *c1cnc(*)cn1]

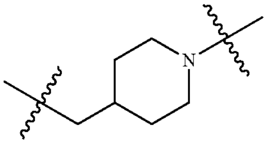

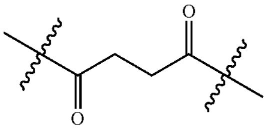 [SMILES: *C(=O)CCC(*)=O]

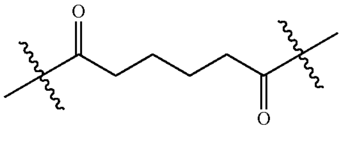 [SMILES: *C(=O)CCCCC(*)=O]

TABLE 1-continued
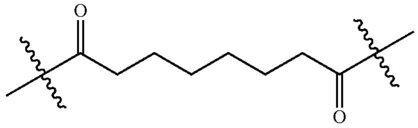 [SMILES: *C(=O)CCCCCCC(*)=O]
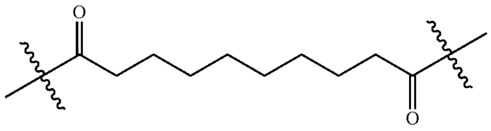 [SMILES: *C(=O)CCCCCCCCC(*)=O]
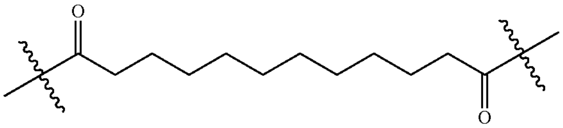 [SMILES: *C(=O)CCCCCCCCCCC(*)=O]
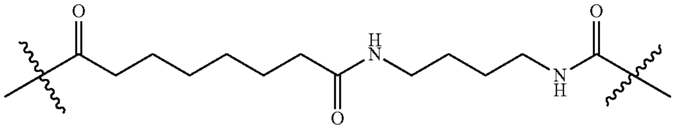 [SMILES: *C(=O)CCCCCCC(=O)NCCCCNC(*)=O]
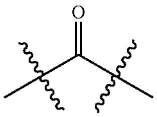 [SMILES: *C(*)=O]
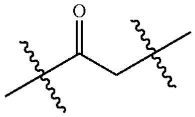 [SMILES: *CC(*)=O]
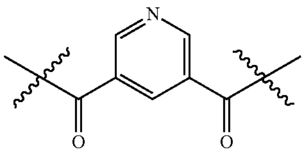 [SMILES: *C(=O)c1cncc(C(*)=O)c1]
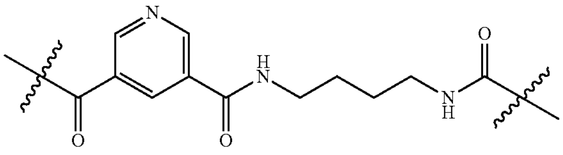 [SMILES: *C(=O)NCCCCNC(=O)c1cncc(C(*)=O)c1]
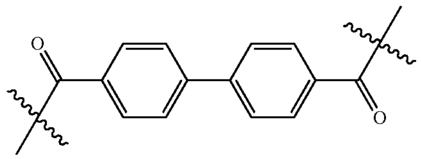 [SMILES: *C(=O)c1ccc(-c2ccc(C(*)=O)cc2)cc1]
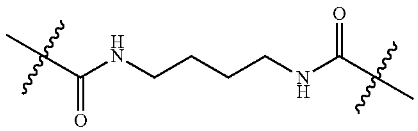 [SMILES: *C(=O)NCCCCNC(*)=O]
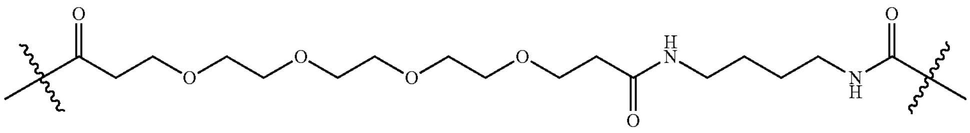 [SMILES: *C(=O)CCOCCOCCOCCOCCC(=O)NCCCCNC(*)=O]

TABLE 1-continued
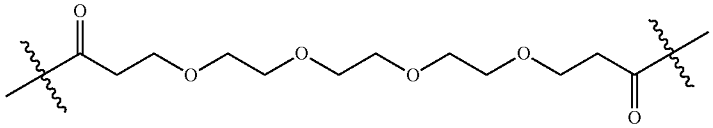 [SMILES: *C(=O)CCOCCOCCOCCOCCC(*)=O]
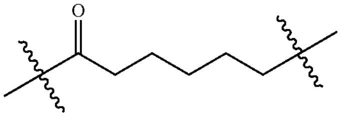 [SMILES: *CCCCCC(*)=O]
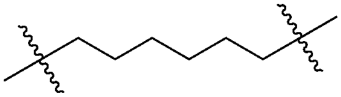 [SMILES: *CCCCCC*]
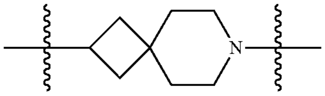 [SMILES: *C1CC2(CCN(*)CC2)C1]
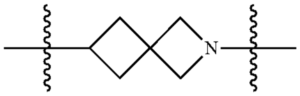 [SMILES: *C1CC2(C1)CN(*)C2]
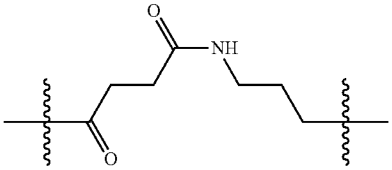 [SMILES: *CCCNC(=O)CCC(*)=O]
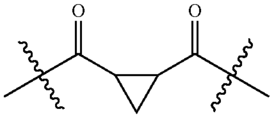 [SMILES: *C(=O)C1CC1C(*)=O]
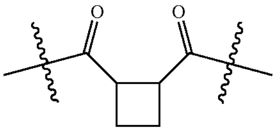 [SMILES: *C(=O)C1CCC1C(*)=O]
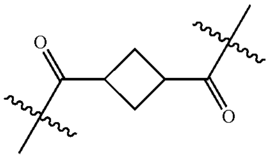 [SMILES: *C(=O)C1CC(C(*)=O)C1]
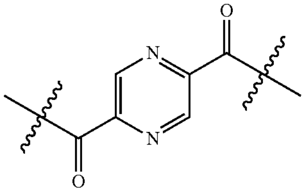 [SMILES: *C(=O)c1cnc(C(*)=O)cn1]
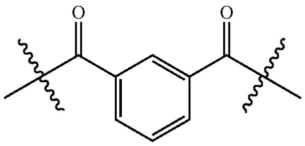 [SMILES: *C(=O)c1cccc(C(*)=O)c1]

TABLE 1-continued

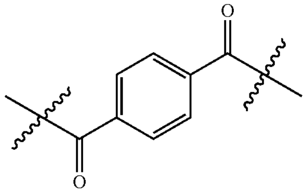 [SMILES: *C(=O)c1ccc(C(*)=O)cc1]

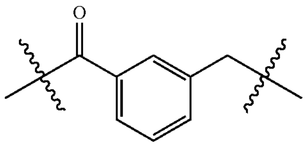 [SMILES: *Cc1cccc(C(*)=O)c1]

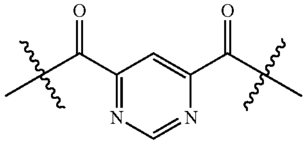 [SMILES: *C(=O)c1cc(C(*)=O)ncn1]

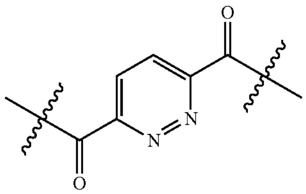 [SMILES: *C(=O)c1ccc(C(*)=O)nn1]

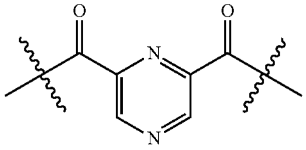 [SMILES: *C(=O)c1cncc(C(*)=O)n1]

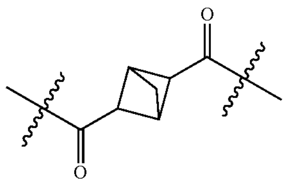 [SMILES: *C(=O)C1C2CC1C2C(*)=O]

Z is an E3-ligase binding moiety or ligase-binding moiety. There are several E3 ligases, and Z may bind to any one or more of the E3 ligases. E3 ligases include the von Hippel-Lindau ligase (VHL), cereblon, the inhibitor of apoptosis protein (IAP; includes cIAPI—cellular inhibitor of apoptosis protein 1, and xIAP—X-linked IAP), and mouse double minute 2 homolog (MDM2). Exemplary Z moieties include, but are not limited to the VHL ligase-binding moiety, the cereblon ligase-binding moiety, the IAP ligase-binding moiety, the MDM2 ligase-binding moiety, and derivatives thereof. In some embodiments, Z is:

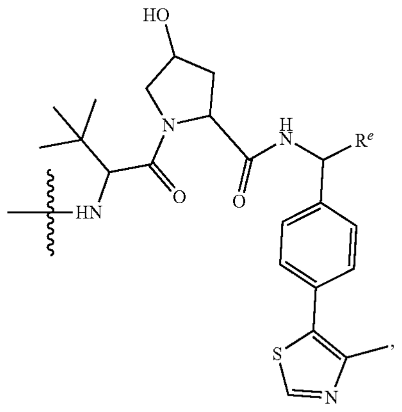

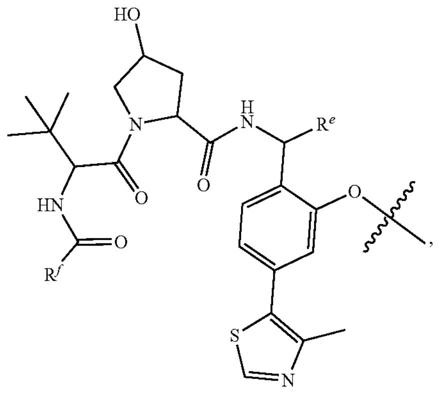

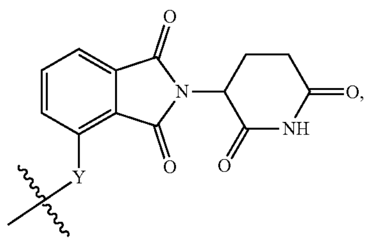

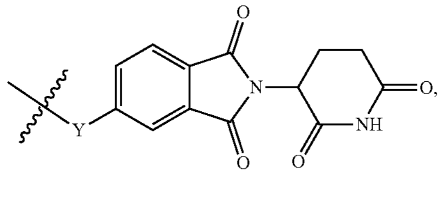

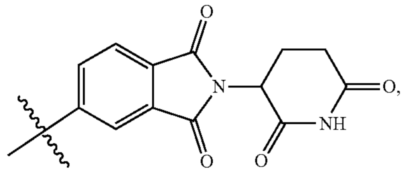

-continued

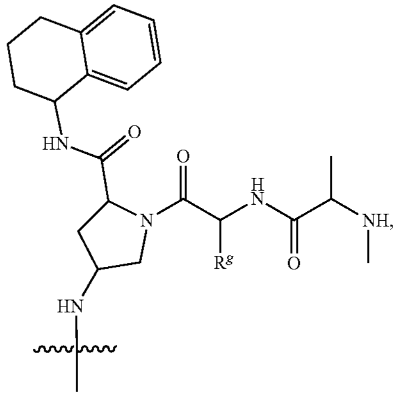

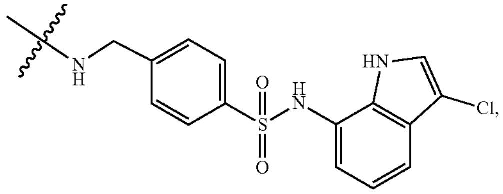

or

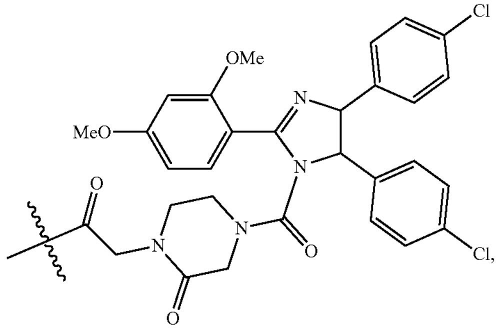

where each $R^e$ independently is substituted or unsubstituted $C_1$-$C_3$ alkyl or H; $R^f$ is substituted or unsubstituted $C_1$-$C_3$ alkyl or —$N(R^e)_2$; and Y is O or $NR^e$, or Y is absent. In certain embodiments, each $R^e$ independently is methyl, ethyl, n-propyl, isopropyl, cyclopropyl, or H. In some examples, each $R^e$ is methyl or H. In some embodiments, $R^f$ is substituted or unsubstituted cyclopropyl. In certain examples, the cyclopropyl group is halogenated (e.g., fluorinated) or substituted with a cyano group. In some embodiments, Z is a stereoisomer:

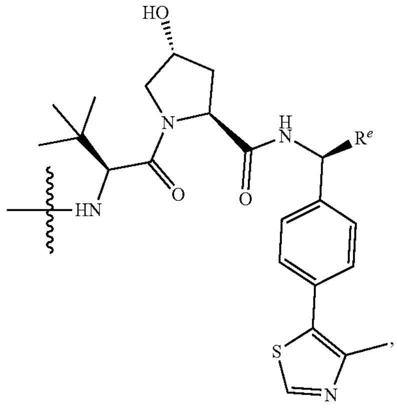

-continued
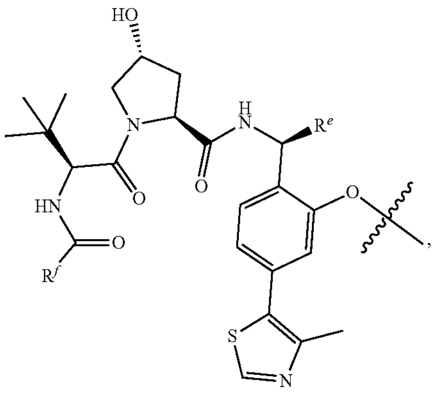
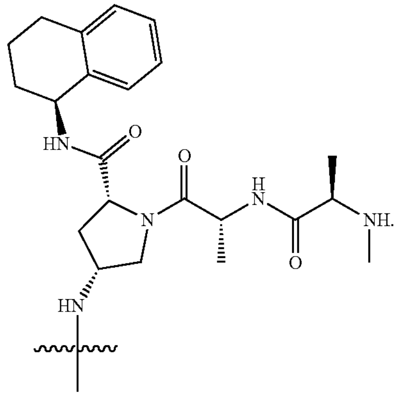
Several non-limiting examples of Z are shown in Table 2.
TABLE 2
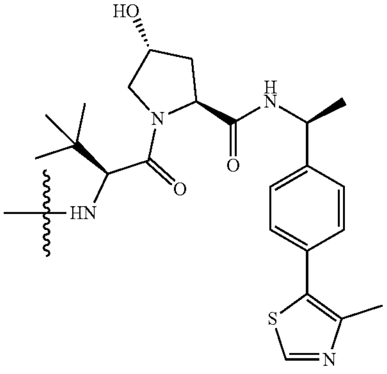 [SMILES: *N[C@H](C(=O)N1C[C@H](O)C[C@H]1C(=O)N[C@@H](C)c1ccc(-c2scnc2C)cc1)C(C)(C)C]
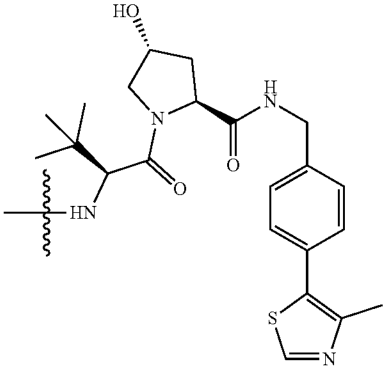 [SMILES: *N[C@H](C(=O)N1C[C@H](O)C[C@H]1C(=O)NCc1ccc(-c2scnc2C)cc1)C(C)(C)C]
TABLE 2-continued
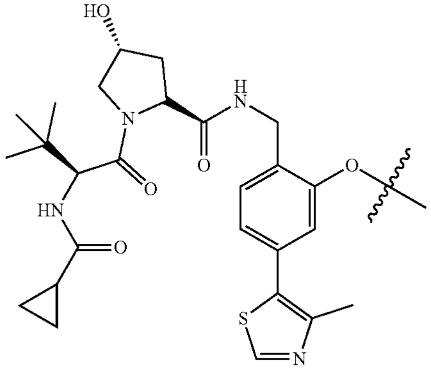
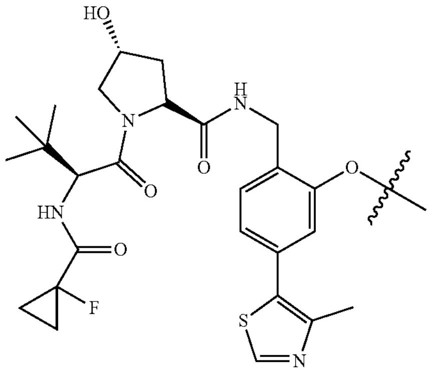
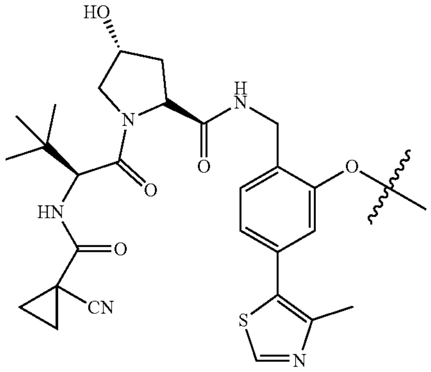
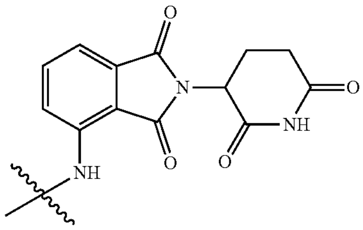 [SMILES: *Nc1cccc2c1C(=O)N(C1CCC(=O)NC1=O)C2=O]
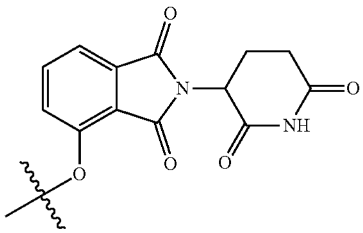 [SMILES: *Oc1cccc2c1C(=O)N(C1CCC(=O)NC1=O)C2=O]

TABLE 2-continued

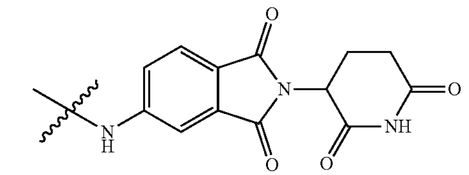 [SMILES: *Nc1ccc2c(c1)C(=O)N(C1CCC(=O)NC1=O)C2=O]

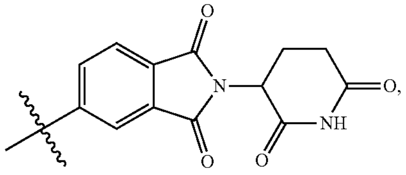 [SMILES: *c1ccc2c(c1)C(=O)N(C1CCC(=O)NC1=O)C2=O]

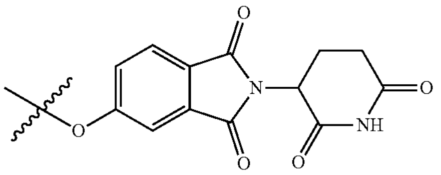 [SMILES: *Oc1ccc2c(c1)C(=O)N(C1CCC(=O)NC1=O)C2=O]

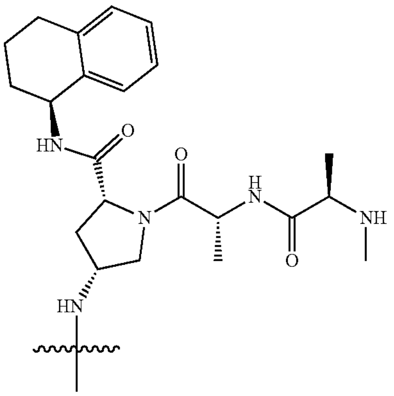 [SMILES: *N[C@@H]1C[C@H](C(=O)N[C@H]2CCCc3ccccc32)N(C(=O)[C@@H](C)NC(=O)[C@@H](C)NC)C1]

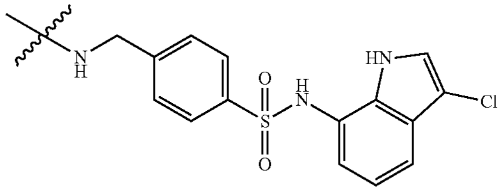 [SMILES: *NCc1ccc(S(=O)(=O)Nc2cccc3c(Cl)c[nH]c23)cc1]

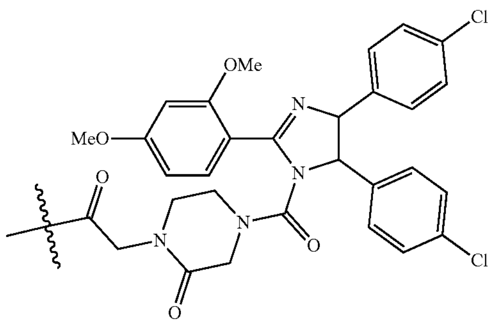 [SMILES: *C(=O)CN1CCN(C(=O)N2C(c3ccc(OC)cc3OC)=NC(c3ccc(Cl)cc3)C2c2ccc(Cl)cc2)CC1=O]

Q is an LZK binding moiety. In some implementations, Q is not foretinib. In some embodiments, Q is an LZK inhibitor. In certain embodiments, Q is:

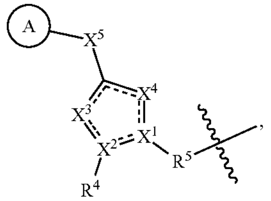

where each bond represented by ---- is a single or double bond as needed to satisfy valence requirements. Ring A is a monocyclic or bicyclic heteroaryl ring. In some embodiments, Ring A is

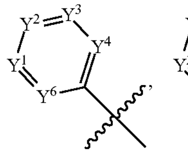 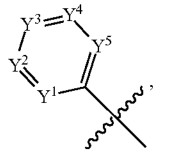 or 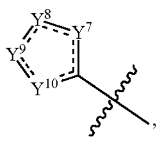

where each bond represented by ---- is a single or double bond as needed to satisfy valence requirements. The —$X^1$($R^5$)— moiety is —C($R^5$)—, —C($R^5$)—C(H)—, —C(H)—C($R^5$)—, —C($R^5$)—N—, —N—C($R^5$)—, or —N($R^5$)—. $X^2$ is N or C. $X^3$ is N or C(H). One or two of $X^1$—$X^3$ comprises N. $X^4$ is C(H) or S. $X^5$ is —N(H)— or absent. $Y^1$ is C($R^1$) or N. $Y^2$ is C($R^2$) or N. $Y^3$ is C($R^3$) or N. $Y^4$ is C($R^6$) or N. $Y^5$ is C($R^7$) or N. $Y^6$ is C($R^8$) or N. One or two of $Y^1$-$Y^6$ are N. If two of $Y^1$-$Y^6$ are N, the nitrogens may not be immediately adjacent to one another. Two, three, or four of $Y^7$-$Y^{10}$ independently are N or N($R^9$) and the others of $Y^7$-$Y^{10}$ are C($R^{10}$); the nitrogen atoms may be immediately adjacent one another or separated by at least one carbon atom. In some embodiments, two of $Y^7$-$Y^{10}$ independently are N or N($R^9$), and the other two of $Y^7$-$Y^{10}$ are C($R^{10}$).

In any of the foregoing or following embodiments, $Y^4$ may be N. In some embodiments, $Y^1$ and $Y^4$ are N. In any of the foregoing or following embodiments, at least one of $Y^1$-$Y^3$ or $Y^6$ is other than C(H).

$R^1$ is cyano, perhaloalkyl, H, alkyl, or perhaloalkoxy. Exemplary $R^1$ groups include, but are not limited to, cyano, H, —$OCF_3$, or —$CF_3$. In particular implementations, $R^1$ is cyano or H.

$R^2$ is H, alkoxy, perhaloalkyl, perhaloalkoxy, haloalkoxy, haloalkyl, cyanoalkyl, alkyl, cyano, amino, or heteroarylalkoxy, or $R^1$ and $R^2$ together with the atoms to which they are attached form a 5- or 6-membered substituted or unsubstituted aryl or substituted or unsubstituted heteroaryl ring. In some embodiments, the alkyl or alkoxy portion of $R^2$ is $C_1$-$C_6$ alkyl or alkoxy. For example, $R^2$ may be methoxy, fluoromethoxy, or trifluoromethoxy. In some implementations, the at least a portion of the alkyl portion of $R^2$ is cycloalkyl, such as cyclopropyl or bicyclo[1.1.1]pentyl. The alkyl or alkoxy portion may be halogenated. In certain implementations, $R^2$ is fluorinated. Exemplary $R^2$ groups include, but are not limited to —$OCH_3$, —$OCF_3$, —$CF_3$, —CN, —H, —$OCHF_2$,

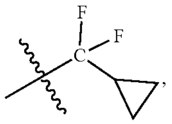
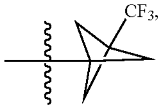
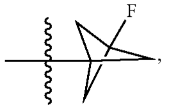
or
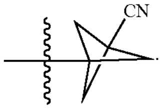

In some implementations, $R^1$ and $R^2$ together with the atoms to which they are attached form a 5- or 6-membered substituted or unsubstituted aryl or substituted or unsubstituted heteroaryl ring. In one example, ring A is

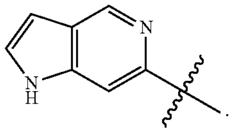 [SMILES: *c1cc2[nH]ccc2cn1]

$R^3$ is H, amino, alkylamino, aminoalkyl, alkoxy, or —N(H)C(O)R' where R' is alkyl, or $R^2$ and $R^3$ together with the atoms to which they are attached form a 5- or 6-membered substituted or unsubstituted aryl or substituted or unsubstituted heteroaryl ring. In some embodiments, $R^3$ is H, —$NH_2$, —N(H)C(O)$CH_3$, methyl,

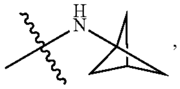
, or
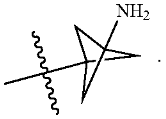

In some implementations, $R^2$ and $R^3$ together with the atoms to which they are attached form a 5- or 6-membered substituted or unsubstituted aryl or substituted or unsubstituted heteroaryl ring. In one example, ring A is

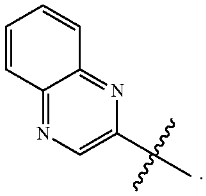 [SMILES: *c1cnc2ccccc2n1]

$R^4$ is substituted or unsubstituted aliphatic, substituted or unsubstituted azaalkyl, or aryl. In some implementations, $R^4$ is 3,3-difluoro-1-pyrrolidinyl, isopropyl, 2-methylpropyl, cyclopropylmethyl, —C(H)(OH)—C($CH_3$)$_2$, cyclopropyl, or

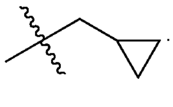

$R^5$ is substituted or unsubstituted aliphatic, substituted or unsubstituted heteroaliphatic, substituted or unsubstituted aminoalkyl, or substituted or unsubstituted alkylamino. In some embodiments, $R^5$ is

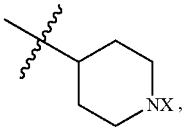
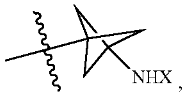
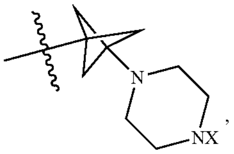
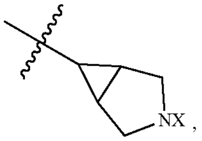
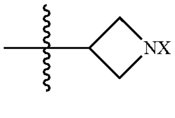
,
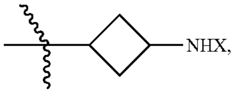
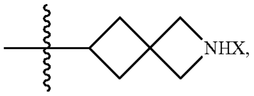
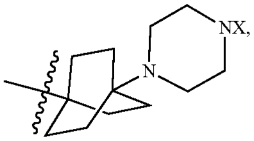
or
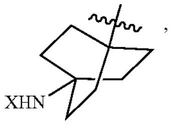

where X is a bond or alkyl group binding Q to L. In some implementations, $R^5$ is

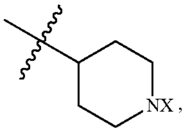
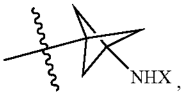
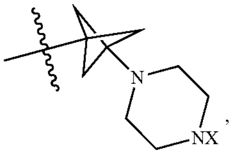
or
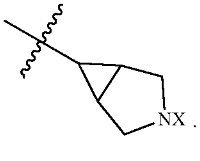

$R^6$-$R^8$ independently are H, alkyl, alkoxy, perhaloalkyl, perhaloalkoxy, or cyano. In some embodiments, $R^6$-$R^8$ are H, methyl, —$OCH_3$, —$CF_3$, —$OCF_3$, or —CN. In certain implementations, $R^6$-$R^8$ are H. In some implementations, $Y^4$ is N and $R^6$ is therefore absent. Ring A binds to remainder of Q through $Y^5$ or $Y^6$. Thus, either $R^7$ or $R^8$ will be absent.

Each $R^9$ independently is H or alkyl. In some embodiments, each $R^9$ independently is H or methyl. Each $R^{10}$ independently is H, alkyl, or cyano. In some implementations, $R^{10}$ independently is H, methyl, or cyano.

In any of the foregoing or following embodiments, unless otherwise specified, the aliphatic, heteroaliphatic, or azaalkyl groups may be straight, branched, cyclic, or any combination thereof. In some embodiments, ring A is:

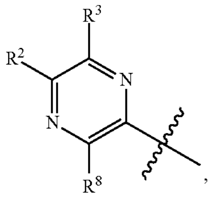, 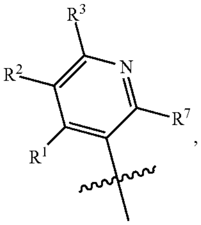,
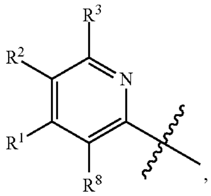, 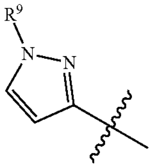,
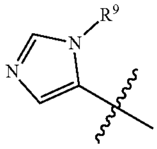, 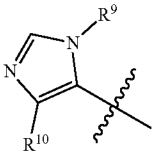,
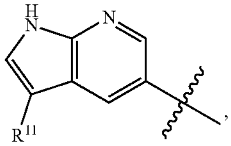, 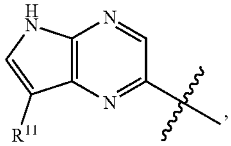,
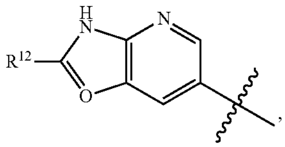,
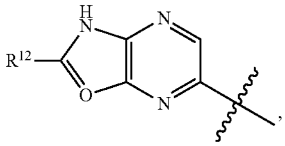,
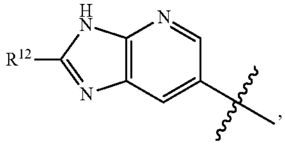,
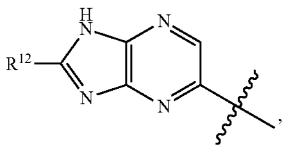, or
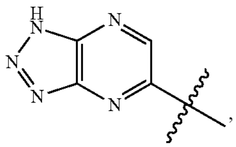,
where $R^{11}$ and $R^{12}$ are H, alkyl, perhaloalkyl, alkoxy, perhaloalkoxy, cyano, or amino.
In certain examples, ring A is:
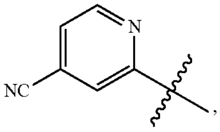, 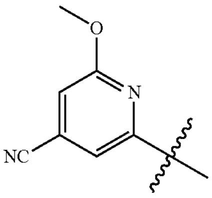,
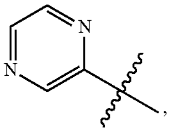, 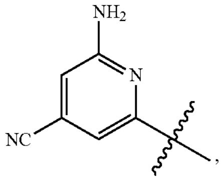,
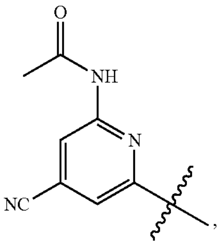, 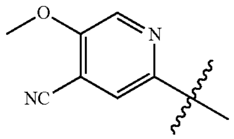,
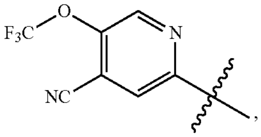,
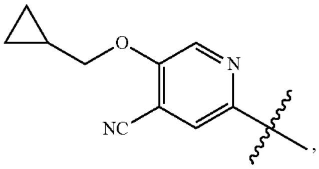,
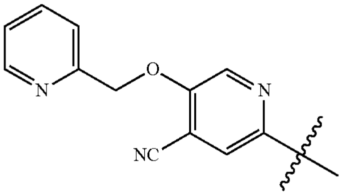, 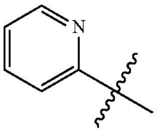,
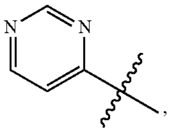, 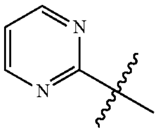,
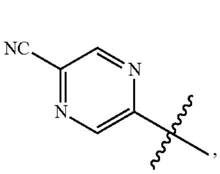, 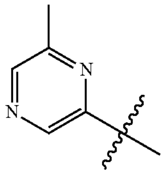,
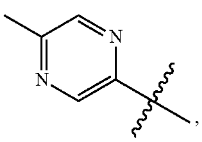, 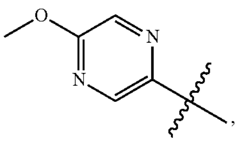, -continued
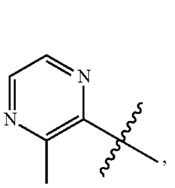
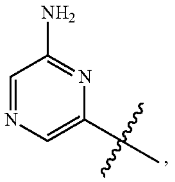
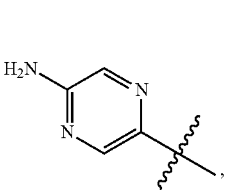
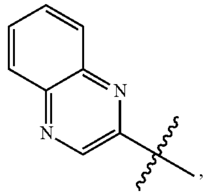
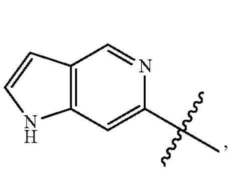
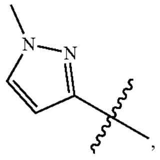
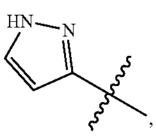
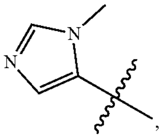
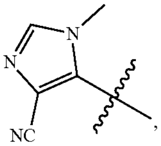
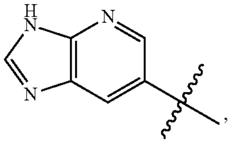
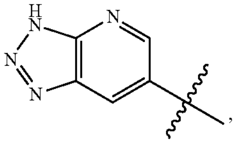
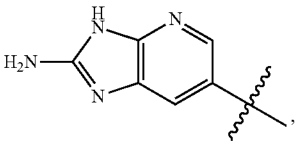
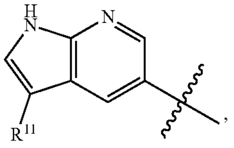
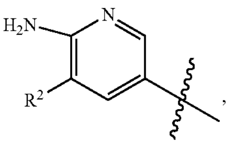
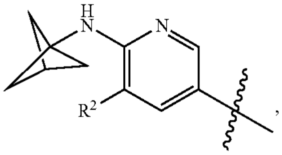
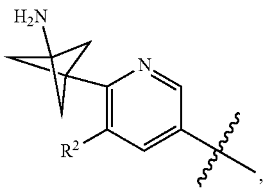
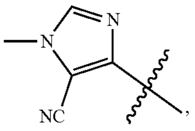
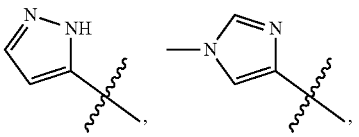 or
-continued
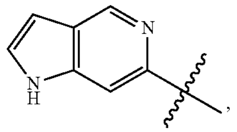
where $R^2$ is —$CF_3$, —$OCF_3$, —$OCHF_2$, —$OCH_3$, —CN, or —H, and $R^{11}$ is —$CF_3$, —$OCF_3$, —CN, or —H. In some embodiments, Q has a structure according to formula Q1 or formula Q2:
(Q1)
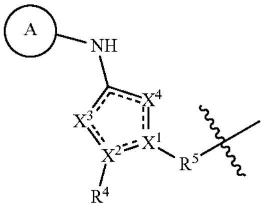
or
(Q2)
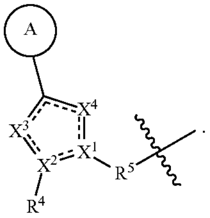
In some implementations, Q has a structure according to formula Q1A, Q1B, Q2A, or Q2B:
(Q1A)
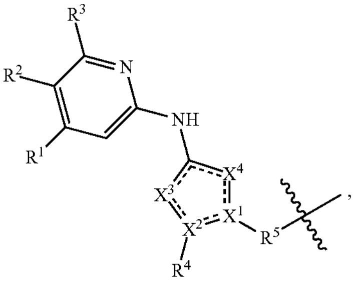
Q(1B)
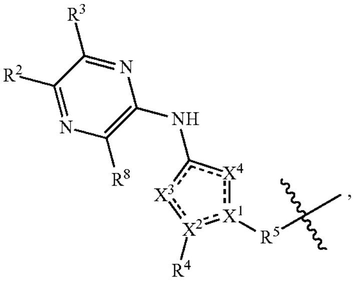

-continued (Q2A)

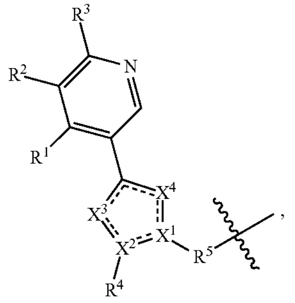

, or (Q2B)

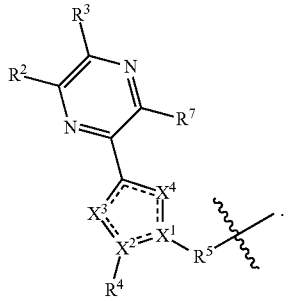

.

In any of the foregoing or following embodiments, —$X^1(R^5)$— is —$C(R^5)$—, —$C(R^5)$—C(H)—, —C(H)—$C(R^5)$—, —$C(R^5)$—N—, —N—$C(R^5)$—, or —$N(R^5)$—. In some embodiments, —$X^1(R^5)$— is —C(H)—$C(R^5)$—.

In some embodiments, Q has formula Q1A, $R^1$ is cyano or perhaloalkyl, and $R^2$ and $R^3$ are H. $R^1$ may be cyano or trifluoromethyl. In certain embodiments, $R^1$ is cyano. In certain implementations, Q has formula Q1A, $R^1$ is H, and $R^1$ and $R^2$ together with the atoms to which they are bound form a 5- or 6-membered aryl or heteroaryl ring.

In some embodiments, Q has formula Q2A, $R^1$ is H, and $R^2$ and $R^3$ are other than H. In some embodiments, Q has formula Q2A, $R^2$ is H, and $R^1$ and $R^3$ are other than H. In certain implementations, Q has formula Q2A, $R^1$ is H, and $R^2$ and $R^3$ together with the atoms to which they are bound form a 5- or 6-membered aryl or heteroaryl ring. In some implementations, $R^3$ is amino, aminoalkyl, or alkylamino, and $R^2$ is alkoxy, haloalkoxy, perhaloalkoxy, perhaloalkyl, haloalkyl, or cyano. In certain embodiments, $R^3$ is —$NH_2$, and $R^2$ is —$OCH_3$, —$OCF_3$, —$CF_3$, —CN, —$OCHF_2$,

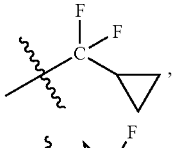

,

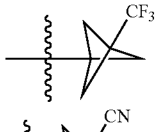

,

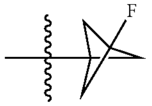

,

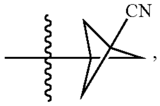

, or H. In some examples, $R^2$ is —$OCF_3$, —$CF_3$, or —CN.

In some embodiments, Q has formula Q1B, $R^2$ is H, alkyl, alkoxy, amino, or cyano, $R^3$ is H, amino, or alkyl, and $R^8$ is H or alkyl. In some examples, the alkyl or alkoxy is methyl or methoxy, respectively.

In some embodiments, Q has formula Q2B, $R^2$ is haloalkyl, perhaloalkyl, alkoxy, haloalkoxy, perhaloalkoxy, cyano, or H, $R^3$ is amino, aminoalkyl, or alkylamino, and $R^7$ is H or alkyl. In certain implementations, $R^7$ is H, $R^3$ is —$NH_2$,

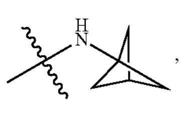

, or

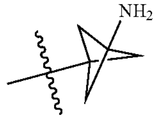

, and $R^2$ is —$CF_3$, —CN, —H, —$OCH_3$, —$OCHF_2$, $OCF_3$,

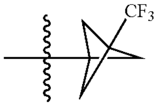

,

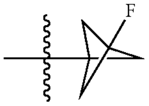

, or

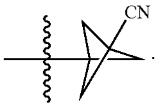

.

In any of the foregoing or following embodiments,

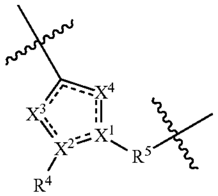

may be:

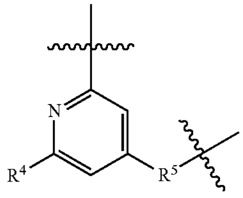

,

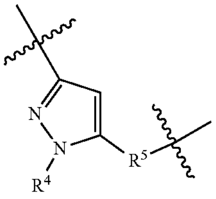

,

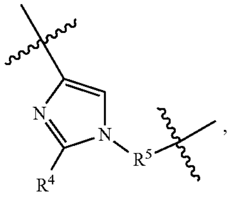

,

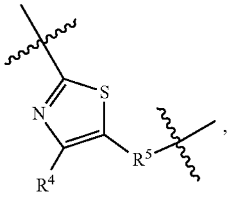

, where $R^4$ and $R^5$ are defined as above. In some embodiments, $R^4$ is substituted or unsubstituted alkyl, substituted or unsubstituted azaalkyl, or aryl. In certain embodiments, $R^4$ is substituted or unsubstituted $C_1$-$C_5$ alkyl or substituted cycloazaalkyl. In some examples, $R^4$ is substituted pyrrolidinyl (e.g., 3,3-difluoro-1-pyrrolidinyl), isopropyl, or —C(H)(OH)—$C(CH_3)_2$.

$R^5$ is substituted or unsubstituted aliphatic, substituted or unsubstituted heteroaliphatic, or substituted or unsubstituted alkylamino. In some embodiments, $R^5$ is substituted or unsubstituted alkyl, substituted or unsubstituted heteroalkyl, or substituted or unsubstituted alkylamino. In certain embodiments, $R^5$ comprises a cycloalkyl moiety, a cycloheteroalkyl moiety, or both. The cycloalkyl or heterocycloalkyl moieties may be bicycloalkyl or bicycloheteroalkyl. Exemplary $R^5$ groups include, but are not limited to

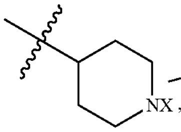,
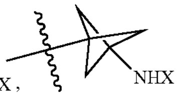,
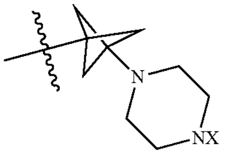,
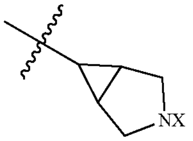,
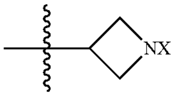,
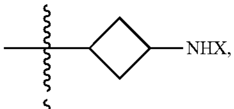
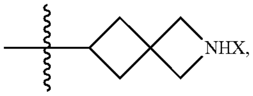
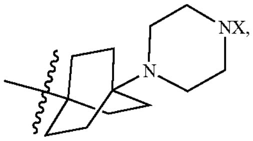 or
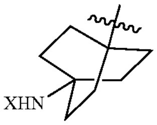,
where X is a bond or alkyl group binding Q to L. In some implementations, $R^5$ is
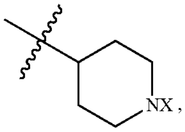,
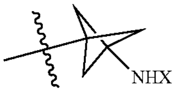,
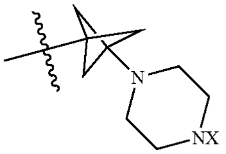, or
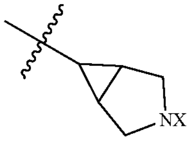.
In some embodiments,
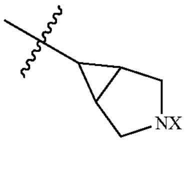
has a stereochemistry
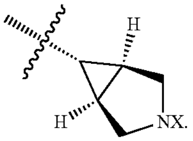
In some embodiments, Q is:
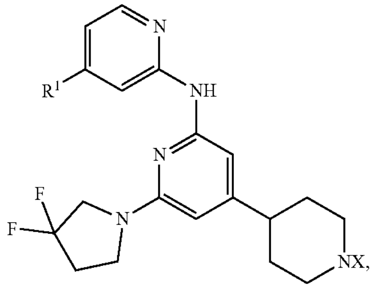
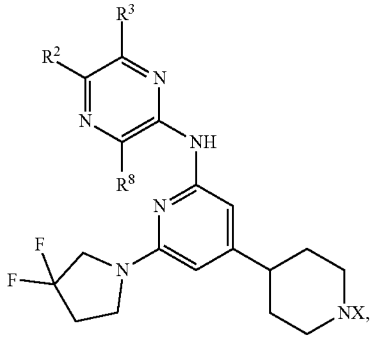
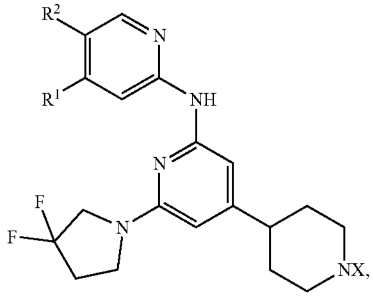
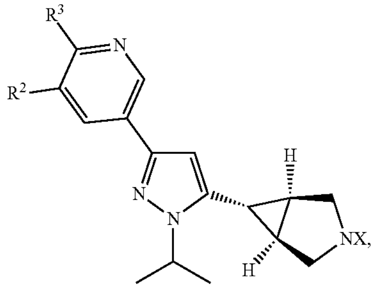
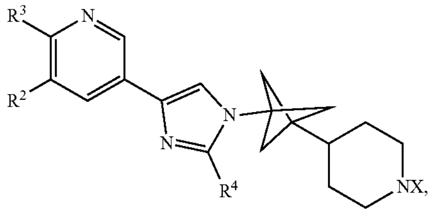
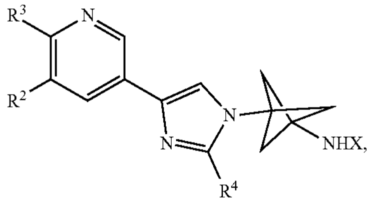

-continued
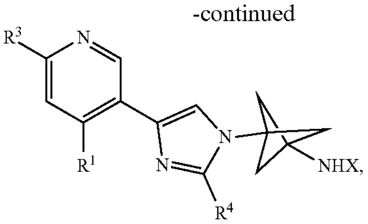
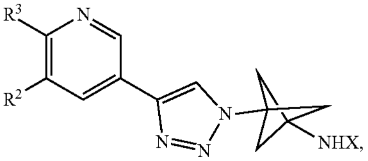
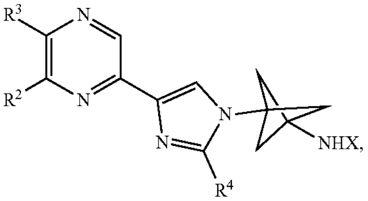
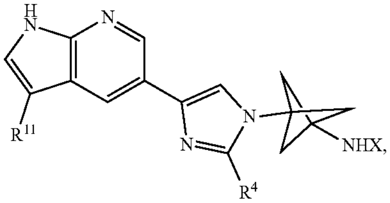
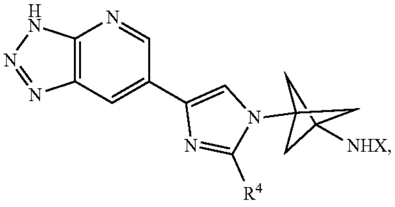
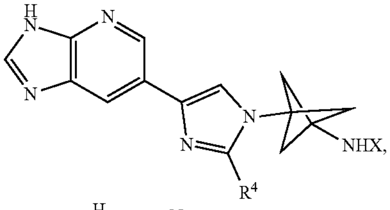
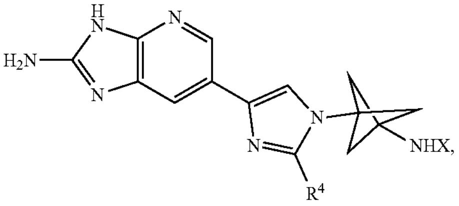
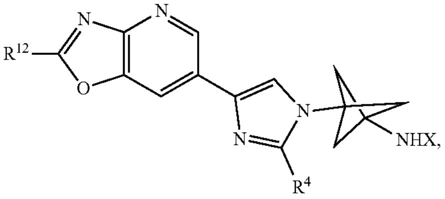
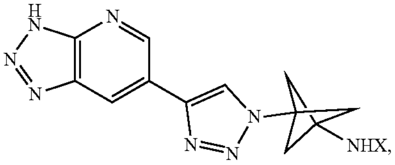
-continued
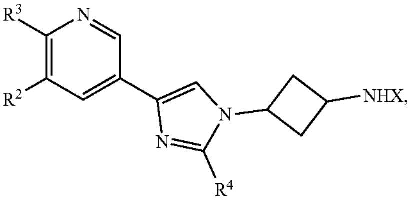
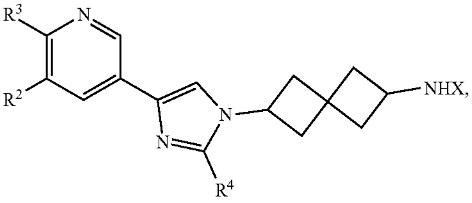
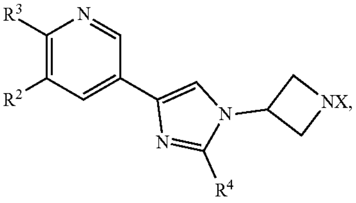
or
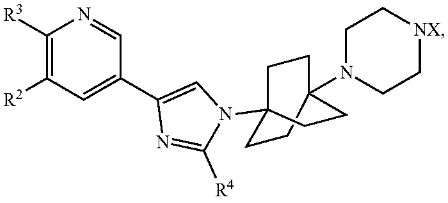
where $R^1$-$R^4$ and $R^8$ are as previously defined, and $R^{11}$ and $R^{12}$ are H, alkyl, perhaloalkyl, alkoxy, perhaloalkoxy or cyano. In some embodiments, $R^4$ is isopropyl, —C(H)(OH)—C($CH_3$)$_2$, cyclopropyl, or
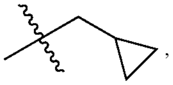 [SMILES: *CC1CC1]
In certain implementations 1 is —CN or —$CF_3$; $R^2$ is —$OCH_3$, —$OCF_3$, —$CF_3$, —CN, —$OCHF_2$,
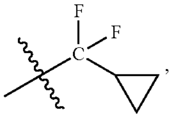
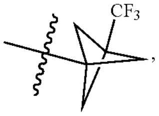
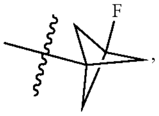
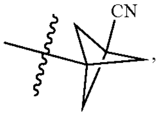

or H; $R^3$ is —$NH_2$,

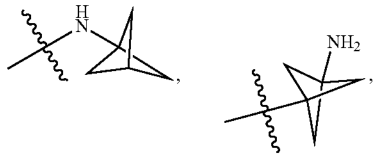 [SMILES: *NC12CC(C1)C2 ; *C12CC(N)(C1)C2]

or H; $R^8$ is —$OCF_3$, —CN, —$CH_3$, or H; $R^{11}$ and $R^{12}$ independently are —$CF_3$, —CN, —H, —$OCH_3$, or —$OCF_3$; and X is a bond.

In any of the foregoing embodiments, the targeted degrader may exhibit membrane permeability and/or water solubility. Permeability and solubility are related to the topological polar surface area (TPSA) and molecular weight of the targeted degrader. A desirable solubility may be provided by molecules having a TPSA of ≥0.1×MW (or TPSA/MW ratio ≥0.1) (see, e.g., Maple et al., *Med Chem Commun* 2019, 10:1755-1764). In some embodiments, water solubility is enhanced by forming the targeted degrader as a common salt (e.g., acetates, oxalates, methane sulfonates), or from common acids such as hydrochloric acid or sulfuric acid. Advantageously, because some embodiments of the targeted degraders are catalytic in nature, a relatively low aqueous solubility may not be a deterrent. A desirable permeability may be provided by molecules having a TPSA of <140 (Ibid.). Thus, in some embodiments, the targeted degrader has a TPSA of from 0.1×MW to 140.

Exemplary LZK-targeting degraders include the compounds shown in Table 3, as well as other stereoisomers, tautomers, and pharmaceutically acceptable salts thereof.

TABLE 3

| | |
|---|---|
| 3 | 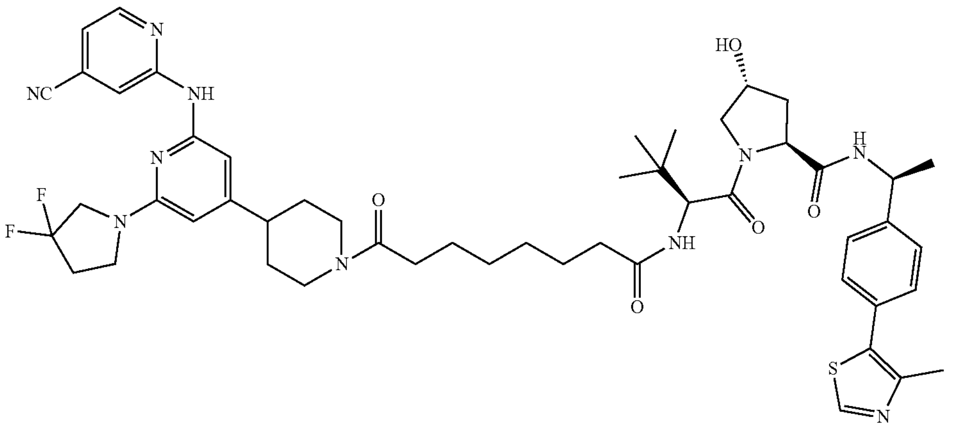 [SMILES: Cc1ncsc1-c1ccc([C@H](C)NC(=O)[C@@H]2C[C@@H](O)CN2C(=O)[C@@H](NC(=O)CCCCCCC(=O)N2CCC(c3cc(Nc4cc(C#N)ccn4)nc(N4CCC(F)(F)C4)c3)CC2)C(C)(C)C)cc1] |
| 4 | 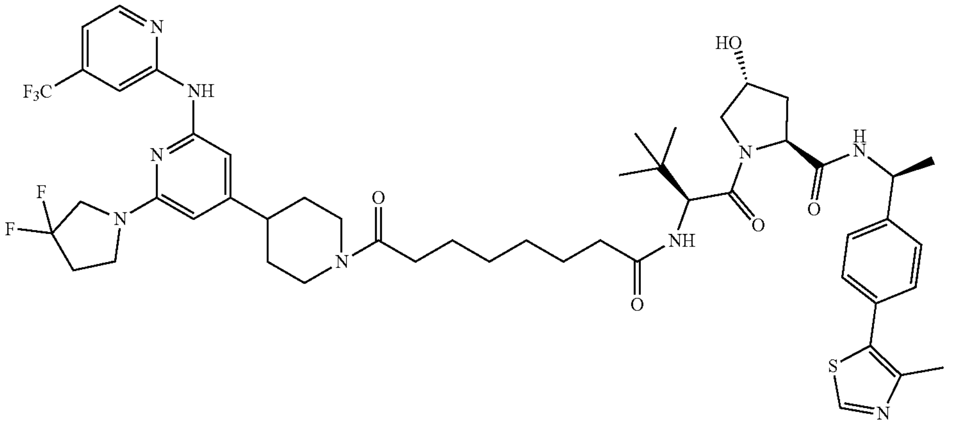 [SMILES: Cc1ncsc1-c1ccc([C@H](C)NC(=O)[C@@H]2C[C@@H](O)CN2C(=O)[C@@H](NC(=O)CCCCCCC(=O)N2CCC(c3cc(Nc4cc(C(F)(F)F)ccn4)nc(N4CCC(F)(F)C4)c3)CC2)C(C)(C)C)cc1] |
| 5 | 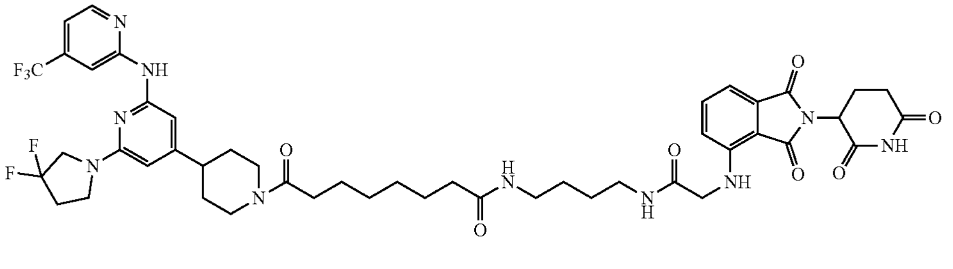 [SMILES: N#Cc1ccnc(Nc2cc(C3CCN(C(=O)CCCCCCC(=O)NCCCCNC(=O)CNc4cccc5c4C(=O)N(C4CCC(=O)NC4=O)C5=O)CC3)cc(N3CCC(F)(F)C3)n2)c1] |

TABLE 3-continued
6
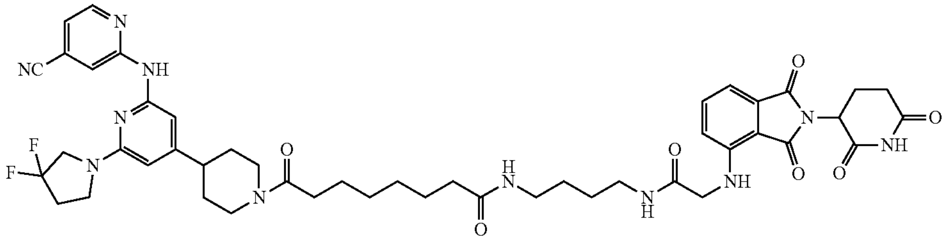
7
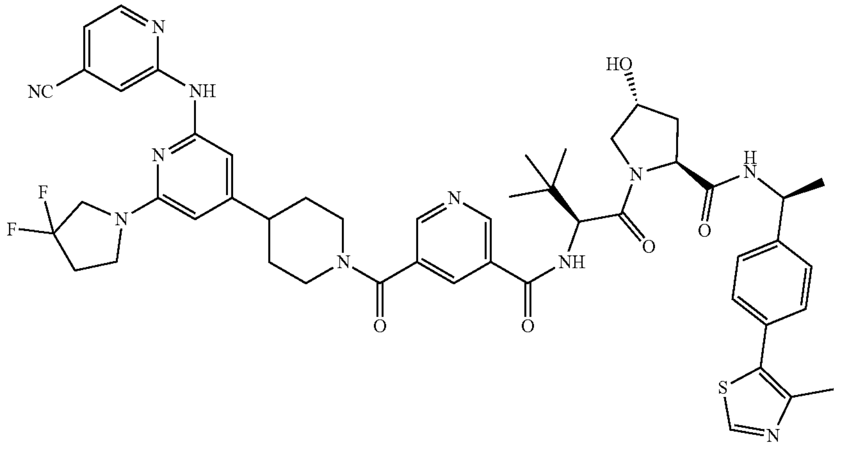 [SMILES: Cc1ncsc1-c1ccc([C@H](C)NC(=O)[C@@H]2C[C@@H](O)CN2C(=O)[C@@H](NC(=O)c2cncc(C(=O)N3CCC(c4cc(Nc5cc(C#N)ccn5)nc(N5CCC(F)(F)C5)c4)CC3)c2)C(C)(C)C)cc1]
8
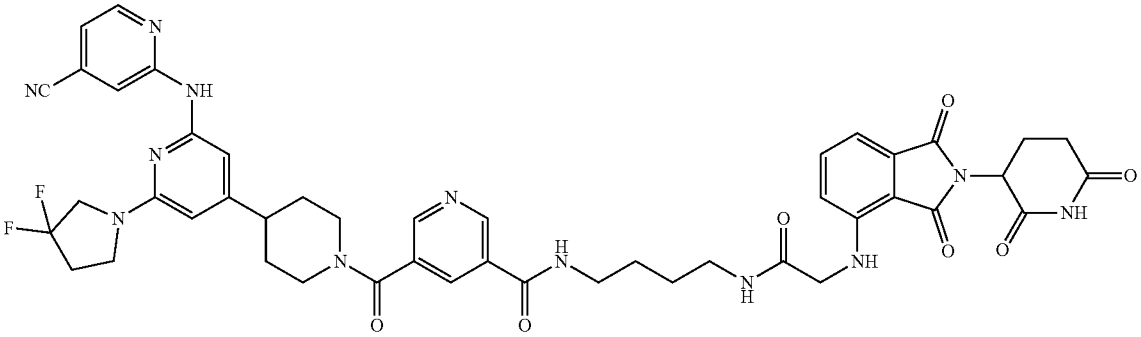 [SMILES: N#Cc1ccnc(Nc2cc(C3CCN(C(=O)c4cncc(C(=O)NCCCCNC(=O)CNc5cccc6c5C(=O)N(C5CCC(=O)NC5=O)C6=O)c4)CC3)cc(N3CCC(F)(F)C3)n2)c1]
9
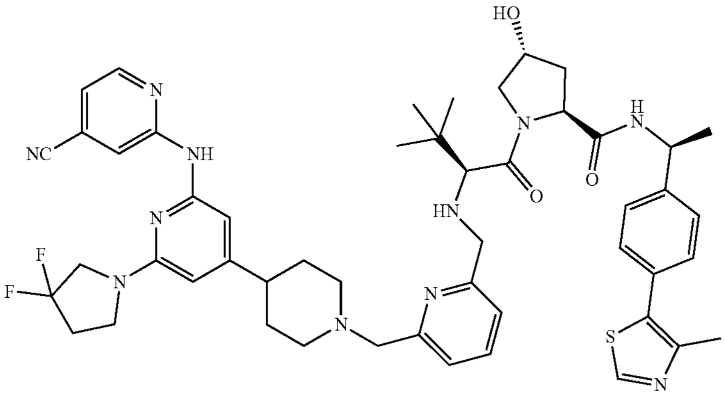 [SMILES: Cc1ncsc1-c1ccc([C@H](C)NC(=O)[C@@H]2C[C@@H](O)CN2C(=O)[C@@H](NCc2cccc(CN3CCC(c4cc(Nc5cc(C#N)ccn5)nc(N5CCC(F)(F)C5)c4)CC3)n2)C(C)(C)C)cc1]

TABLE 3-continued
10
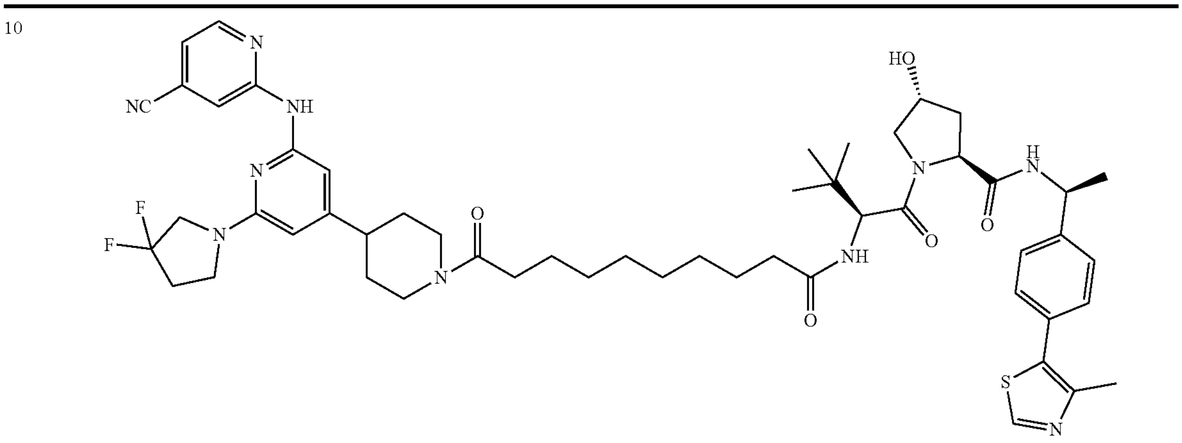
11
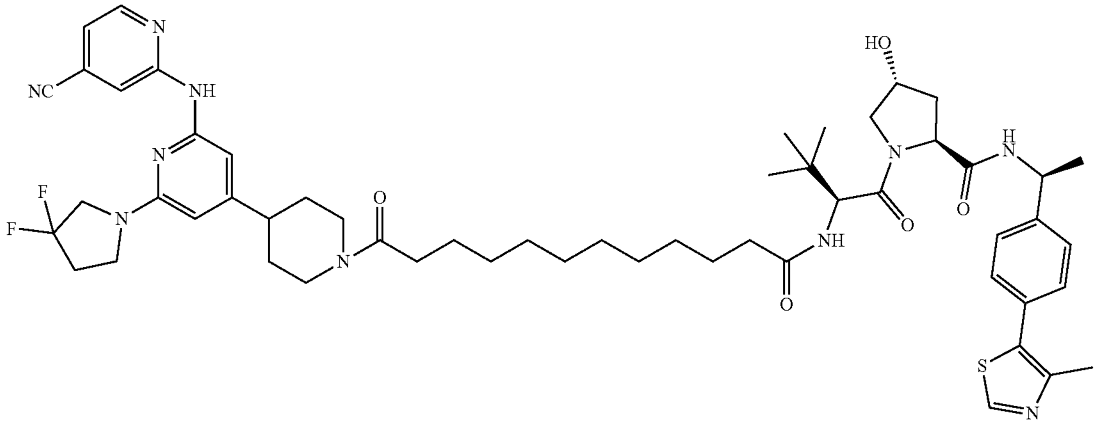 [SMILES: Cc1ncsc1-c1ccc([C@H](C)NC(=O)[C@@H]2C[C@@H](O)CN2C(=O)[C@@H](NC(=O)CCCCCCCCCCC(=O)N2CCC(c3cc(Nc4cc(C#N)ccn4)nc(N4CCC(F)(F)C4)c3)CC2)C(C)(C)C)cc1]
12
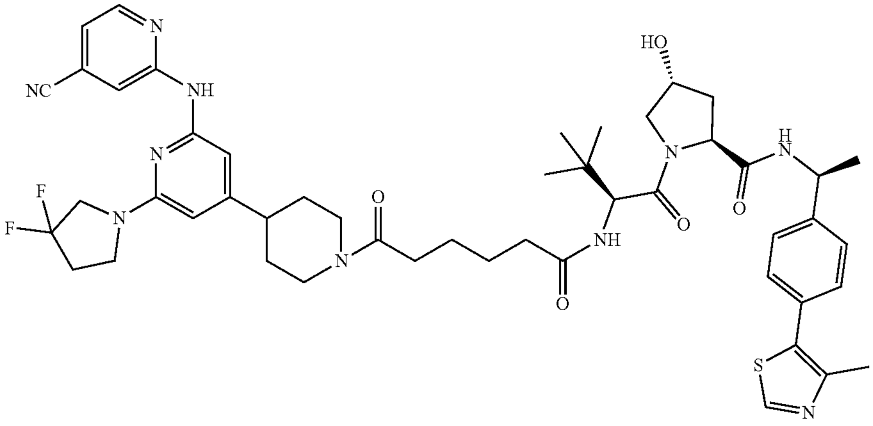 [SMILES: Cc1ncsc1-c1ccc([C@H](C)NC(=O)[C@@H]2C[C@@H](O)CN2C(=O)[C@@H](NC(=O)CCCCC(=O)N2CCC(c3cc(Nc4cc(C#N)ccn4)nc(N4CCC(F)(F)C4)c3)CC2)C(C)(C)C)cc1]

TABLE 3-continued
13
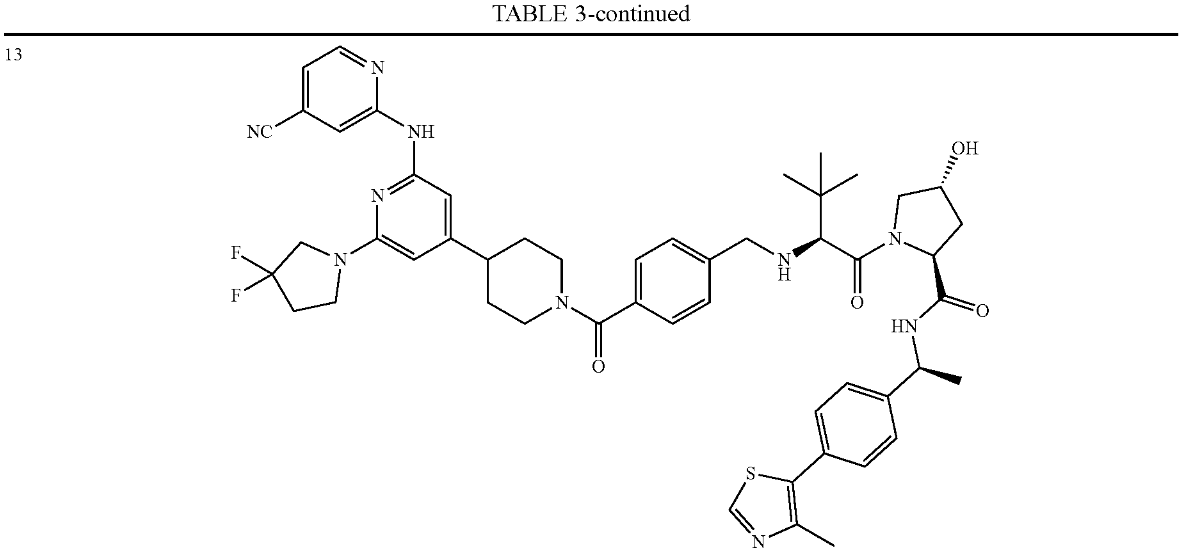
14
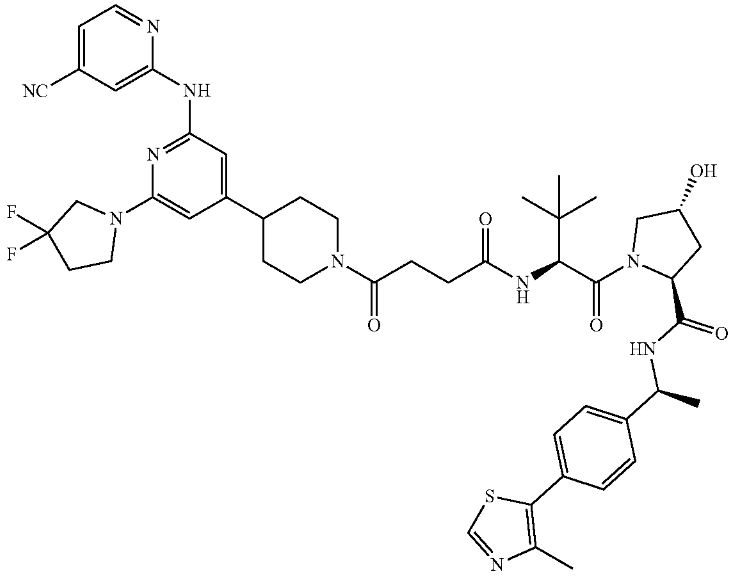 [SMILES: Cc1ncsc1-c1ccc([C@H](C)NC(=O)[C@@H]2C[C@@H](O)CN2C(=O)[C@@H](NC(=O)CCC(=O)N2CCC(c3cc(Nc4cc(C#N)ccn4)nc(N4CCC(F)(F)C4)c3)CC2)C(C)(C)C)cc1]
15
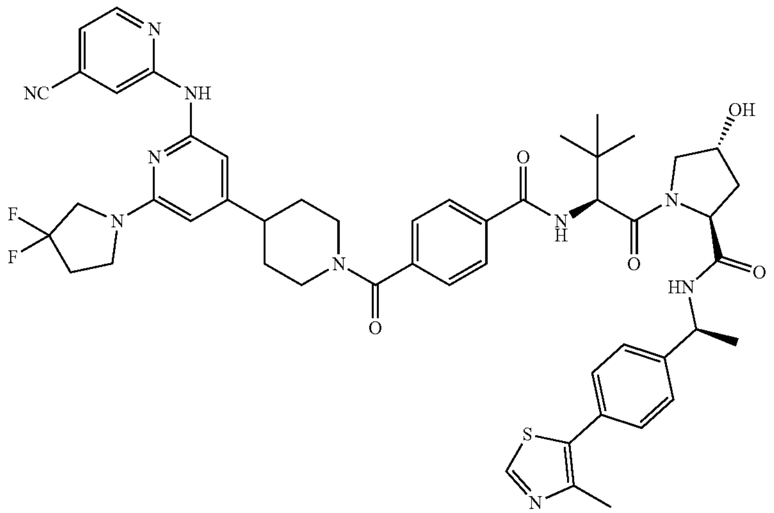 [SMILES: Cc1ncsc1-c1ccc([C@H](C)NC(=O)[C@@H]2C[C@@H](O)CN2C(=O)[C@@H](NC(=O)c2ccc(C(=O)N3CCC(c4cc(Nc5cc(C#N)ccn5)nc(N5CCC(F)(F)C5)c4)CC3)cc2)C(C)(C)C)cc1]

TABLE 3-continued
16
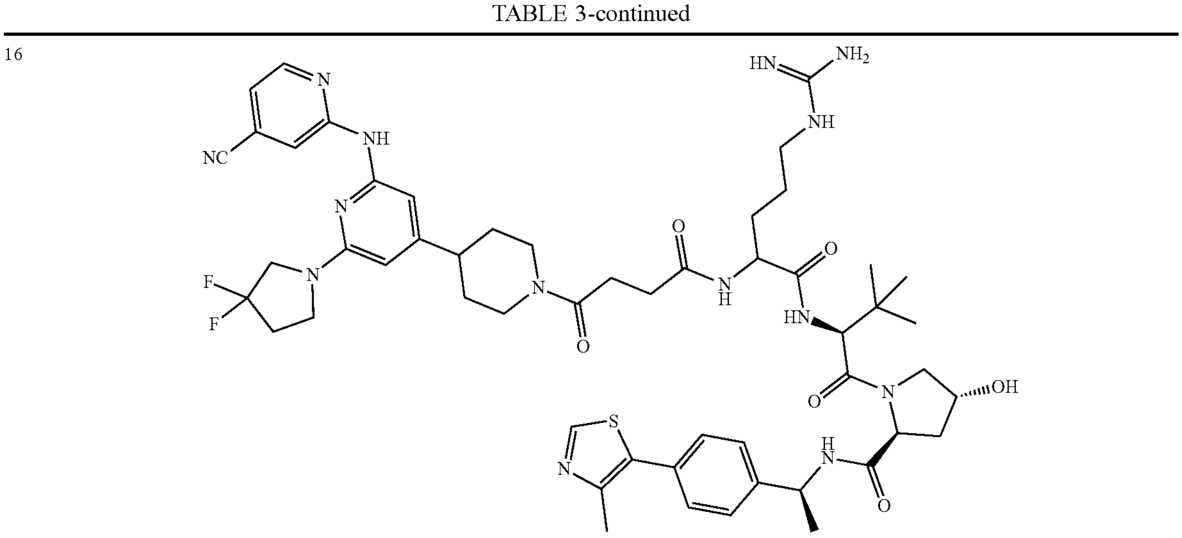
17
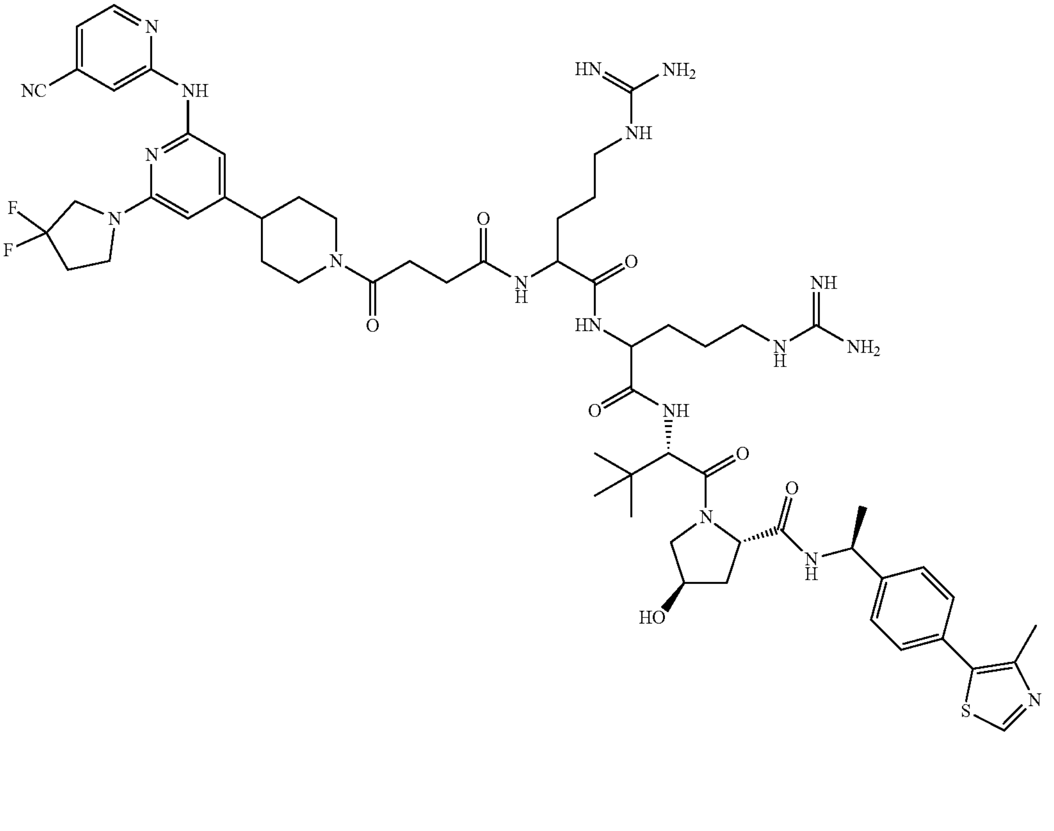 [SMILES: Cc1ncsc1-c1ccc([C@H](C)NC(=O)[C@@H]2C[C@@H](O)CN2C(=O)[C@@H](NC(=O)C(CCCNC(=N)N)NC(=O)C(CCCNC(=N)N)NC(=O)CCC(=O)N2CCC(c3cc(Nc4cc(C#N)ccn4)nc(N4CCC(F)(F)C4)c3)CC2)C(C)(C)C)cc1]

TABLE 3-continued
18
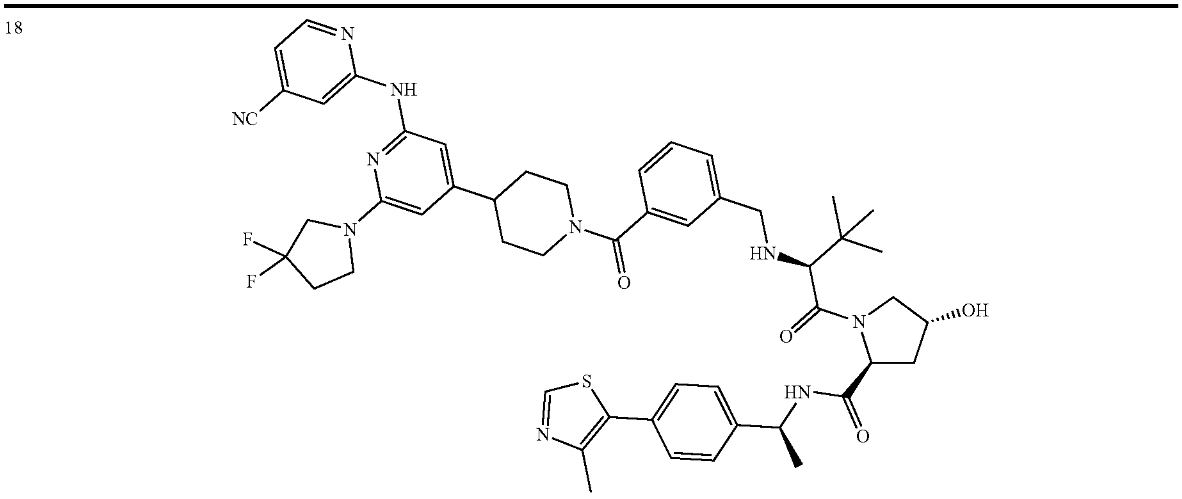
19
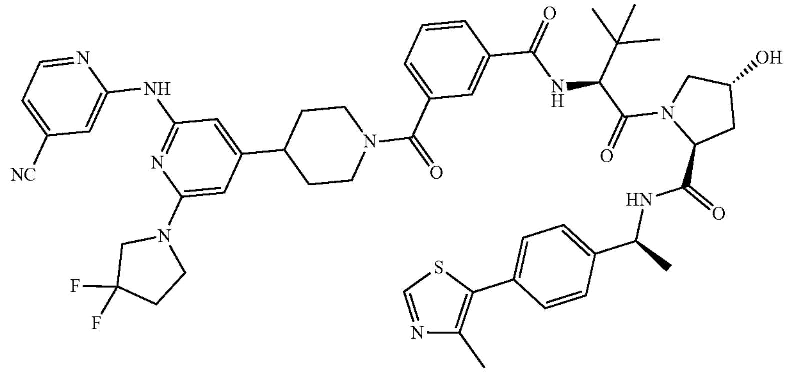 [SMILES: Cc1ncsc1-c1ccc([C@H](C)NC(=O)[C@@H]2C[C@@H](O)CN2C(=O)[C@@H](NC(=O)c2cccc(C(=O)N3CCC(c4cc(Nc5cc(C#N)ccn5)nc(N5CCC(F)(F)C5)c4)CC3)c2)C(C)(C)C)cc1]
20
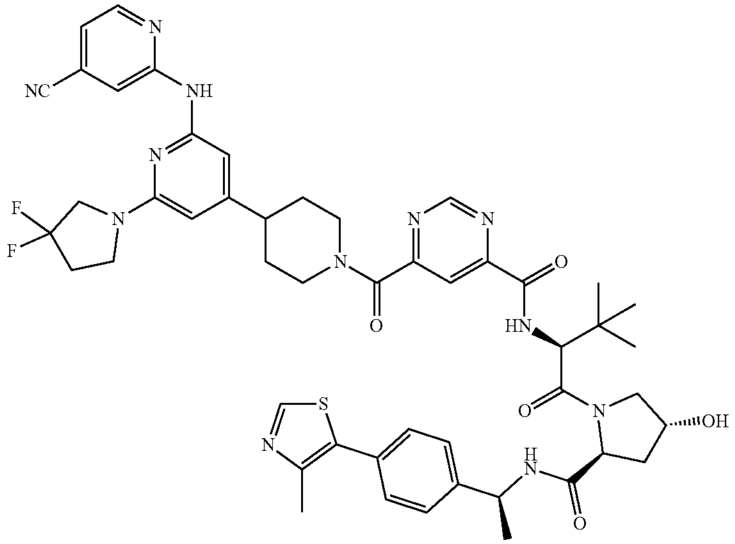 [SMILES: Cc1ncsc1-c1ccc([C@H](C)NC(=O)[C@@H]2C[C@@H](O)CN2C(=O)[C@@H](NC(=O)c2cc(C(=O)N3CCC(c4cc(Nc5cc(C#N)ccn5)nc(N5CCC(F)(F)C5)c4)CC3)ncn2)C(C)(C)C)cc1]

TABLE 3-continued
21
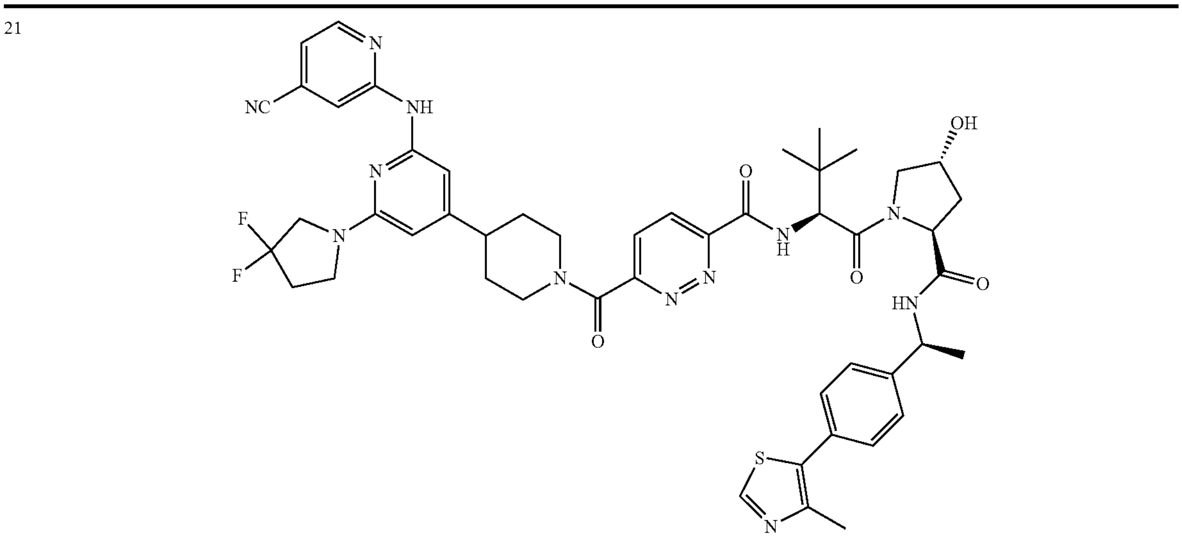
22
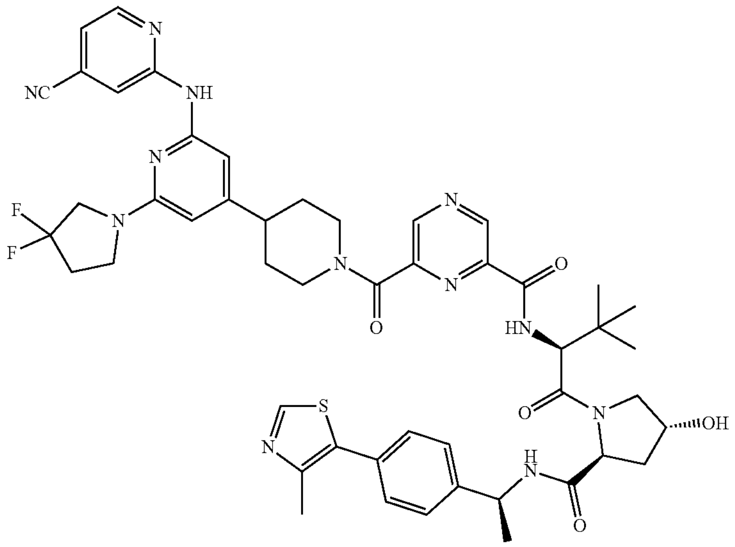 [SMILES: Cc1ncsc1-c1ccc([C@H](C)NC(=O)[C@@H]2C[C@@H](O)CN2C(=O)[C@@H](NC(=O)c2cncc(C(=O)N3CCC(c4cc(Nc5cc(C#N)ccn5)nc(N5CCC(F)(F)C5)c4)CC3)n2)C(C)(C)C)cc1]
23
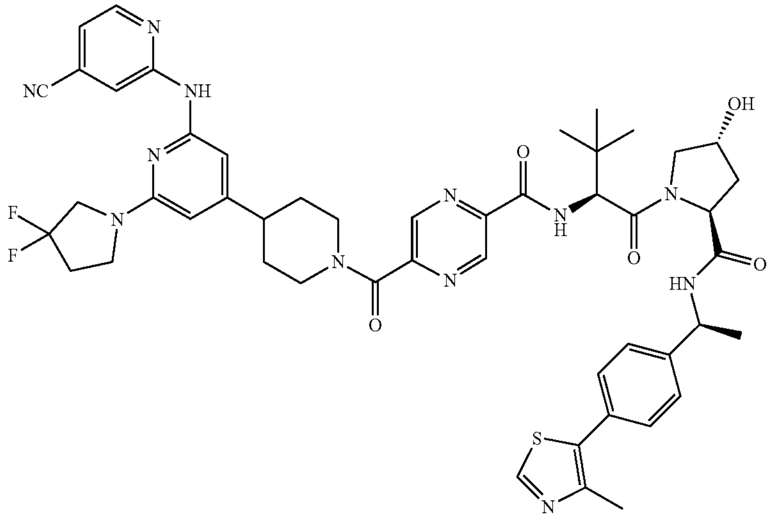 [SMILES: Cc1ncsc1-c1ccc([C@H](C)NC(=O)[C@@H]2C[C@@H](O)CN2C(=O)[C@@H](NC(=O)c2cnc(C(=O)N3CCC(c4cc(Nc5cc(C#N)ccn5)nc(N5CCC(F)(F)C5)c4)CC3)cn2)C(C)(C)C)cc1]

TABLE 3-continued
24
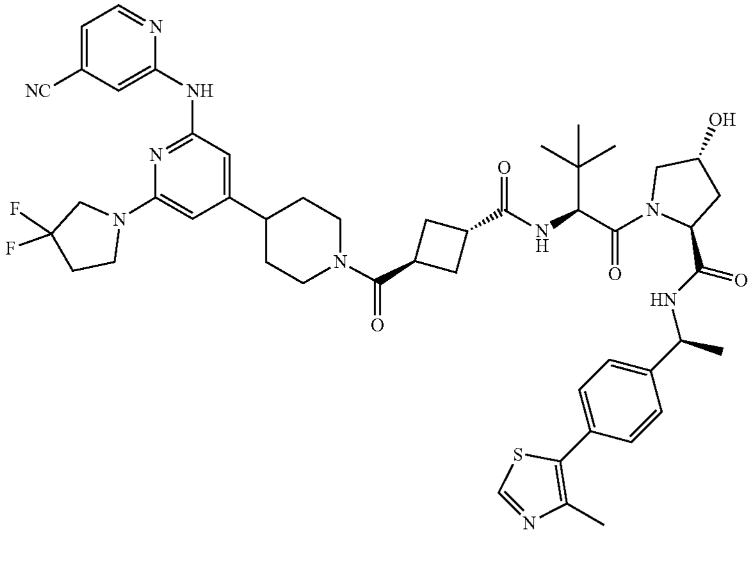 [SMILES: Cc1ncsc1-c1ccc([C@H](C)NC(=O)[C@@H]2C[C@@H](O)CN2C(=O)[C@@H](NC(=O)[C@H]2C[C@H](C(=O)N3CCC(c4cc(Nc5cc(C#N)ccn5)nc(N5CCC(F)(F)C5)c4)CC3)C2)C(C)(C)C)cc1]
25
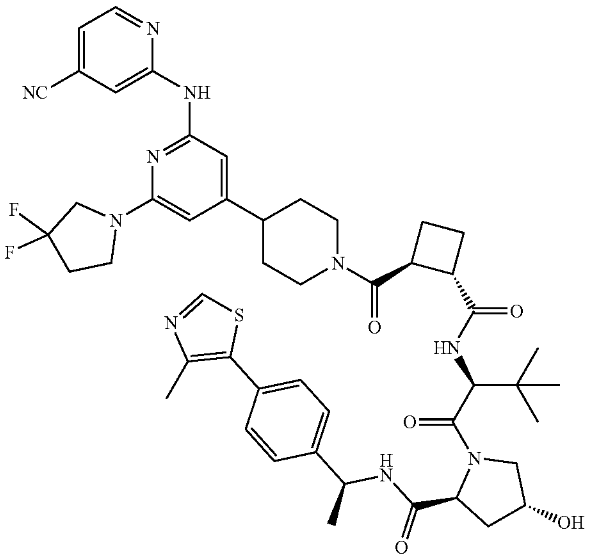 [SMILES: Cc1ncsc1-c1ccc([C@H](C)NC(=O)[C@@H]2C[C@@H](O)CN2C(=O)[C@@H](NC(=O)[C@H]2CC[C@@H]2C(=O)N2CCC(c3cc(Nc4cc(C#N)ccn4)nc(N4CCC(F)(F)C4)c3)CC2)C(C)(C)C)cc1]
26
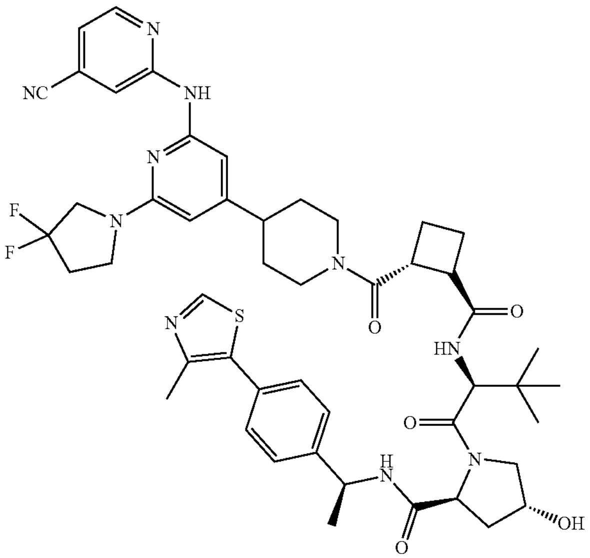

TABLE 3-continued
27
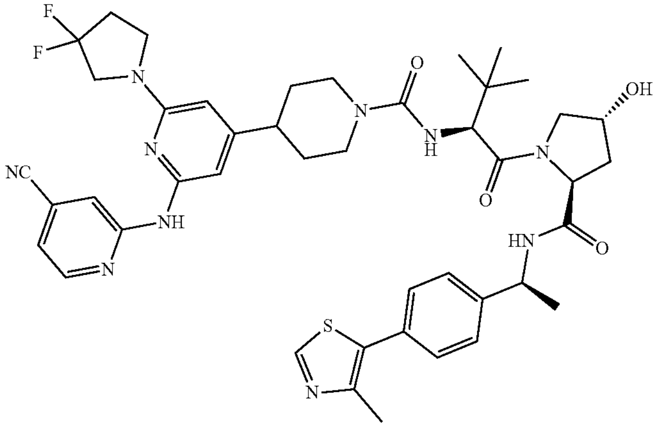 [SMILES: Cc1ncsc1-c1ccc([C@H](C)NC(=O)[C@@H]2C[C@@H](O)CN2C(=O)[C@@H](NC(=O)N2CCC(c3cc(Nc4cc(C#N)ccn4)nc(N4CCC(F)(F)C4)c3)CC2)C(C)(C)C)cc1]
28
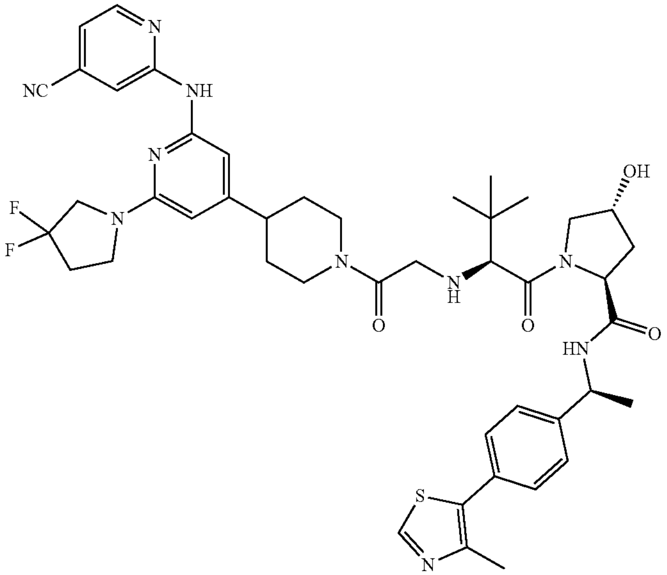 [SMILES: Cc1ncsc1-c1ccc([C@H](C)NC(=O)[C@@H]2C[C@@H](O)CN2C(=O)[C@@H](NCC(=O)N2CCC(c3cc(Nc4cc(C#N)ccn4)nc(N4CCC(F)(F)C4)c3)CC2)C(C)(C)C)cc1]
29
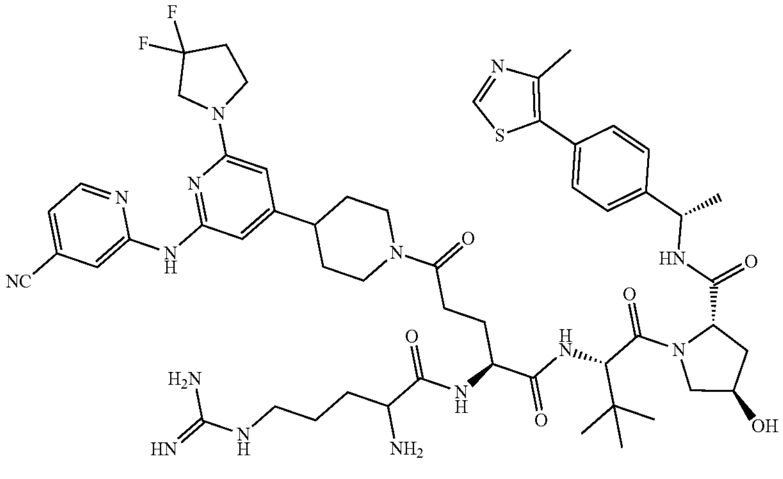 [SMILES: Cc1ncsc1-c1ccc([C@H](C)NC(=O)[C@@H]2C[C@@H](O)CN2C(=O)[C@@H](NC(=O)[C@H](CCC(=O)N2CCC(c3cc(Nc4cc(C#N)ccn4)nc(N4CCC(F)(F)C4)c3)CC2)NC(=O)C(N)CCCNC(=N)N)C(C)(C)C)cc1]

TABLE 3-continued
30
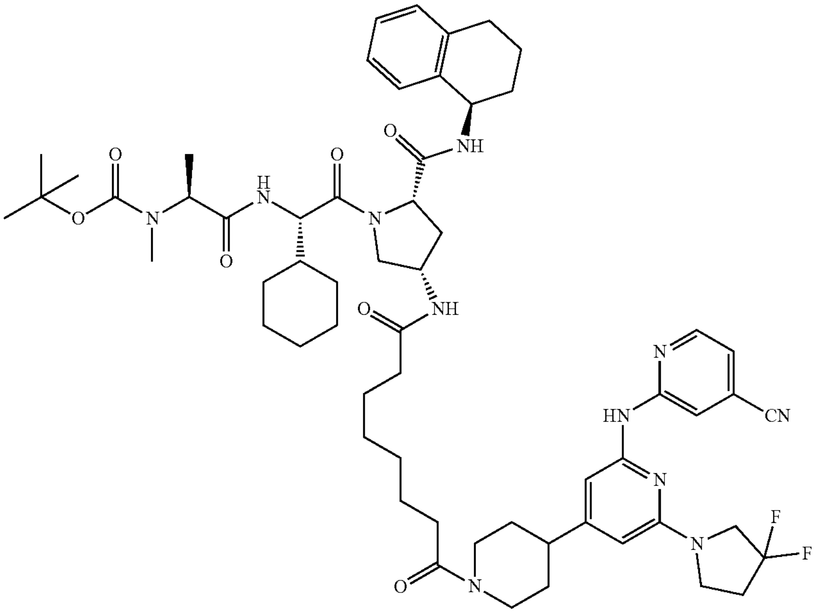 [SMILES: C[C@@H](C(=O)N[C@H](C(=O)N1C[C@@H](NC(=O)CCCCCCC(=O)N2CCC(c3cc(Nc4cc(C#N)ccn4)nc(N4CCC(F)(F)C4)c3)CC2)C[C@H]1C(=O)N[C@@H]1CCCc2ccccc21)C1CCCCC1)N(C)C(=O)OC(C)(C)C]
31
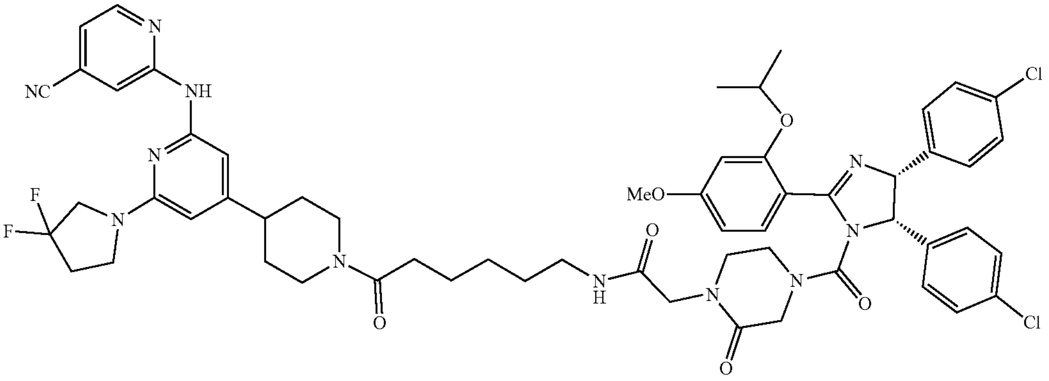 [SMILES: COc1ccc(C2=N[C@H](c3ccc(Cl)cc3)[C@H](c3ccc(Cl)cc3)N2C(=O)N2CCN(CC(=O)NCCCCCC(=O)N3CCC(c4cc(Nc5cc(C#N)ccn5)nc(N5CCC(F)(F)C5)c4)CC3)C(=O)C2)c(OC(C)C)c1]
32
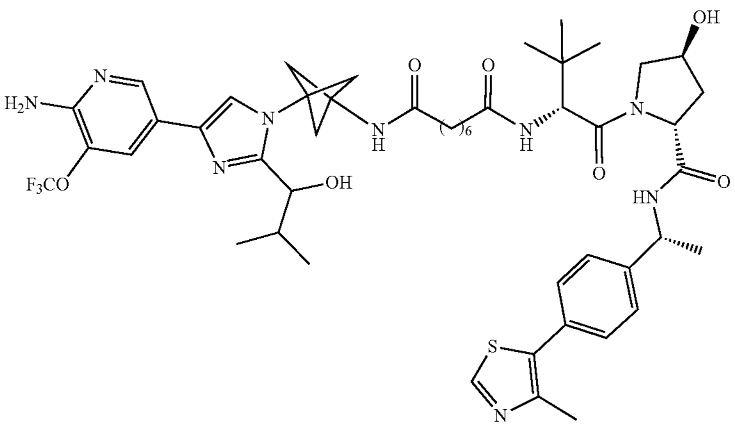

TABLE 3-continued
33
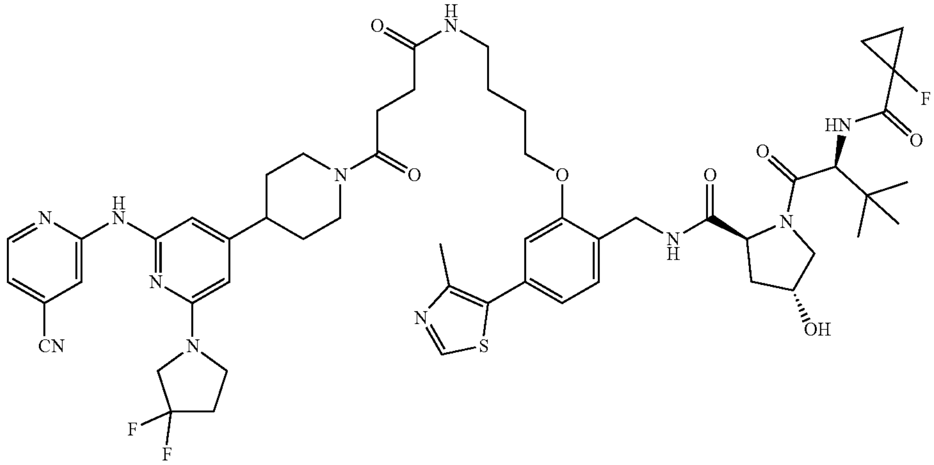 [SMILES: Cc1ncsc1-c1ccc(CNC(=O)[C@@H]2C[C@@H](O)CN2C(=O)[C@@H](NC(=O)C2(F)CC2)C(C)(C)C)c(OCCCCNC(=O)CCC(=O)N2CCC(c3cc(Nc4cc(C#N)ccn4)nc(N4CCC(F)(F)C4)c3)CC2)c1]
34
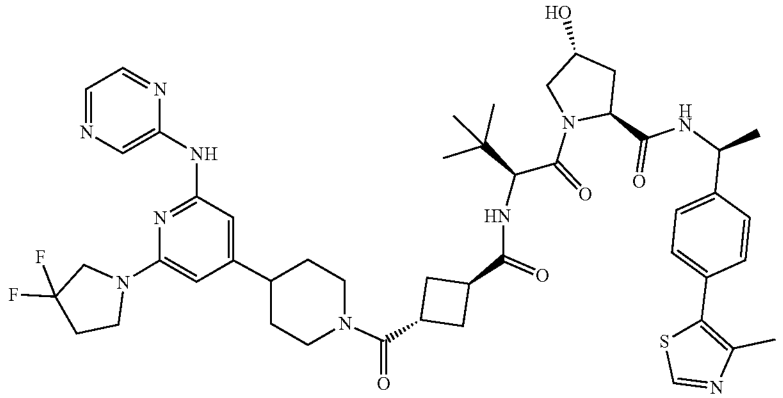 [SMILES: Cc1ncsc1-c1ccc([C@H](C)NC(=O)[C@@H]2C[C@@H](O)CN2C(=O)[C@@H](NC(=O)[C@H]2C[C@H](C(=O)N3CCC(c4cc(Nc5cnccn5)nc(N5CCC(F)(F)C5)c4)CC3)C2)C(C)(C)C)cc1]
35
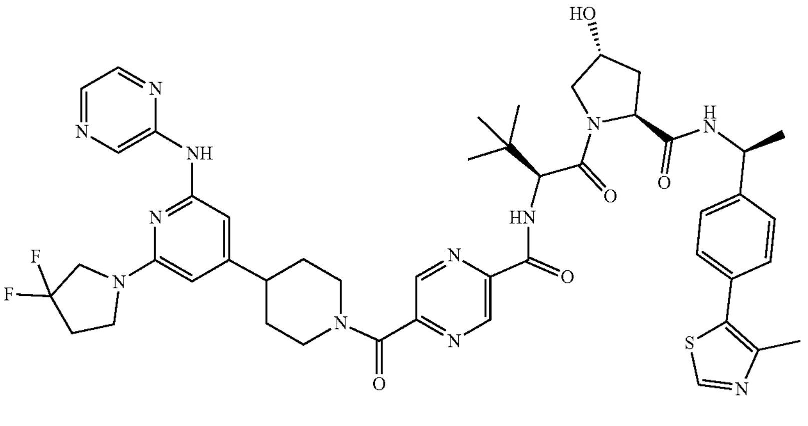 [SMILES: Cc1ncsc1-c1ccc([C@H](C)NC(=O)[C@@H]2C[C@@H](O)CN2C(=O)[C@@H](NC(=O)c2cnc(C(=O)N3CCC(c4cc(Nc5cnccn5)nc(N5CCC(F)(F)C5)c4)CC3)cn2)C(C)(C)C)cc1]

TABLE 3-continued
36
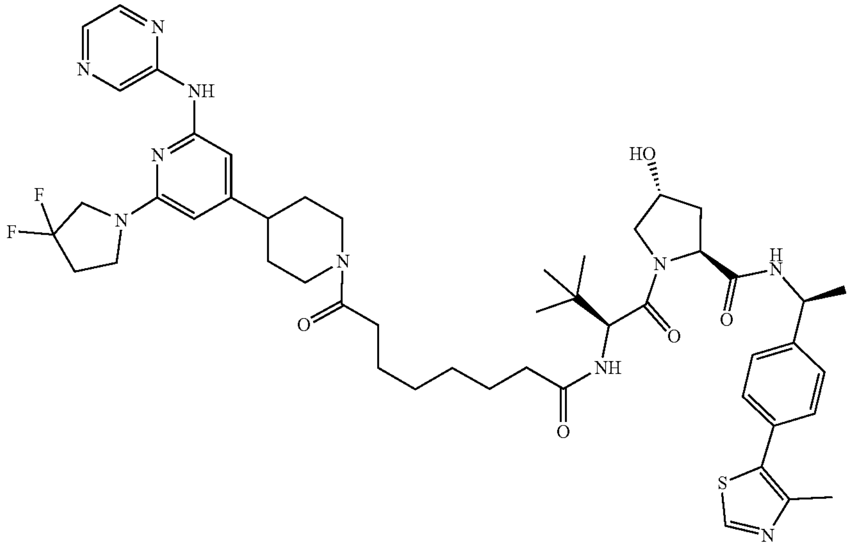 [SMILES: Cc1ncsc1-c1ccc([C@H](C)NC(=O)[C@@H]2C[C@@H](O)CN2C(=O)[C@@H](NC(=O)CCCCCCC(=O)N2CCC(c3cc(Nc4cnccn4)nc(N4CCC(F)(F)C4)c3)CC2)C(C)(C)C)cc1]
37
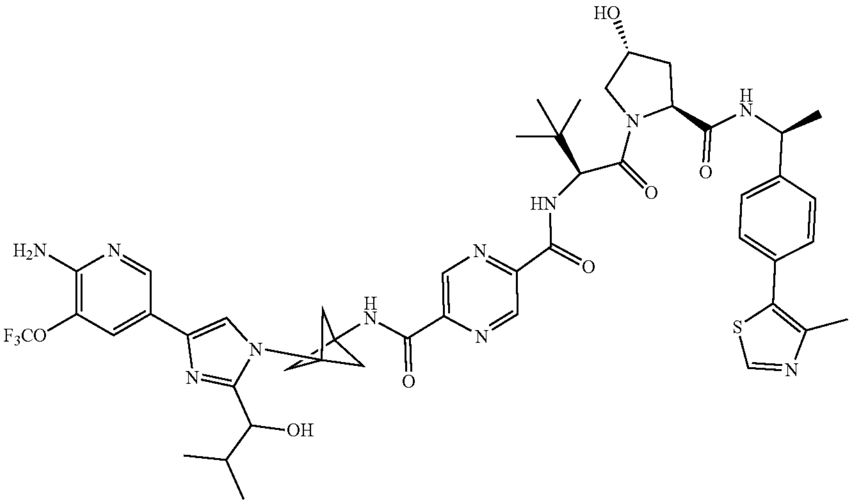 [SMILES: Cc1ncsc1-c1ccc([C@H](C)NC(=O)[C@@H]2C[C@@H](O)CN2C(=O)[C@@H](NC(=O)c2cnc(C(=O)NC34CC(n5cc(-c6cnc(N)c(OC(F)(F)F)c6)nc5C(O)C(C)C)(C3)C4)cn2)C(C)(C)C)cc1]
38
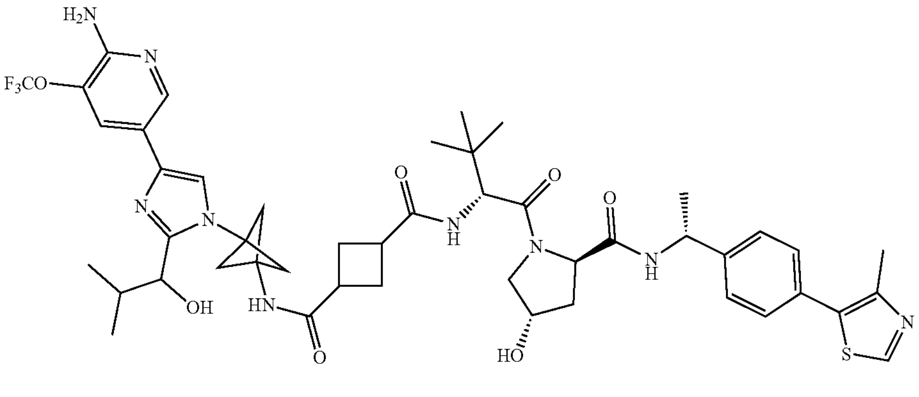 [SMILES: Cc1ncsc1-c1ccc([C@@H](C)NC(=O)[C@H]2C[C@H](O)CN2C(=O)[C@H](NC(=O)C2CC(C(=O)NC34CC(n5cc(-c6cnc(N)c(OC(F)(F)F)c6)nc5C(O)C(C)C)(C3)C4)C2)C(C)(C)C)cc1]

TABLE 3-continued
39
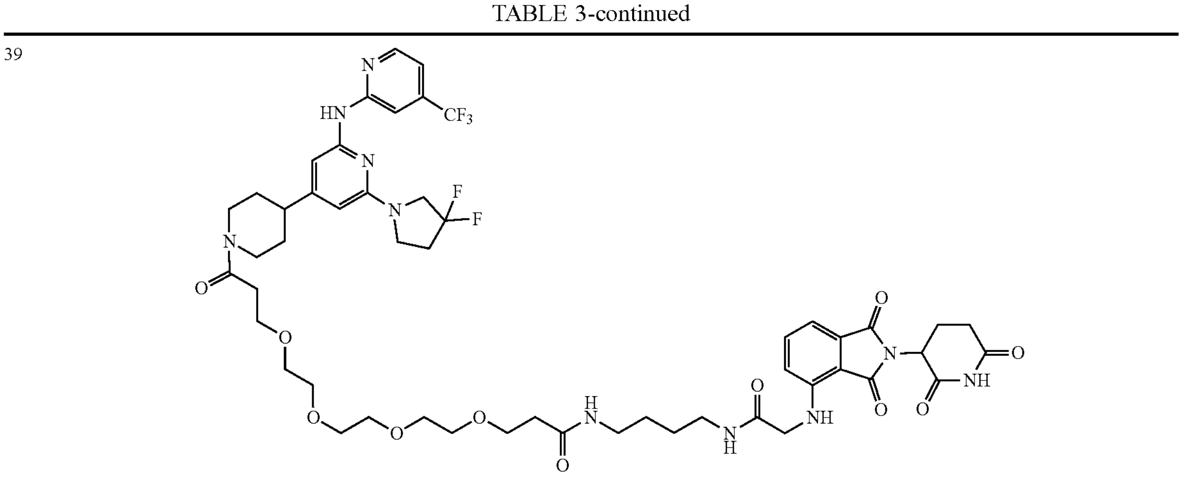
40
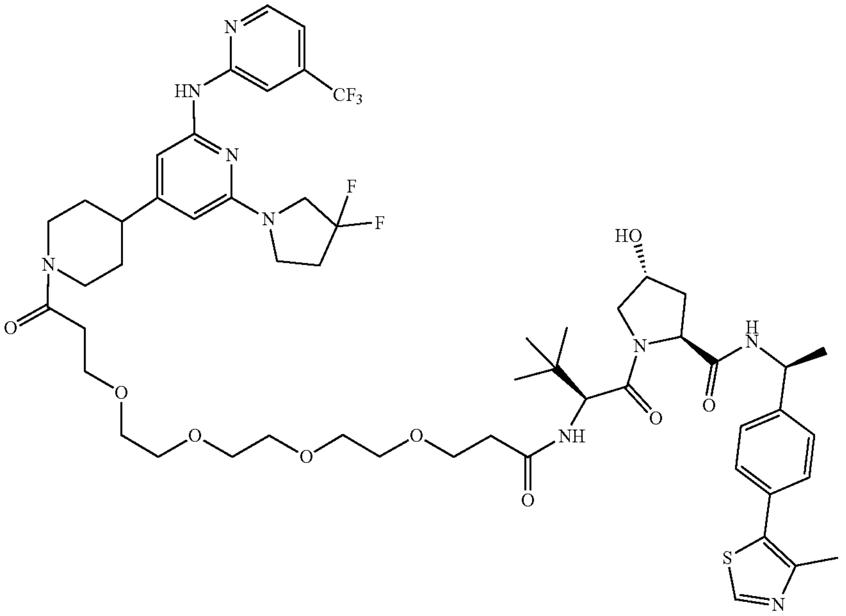 [SMILES: Cc1ncsc1-c1ccc([C@H](C)NC(=O)[C@@H]2C[C@@H](O)CN2C(=O)[C@@H](NC(=O)CCOCCOCCOCCOCCC(=O)N2CCC(c3cc(Nc4cc(C(F)(F)F)ccn4)nc(N4CCC(F)(F)C4)c3)CC2)C(C)(C)C)cc1]
41
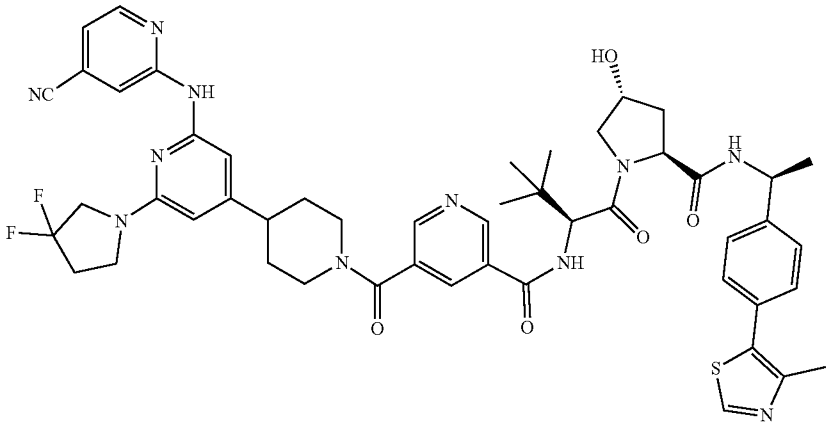 [SMILES: Cc1ncsc1-c1ccc([C@H](C)NC(=O)[C@@H]2C[C@@H](O)CN2C(=O)[C@@H](NC(=O)c2cncc(C(=O)N3CCC(c4cc(Nc5cc(C#N)ccn5)nc(N5CCC(F)(F)C5)c4)CC3)c2)C(C)(C)C)cc1]

TABLE 3-continued
42
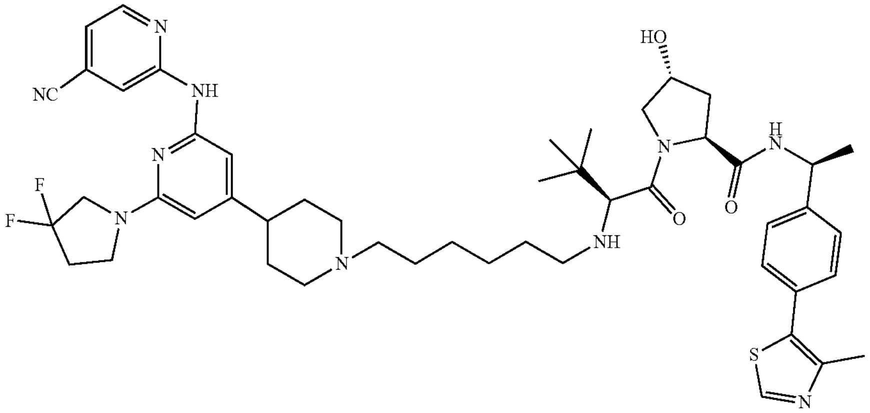 [SMILES: Cc1ncsc1-c1ccc([C@H](C)NC(=O)[C@@H]2C[C@@H](O)CN2C(=O)[C@@H](NCCCCCCN2CCC(c3cc(Nc4cc(C#N)ccn4)nc(N4CCC(F)(F)C4)c3)CC2)C(C)(C)C)cc1]
43
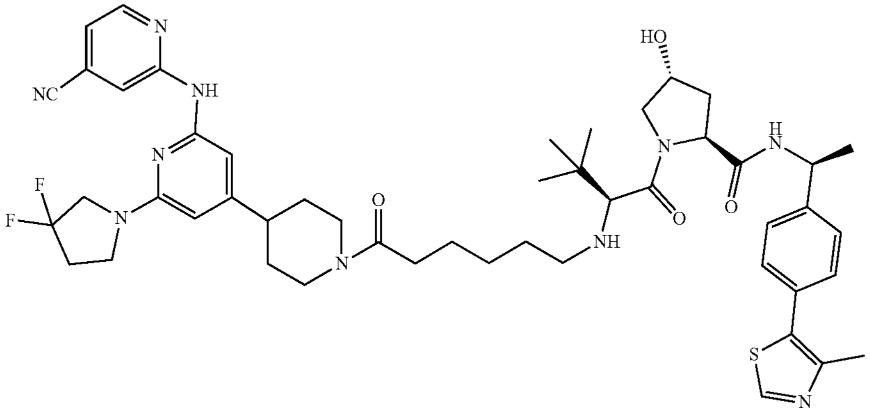 [SMILES: Cc1ncsc1-c1ccc([C@H](C)NC(=O)[C@@H]2C[C@@H](O)CN2C(=O)[C@@H](NCCCCCC(=O)N2CCC(c3cc(Nc4cc(C#N)ccn4)nc(N4CCC(F)(F)C4)c3)CC2)C(C)(C)C)cc1]
44
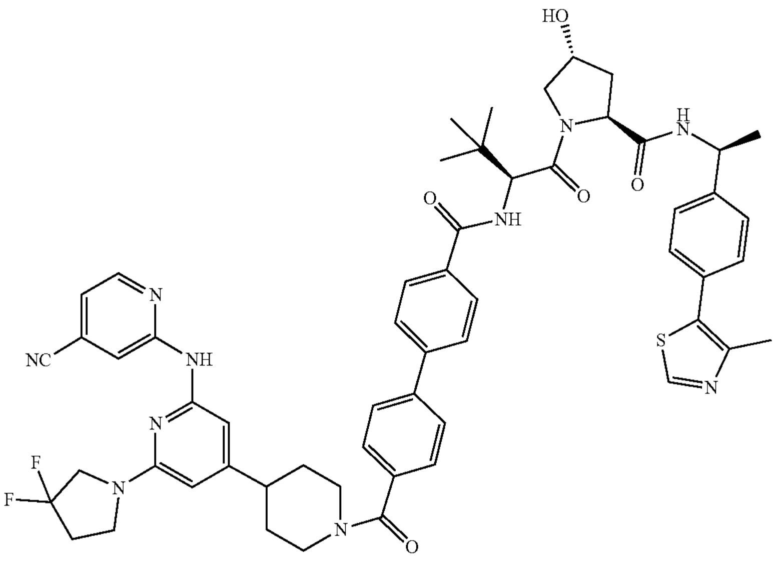 [SMILES: Cc1ncsc1-c1ccc([C@H](C)NC(=O)[C@@H]2C[C@@H](O)CN2C(=O)[C@@H](NC(=O)c2ccc(-c3ccc(C(=O)N4CCC(c5cc(Nc6cc(C#N)ccn6)nc(N6CCC(F)(F)C6)c5)CC4)cc3)cc2)C(C)(C)C)cc1]

TABLE 3-continued
45
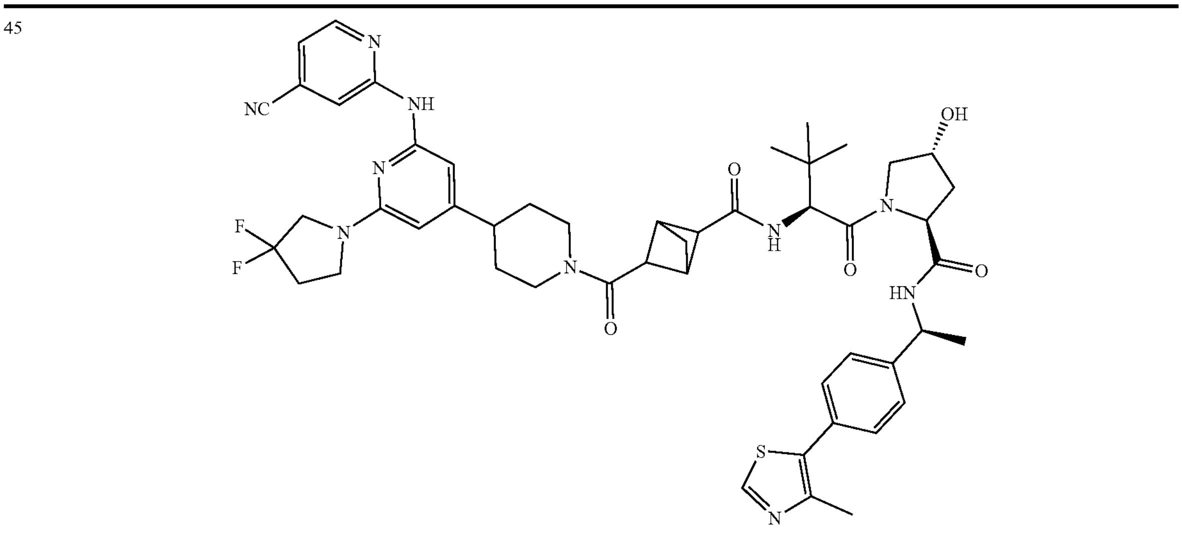
46
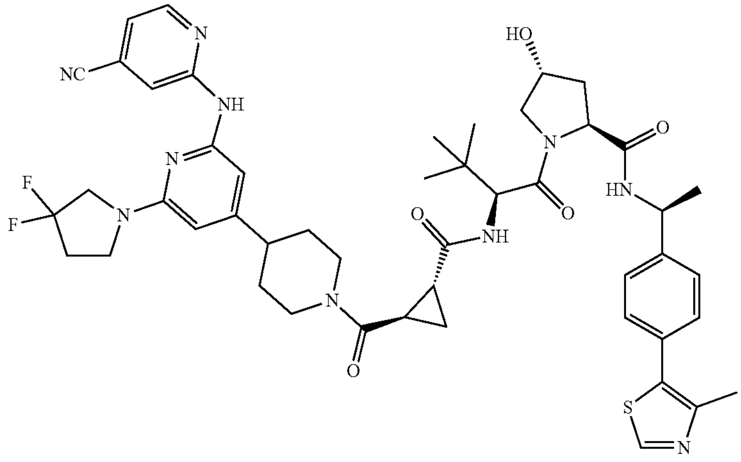 [SMILES: Cc1ncsc1-c1ccc([C@H](C)NC(=O)[C@@H]2C[C@@H](O)CN2C(=O)[C@@H](NC(=O)[C@@H]2C[C@H]2C(=O)N2CCC(c3cc(Nc4cc(C#N)ccn4)nc(N4CCC(F)(F)C4)c3)CC2)C(C)(C)C)cc1]
47
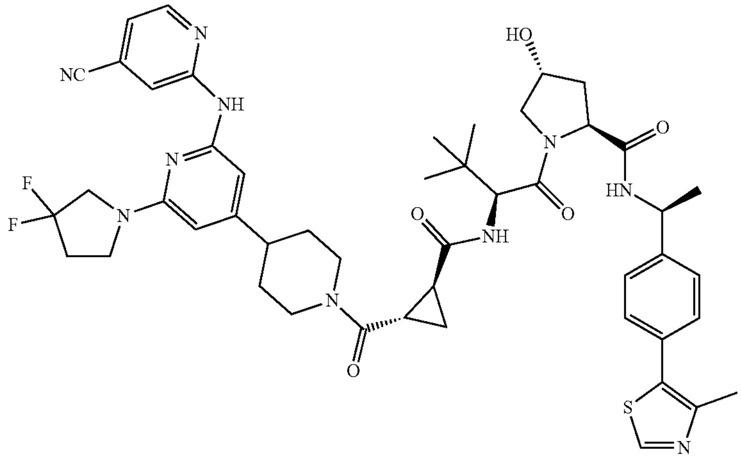 [SMILES: Cc1ncsc1-c1ccc([C@H](C)NC(=O)[C@@H]2C[C@@H](O)CN2C(=O)[C@@H](NC(=O)[C@H]2C[C@@H]2C(=O)N2CCC(c3cc(Nc4cc(C#N)ccn4)nc(N4CCC(F)(F)C4)c3)CC2)C(C)(C)C)cc1]

TABLE 3-continued
48
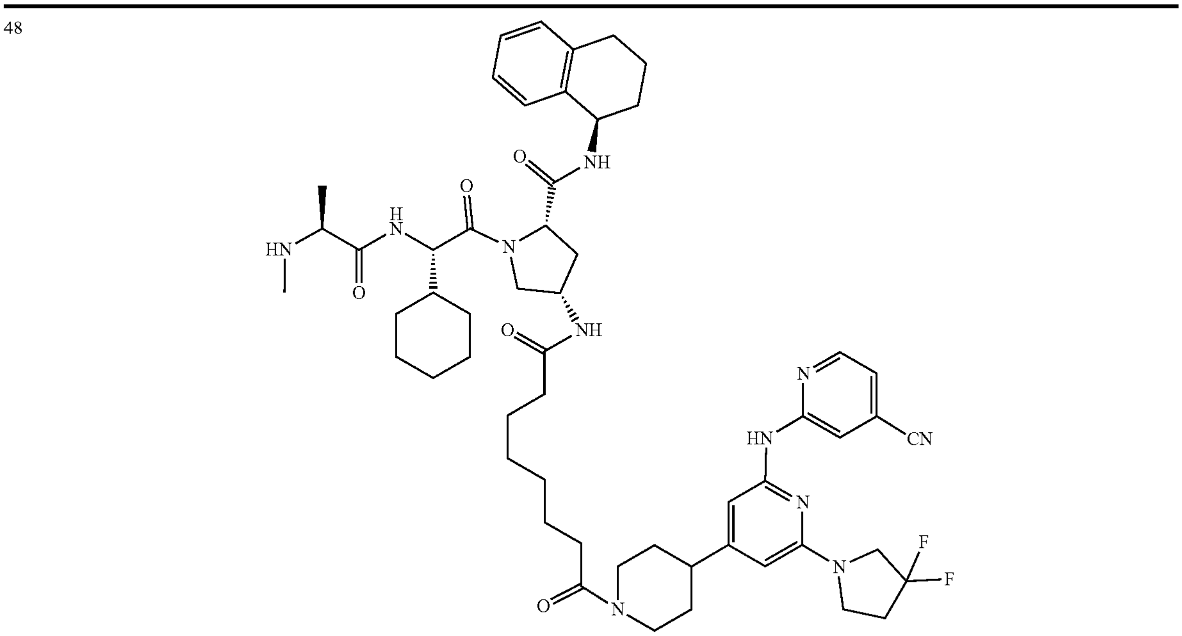
49
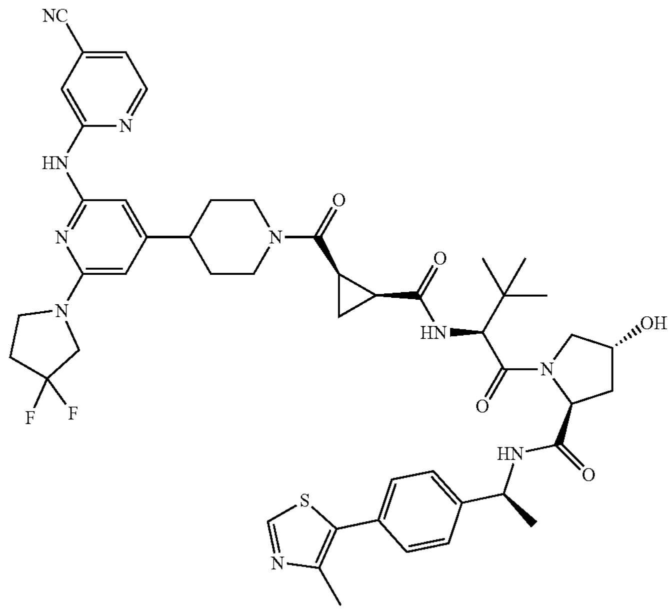 [SMILES: Cc1ncsc1-c1ccc([C@H](C)NC(=O)[C@@H]2C[C@@H](O)CN2C(=O)[C@@H](NC(=O)[C@H]2C[C@H]2C(=O)N2CCC(c3cc(Nc4cc(C#N)ccn4)nc(N4CCC(F)(F)C4)c3)CC2)C(C)(C)C)cc1]

TABLE 3-continued
50
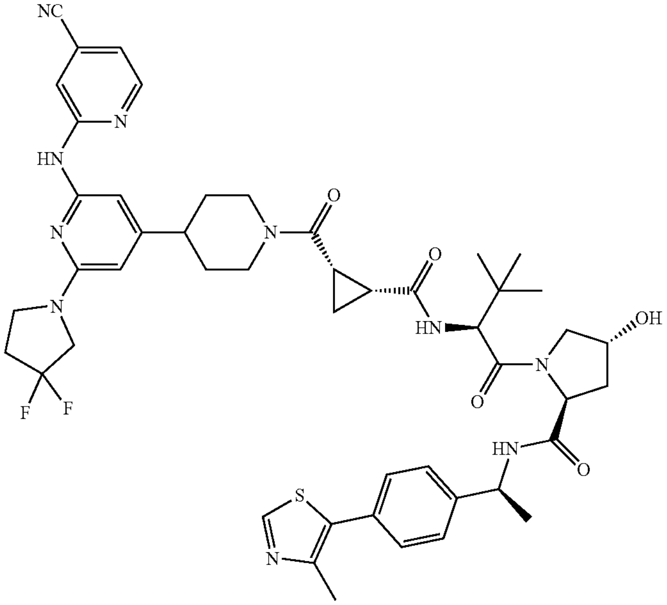 [SMILES: Cc1ncsc1-c1ccc([C@H](C)NC(=O)[C@@H]2C[C@@H](O)CN2C(=O)[C@@H](NC(=O)[C@@H]2C[C@@H]2C(=O)N2CCC(c3cc(Nc4cc(C#N)ccn4)nc(N4CCC(F)(F)C4)c3)CC2)C(C)(C)C)cc1]
51
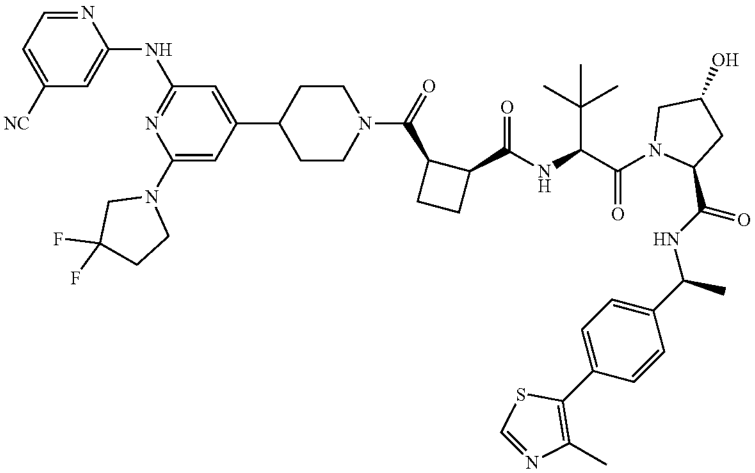 [SMILES: Cc1ncsc1-c1ccc([C@H](C)NC(=O)[C@@H]2C[C@@H](O)CN2C(=O)[C@@H](NC(=O)[C@H]2CC[C@H]2C(=O)N2CCC(c3cc(Nc4cc(C#N)ccn4)nc(N4CCC(F)(F)C4)c3)CC2)C(C)(C)C)cc1]
52
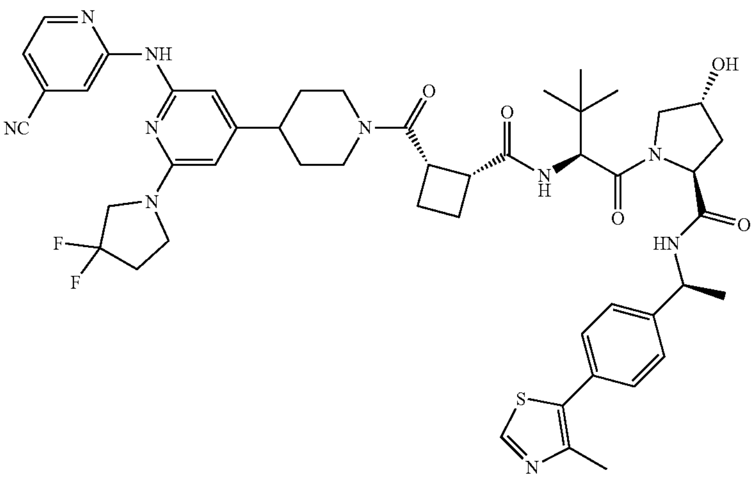 [SMILES: Cc1ncsc1-c1ccc([C@H](C)NC(=O)[C@@H]2C[C@@H](O)CN2C(=O)[C@@H](NC(=O)[C@@H]2CC[C@@H]2C(=O)N2CCC(c3cc(Nc4cc(C#N)ccn4)nc(N4CCC(F)(F)C4)c3)CC2)C(C)(C)C)cc1]

TABLE 3-continued
53
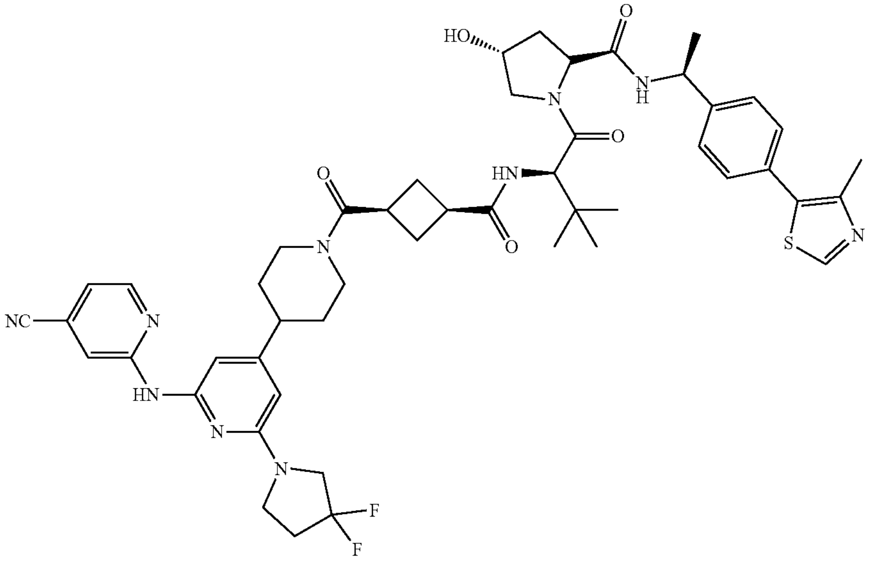
54
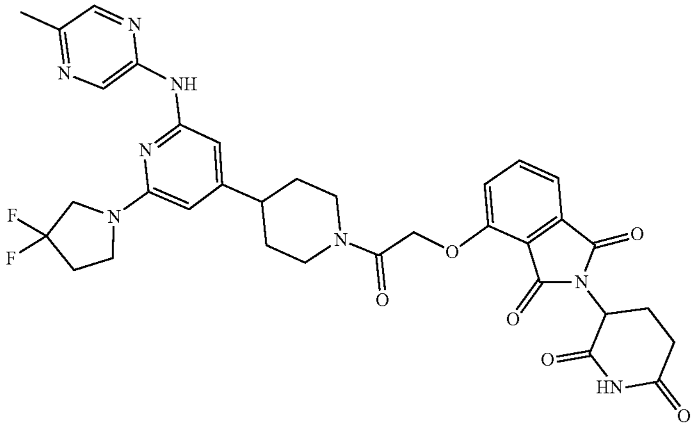 [SMILES: Cc1cnc(Nc2cc(C3CCN(C(=O)COc4cccc5c4C(=O)N(C4CCC(=O)NC4=O)C5=O)CC3)cc(N3CCC(F)(F)C3)n2)cn1]
55
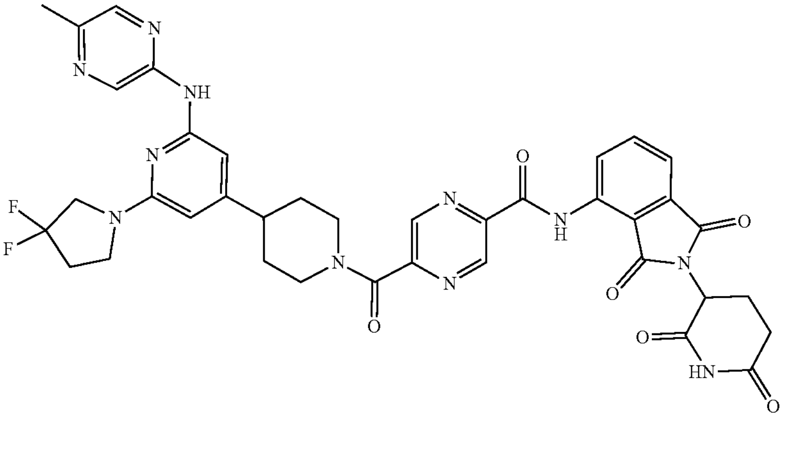 [SMILES: Cc1cnc(Nc2cc(C3CCN(C(=O)c4cnc(C(=O)Nc5cccc6c5C(=O)N(C5CCC(=O)NC5=O)C6=O)cn4)CC3)cc(N3CCC(F)(F)C3)n2)cn1]

TABLE 3-continued
56
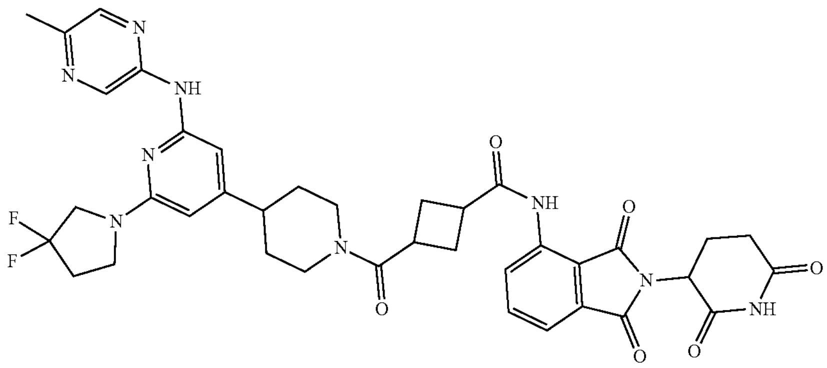 [SMILES: Cc1cnc(Nc2cc(C3CCN(C(=O)C4CC(C(=O)Nc5cccc6c5C(=O)N(C5CCC(=O)NC5=O)C6=O)C4)CC3)cc(N3CCC(F)(F)C3)n2)cn1]
57
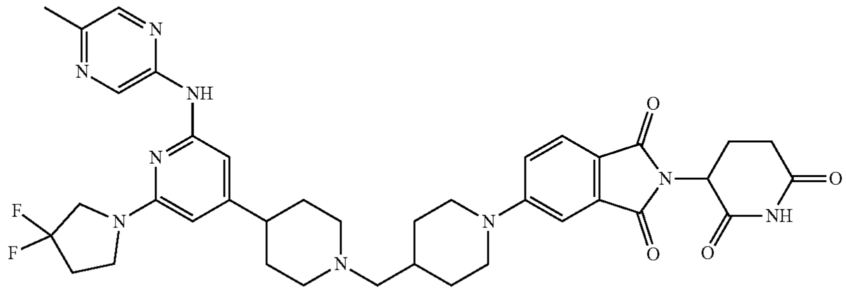 [SMILES: Cc1cnc(Nc2cc(C3CCN(CC4CCN(c5ccc6c(c5)C(=O)N(C5CCC(=O)NC5=O)C6=O)CC4)CC3)cc(N3CCC(F)(F)C3)n2)cn1]
58
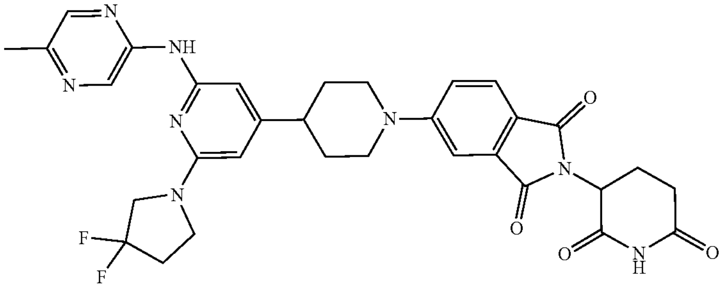 [SMILES: Cc1cnc(Nc2cc(C3CCN(c4ccc5c(c4)C(=O)N(C4CCC(=O)NC4=O)C5=O)CC3)cc(N3CCC(F)(F)C3)n2)cn1]
59
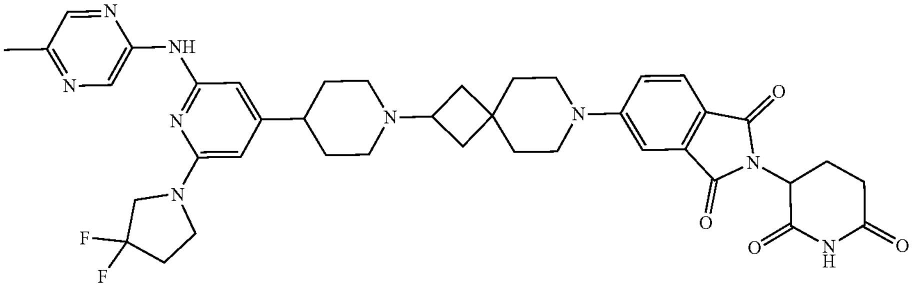 [SMILES: Cc1cnc(Nc2cc(C3CCN(C4CC5(CCN(c6ccc7c(c6)C(=O)N(C6CCC(=O)NC6=O)C7=O)CC5)C4)CC3)cc(N3CCC(F)(F)C3)n2)cn1]
60
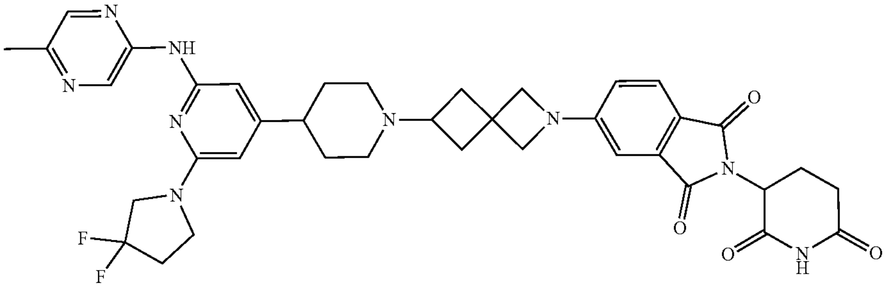 [SMILES: Cc1cnc(Nc2cc(C3CCN(C4CC5(C4)CN(c4ccc6c(c4)C(=O)N(C4CCC(=O)NC4=O)C6=O)C5)CC3)cc(N3CCC(F)(F)C3)n2)cn1]

TABLE 3-continued

61 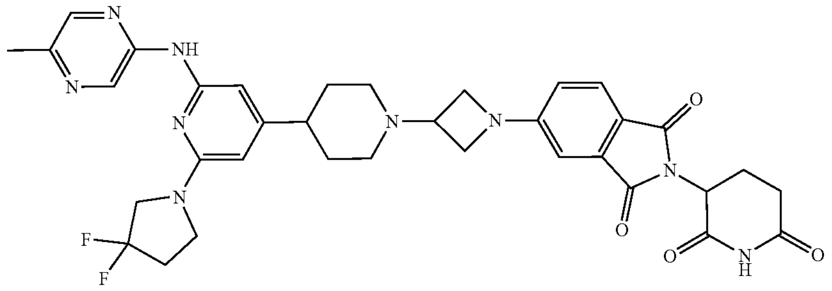 [SMILES: Cc1cnc(Nc2cc(C3CCN(C4CN(c5ccc6c(c5)C(=O)N(C5CCC(=O)NC5=O)C6=O)C4)CC3)cc(N3CCC(F)(F)C3)n2)cn1]

III. Pharmaceutical Compositions

The disclosure also encompasses pharmaceutical compositions comprising one or more of the disclosed LZK-targeting degraders. A pharmaceutical composition comprises a compound as disclosed herein and a pharmaceutically acceptable excipient.

The compounds described herein can be used to prepare therapeutic pharmaceutical compositions. The compounds may be added to the compositions in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and b-glycerophosphate. Suitable inorganic salts may also be formed, including hydrochloride, halide, sulfate, nitrate, bicarbonate, and carbonate salts.

Pharmaceutically acceptable salts may be obtained using procedures known to persons of ordinary skill in the art, for example by reacting a sufficiently basic compound, such as an amine, with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human or veterinary patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 2% to about 60% of the weight of a given unit dosage form. The amount of active compound in such therapeutically useful compositions is such that an effective dosage level can be obtained.

The tablets, troches, pills, capsules, and the like may also contain one or more of the following excipients: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, methods of preparation can include vacuum drying and freeze drying techniques, which yield a powder of the active ingredient plus any additional desired ingredient present in the previously sterile-filtered solutions.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

IV. Methods of Use

Embodiments of the disclosed LZK-targeting degraders target and inhibit LZK activity. In some embodiments, the LZK-targeting degrader inhibit LZK activity by degrading LZK molecules. The LZK-targeting targeted degrader may be catalytic. In some embodiments, a single molecule of a disclosed LZK-targeting degrader may sequentially bind to and degrade a plurality of LZK molecules.

In some embodiments, a method of inhibiting LZK activity includes contacting a cell expressing LZK with an effective amount of a compound as disclosed herein, thereby inhibiting LZK activity. Contacting may be performed in vivo, in vitro, or ex vivo. In some embodiments, inhibiting the LZK activity further comprises degrading LZK. In any of the foregoing or following embodiments, inhibiting LZK activity may further inhibit cell cycle progression, reduce c-MYC expression, reduce GOF mutant p53 expression, inhibit c-Jun N-terminal kinase (JNK) pathway signaling, inhibit PI3K/AKT pathway signaling, inhibit cyclin dependent kinase 2 (CDK2) activity, or any combination thereof. In some embodiments, the inhibition or reduction is at least 10%, at least 25%, at least 50%, or at least 75% compared to the cell cycle progression, c-MYC expression, GOF-p53 expression, JNK pathway signaling, PI3K/AKT pathway signaling, or CDK2 activity in the absence of the LZK-targeting degrader. In any of the foregoing or following embodiments, the cell may be characterized by amplification of chromosome 3q, overexpression of mitogen-activated protein kinase kinase kinase 13 (MAP3K13), or both. In any of the foregoing or following embodiments, the cell may be a cancer cell. In some embodiments, the cell is a head and neck squamous cell carcinoma (HNSCC) cell, a lung squamous cell carcinoma (LSCC) cell, a hepatocellular carcinoma cell, an ovarian cancer cell, a small cell lung cancer cell, a neuroendocrine prostate cancer cell, or an esophageal cancer cell (e.g., esophageal adenocarcinoma). In certain embodiments, the cell is an HNSCC or LSCC cell.

In any of the foregoing embodiments, contacting the cell with the compound may comprise administering a therapeutically effective amount of the compound, or an amount of a pharmaceutical composition comprising the therapeutically effective amount of the compound, to a subject. The subject may be identified as a subject that may benefit from LZK inhibition. In some embodiments, the subject has a disease or condition characterized at least in part by LZK overexpression. In certain embodiments, the disease or condition is cancer. In some examples, the cancer is HNSCC, LSCC, hepatocellular carcinoma, ovarian cancer, small cell lung cancer, neuroendocrine prostate cancer, or esophageal cancer cell (e.g., esophageal adenocarcinoma). In certain embodiments, the cancer is HNSCC or LSCC. In any of the foregoing embodiments, administering the therapeutically effective amount of the compound, or the amount of the pharmaceutical composition, may decrease viability of the cancer cells, inhibit tumor growth, or a combination thereof. In some embodiments, the viability is decreased or the tumor growth is inhibited by at least 10%, at least 25%, at least 50%, or at least 75% compared to viability or tumor growth in the absence of the LZK targeted degrader.

The compound or pharmaceutical composition may be administered to the subject through any suitable route. In some embodiments, the compound or pharmaceutical composition is administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). In some embodiments, the compound or pharmaceutical composition is administered to the subject by injection. The therapeutically effective dosages of the agents can be provided as repeated doses within a prolonged prophylaxis or treatment regimen that will yield clinically significant results to alleviate one or more symptoms or detectable conditions associated with a targeted condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to elicit a desired immune response or alleviate one or more symptoms of a targeted disease). In alternative embodiments, an effective amount or effective dose of the agents may simply inhibit or enhance one or more selected biological activities correlated with a disease or condition, as set forth herein, for either therapeutic or diagnostic purposes.

The actual dosages of the agents will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the agent for eliciting the desired activity or biological response in the subject. Dosage regimens can be adjusted to provide an optimum prophylactic or therapeutic response. A therapeutically effective amount is also one in which any toxic or detrimental side effects of the agent is outweighed in clinical terms by therapeutically beneficial effects. A non-limiting range for a therapeutically effective amount of a compound according to any one of formulas I-IV within the methods and formulations of the disclosure is 0.001 mg/kg body weight to 100 mg/kg body weight, such as 0.01 mg/kg body weight to 20 mg/kg body weight, 0.01 mg/kg body weight to 10 mg/kg body weight 0.05 mg/kg to 5 mg/kg body weight, or 0.1 mg/kg to 2 mg/kg body weight. Dosage can be varied by the attending clinician to maintain a desired concentration at a target site (for example, systemic circulation). Higher or lower concentrations can be selected based on the mode of delivery, for example, trans-epidermal or oral delivery versus intravenous or subcutaneous delivery. Dosage can also be adjusted based on the release rate of the administered formulation, for example, of sustained release oral versus injected particulate or transdermal delivery formulations, and so forth.

In any of the foregoing or following embodiments, the therapeutically effective amount may be administered at intervals for a period of time effective to provide a therapeutic effect, e.g., decreased cancer cell viability and/or tumor growth inhibition. In some embodiments, the intervals are once daily. In other embodiments, the therapeutically effective amount may be divided into two or more doses administered at intervals in a 24-hour period. In some embodiments, the effective period of time is from one day to several months, such as from one day to 12 months, three days to six months, seven days to three months, 7-30 days, or 7-14 days. In certain embodiments, the effective period of time may be even longer than 12 months, such as a period of years.

V. Representative Embodiments

Certain representative embodiments are exemplified in the following numbered clauses.

1. A compound, or a stereoisomer, tautomer, or pharmaceutically acceptable salt thereof, having a general formula:

Q-L-Z where Q is a leucine zipper kinase (LZK) binding moiety; Z is an E3-ligase binding moiety; and L is a linker having a general formula

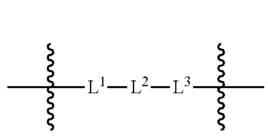

, wherein $L^1$ is —C(O)—, —$S(O)_2$—, —$CH_2$—, —$C(R^b)(R^c)$—, —$(CH_2)_nC(O)$—, —C(O)—$(CH_2)_n$—, —$N(R^c)$—, —$N(R^c)$—$(C(H)(R^a))_s$—C(O)—, or —C(O)—$(C(H)(R^a))_s$—$N(R^c)$—, and $L^1$ binds to Q, or $L^1$ is absent and $L^2$ binds to Q; $L^3$ is —C(O)—, —$S(O)_2$—, —$CH_2$—, —$C(R^b)(R^c)$—, —C(O)—$(CH_2)_n$—, —$(CH_2)_n$—C(O)—, —$N(R^c)$—, —$N(R^c)$—$(C(H)(R^a))_s$—C(O)—, or —C(O)—$(C(H)(R^a))_s$—$N(R^c)$—, and -$L^3$ binds to Z, or $L^3$ is absent and $L^2$ binds to Z; $L^2$ is —$(R^d)_p$—, —$N(R^b)$—$(R^d)_p$—, —$(R^d)_p$—$N(R^b)$—, —$N(R^b)$—$(R^d)_p$—$N(R^b)$—, —$(N(R^b)$—$(C(H)(R^a))_s$—$C(O))_m$—$N(R^b)$—$C(H)(R^a)$—, or —$C(H)(R^a)$—$N(R^b)$—$(C(O)$—$(C(H)(R^a))_s$—$N(R^b))_m$—; each $R^a$ independently is an amino acid side chain; each $R^b$ independently is H or $R^c$; each $R^c$ independently is substituted or unsubstituted aliphatic, substituted or unsubstituted heteroaliphatic, substituted or unsubstituted aryl, substituted or unsubstituted heteroaryl, substituted or unsubstituted arylalkyl, or substituted or unsubstituted alkylaryl; each $R^d$ independently is substituted or unsubstituted aliphatic, substituted or unsubstituted heteroaliphatic, substituted or unsubstituted aryl, substituted or unsubstituted heteroaryl, —$(CH_2$—$CH_2$—$O)_r$—, —$(C(H)(R^a))_s$—C(O)—, —C(O)$N(R^b)$—, or —$N(R^b)C(O)$—; each $R^c$ independently is substituted or unsubstituted $C_1$-$C_3$ alkyl or H; m is an integer from 0-11; n is an integer from 1-10; p is an integer from 1-5; r is an integer from 2-20; and s is an integer from 1-20, wherein (i) $L^2$ is not solely —C(O)$N(R^b)$— or —$N(R^b)C(O)$—, and (ii) if $L^2$ terminates in —$C(H)(R^a)$—C(O)— or —$N(R^b)C(O)$—, then $L^3$ is not —C(O)— or —$S(O)_2$—.

2. The compound of clause 1, wherein: each $R^c$ independently is substituted or unsubstituted alkyl, substituted or unsubstituted heteroalkyl, substituted or unsubstituted aryl, substituted or unsubstituted heteroaryl, substituted or unsubstituted arylalkyl, or substituted or unsubstituted alkylaryl; and each $R^d$ independently is substituted or unsubstituted alkyl, substituted or unsubstituted alkyl, substituted or unsubstituted aryl, substituted or unsubstituted heteroaryl, —$(CH_2$—$CH_2$—$O)_r$—, —$(C(H)(R^a))_s$—C(O)—, or —C(O)$N(R^b)$—.

3. The compound of clause 1 or clause 2, wherein: (i) $N(R^b)$ is NH; or (ii) $R^c$ is unsubstituted $C_1$-$C_5$ alkyl, unsubstituted heteroalkyl comprising 1-4 carbon atoms and 1-3 heteroatoms selected from O, N, and S, unsubstituted phenyl, unsubstituted heteroaryl comprising 1-3 heteroatoms selected from O, N, and S, unsubstituted arylalkyl comprising from 1-3 carbon atoms in the alkyl portion, or unsubstituted alkylaryl comprising from 1-3 carbon atoms in the alkyl portion; or (iii) each $R^d$ independently is alkyl, alkylamino, aminoalkyl, amino-alkyl-amino, piperazinyl, piperidinyl, phenyl, —$(CH_2$—$CH_2$—$O)_r$—, or —C(O)N(H)—; or (iv) any combination of (i), (ii), and (iii).

4. The compound of clause 1, wherein $L^2$ comprises: one or more of

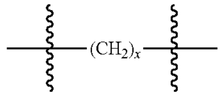

,

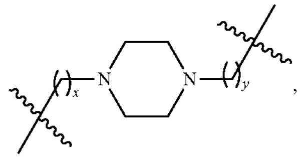

,

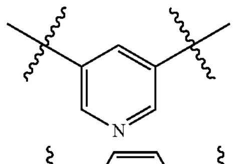

,

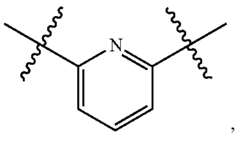

,

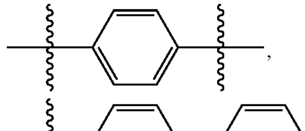

,

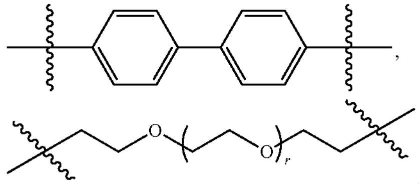

,

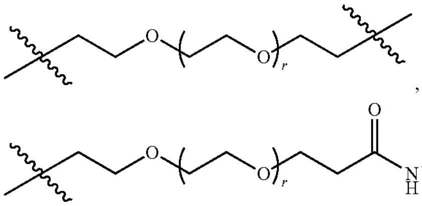

,

,

-continued
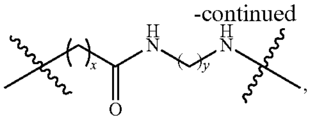,
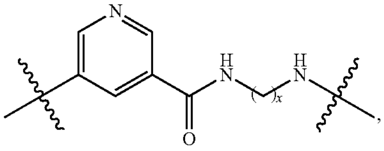, and
-continued
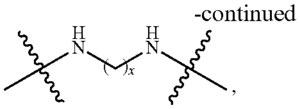,
where x and y independently are integers from 1-20, optionally in combination with one or more of —C(O)N(H)— and —N(H)C(O)—.
5. The compound of clause 1, wherein L is:
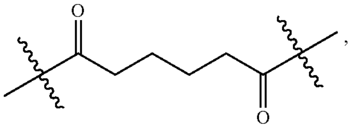, 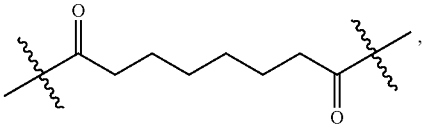,
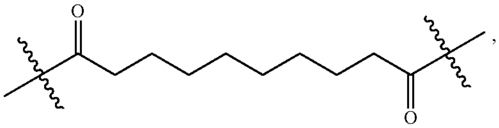, 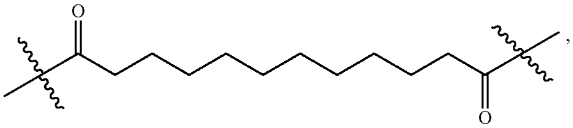,
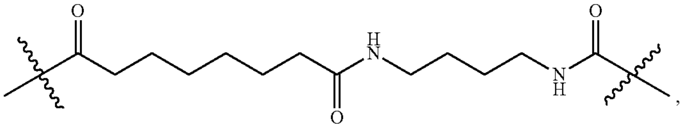, 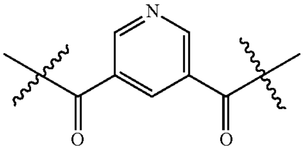,
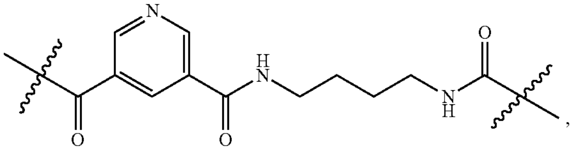, 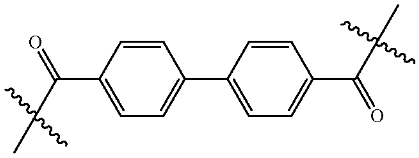,
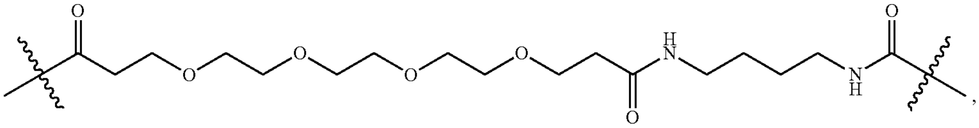,
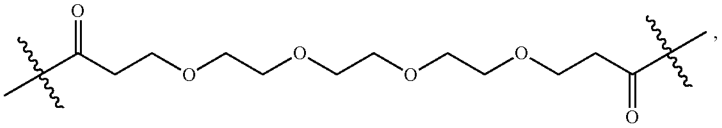,
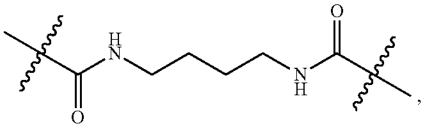, 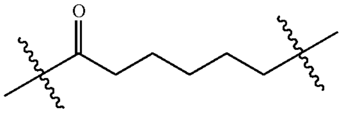, or
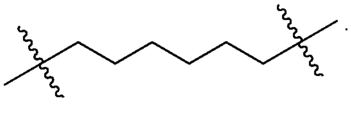.

6. The compound of any one of clauses 1-5, wherein Z is:
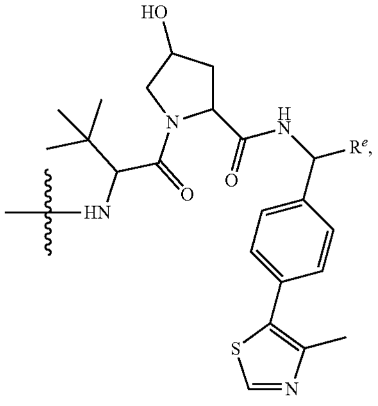
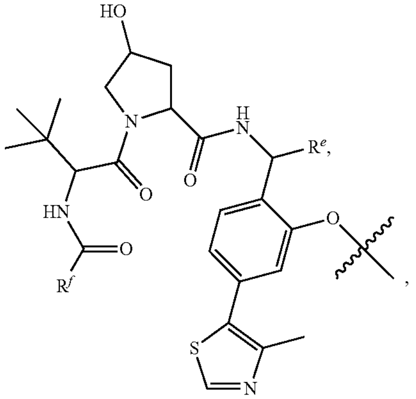
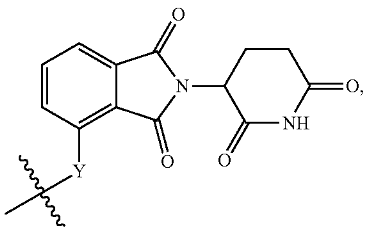
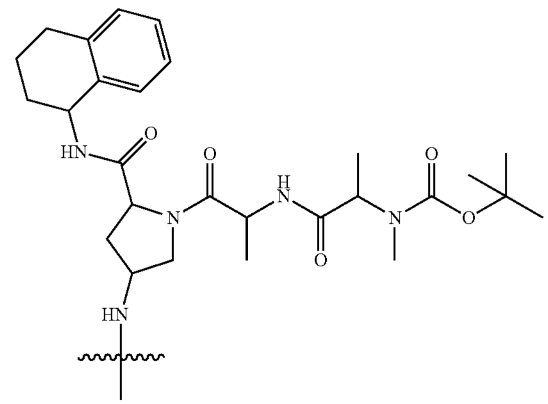
,
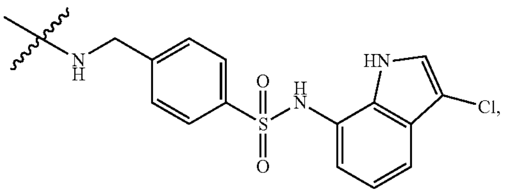
or
-continued
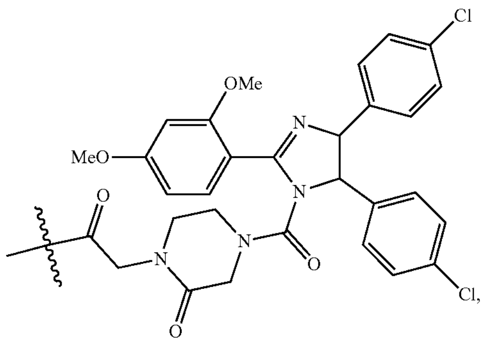
where each $R^e$ independently is substituted or unsubstituted $C_1$-$C_3$ alkyl or H; $R^f$ is substituted or unsubstituted $C_1$-$C_3$ alkyl or —$N(R^e)_2$; and Y is O or $N(R^e)$.
7. The compound of clause 6, wherein Z is:
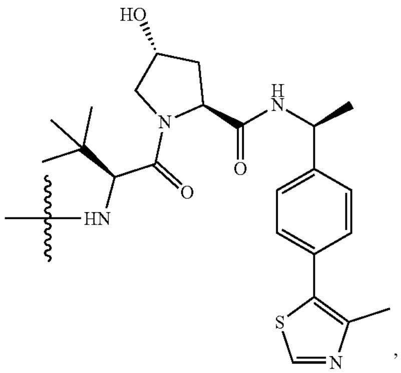
,
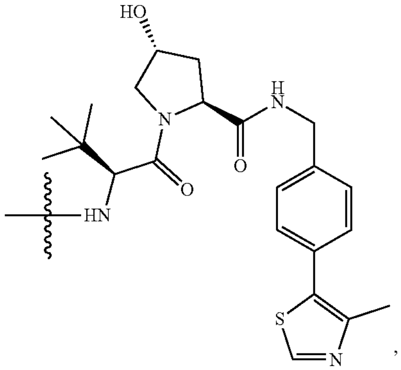
,
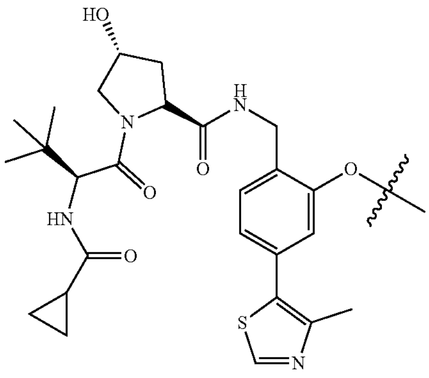
, -continued

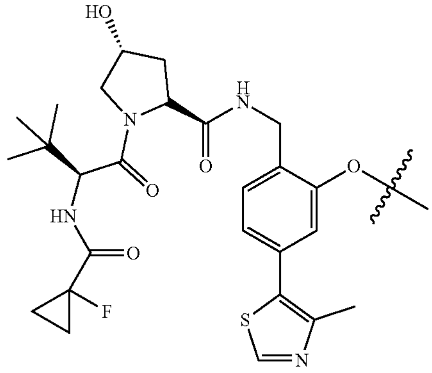

,

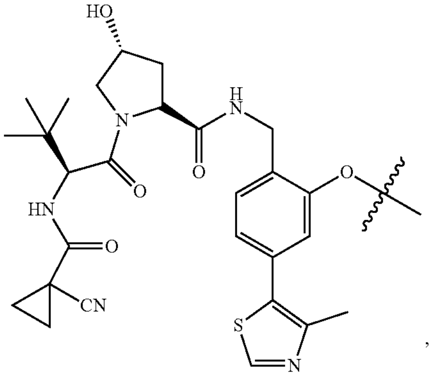

,

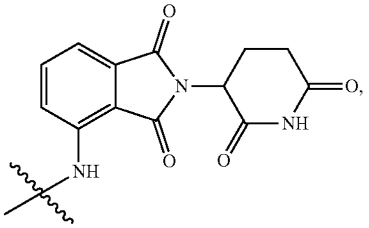

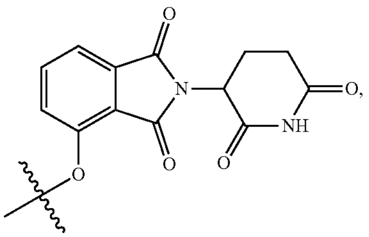

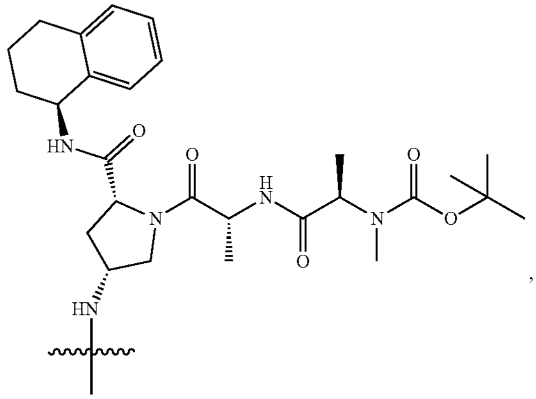

,

-continued

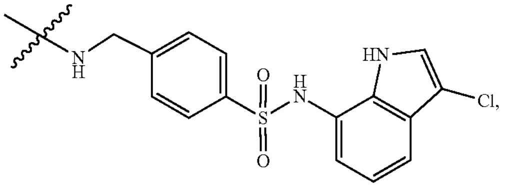

or

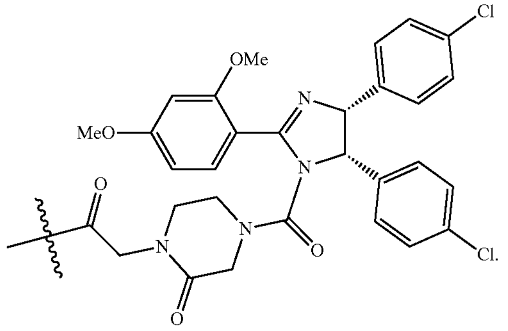

8. The compound of any one of clauses 1-7, wherein Q is:

(Q1)

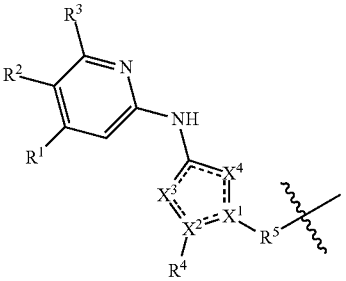

or (Q2)

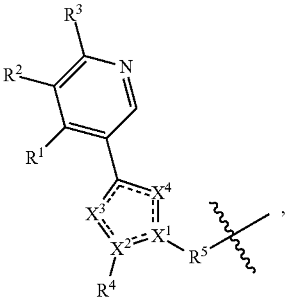

, where each bond represented by - - - - is a single or double bond as needed to satisfy valence requirements; —$X^1(R^5)$— is —$C(R^5)$—, —$C(R^5)$—C(H)—, —C(H)—$C(R^5)$—, —$C(R^5)$—N—, —N—$C(R^5)$—, or —$N(R^5)$—; $X^2$ is N or C; $X^3$ is N or C(H), wherein one or two of $X^1$—$X^3$ comprises N; $X^4$ is C(H) or S; $R^1$ is H, cyano, perhaloalkyl, or alkyl; $R^2$ is H, perhaloalkyl, perhaloalkoxy, alkyl, alkoxy, or cyano; $R^3$ is H, amino, alkylamino, or aminoalkyl, wherein at least one of $R^1$-$R^3$ is other than H; $R^4$ is substituted or unsubstituted aliphatic, substituted or unsubstituted azaalkyl, or aryl; and $R^5$ is substituted or unsubstituted aliphatic, substituted or unsubstituted heteroaliphatic, or substituted or unsubstituted alkylamino.

9. The compound of clause 8, wherein

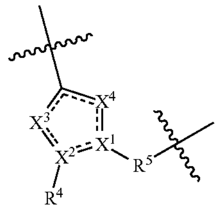

is:

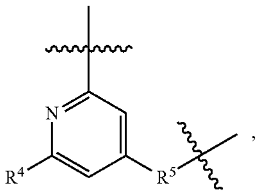

,

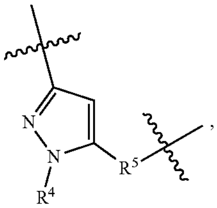

,

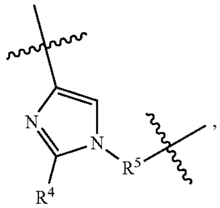

, or

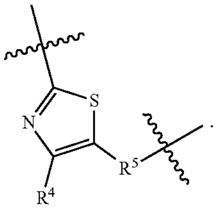

.

10. The compound of clause 8 or clause 9, wherein: (i) $R^4$ is 3,3-difluoro-1-pyrrolidinyl, isopropyl, or —C(H)(OH)—$C(CH_3)_2$; or (ii) $R^5$ is

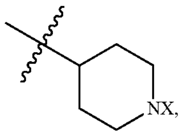

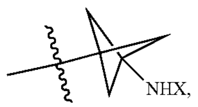

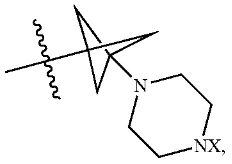

or

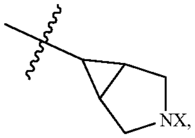

where X is a bond or alkyl group binding Q to L; or (iii) both (i) and (ii).

11. The compound of clause 10, wherein Q is:

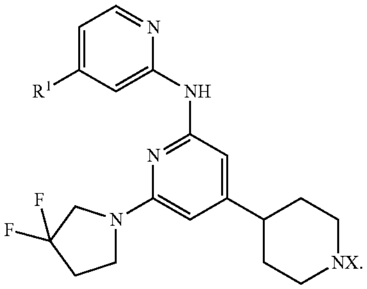

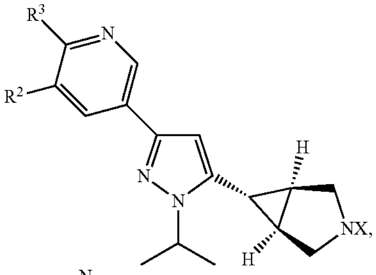

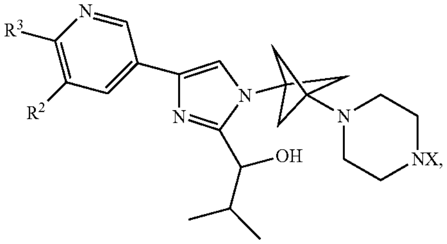

or

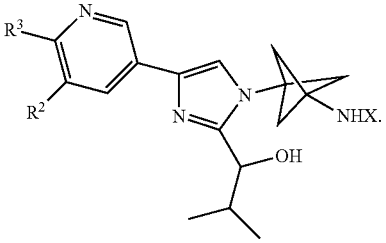

12. The compound of clause 11, wherein: $R^1$ is —$CF_3$ or —CN; $R^2$ is —$OCF_3$, —$CF_3$, or CN; $R^3$ is —$NH_2$; and X is a bond.

13. The compound of clause 1, wherein the compound is:

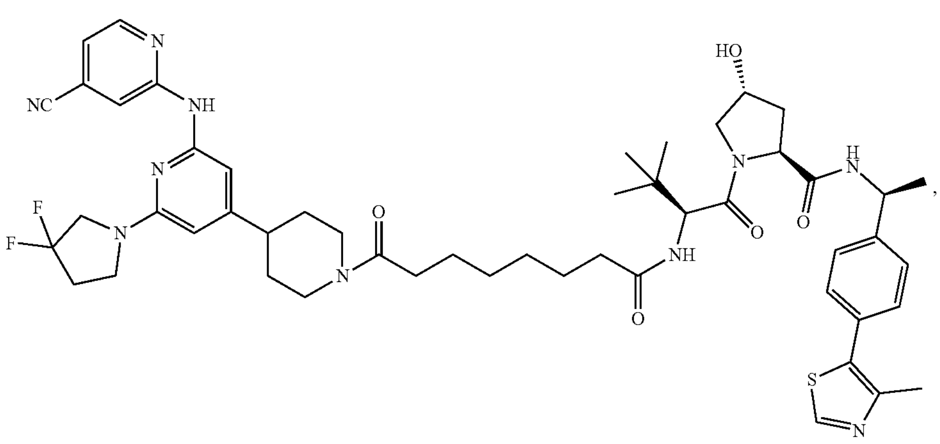

,

-continued
4
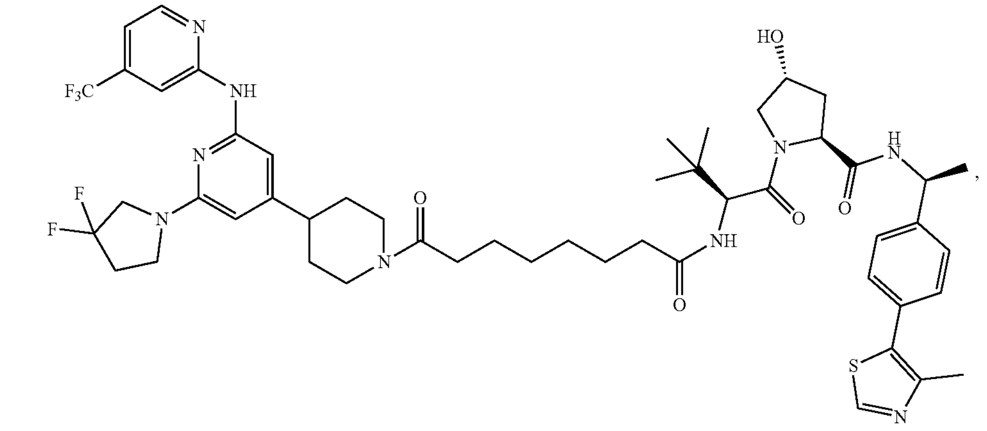
5
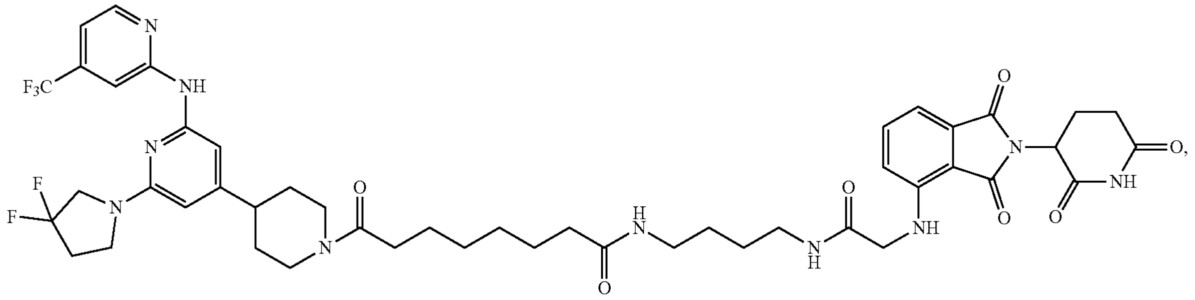
6
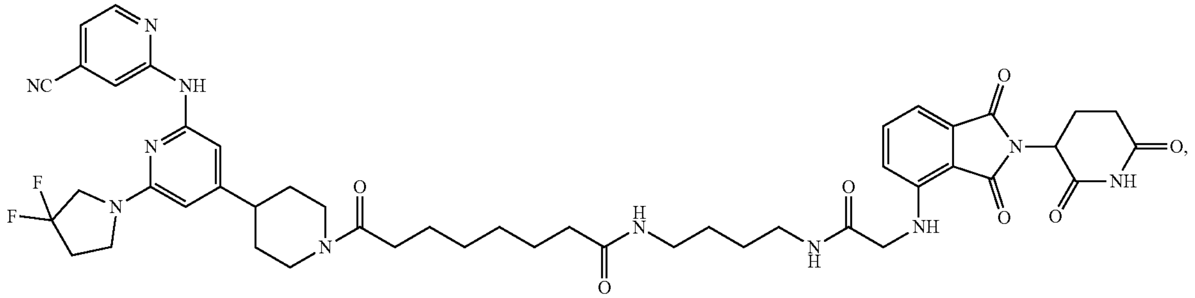
7
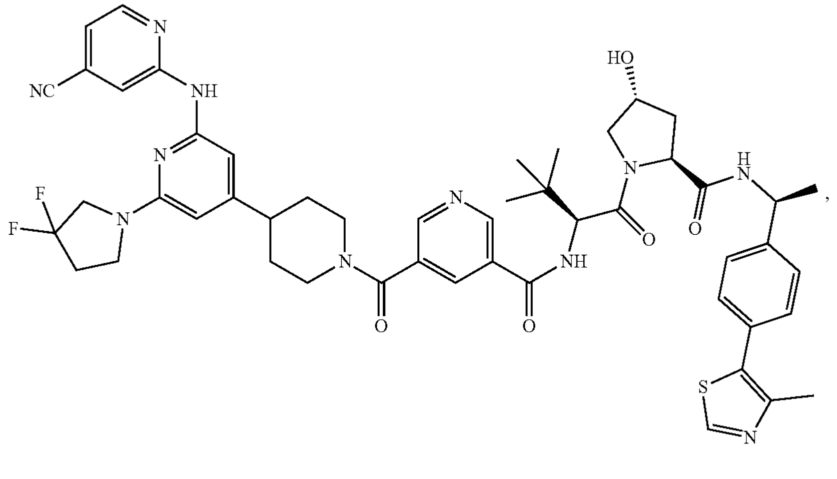

-continued
8
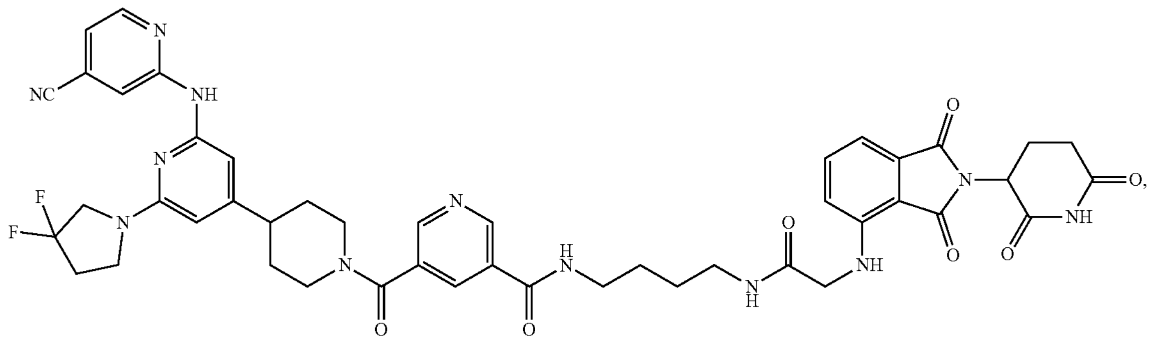
9
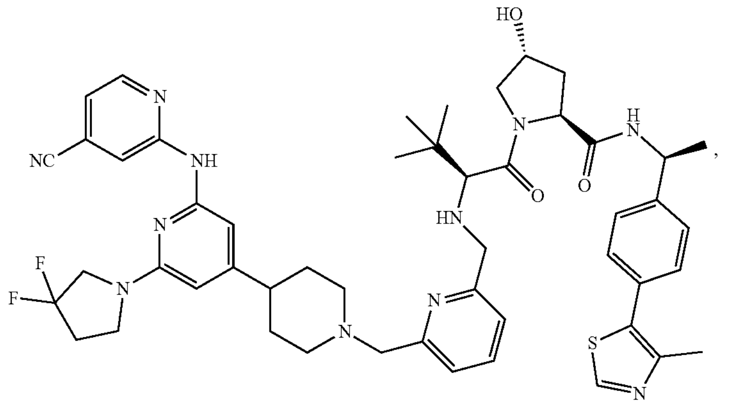
12
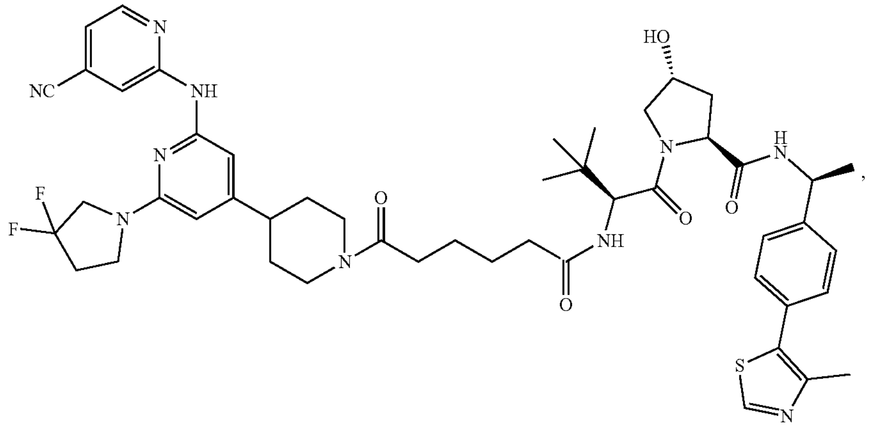
10
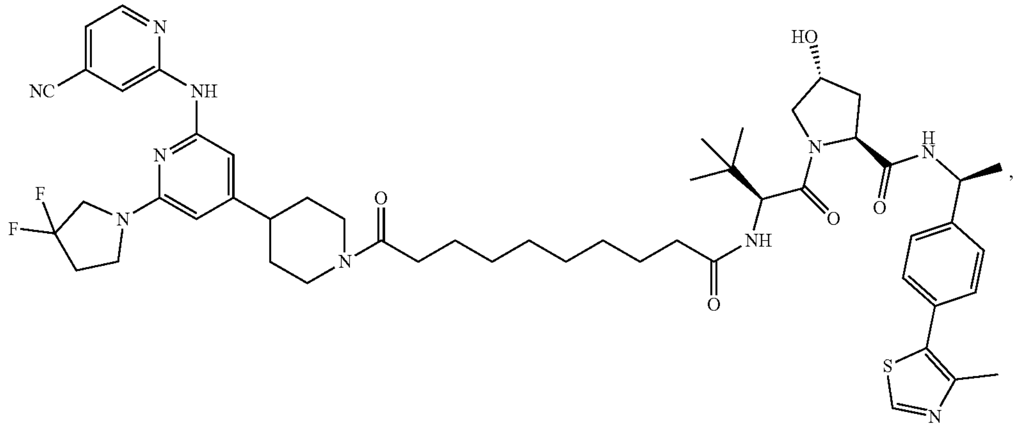

-continued
11
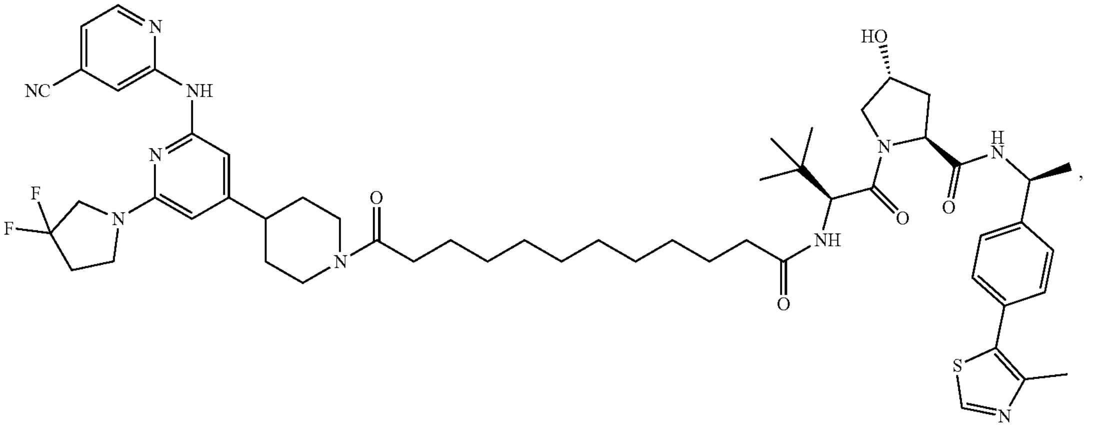
39
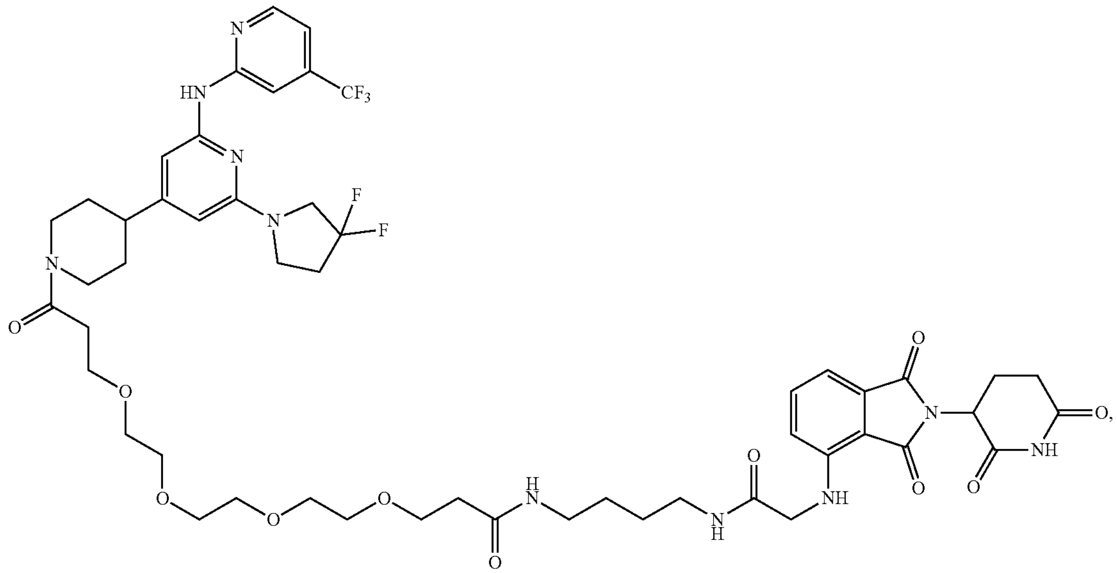
40
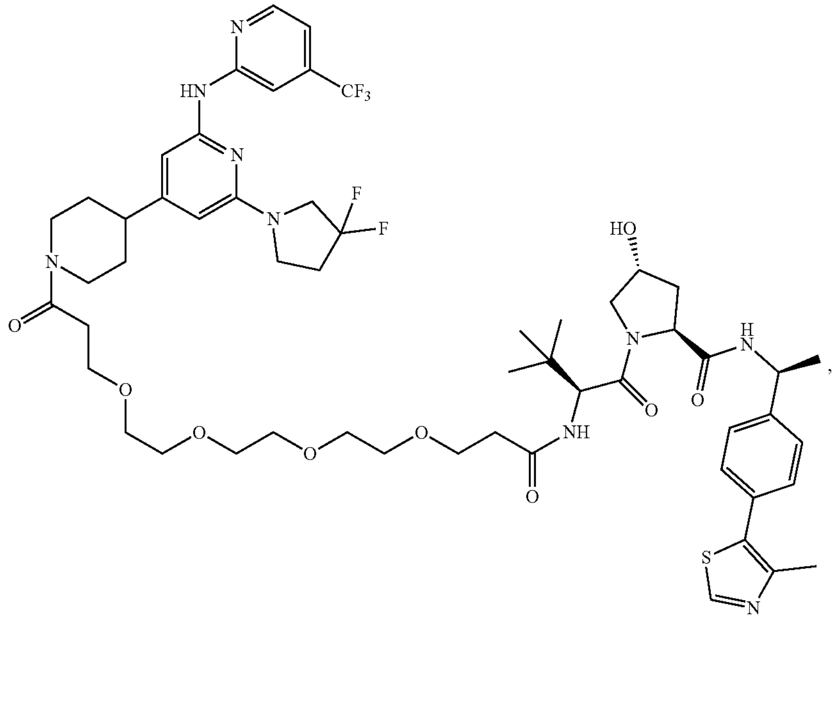

-continued
41
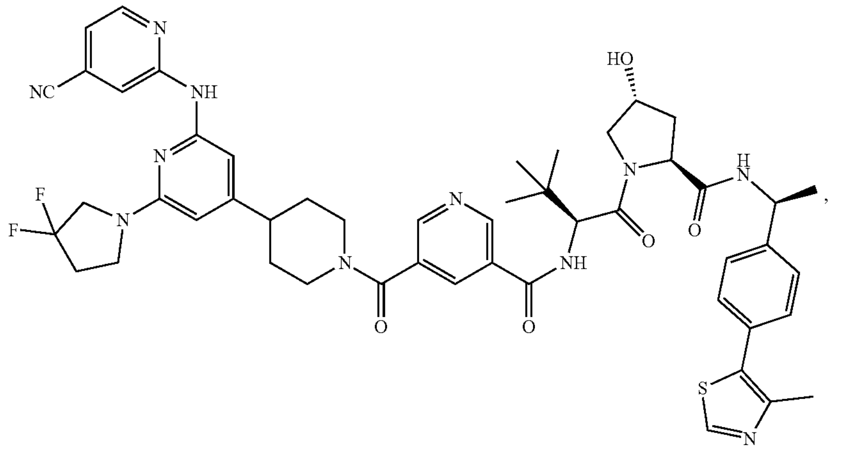
8
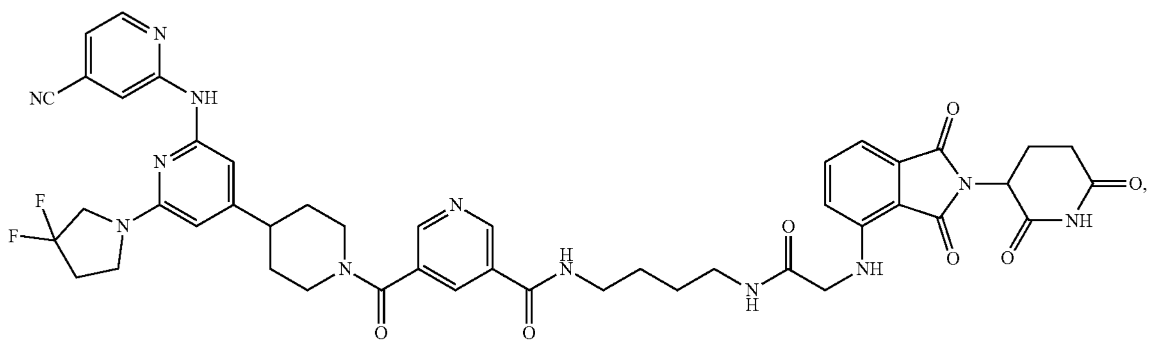
42
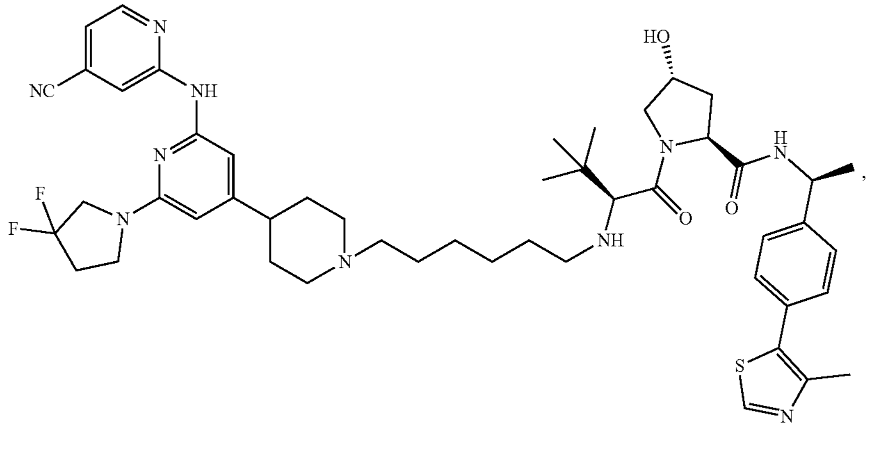

-continued

43

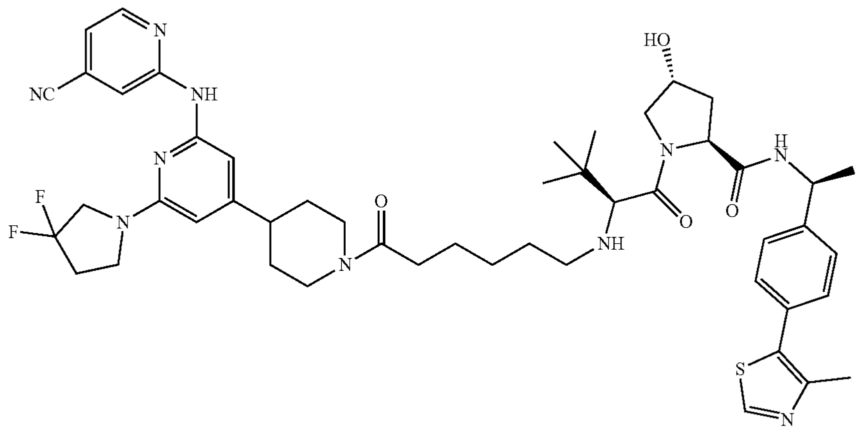

, or

44

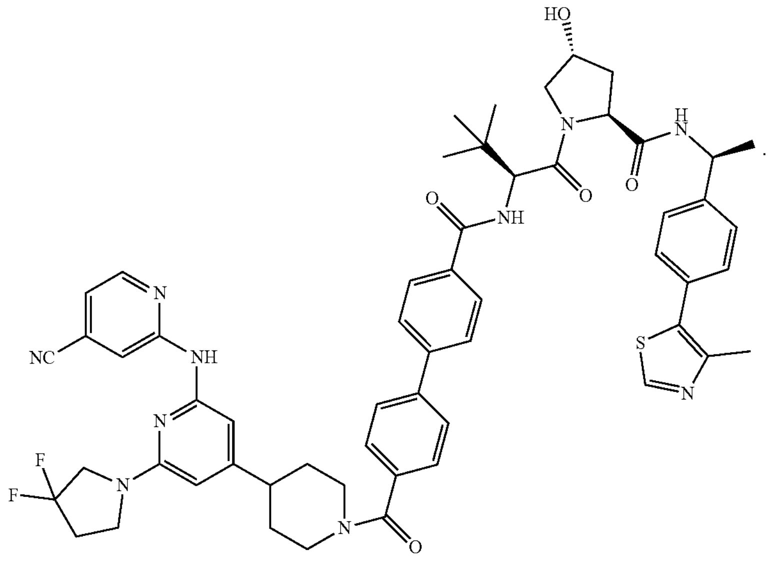

14. A pharmaceutical composition comprising a compound according to any one of clauses 1-13 and at least one pharmaceutically acceptable carrier.

15. A method of inhibiting leucine zipper-bearing kinase (LZK) activity, comprising:

contacting a cell expressing LZK with an effective amount of a compound according to any one of clauses 1-13, thereby inhibiting LZK activity.

16. The method of clause 15, wherein inhibiting LZK activity comprises degrading LZK.

17. The method of clause 15 or clause 16, wherein inhibiting LZK activity inhibits cell cycle progression, reduces c-MYC expression, reduces gain-of-function (GOF) mutant p53 expression, inhibits c-Jun N-terminal kinase (JNK) pathway signaling, inhibits PI3K/AKT pathway signaling, inhibits cyclin dependent kinase 2 (CDK2) activity, or any combination thereof.

18. The method of any one of clauses 15-17, wherein the cell is characterized by amplification of chromosome 3q, overexpression of mitogen-activated protein kinase kinase kinase 13 (MAP3K13), or both.

19. The method of any one of clauses 15-18, wherein the cell is a head and neck squamous cell carcinoma (HNSCC) cell, a lung squamous cell carcinoma (LSCC) cell, a hepatocellular carcinoma cell, an ovarian cancer cell, a small cell lung cancer cell, a neuroendocrine prostate cancer cell, or an esophageal cancer cell.

20. The method of any one of clauses 15-19, wherein contacting the cell with the compound comprises administering a therapeutically effective amount of the compound, or an amount of a pharmaceutical composition comprising the therapeutically effective amount of the compound, to a subject.

21. The method of clause 20, wherein the subject has a disease or condition characterized at least in part by LZK overexpression.

22. The method of clause 21, wherein the disease or condition is cancer.

23. The method of clause 22, wherein the cancer is HNSCC, LSCC, hepatocellular carcinoma, ovarian cancer, small cell lung cancer, neuroendocrine prostate cancer, or esophageal cancer.

24. The method of clause 23, wherein the cancer is HNSCC or LSCC.

25. The method of any one of clauses 22-24, wherein administering the therapeutically effective amount of the compound, or the amount of the pharmaceutical composition, decreases viability of the cancer cells, inhibits tumor growth, or a combination thereof.

26. The method of any one of clauses 20-25, wherein administering is performed parenterally, orally, or topically.

VI. Examples

Methods

Plasmids and Transfections

LZK cDNA was prepared from RNA extracted from 293T cells, attB flanking regions were added by PCR, and the BP Clonase reaction was used to insert LZK into pDONR221. From here, the Invitrogen Gateway system was used for cloning into destination vectors. FLAG-tagged (pReceiver-M12, GeneCopoeia) destination vector was converted into Gateway destination vector for use in transient overexpression assays. The pLenti6.3/TO/V5-DEST vector was used to generate stable overexpression. The drug-resistant construct for LZK was a Q240S mutation that was introduced using a Site-Directed Mutagenesis Kit (Stratagene). The oligonucleotides are listed below in Table 4. 293T cells were transiently transfected using Lipofectamine 2000 (Invitrogen), according to the manufacturer's protocol, with OptiMEM (Gibco). A pcDNA3.1(+) vector (Invitrogen) was used as an empty vector control where required. The CDK2 sensor vector CSII-pEF1a-DHB(aa994-1087)-mVenus and the nuclear marker vector CSII-pEF1a-H2B-mTurquoise were described previously (Spencer et al., *Cell* 2013, 155:369-383).

TABLE 4

| SEQ ID NO | Primer | Sequence |
|---|---|---|
| 1 | LZK Q240S Forward (c718t_a719c_) | 5'-CTGTGCCCATGGATC ACTCTACGAGG-3' |
| 2 | LZK Q240S Reverse (c718t_a719c_) | 5'-CCTCGTAGAGTGATC CATGGGCACAG-3' |
| 3 | LZK K195M Forward (a584t) | 5'-GAGGTGGCCATCAAG AAAGTGAGAG-3' |
| 4 | LZK K195M Reverse (a584t) | 5'-CTCTCACTTTCTTGA TGGCCACCTC-3' |
| 5 | XbaI to start of LZK Forward | 5'-TAATCTAGAATGGCCA ACTTTCAGGAGCACCT-3' |
| 6 | NotI to end of LZK Reverse | 5'-TTAGCGGCCGCTTACCA GGTAGCAGAGCTGTAGT-3' |
| 7 | T7 promoter | 5'-TAATACGACTCACTAT AGGG-3' |
| 8 | BGH reverse | 5'-TAGAAGGCACAGTCGA GG-3' |
| 9 | XbaI to LZK kinase domainForward | 5'-TAATCTAGAATGCTGG GTAGTGGAGCCCAAGG-3' |
| 10 | NotI to LZK end kinase domain Reverse | 5'-TTAGCGGCCGCTTAGGC AATGTCTAAATGCATGA-3' |
| 11 | NotI to LZK end zipper domains Reverse | 5'-TTAGCGGCCGCTTACACTGC TTGCTCACGCTTAA-3' |
| 12 | NotI to LZK end stop codon Reverse | 5'-TTAGCGGCCGCTTACCAGGT AGCAGAGCTGTAGT-3' |

Cell Culture

CAL33 (German Collection of Microorganisms and Cell Cultures [DSMZ], obtained October 2012) and 293T (American Type Culture Collection [ATCC], July 2012) cells were maintained in DMEM (Sigma-Aldrich) supplemented with 1000 tetracycline-tested fetal bovine serum (FBS) (Atlanta Biologicals), 1% penicillin-streptomycin (Gibco), and 2 mM GlutaMAX (Gibco). BICR56 cells (Public Health England, November 2012 and April 2014) were grown in DMEM with 10% tetracycline-tested FBS, 1% penicillin-streptomycin, 0.4 μg/mL hydrocortisone (Sigma-Aldrich), and 2 mM GlutaMAX. MSK921 (Memorial Sloan Kettering Cancer Center, July 2014), BEAS-2B (ATCC, October 2012), LK2 (Japanese Collection of Research Bioresources [JCRB] Cell Bank, February 2015), and NCI-H520 (ATCC) cells were maintained in RPMI 1640 (Quality Biological) with 10% tetracycline-tested FBS, 2 mM GlutaMAX, and 1% penicillin-streptomycin. Detroit 562 cells (ATCC, November 2014) were maintained in EMEM (Sigma-Aldrich) with 10% tetracycline-tested FBS, 2 mM GlutaMAX, and 1% penicillin-streptomycin. 293FT cells (Invitrogen, November 2011) were maintained in DMEM with 10% tetracycline-tested FBS, 4 mM GlutaMAX, 1 mM sodium pyruvate (Gibco), and 0.1 mM NEAA (Gibco). SCC-15 cells (ATCC, 2019) were maintained in DMEM (Gibco) with bicarbonate buffer (3.7 g/L), 10% FBS, and 1% penicillin-streptomycin. All cells were incubated at 37° C. and 5% $CO_2$. Cell lines in regular use were subject to authentication by yearly Short Tandem Repeat (STR) profiling (conducted by multiplex PCR assay by an Applied Biosystems AmpFLSTR system). STR profiles were compared to ATCC and DSMZ databases. However, no profile was available for MSK921. The 3q status of all HNSCC and immortalized control cell lines was verified in-house. All cell lines were used in experiments for fewer than 20 passages (10 weeks) after thawing, before a fresh vial was taken from freeze. Cell lines in use were confirmed to be *mycoplasma*-negative using a Visual-PCR *Mycoplasma* Detection Kit (GM Biosciences).

Generation of Doxycycline-Inducible Knockdown Cell Lines

CAL33 and BICR56 inducible knockdown cells were generated by SIRION Biotech. MSK921 was generated in-house using lentiviral particles provided by SIRION (generated by transfection of 293TN cells with expression vectors and lentiviral packaging plasmids). Transduction occurred at MOI 5 with 8 μg/mL polybrene. After 24 hours, medium was replaced with fresh medium containing puromycin (Invitrogen) to select for cells that had been effectively transduced. shRNA sequences were CGGAATGAACCTGTCTCTGAA (sh1; SEQ ID NO: 19) and GATGTAGATTCTTCAGCCATT (sh2; SEQ ID NO: 20). The lentiviral expression plasmid was pCLVi(3G)-MCS-Puro, which expresses a doxycycline-responsive transactivator and the shRNA from the same vector. Expression of the transactivator is constitutive, while shRNA expression depends on a doxycycline-inducible promoter. Binding doxycycline to the transactivator allows it to bind the doxycycline-inducible promoter and promote shRNA expression. Doxycycline (Sigma-Aldrich) was used at 1 μg/mL to induce LZK knockdown.

Generation of Tetracycline-Inducible Expression Cell Lines

The ViraPower HiPerform T-REx Gateway Expression System (Invitrogen) was used to generate cells with tetracycline-inducible expression of LZK. In brief, wild-type (WT) or drug-resistant mutant (Q240S) LZK (cloned into pLenti6.3/TO/V5-DEST vector) and pLenti3.3/TR (for tetracycline repressor expression) were transfected into 293FT cells using Lipofectamine 2000 to generate lentiviral stock. Cell lines were generated by antibiotic selection (blasticidin [Gibco] and geneticin [Gibco]). Doxycycline (Sigma-Aldrich) was used at 1 μg/mL to induce LZK expression.

RNA Preparation

Cells were lysed using Buffer RLT (Qiagen) with 1% v/v 2-mercaptoethanol (Bio-Rad) 48 hours after treatment (tetracycline-induced overexpression or doxycycline-induced knockdown). Genomic DNA was removed and RNA was prepared using an RNeasy kit (Qiagen) according to the manufacturer's protocol. The RNA quantity was determined using a NanoDrop™ One Spectrophotometer (Thermo Scientific).

RT-PCR

RT-PCR was performed using a SuperScript III One-Step RT-PCR kit (Invitrogen). Primers used were as follows: AACTGATTCGAAGGCGCAGA (LZK forward; SEQ ID NO: 13), GGGCGTT_TCCAAGAGAGGA (LZK reverse. SEQ ID NO: 14), GGCACCACACCTTCTACAATG (β-actin forward; SEQ ID NO: 15), GTGGTGGTGAAGCTGTAGCC (β-actin reverse; SEQ ID NO: 16), CCATGGAGAAGGCTGGGG (GAPDH forward; SEQ ID NO: 17), GTCCACCACCCTGTTGCTGTA (GAPDH reverse; SEQ ID NO: 18). The cycling conditions for PCR were as follows: cDNA synthesis and pre-denaturation (one cycle at 55° C. for 30 minutes followed by 94° C. for two minutes), PCR amplification (25 cycles of denaturing at 94° C. for 15 seconds, annealing at 55° C. for 30 seconds, and extension at 68° C. for 60 seconds), and a final extension at 68° C. for five minutes using C1000 TOUCH CYCLER w/48W FS RM (Bio-Rad). PCR products were resolved on 2% agarose gel and visualized with Nancy-520 (Sigma-Aldrich) DNA gel stain under ultraviolet light using ChemiDoc™ MP Imaging System (Bio-Rad).

Inhibitor Treatment

GNE-3511 (#19174) was purchased from Cayman Chemical or from Synnovator (#SYNNAA108230) in large quantities for the mouse studies. MG132 (#S2619) was purchased from Selleck Chemicals. Pevonedistat or MLN4924 (#HY-70062) was purchased from MedChemExpress. All compounds were dissolved in DMSO (Fisher), and DMSO was used as the vehicle control in the cell-based assays.

Protein Lysate Preparation and Immunoblots

Generally, cells were plated in six-well or 35-mm plates for 24 hours, after which doxycycline was added or treatment with specific inhibitor was administered using 50 FBS media for 48 hours. After appropriate treatment time, cells were washed with ice-cold phosphate-buffered saline without Ca and Mg (Quality Biological) and then lysed on ice with RIPA buffer (50 mM NaCl, 1.0% IGEPAL® CA-630, 0.5% sodium deoxycholate, 0.10% SDS, 50 mM Tris, pH 8.0) (Sigma-Aldrich) supplemented with protease inhibitor tablet (Sigma-Aldrich) and phosphatase inhibitor cocktails 2 and 3 (Sigma-Aldrich) followed by centrifugation at 15,000 rpm for 10 minutes at 4° C. Protein concentrations were determined from the cell lysate by using 660 nm Protein Assay Reagent (Pierce). Cell extracts were denatured, subjected to SDS-PAGE, transferred to PVDF membranes (Bio-Rad) and blocked for 2 hours using 5 bovine serum albumin (BSA) in phosphate-buffered saline and 0.10 Tween® 20 (PBS-T). The membranes were incubated with the specific antibodies overnight in 500 BSA/PBST at 4° C. followed by a 1 hour incubation with the appropriate horseradish peroxidase-conjugated secondary antibodies and signal was detected by chemiluminescence (Thermo Fisher). The antibodies are listed in Table 5.

TABLE 5

| Antibody | Source | Identifier |
|---|---|---|
| Rabbit anti-phospho-SAPK/JNK (Thr183/Tyr185) (81E11) | Cell Signaling Technology | Cat# 4668, RRID: AB_823588 |
| Rabbit anti-SAPK/JNK | Cell Signaling Technology | Cat# 9252, RRID: AB_2250373 |
| Rabbit anti-GAPDH (14C10) | Cell Signaling Technology | Cat# 2118, RRID: AB_561053 |
| Rabbit anti-phospho-MKK7 (Ser271/Thr275) | Cell Signaling Technology | Cat# 4171, RRID: AB_2250408 |
| Rabbit anti-MKK7 | Cell Signaling Technology | Cat# 4172, RRID: AB_330914 |
| Mouse anti-GST (26H1) | Cell Signaling Technology | Cat# 2624, RRID: AB_2189875 |
| Rabbit anti-c-Myc (Y69) | Abcam | Cat# ab32072, RRID: AB_731658 |
| Mouse anti-p53 (DO-1) | Santa Cruz Biotechnology | Cat# sc-126, RRID: AB_628082 |
| Rabbit anti-LZK | YenZym Antibodies | Cat# YZ6696 |
| Mouse anti-cdc2 (POH1) | Cell Signaling Technology | Cat# 9116, RRID: AB_2074795 |
| Rabbit anti-CDK2 (78B2) | Cell Signaling Technology | Cat# 2546, RRID: AB_2276129 |
| Rabbit anti-CDK4 (D9G3E) | Cell Signaling Technology | Cat# 12790, RRID: AB_2631166 |
| Mouse anti-CDK6 (B-10) | Santa Cruz Biotechnology | Cat# sc-7961, RRID: AB_627242 |
| Mouse anti-cyclin A2 (BF683) | Cell Signaling Technology | Cat# 4656, RRID: AB_2071958 |
| Rabbit anti-cyclin B1 | Cell Signaling Technology | Cat# 4138, RRID: AB_2072132 |
| Mouse anti-cyclin D1 (DCS6) | Cell Signaling Technology | Cat# 2926, RRID: AB_2070400 |
| Mouse anti-cyclin E1 (HE12) | Cell Signaling Technology | Cat# 4129, RRID: AB_2071200 |
| Rat anti-FLAG (L5) | BioLegend | Cat# 637302, RRID: AB_1134268 |
| Rabbit anti-FLAG (D6W5B) | Cell Signaling Technology | Cat# 14793, RRID: AB_2572291 |
| Sheep anti-mouse IgG, secondary, HRP | GE Healthcare Life Sciences | Cat# NA931, RRID: AB_772210 |
| Donkey anti-rabbit IgG, secondary, HRP | GE Healthcare Life Sciences | Cat# NA934, RRID: AB_772206 |

Reverse Phase Protein Arrays

Cells were seeded in 10 cm dishes, at $6\times10^5$ for CAL33 and BICR56, and $6.25\times10^5$ for MSK921, before addition of doxycycline (to induce LZK knockdown) the following day. Cells were lysed on ice with 1× Triton X-100 cell lysis buffer (#9803, Cell Signaling Technology) supplemented with protease and phosphatase inhibitors (Roche Applied Science, #05056489001 and 04906837001, respectively) and 1.5 mM $MgCl_2$, 48 hours after induction with doxycycline. Cell lysates were centrifuged, and the supernatant was collected. Protein concentration was measured using 660 nm Protein Assay Reagent (Pierce), and adjusted to 2 mg/mL. Then 4× reducing sodium dodecyl sulfate (SDS) sample buffer was added (40% glycerol, 8% SDS, and 0.25 M Tris HCl, pH 6.8, with 10% β-mercaptoethanol added before use), and the samples were incubated at 80° C. for three minutes. Lysates from three independent experiments were sent for RPPA analysis. The Host and Tumour Profiling Unit at Cancer Research UK Edinburgh Centre (MRC Institute of Genetics and Molecular Mechanism, The University of Edinburgh) performed a nitrocellulose slide format RPPA with a panel of 60 antibodies according to established protocols (Sriskandarajah et al., *BMC Cancer* 2020, 20:269). Results were compared to samples without dox-induction of LZK knockdown.

MTS Cell Viability Assays

A Cell Titer 96 AQueous One Solution Cell Proliferation Assay (Promega) was used for MTS assays following the manufacturer's protocol. In brief, 5,000 cells were plated in triplicate in 96-well plates and treated with drug compounds 24 hours later using 5% FBS media. Doxycycline was added where appropriate, and cells were incubated for 72 hours. MTS was added, cells were incubated for two hours, and absorbance was measured at 490 nm using iMark™ Microplate Absorbance Reader (Bio-Rad). Graphs display percent cell viability relative to the DMSO-treated control sample. EC50 values were determined using GraphPad Prism 8.

Colony Formation Assays

Crystal violet assays were used to assess relative cell growth and survival after treatment with specific compounds. In general, cells were plated in triplicate in 12-well plates for 24 hours before drug treatments were added using 10% FBS media. The plates were incubated for 14 days, with the media and drug being replaced every 48 hours. The cells were then washed with phosphate-buffered saline and fixed in ice-cold methanol before being stained with 0.5% crystal violet (Sigma-Aldrich) in 25% methanol. Images were taken using a ChemiDoc MP Imaging System (Bio Rad), and for quantification, the crystal violet stain was dissolved in 33% acetic acid, incubated for 20 minutes with shaking, and read at 595 nm using iMark™ Microplate Absorbance Reader (Bio-Rad). Graphs display percent colony formation relative to the DMSO-treated control sample.

In Vitro Kinase Assay

One hundred nanograms of glutathione S-transferase (GST)-tagged human LZK pure protein (Carna Biosciences, #09-114) was incubated with 100 ng of GST-tagged human inactive MKK7 pure protein (Carna Biosciences, #07-147-10) in kinase buffer (Cell Signaling Technology, #9802). The assay was performed with 100 μM ATP at 37° C. for 30 minutes. Following the addition of 4× reducing SDS sample buffer, proteins were resolved by sodium dodecyl sulfate-polyacrylamide gel electrophoresis (SDS-PAGE) and immunoblot analysis was performed as stated previously.

ELISA Assay

A PathScan® Phospho-SAPK/JNK (Thr183/Tyr185) Sandwich ELISA Assay (Cell Signaling Technology) was used for ELISA assays following the manufacturer's protocol. In general, 500,000 cells were plated and treated with doxycycline the following day where appropriate and incubated at 37° C. for 48 hours. Cells were treated with the drug compound or control in 5% FBS media for 1 hour. After appropriate treatment time, cells were lysed on ice with 1× Cell Lysis Buffer (Cell Signaling Technology) supplemented with phosphatase and protease inhibitors (Sigma). Each diluted cell lysate was added to Phospho-SAPK/JNK (Thr183/Tyr185)Rabbit mAb Coated microwells in triplicate and incubated overnight at 4° C. Samples were treated with the following antibodies and incubated at 37° C. for 1 hour and 30 minutes, respectively: Detection Antibody and HRP-Linked secondary antibody. Samples were washed between treatments using 1× Wash Buffer according to the manufacturer's protocol. TMB substrate was added to each well and incubated at 37° C. for 10 minutes. Following this, STOPsolution was added to each well and absorbance was measured at 450 nm using iMark™ Microplate Absorbance Reader (Bio-Rad). Graphs display relative phospho-JNK levels.

Mice

Animal work was approved by the National Cancer Institute (NCI) Animal Care and Use Committee (ACUC). All mice were maintained under pathogen-free conditions in the NCI-Frederick immunocompromised suite. Animal handling and experimental procedures were approved by the National Cancer Institute (NCI) Animal Care and Use Committee (ACUC) and was performed within the limits of a license granted by the Home Office according to the Animals (Scientific Procedures) Act 1986. For the drug studies, mice were randomly assigned experimental groups to prevent bias towards to tumor size. After, an identification number was assigned to each animal and the researchers were not blinded to subsequent treatment and data collection. For the outsourced PDX mouse experiment, Crown Bioscience San Diego obtained six- to eight-week-old female NSG mice from The Jackson Laboratory. The Crown Bioscience study indicated animal welfare followed the U.S. Department of Agriculture's Animal Welfare Act (9 CFR Parts 1, 2 and 3) and the protocol was reviewed and approved by the IACUC prior to execution. Additionally, the care forthe animals was conducted in accordance with the regulations of the Association for Assessment and Accreditation of Laboratory Animal Care (AAALAC). For the pharmacokinetic(PK) analysis of PROTACs 3 and 7, female NSG mice between the weight of 17-25 grams wereobtained from The Jackson Laboratory. The PK animal study protocol was approved by ACUCof Division of Veterinary Resources at the National Institutes of Health (NIH).

For the HNSCC xenograft mouse model, $2\times10^6$ CAL33 cells were injected subcutaneously into the right posterior flank of 6-8-week-old immunodeficient NOD-scid IL2Rgamma$^{null}$ (NSG) female mice (obtained from the NCI Center for Cancer Research Animal Resource Program). When tumors reached a volume of approximately 100-150 $mm^3$, mice (10 per group) were randomly assigned to treatment with control or GNE-3511 treatment. The animals were treated for approximately 4-8 weeks, with study endpoints of over 20% body weight loss, tumor volume exceeding 2.0 $cm^3$ in diameter, or significant (greater than 80%) tumor regression observed with specific treatment. For the GNE-3511 study, the compound was dissolved with 60% polyethylene glycol (PEG) 300 MW, 3 eq of 0.1 M HCl, saline (vehicle) and administered twice daily through oral gavage at 100 mg/kg. Body weights and tumor size (tumor volume=[length×width×height]/2) were measured twice weekly. At the endpoint of each study, tumors were harvested, cleaned, weighed, and photographed for analysis.

Tumor fragments from an HNSCC patient containing amplified MAP3K13 were obtained from the National Institutes of Health (NIH) Patient-Derived Models Repository (PDMR), #391396-364-R (pharyngeal squamous cell carcinoma, MAP3K13 gene expression >5). Tumor pieces at approximately 2×2×2 $mm^3$ were implanted subcutaneously with Matrigel (Corning, #356231, lot #8002330) in 6-8-week-old NSG female mice (obtained from the NCI Center for Cancer Research Animal Resource Program) according to the SOP50101 Implantation and Cryopreservation of Tissue for PDX Generation protocol from the NIH PDMR. Five NSG mice were used for initial implantation of the cryopreserved tumor fragments. Body weights and tumor size were measured twice weekly. The tumors were harvested when they reached approximately 1,000 $mm^3$ and were used to generate the PDX mouse model to test GNE-3511. For the efficacy study, passage one of the fresh PDX tumor fragments were implanted into NSG mice using the protocol stated previously. Twenty NSG mice were used (10 for vehicle control and 10 for GNE-3511 treatment). Body weights and tumor sizes were measured twice weekly until tumors reached approximately 150-200 $mm^3$, at which point the mice were randomly assigned to treatment cohorts with control or GNE-3511 for approximately 4-8 weeks. The study endpoints were over 20% body weight loss, tumor volume exceeding 2.0 $cm^3$ in diameter, or significant (greater than 80%) tumor regression observed with treatment. The GNE-3511 was dissolved with 60% PEG 300 MW, 3 eq of 0.1 M HCl, saline (vehicle) and administered daily via intratumoral injection at 50 mg/kg. Body weights and tumor sizes were measured twice weekly. At the endpoint of each study, tumors were harvested, cleaned, weighed, and photographed for analysis.

For the PDX mouse model HN5120 from Crown Biosciences (squamous cell mouth, MAP3K13 gene expression 5.4542), tumor pieces (2×2 mm) from revival mice were implanted subcutaneously in the mice initially from an HNSCC patient containing amplified MAP3K13. Twenty NSG mice were used (10 for vehicle control and 10 for PROTAC 3 treatment). Body weights and tumor sizes were measured twice weekly until tumors reached approximately 100-150 $mm^3$, at which point the mice were randomly assigned to treatment cohorts with control or 3 for up to 8 weeks. The study endpoints were over 20% bodyweight loss, tumor volume exceeding 3000 $mm^3$, or ten days after last dose. Compound 3 was dissolved with 5% DMSO, 45% PEG300, 14.3% 0.1 M HCl, 35.7% saline, pH 7.0 (vehicle) and administered daily via intratumoral injection at 50 mg/kg. Body weights and tumor sizes were measured twice weekly. At the endpoint of each study, tumors were harvested, cleaned, weighed, and photographed for analysis.

For the PK analysis of PROTACs 3 and 7, the in vitro ADME properties of PROTAC 3 and 7 were studied with the standard Tier I assays, i.e. kinetic solubility assay, parallel artificial membrane permeability assay (PAMPA) and rat liver microsomal (RLM) stability assay (36-38). The pharmacokinetics (PK) of PROTACs 3 and 7 were determined in female NSG mice after a single intraperitoneal injection of 50 mg/kg. Mice used in this study (n=3 per time point) were not fasted. PROTACs 3 and 7 were dissolved with a formulation of 40% PEG 300 MW, 3 eq of 0.1 M HCl, saline. The dosing solutions were prepared fresh prior to the drug administration. The injection volume was 10 mL/kg. Blood samples were collected from each mouse before dosing (t=0) and at 0.083, 0.25, 0.5, 1, 2, 4, 7 and 24 hour for PROTAC 3; and at 0.083, 0.25, 0.5, 1, 2, 4, 7, 24 and 48 hour for PROTAC 7. K2EDTA was used as the anti-coagulant. Blood samples was centrifuged at 14,000 rpm at 4° C. to obtain plasma. After blood collection, liver, kidney, lung, and brain tissues were collected, weighed and snap frozen with dry ice. All samples were stored at −80° C. until the analysis.

Quantification and Statistical Analysis

All samples represent biological replicates. Data are presented as the mean with error bars shown on graphs representing ±SEM unless otherwise noted. Two-tailed Student's t-test was used to assess significance of differences between groups for assays and used to measure significance of the mouse tumor volumes at the last day of treatment. Values of $p<0.05$ were considered as significantly different.

Drug Concentrations in Plasma and Tissue Samples

Drug concentrations in plasma and tissue samples were measured by a qualified UPLC-MS/MS method with a Waters Acquity I-Class UPLC interfaced with a Waters TQ-S mass spectrometer. The lower limit of quantitation (LLOQ) was 1 ng/mL for plasma and 1 ng/g tissue for liver, kidney, lung and brain. PK parameters were calculated using the non-compartmental method of the pharmacokinetic software package Phoenix WinNonlin, version 6.2 (Certara, St. Louis, MO). The area under the plasma concentration versus time curve (AUC) was calculated using the linear trapezoidal method. Where warranted, the slope of the apparent terminal phase was estimated by log-linear regression using at least 3 data points, and the terminal rate constant ($\lambda$) was derived from the slope. $AUC_{0-\infty}$ was estimated as the sum of the $AUC_{0-t}$ (where t is the time of the last measurable concentration) and $C_t/\lambda$. The apparent terminal half-life ($t_{1/2}$) was calculated as $0.693/\lambda$.

Histological Analysis

For the IHC analysis for the studies involving the CAL33 xenograft and PDX 391396-364-R mousemodels, staining was performed by the Molecular Histopathology Laboratory (MHL) at the National Cancer Institute at Frederick. Briefly, tissues were fixed in buffered 10% formalin, embedded in paraffin, and sectioned at 5 μm before staining with hematoxylin and eosin (H&E). Additionally, sections were stained using the Leica Biosystems' BondRX auto-stainer with an antibody for cleaved caspase-3 (Cell Signaling Technology, #9661, 1:100, 60 minutes). Slides were blinded and scanned using an Aperio AT2 scanner (Leica Biosystems). Image analysis wasperformed using HALO imaging software (Indica Labs). The shown tumor regions exclude artifacts and necrotic regions. IHC analysis performed by Crown Biosciences San Diego for the PDX HN5120 study was similar except for the cleaved caspase-3 antibody (Cell Signaling Technology, #96645, 1:500, 20 minutes).

In Vitro ADME Assays and In Vivo Pharmacokinetic Studies of Targeted Degraders 3 and 7

In vitro ADME properties of targeted degraders 3 and 7 were studied with the standard Tier I assays, i.e. kinetic solubility assay, parallel artificial membrane permeability assay (PAMPA) and rat liver microsomal (RLM) stability assay (Sun et al., *Bioorg Med Chem* 2019, 27(14):3110-4; Sun et al., *Bioorg Med Chem* 2017, 25(3):1266-76; Shah et al., *Drug Metab Dispos* 2016, 44(10):1653-61). The pharmacokinetics (PK) of targeted degraders 3 and 7 were determined in female NSG mice (The Jackson Laboratory; body weight range from 17-25 grams) after a single intraperitoneal injection of 50 mg/kg. The animal study protocol was approved by ACUC of Division of Veterinary Resources at the National Institutes of Health (NIH). Mice used in this study (n=3 per time point) were not fasted. targeted degraders 3 and 7 were dissolved with a formulation of 40% PEG 300 MW, 3 eq of 0.1 M HCl, saline. The dosing solutions were prepared fresh prior to the drug administration. The injection volume was 10 mL/kg. Blood samples were collected from each mouse before dosing (t=0) and at 0.083, 0.25, 0.5, 1, 2, 4, 7 and 24 hour for targeted degrader 3; and at 0.083, 0.25, 0.5, 1, 2, 4, 7, 24 and 48 hour for targeted degrader 7. K2EDTA was used as the anti-coagulant. Blood samples was centrifuged at 14,000 rpm at 4° C. to obtain plasma. After blood collection, liver, kidney, lung and brain tissues were collected, weighed and snap frozen with dry ice. All samples were stored at −80° C. until the analysis.

Time-Lapse Microscopy

Cells were plated in 96-well plates with full growth media more than 24 hours prior to imaging, such that the density would remain sub-confluent until the end of the imaging period. Time-lapse imaging was performed in 290 μL full growth media. Images were taken in CFP and YFP channels every 12 minutes on a Nikon Ti2-E inverted microscope (Nikon) with a 20×0.45NA objective. Total light exposure time was kept under 600 milliseconds for each time point. Cells were imaged in a humidified, 37° C. chamber at 5% $CO_2$.

Image Analysis

All image analyses were performed with custom MATLAB scripts as previously described (Cappell et al., *Cell* 2016, 166:167-180). In brief, optical illumination bias was empirically derived by sampling background areas across all wells in an imaging session, and was subsequently used to flatten all images. This enabled measurement and subtraction of a global background for each image. Cells were segmented for their nuclei based on H2B-mTurquoise. CDK2 activity was calculated by measuring the nuclear and cytoplasmic fluorescence of the DHB-mVenus protein. Cells were segmented for their cytoplasmic regions by spatially approximating a ring with an inner radius of 2 μm outside of the nuclear mask and an outer radius with a maximum of 10 μm outside of the nuclear mask. Regions within 10 μm of another nucleus were excluded. Cytoplasmic DHB-mVenus was calculated as the median intensity within the cytoplasmic ring, excluding pixel intensities indistinguishable from background.

Mitosis events were automatically identified using H2B-mTurquoise and called at anaphase when one cell split into two daughter cells, each with approximately 45-55% of the size of the mother cell. Cells were considered to have been arrested in the G2 phase if a second mitosis was not detected for more than 30 hours after the first mitosis. Following drug treatment, cells were categorized by their CDK2 activity two hours after anaphase. Cells with high CDK2 activity (defined as greater than 0.6) are considered to have immediately re-entered the cell cycle, cells with transiently low CDK2 activity (defined as less than 0.6 two hours after anaphase but rising to greater than 0.6 within the viewing time) are considered to have entered into a transient G0 state before eventually re-entering the cell cycle, and cells with low CDK2 activity (defined as less than 0.6 within the viewing time) are considered to have entered a prolonged G0 state (Arora et al., *Cell Rep* 2017, 19:1351-1364).

Human Samples

Tumor fragments from HNSCC patients containing amplified MAP3K13 were obtained from the NIH PDMR, #391396-364-R, or from Crown Biosciences San Diego, #HN5120.

Bioinformatic Analyses of HNSCC PDX Mouse Models of NCI PDMR

For nucleic acid extraction, library prep, whole-exome sequencing, and whole-transcriptome sequencing, please see the documents from the NIH PDMR SOPs. An in-house bioinformatics pipeline was used to process WES and RNA-seq data. FASTQ data were generated using the bcl2fastq tool (Illumina, v2.18) and then run through FASTQC for quality confirmation. For WES, reads were mapped to the human hgl9 reference genome by the Burrows-Wheeler Alignmenttool. The resulting bam files were processed using GATK best practice workflow (32). Copy number data was inferred from WES data through use of the CNVKit algorithm, using a pool of normal HapMap cell line samples as reference (30). The RSEM pipeline using STAR aligner was implemented to process RNA-seq data to get gene expression data (Li et al., *BMC Bioinformatics* 2011, 12(1):323). In current cohort, fifty-eight PDX head and neck models were performed by WES and RNA-seq bioinformatics analysis. In each PDX model, it includes multiple (4≥PDX) samples. For copy number data, consensus copy number status (2=diploid, >2 and <5=gain, and ≥5=amplification) was called using majority voting among multiple PDX samples from same model. For gene expression data, average of Fragments Per Kilobase Million (FPKM) was taken to get gene expression at model level.

Example 1

Chemical Syntheses and Characterization

Reagents were purchased from commercial sources and used without further purification. Compound 1 and tert-butyl 4-(2-chloro-6-(3,3-difluoropyrrolidin-1-yl)pyridin-4-yl)-piperidine-1-carboxylate were prepared as previously described (Patel et al., *J Med Chem* 2015, 58:401-418).

(Compound 1)

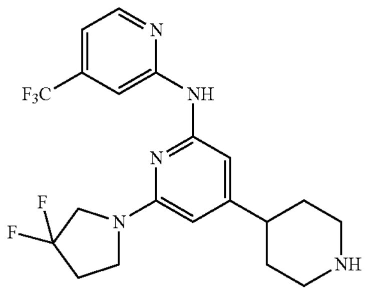

1-(4-(2-Chloro-6-(3,3-difluoropyrrolidin-1-yl)pyridin-4-yl)piperidin-1-yl)ethan-1-one. tert-butyl 4-(2-chloro-6-(3,3-difluoropyrrolidin-1-yl)pyridin-4-yl)piperidine-1-carboxylate (0.55 g, 1.37 mmol) was dissolved in 3 mL of DCM and the solution was cooled in an ice bath and treated with 3 mL of TFA. After 20 min the reaction was concentrated under reduced pressure. The resulting residue was taken up in 15 mL of DCM and treated with N-methylmorpholine (754 uL, 693 mg, 5 equiv) and acetic anhydride (136 uL, 147 mg, 1.05 equiv) and stirred at RT for 1 h. The reaction was then diluted with DCM and washed with 50 mL H2O. The aqueous layer was extracted with 2×40 mL DCM and the combined organic layers were dried over $Na_2SO_4$ and evaporated to yield the desired material.

General Procedure for RuPHOS coupling. 1-(4-(2-chloro-6-(3,3-difluoropyrrolidin-1-yl)pyridin-4-yl)piperidin-1-yl)ethan-1-one (50 mg, 145 umol), RuPHOS ligand (8.8 mg, 18.9 umol, 0.13 equiv) Pd—RuPHOS (9.4 mg, 12.9 umol, 0.09 equiv), and tBuOK (24.5 mg, 218 umol, 1.5 equiv) were combined with the amine (1.22 equiv) in a microwave vial and sealed. The vial was evacuated and backfilled with argon 3×. 2 mL of dioxane was added and the reaction was heated to 135 C for 1 h. The reaction was then cooled and filtered; the filter cake was washed with EtOAc, and the resulting filtrate was adsorbed onto Celite. The desired product was isolated by flash chromatography.

Synthetic details are provided for compound 3; compounds 4-8 were synthesized following a similar protocol. Final products were purified by flash chromatography or preparative high-performance liquid chromatography (HPLC). All tested compounds were characterized by liquid chromatography/mass spectrometry (LC/MS). Nuclear magnetic resonance (NMR) spectra were obtained on a 400 MHz Varian NMR and processed using MestreNova software. LC/MS data for small molecules were acquired on an Agilent Technologies 1290 Infinity HPLC system using a 6130 quadrupole LC/MS detector and a Poroshell 120 SB—C18 2.7 μm column (4.6×50 mm) or an Agilent 1200 series HPLC system with an LC/MSC Trap XCT detector and a ZORBAX 300SB-C18 3.5 μm column (4.6×50 mm). Preparative HPLC chromatography was performed on a Shimadzu system using a 30 mm×150 mm Xbridge C18 column (Waters). Flash chromatography was performed on a Teledyne ISCO CombiFlash Rf+. High-resolution mass spectrometry (HRMS) data was acquired on a Waters Xevo G2-XS QTof running MassLynx version 4.1

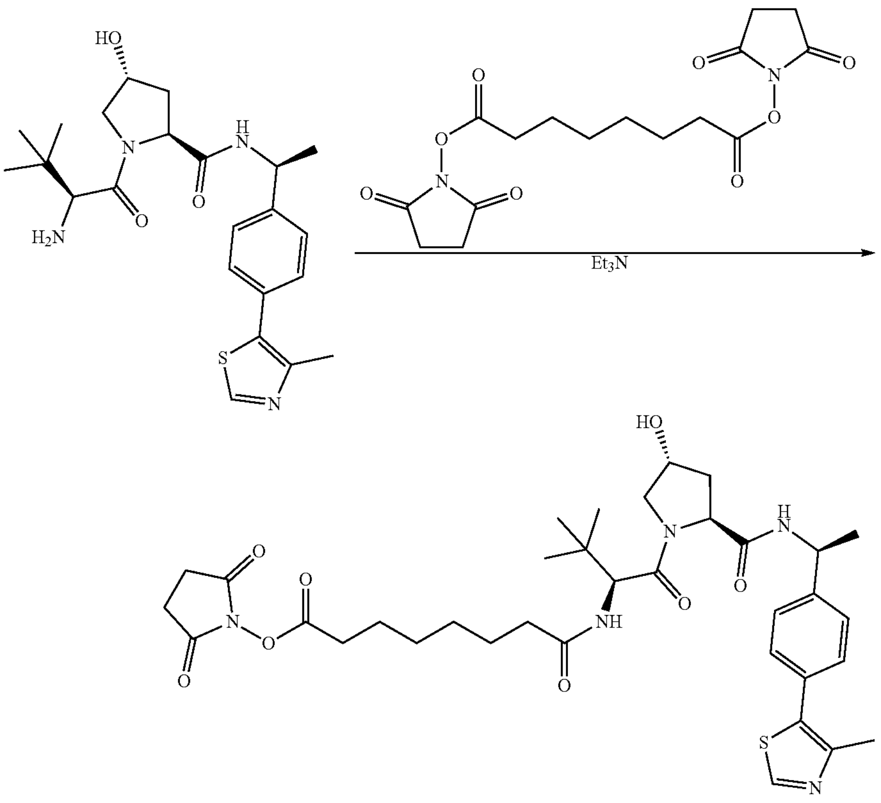

2,5-Dioxopyrrolidin-1-yl 8-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-8-oxooctanoate. A solution of 500 mg of (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (1.04 mmol) and 0.22 mL of triethylamine in 2 mL of dimethylformamide (DMF) was added dropwise to a stirred solution of di-N-succinimidyl suberate (1.53 g, 4.16 mmol) in 10 mL of dry DMF and 10 mL of dry dichloromethane (DCM). The suspension was stirred overnight, then concentrated under reduced pressure. The residue was subjected to flash chromatography (0→15% MeOH in DCM) to yield 522 mg (72% yield) of the desired material as a colorless glassy residue. $^1$H NMR (400 MHz, $CDCl_3$) δ 8.76 (s, 1H), 7.43-7.36 (m, 4H), 6.36 (d, J=8.8 Hz, 1H), 5.09 (p, J=7.0 Hz, 1H), 4.68 (t, J=7.9 Hz, 1H), 4.57 (d, J=8.8 Hz, 1H), 4.51 (s, 1H), 4.15-4.07 (m, 1H), 3.68-3.57 (m, 1H), 2.83 (d, J=3.9 Hz, 4H), 2.60 (t, J=7.3 Hz, 2H), 2.54 (s, 3H), 2.46 (ddd, J=13.4, 7.8, 4.5 Hz, 1H), 2.32-2.17 (m, 2H), 2.13-2.04 (m, 1H), 1.74 (p, J=7.3 Hz, 2H), 1.65 (ddt, J=11.3, 7.3, 3.8 Hz, 2H), 1.48 (d, J=6.9 Hz, 3H), 1.46-1.38 (m, 2H), 1.38-1.27 (m, 2H), 1.04 (s, 9H). $^{13}$C NMR (101 MHz, $CDCl_3$) δ 173.42, 171.83, 170.12, 169.58, 168.70, 150.58, 148.29, 143.42, 131.71, 130.75, 129.54, 126.53, 69.87, 58.78, 57.43, 56.74, 48.78, 36.05, 35.95, 35.40, 30.85, 28.31, 28.09, 26.54, 25.67, 25.20, 24.42, 22.25, 16.06. HRMS: Calcd for $C_{35}H_{48}N_5O_8S^+$ 698.3218, found 698.3215.

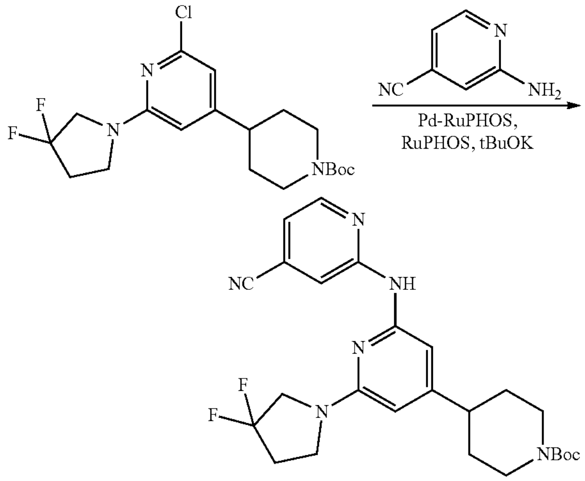

tert-Butyl 4-(2-((4-cyanopyridin-2-yl)amino)-6-(3,3-difluoropyrrolidin-1-yl)pyridin-4-yl)piperidine-1-carboxylate. A microwave flask containing tert-butyl 4-(2-chloro-6-(3,3-difluoropyrrolidin-1-yl)pyridin-4-yl)piperidine-1-carboxylate (109 mg, 0.271 mmol), RuPhos (16.5 mg, 0.0353 mmol), chloro{[RuPhos][2-(2-aminoethylphenyl]palladium (II)}/[RuPhos] admixture (17.6 mg, 0.024 mmol), potassium t-butoxide (45.7 mg, 0.407 mmol), 2-amino-4-cyanopyridine (39.4 mg, 0.331 mmol), and a stir bar was sealed, evacuated, and backfilled with argon three times. Dioxane (3 mL) was added, and the mixture was heated for 45 minutes at 125° C. Upon completion of the reaction, the mixture was adsorbed onto Celite and subjected to flash chromatography (15→60% EtOAc in hexanes). The product was obtained as a yellow solid (107 mg, 82% yield). $^1$H NMR (400 MHz, $CDCl_3$) δ 8.42 (d, J=1.2 Hz, 1H), 8.36-8.30 (m, 1H), 7.49 (s, 1H), 7.00 (dd, J=5.1, 1.4 Hz, 1H), 6.22 (s, 1H), 5.80 (d, J=1.0 Hz, 1H), 4.25 (br s, 1H), 3.84 (t, J=13.1 Hz, 2H), 3.74 (t, J=7.2 Hz, 2H), 2.79 (t, J=12.7 Hz, 2H), 2.61-2.44 (m, 4H), 1.81 (d, J=13.0 Hz, 2H), 1.68-1.52 (m, 2H), 1.48 (s, 9H). $^{13}$C NMR (101 MHz, $CDCl_3$) δ 158.51, 156.16, 154.97, 154.66, 152.41, 149.20, 127.90 (t, J=248 Hz), 121.52, 117.44, 117.07, 114.18, 98.82, 98.78, 97.48, 79.82, 54.33 (t, J=32 Hz), 44.72, 44.26, 42.87, 34.26 (t, J=24 Hz), 28.67. HRMS: Calcd for $C_{25}H_{31}F_2N_{16}O_2^+$ 485.2471, found 485.2468.

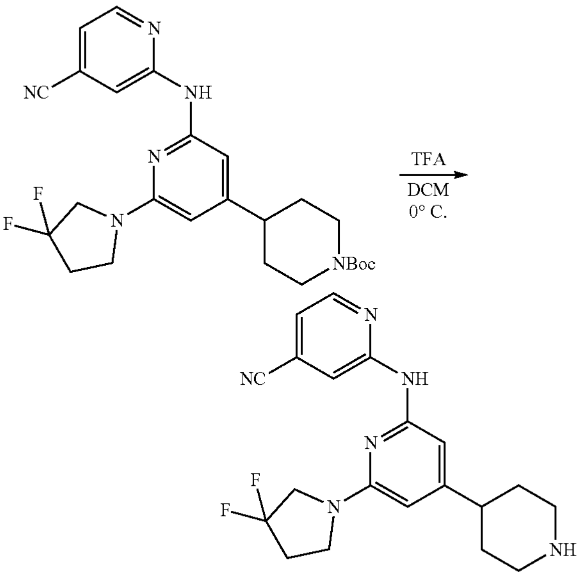

2-((6-(3,3-Difluoropyrrolidin-1-yl)-4-(piperidin-4-yl)pyridin-2-yl)amino)isonicotinonitrile. tert-Butyl 4-(2-((4-cyanopyridin-2-yl)amino)-6-(3,3-difluoropyrrolidin-1-yl)pyridin-4-yl)piperidine-1-carboxylate (81 mg, 0.167 mmol) was dissolved in 0.7 mL of DCM and stirred in an ice bath. Trifluoroacetic acid (0.7 mL) was added, and the reaction was stirred at 0° C. for 20 minutes. Upon completion of the reaction as determined by LC/MS, all volatiles were removed under reduced pressure. The resulting residue was used without further purification.

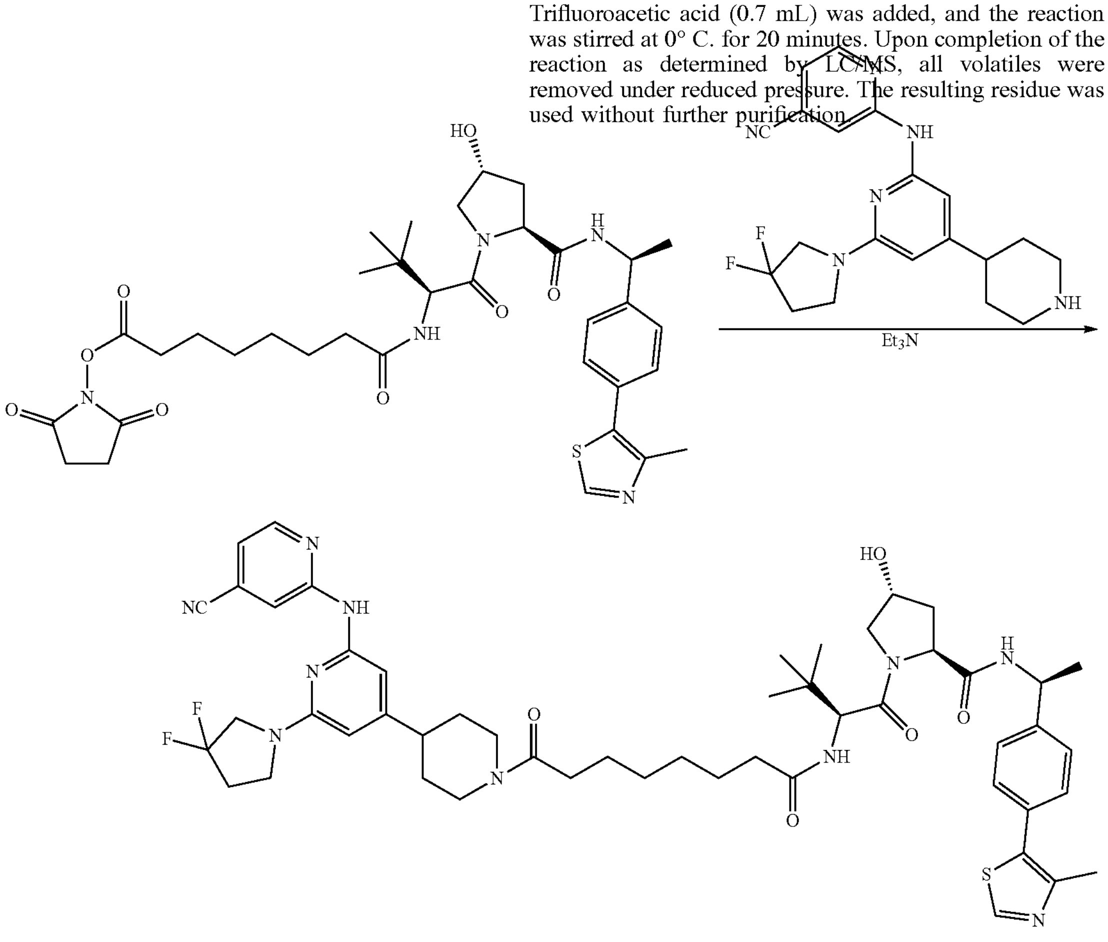

Compound 3 (VHL-Suberoyl-DLK). 2,5-Dioxopyrrolidin-1-yl 8-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-8-oxooctanoate (522 mg, 0.75 mmol) was combined with 2-((6-(3,3-Difluoropyrrolidin-1-yl)-4-(piperidin-4-yl)pyridin-2-yl)amino)isonicotinonitrile trifluoroacetic acid salt (361 mg equivalent weight, 0.75 mmol) and N-methylmorpholine (0.5 mL) in 7 mL of DMF. After stirring overnight, the reaction was diluted with 75 mL each of DCM and water. The aqueous phase was separated and extracted with 2×50 mL DCM; the combined organic extracts were washed with saturated brine solution and dried over $Na_2SO_4$. Flash chromatography (5→25% MeOH in DCM) afforded 550 mg (76% yield) of the desired material as a yellow solid. $^1H$ NMR (400 MHz, $CDCl_3$) δ 8.66 (d, J=0.4 Hz, 1H), 8.47 (s, 1H), 8.31 (d, J=5.1 Hz, 1H), 7.88 (s, 1H), 7.59-7.51 (m, 1H), 7.39-7.30 (m, 4H), 6.98 (dd, J=5.1, 1.4 Hz, 1H), 6.54-6.46 (m, 1H), 6.24 (s, 1H), 5.76 (s, 1H), 5.09 (p, J=7.0 Hz, 1H), 4.74 (q, J=8.2 Hz, 2H), 4.64 (dd, J=8.9, 2.8 Hz, 1H), 4.49 (s, 1H), 4.06 (d, J=11.3 Hz, 1H), 3.95 (d, J=13.9 Hz, 2H), 3.82 (t, J=13.0 Hz, 2H), 3.72 (t, J=7.2 Hz, 2H), 3.65-3.58 (m, 1H), 3.08 (t, J=13.6 Hz, 2H), 2.68-2.39 (m, 9H), 2.33 (d, J=5.4 Hz, 2H), 2.19 (dq, J=14.4, 7.2 Hz, 2H), 2.09 (dt, J=13.1, 7.5 Hz, 1H), 1.82 (d, J=14.2 Hz, 2H), 1.61-1.51 (m, 4H), 1.46 (d, J=6.9 Hz, 3H), 1.35-1.28 (m, 4H), 1.04 (s, 9H). HRMS: Calcd for $C_{51}H_{65}F_2N_{10}O_5S^+$ 967.4823, found 967.4814.

4

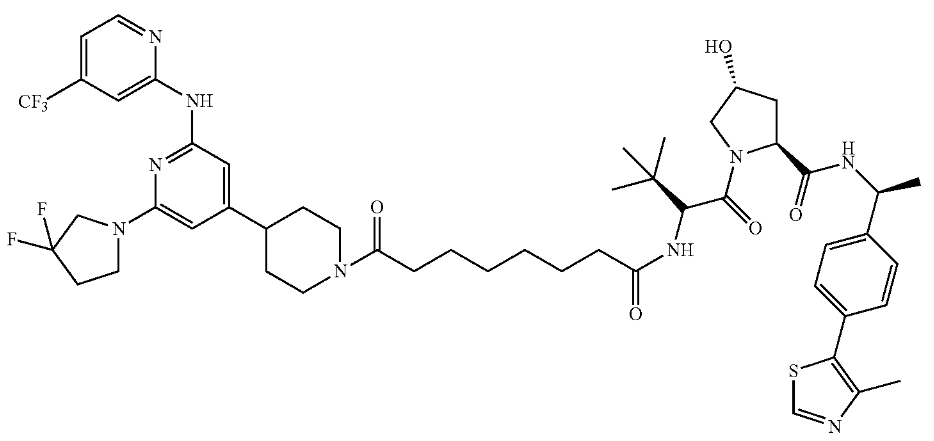

Compound 4. LC/MS: 95.7% pure (280 nm). HRMS: Calcd for $C_{51}H_{65}F_5N_9O_5S^+$ 1010.4750, found 1010.4759

5

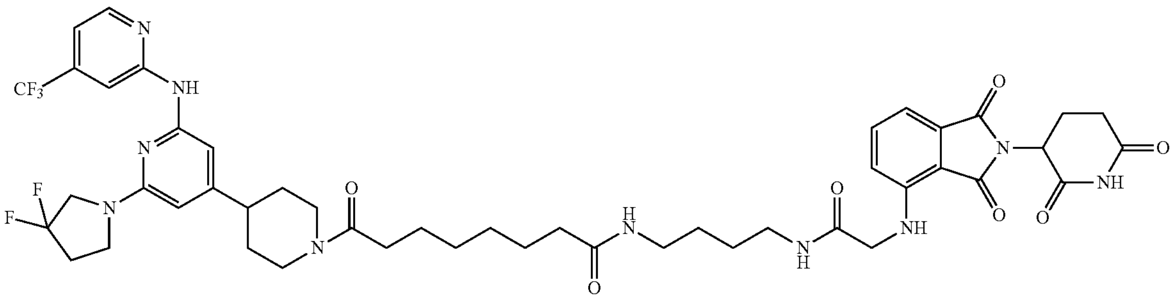

Compound 5. LC/MS: 97.2% pure (280 nm). HRMS: Calcd for $C_{47}H_{56}F_5N_{10}O_7$ 967.4254, found 967.4252
6
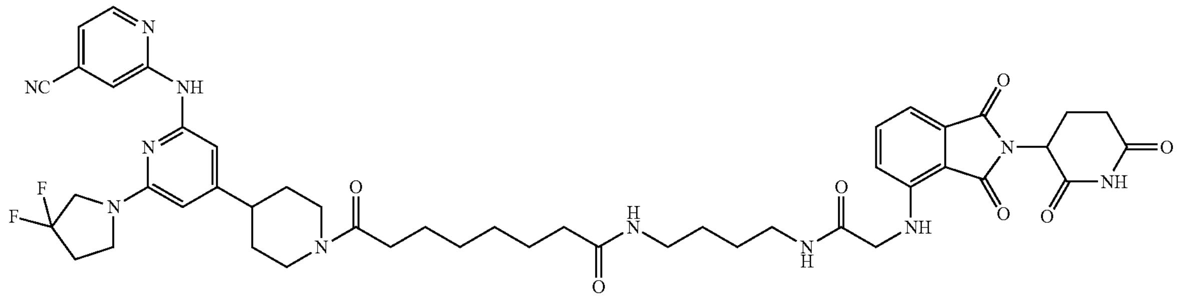
Compound 6. 98.4% pure (254 nm). HRMS: Calcd for $C_{47}H_{56}F_2N_{11}O_7^+$924.4332, found 924.4319.
7
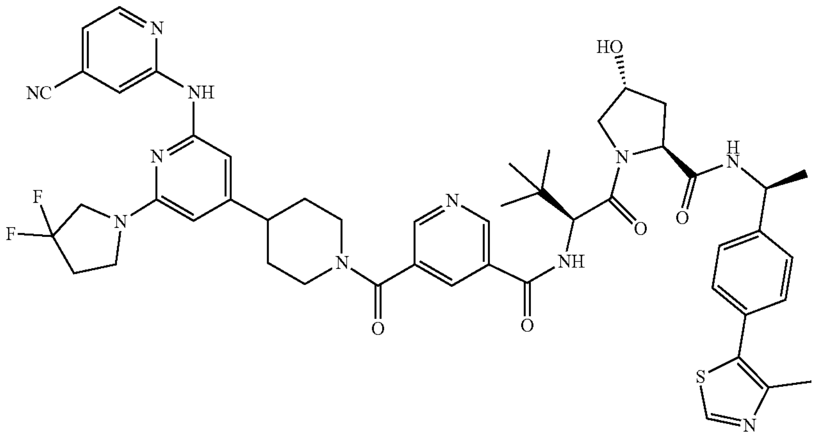
Compound 7. 97.4% pure (254 nm). HRMS: Calcd for $C_{50}H_{56}F_2N_{11}O_5S^+$ 960.4155, found 960.4153.
8
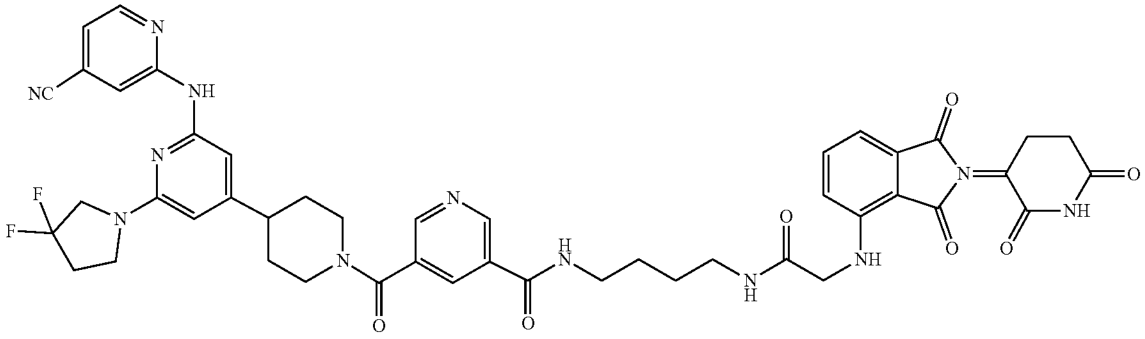
Compound 8. 95.4% pure (254 nm). HRMS: Calcd for $C_{46}H_{47}F_2N_{12}O_7^+$ 917.3659, found 917.3655.

9

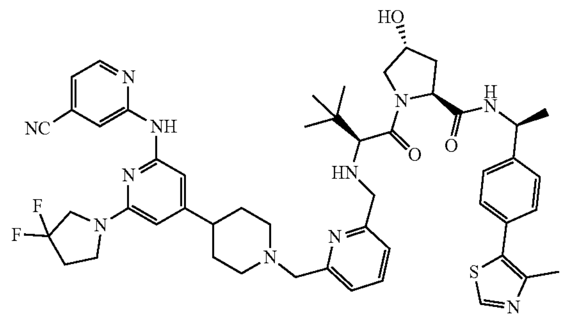

(1 eq) and NMM (4 eq) and the solution was stirred under argon for 5 minutes. HATU was added (1 eq) and the reaction was stirred at room temperature for 30 minutes after which water was added and the mixture was stirred for 20 minutes. The solution was then extracted with dichloromethane, washed with saturated sodium bicarbonate, and brine. The organic layer was then dried over sodium sulfate, filtered, and concentrated in vacuo. The crude residue was purified by flash chromatography using gradient elution (0-10% methanol in dichloromethane) over 20 CV in a 4 g silica column. The compound was further purified by reverse phase HPLC using a Waters XBridge Prep C18 5 μm 19 mm×150 mm column in water (0.05% TFA with an increasing gradient of acetonitrile (0.05% TFA). The combined fractions were lyophilized to afford the product as a fluffy yellow solid.

13

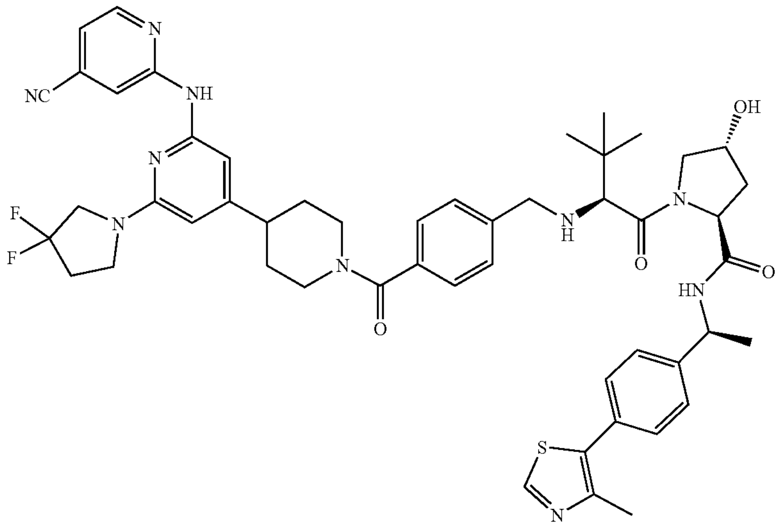

Compound 9. LCMS: 97.5% pure (254 nm). Calcd for $C_{50}H_{60}F_2N_{11}O_3^+$ 932.5, found 932.5.

Compounds 13-29 and 33 were synthesized as follows:

General Method 1A. To a solution of 2-((6-(3,3-difluoropyrrolidin-1-yl)-4-(piperidin-4-yl)pyridin-2-yl)amino)isonicotinonitrile dioxalate salt (1 eq) in dry DMF (1 mL) was added N-methylmorpholine (5 eq) and the solution was stirred under argon for 5 minutes. To a solution of bis-acid (2 eq) in dry DMF (1 mL) was added HATU (2 eq) and N-methylmorpholine (2 eq) and stirred for 5 minutes. The activated acid was added to the DMF solution containing the LZK inhibitor. The reaction was monitored by LCMS until the reaction was complete (0.5-1 hour) and water was added to the reaction mixture and stirred for 30 minutes. The reaction solution was extracted with dichloromethane ×3. The combined organic layer was washed with saturated sodium bicarbonate solution, brine, dried over sodium sulfate, filtered, and concentrated in vacuo. The crude LZK-acid product was used in the next step without further purification.

General Method 1B. To a solution of the LZK-acid (1 eq) in DMF (1 mL) was added (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride Compound 13. To a suspension of (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (22 mg, 0.046 mmol) and 4-formylbenzoic acid (9 mg, 0.06 mmol) was added sodium sulfate (55 mg) and refluxed overnight. The reaction mixture was then cooled in an ice bath and sodium borohydride (4 mg, 0.11 mmol) and the reaction was stirred until conversion was completed, as judged by LCMS. The reaction mixture was then filtered through celite, concentrated, dissolved dichloromethane and loaded onto a silica cartridge and purified by flash chromatography 0 to 25% Methanol in dichloromethane to afford the free acid as a yellow solid.

The above solid (22 mg, 0.038 mmol) was dissolved in DMF (2 mL) followed by the addition of 2-((6-(3,3-difluoropyrrolidin-1-yl)-4-(piperidin-4-yl)pyridin-2-yl)amino) isonicotinonitrile dioxalate salt (21 mg, 0.037 mmol) and N-methylmorpholine (26 μL, 0.23 mmol). HATU (20 mg, 0.053 mmol) was then added and solution was stirred for 1 hour and water and DCM was added. The aqueous layer was extracted with DCM (25 mL×2). The combined organic extracts were washed with saturated sodium bicarbonate, brine, dried over sodium sulfate, filtered, and concentrated. The crude solid was then dissolved in dichloromethane and loaded onto a silica cartridge and purified by flash chromatography 0 to 12% methanol in dichloromethane to afford the product as a yellow solid. The product was further purified by reverse phase HPLC using a Waters XBridge Prep C18 5 μm 19 mm×150 mm column in water (0.05% TFA with an increasing gradient of acetonitrile (0.05% TFA). The combined fractions were lyophilized to afford the product as a fluffy yellow solid. LCMS: 97.5% pure (254 nm). Calcd for $C_{51}H_{59}F_2N_{10}O_4S^+$ 945.4, found 945.5

14

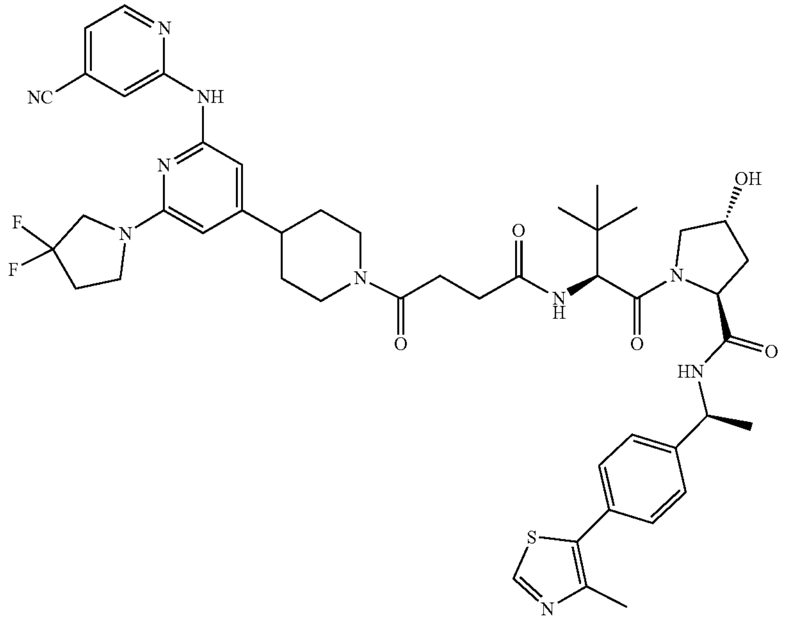

Compound 14. To a solution of 2-((6-(3,3-difluoropyrrolidin-1-yl)-4-(piperidin-4-yl)pyridin-2-yl)amino)isonicotinonitrile dioxalate salt (107 mg, 0.19 mmol) in anhydrous dimethylformamide (3 mL) was added N-methylmorpholine (107 μL, 0.95 mmol) and succinic anhydride (25 mg, 0.25 mmol) and the reaction was stirred overnight under argon. The crude solid was dissolved in dichloromethane and loaded onto a silica cartridge and purified by flash chromatography 0 to 20% Methanol in dichloromethane to afford the product as a yellow solid.

After 30 minutes was added e3 ligase VHL warhead hydrochloride (44 mg, 0.078 mmol) and anhydrous diisopropylethylamine (27 μL, 0.24 mmol) and the reaction was stirred for 1 hour under argon at room temperature. The reaction mixture was poured into water and extracted with dichloromethane. The combined organic extracts were washed with brine, dried over sodium sulfate, filtered, and concentrated in vacuo. The crude solid was dissolved in dichloromethane and loaded onto a silica cartridge and purified by flash chromatography 0 to 15% Methanol in dichloromethane to afford the product as a yellow solid. The product was further purified by reverse phase HPLC using a Waters XBridge Prep C18 5 μm 19 mm×150 mm column in water (0.05% TFA with an increasing gradient of acetonitrile (0.05% TFA). The combined fractions were lyophilized to afford the product as a fluffy yellow solid. LCMS: 99.1% pure (254 nm). Calcd for $C_{44}H_{53}F_2N_{10}O_4S^+$ 855.4, found 855.3. LCMS: 99.6% pure (254 nm). Calcd for $C_{47}H_{57}F_2N_{10}O_5S^+$ 911.4, found 911.4

15
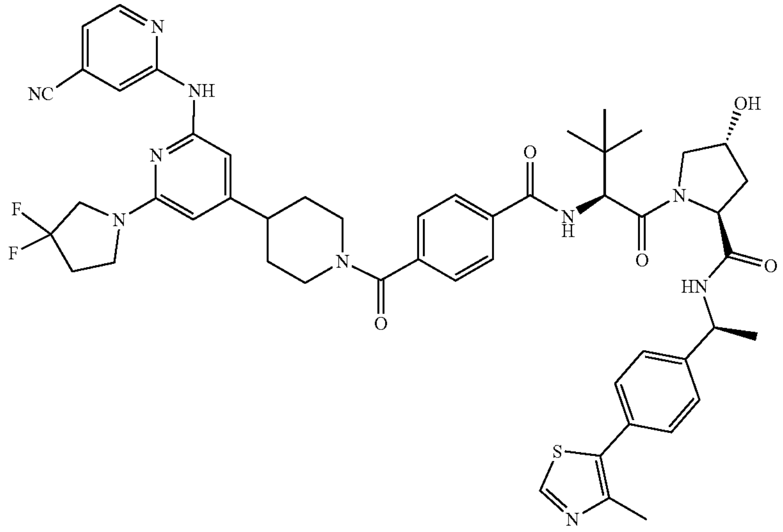
Compound 15. Prepared by General Method 1
LCMS: 98.1% pure (254 nm). Calcd for $C_{51}H_{57}F_2N_{10}O_5S^+$ 959.4, found 959.5
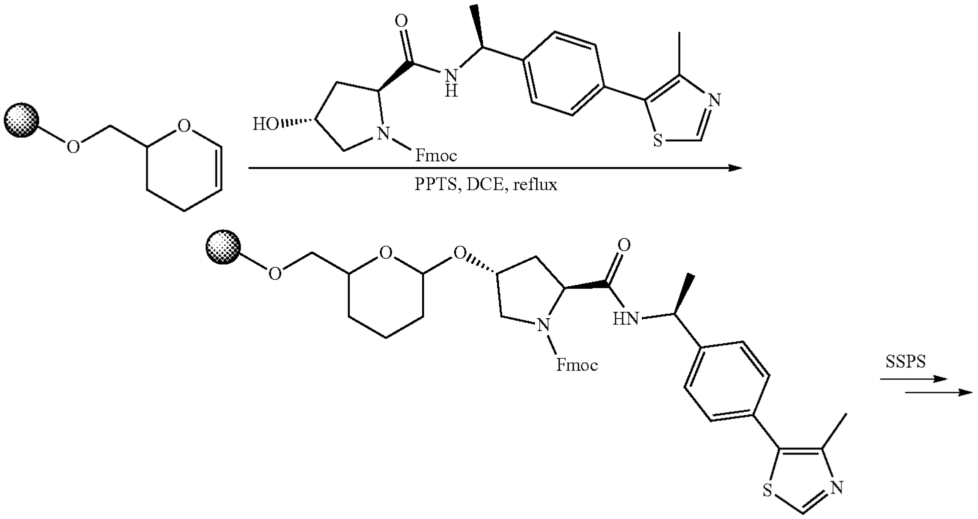

-continued
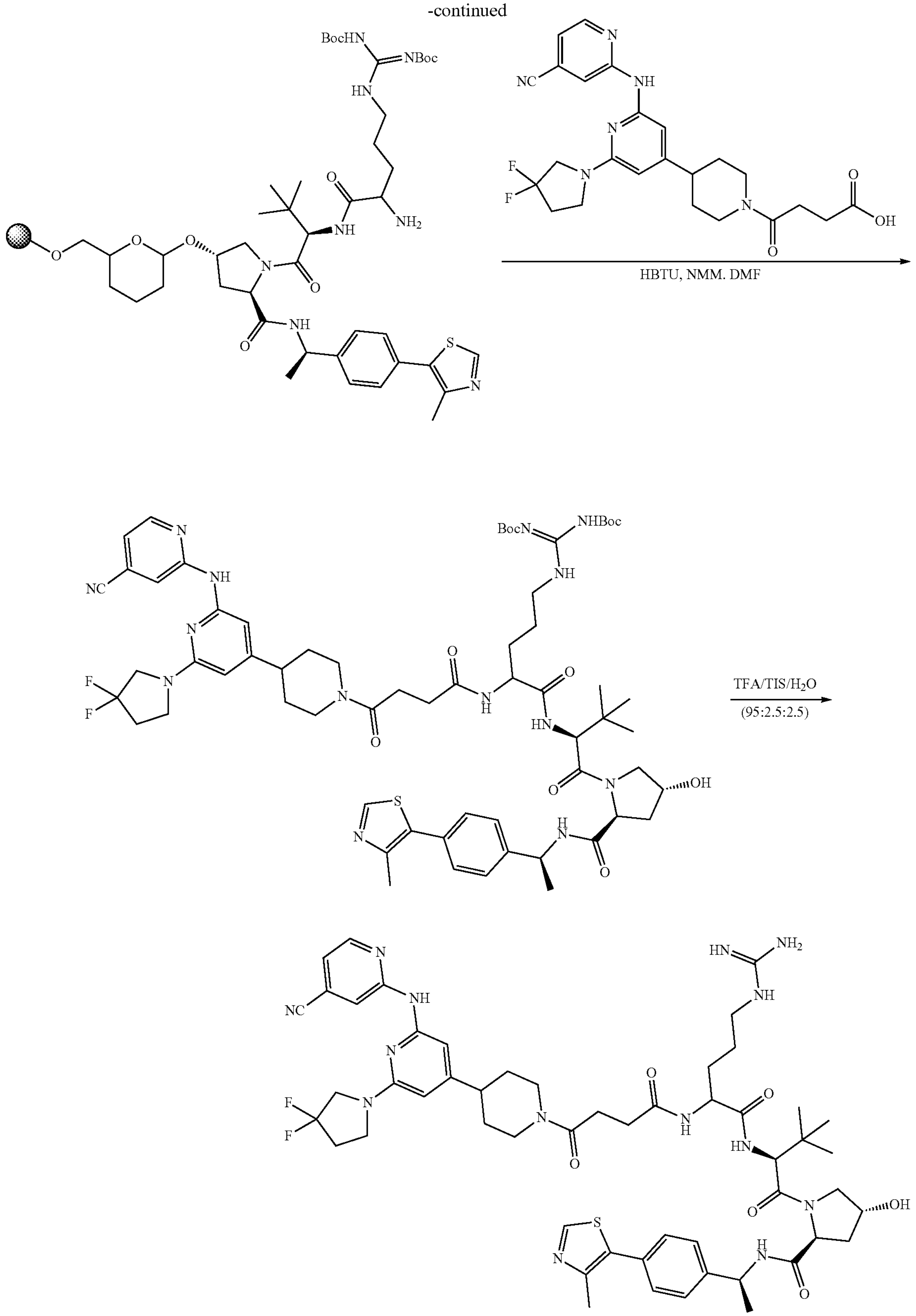

Compound 16. Ellman (730 mg, 1.01 mmol) was swollen in 10 mL of 1,2-dichloroethane under argon for 1 hour. To resin was added (9H-fluoren-9-yl)methyl (2S,4R)-4-hydroxy-2-(((S)-1-(4-(4-methylthiazol-5-yl)phenyl)ethyl)carbamoyl) pyrrolidine-1-carboxylate (673 mg, 1.22 mmol) and pyridinium p-toluene sulfonate (382 mg, 1.52 mmol) and the reaction mixture was stirred at 80° C. overnight under argon. The resin was then washed with ample amounts of dimethylformamide, dichloromethane, and diethyl ether.

The resin with attached (9H-fluoren-9-yl)methyl (2S,4R)-4-hydroxy-2-(((S)-1-(4-(4-methylthiazol-5-yl)phenyl)ethyl) carbamoyl)pyrrolidine-1-carboxylate (516 mg, 0.16 mmol) was treated with 20% piperidine in DMF for 20 minutes twice and washed with DMF. A solution of Fmoc-L-tert-leucine (461 mg, 1.30 mmol), HBTU (495 mg, 1.31 mmol), N-methylmorpholine (0.29 mL, 2.61 mmol) in DMF was added to the resin and the reaction was agitated for 1 hour. The resin was then washed repeatedly with DMF, DCM, and diethyl ether.

The above resin (127 mg, 0.04 mmol) was treated with 20% piperidine in DMF for 20 minutes twice and washed with DMF. A solution of Fmoc-Arg$(Boc)_2$-OH (194 mg, 0.33 mmol), HBTU (116 mg, 0.31 mmol), N-methylmorpholine (72 μL, 0.64 mmol) in DMF was added to the resin and the reaction was agitated for 1 hour. The resin was then washed with DMF, DCM, and DMF again. The resin was then again treated with 20% piperidine in DMF for 20 minutes twice and washed with DMF, DCM, and diethyl ether.

To the above resin (23 mg, 0.007 mmol) was added a solution of 4-(4-(2-((4-cyanopyridin-2-yl)amino)-6-(3,3-difluoropyrrolidin-1-yl)pyridin-4-yl)piperidin-1-yl)-4-oxobutanoic acid (27 mg, 0.056 mmol), HBTU (21 mg, 0.056 mmol), and N-methylmorpholine (13 μL, 0.112 mmol) in DMF and the reaction was agitated for 1 hour. The resin was then washed repeatedly with DMF, DCM, and diethyl ether.

The above resin was treated with a mixture of trifluoroacetic acid, triisopropylsilane, and water (95:2.5:2.5) for 2 hours. The resin was then filtered and the product was precipitated in anhydrous diethyl ether and centrifuged. The product was further purified by reverse phase HPLC using a Waters XBridge Prep C18 5 μm 19 mm×150 mm column in water (0.05% TFA with an increasing gradient of acetonitrile (0.05% TFA). The combined fractions were lyophilized to afford the product as a fluffy yellow solid. LCMS: 96.7% pure (254 nm). Calcd for $C_{53}H_{70}F_2N_{14}O_6^{2+}$ 534.3, found 534.4.

17

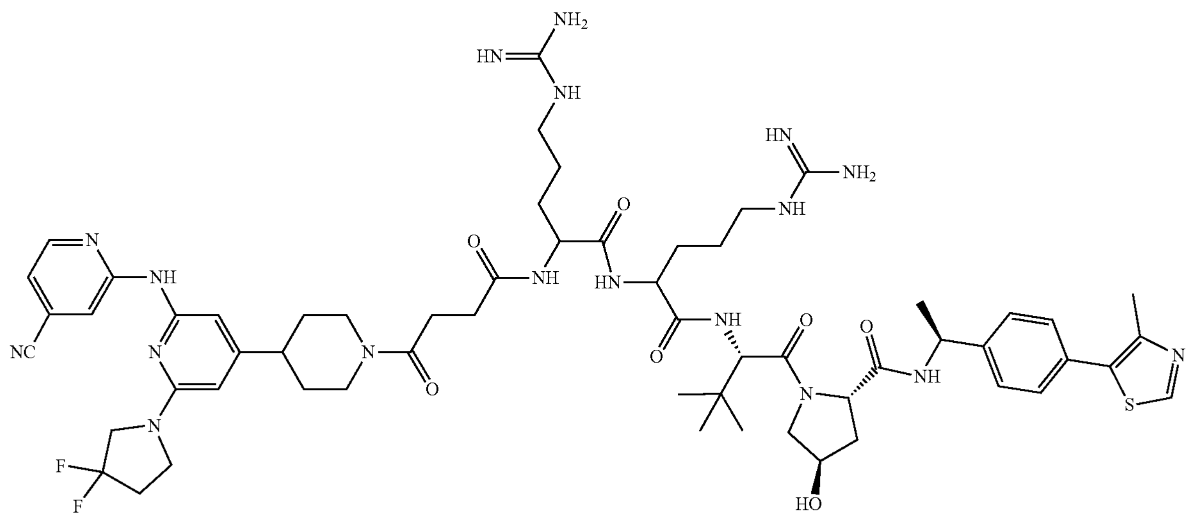

Compound 17. Prepared in a similar way to compound 16. LCMS: 95.8% pure (254 nm). Calcd for $C_{59}H_{52}F_2N_{18}O_7S^{2+}$ 612.3, found 612.5.
18
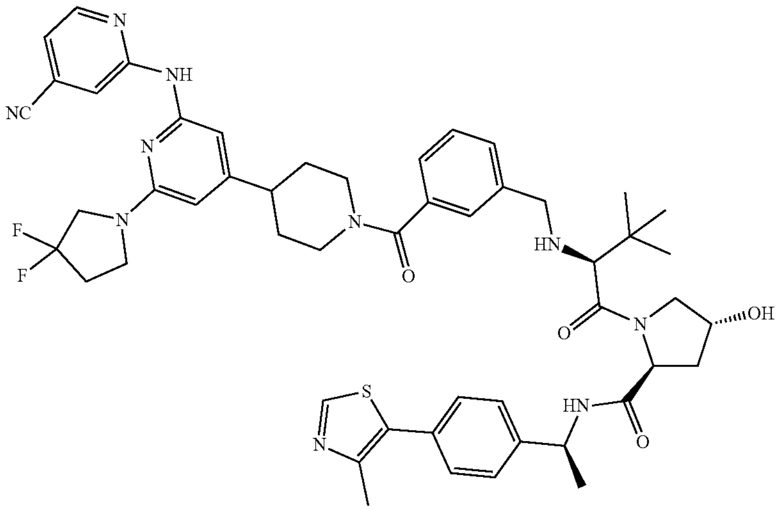
Compound 18. Prepared in same way as Compound 13 LCMS: 96.9% pure (254 nm). Calcd for $C_{51}H_{59}F_2N_{10}O_4S^+$ 945.4, found 945.5
19
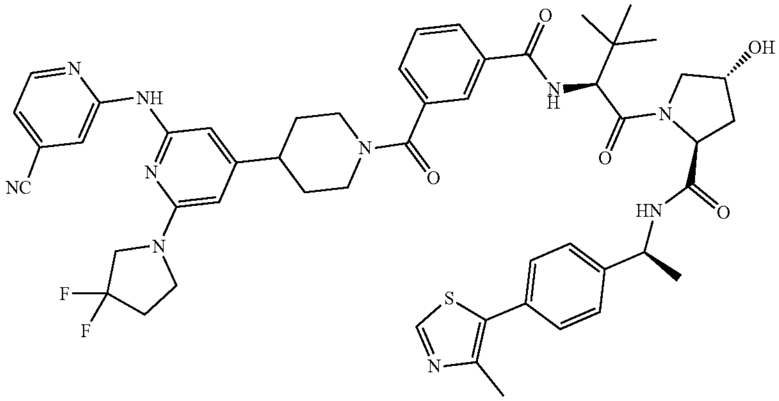

Compound 19. Prepared by General Method 1
LCMS: 97.5% pure (254 nm). Calcd for $C_{51}H_{57}F_2N_{10}O_5S^+$ 959.4, found 959.5
20
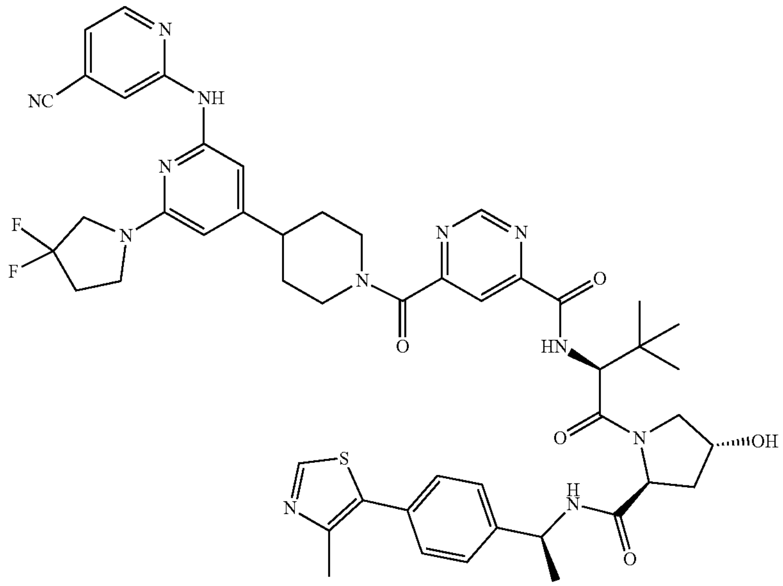
Compound 20. Prepared by General Method 1
LCMS: 97.0% pure (254 nm). Calcd for $C_{49}H_{55}F_2N_{12}O_5S^+$ 961.4, found 961.5.
21
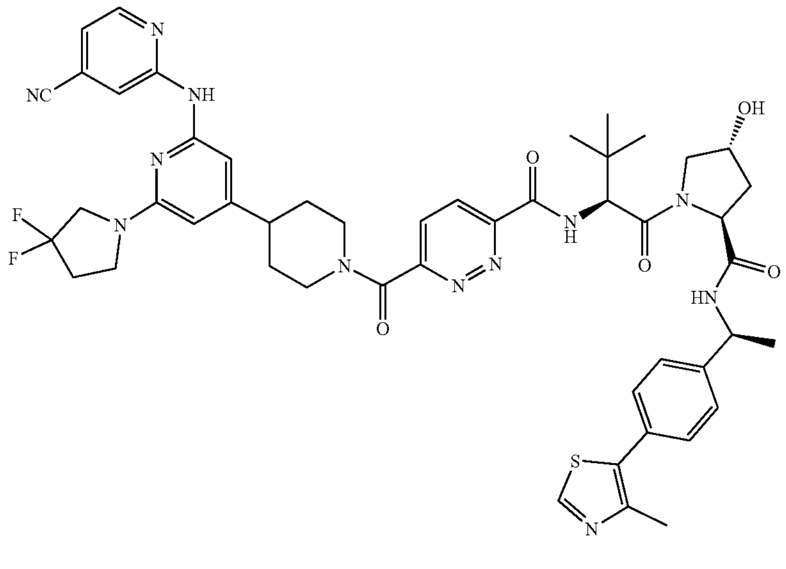

Compound 21. Prepared by General Method 1
LCMS: 99.4% pure (254 nm). Calcd for $C_{49}H_{55}F_2N_{12}O_5S^+$ 961.4, found 961.5
22
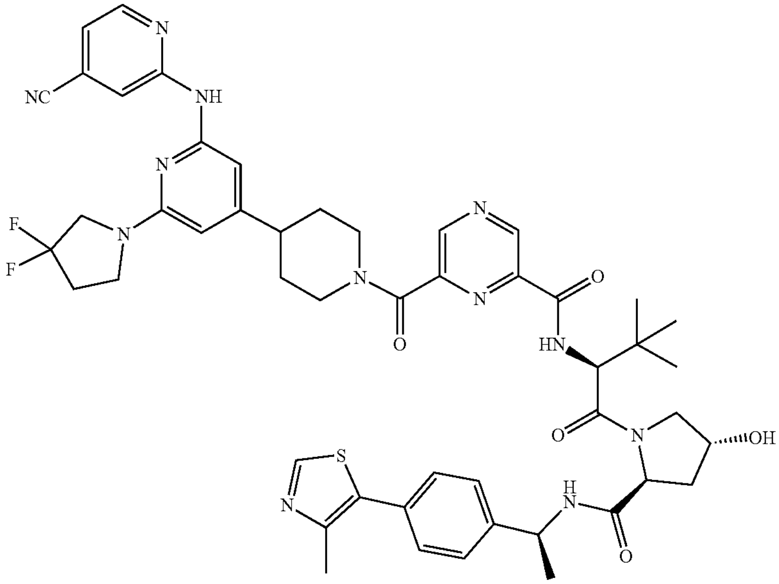
Compound 22. Prepared by General Method 1
LCMS: 96.7% pure (254 nm). Calcd for $C_{49}H_{55}F_2N_{12}O_5S^+$ 961.4, found 961.5
23
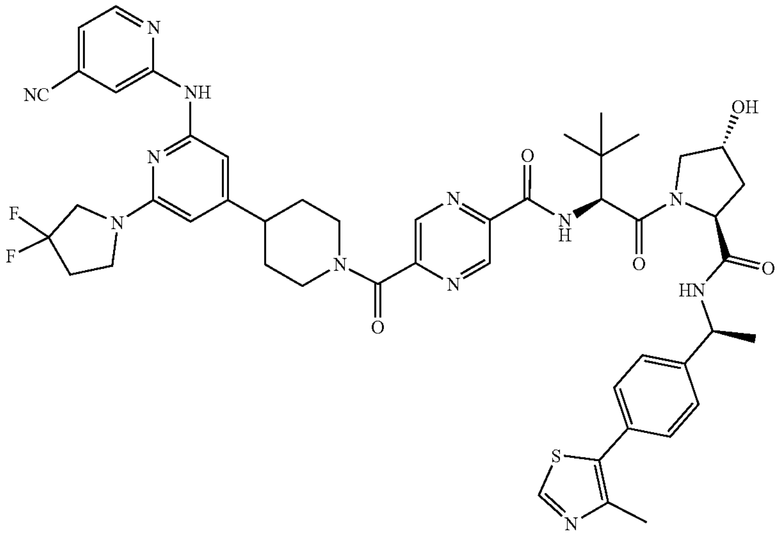

Compound 23. Prepared by General Method 1
LCMS: 95.6% pure (254 nm). Calcd for $C_{49}H_{55}F_2N_{12}O_5S^+$ 961.4, found 961.5.
24
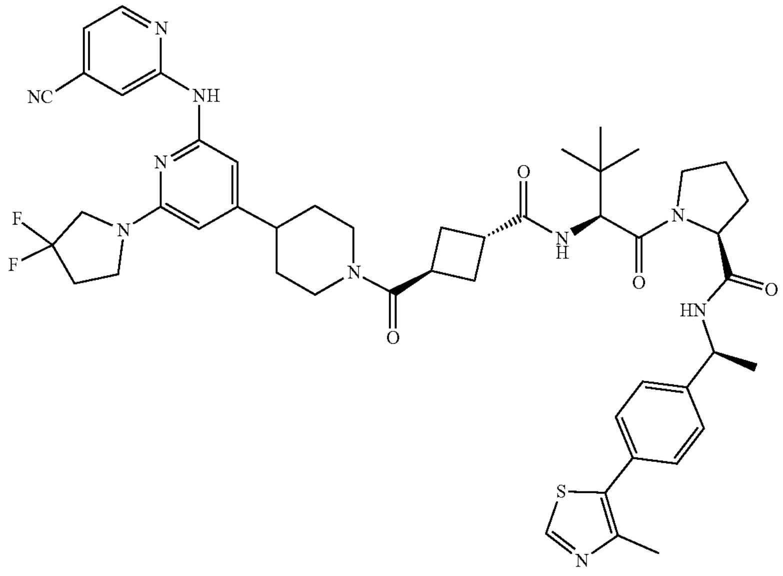
Compound 24. Prepared by General Method 1
LCMS: 98.4% pure (254 nm). Calcd for $C_{49}H_{59}F_2N_{10}O_5S^+$ 937.4, found 937.5.
25
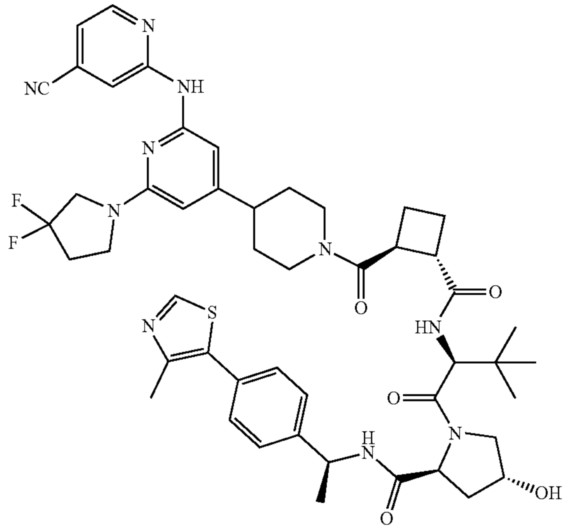
Compound 25. Prepared by General Method 1
LCMS: 98.0% pure (254 nm). Calcd for $C_{49}H_{59}F_2N_{10}O_5S^+$ 937.4, found 937.5.
26
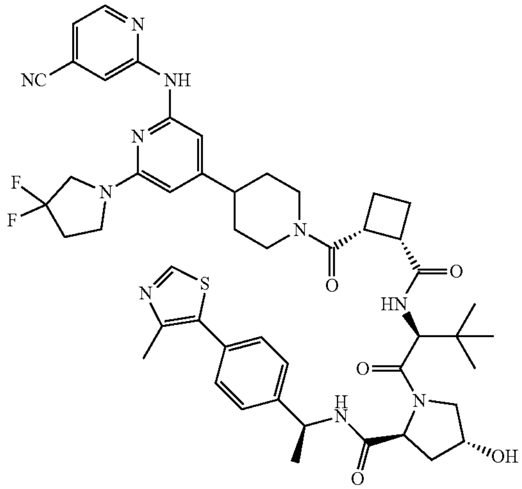

Compound 26. Prepared by General Method 1

LCMS: 98.0% pure (254 nm). Calcd for $C_{49}H_{59}F_2N_{10}O_5S^+$ 937.4, found 937.5.

27

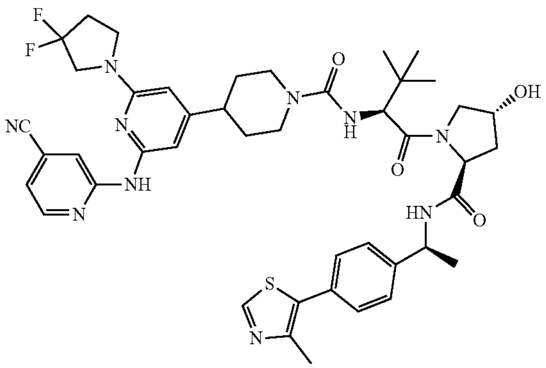

Compound 27. To a solution of 2-((6-(3,3-difluoropyrrolidin-1-yl)-4-(piperidin-4-yl)pyridin-2-yl)amino)isonicotinonitrile dioxalate salt in anhydrous dichloromethane (3 mL) was added triphosgene (37 mg, 0.079 mmol) under argon. Anhydrous diisopropylethylamine (54 μL, 0.48 mmol) was added. After 30 minutes was added (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (44 mg, 0.078 mmol) and anhydrous diisopropylethylamine (27 μL, 0.24 mmol) and the reaction was stirred for 1 hour under argon at room temperature. The reaction mixture was poured into water and extracted with dichloromethane. The combined organic extracts were washed with brine, dried over sodium sulfate, filtered, and concentrated in vacuo. The crude solid was dissolved in dichloromethane and loaded onto a silica cartridge and purified by flash chromatography 0 to 15% Methanol in dichloromethane to afford the product as a yellow solid.

The product was further purified by reverse phase HPLC using a Waters XBridge Prep C18 5 μm 19 mm×150 mm column in water (0.05% TFA with an increasing gradient of acetonitrile (0.05% TFA). The combined fractions were lyophilized to afford the product as a fluffy yellow solid.

LCMS: 99.1% pure (254 nm). Calcd for $C_{44}H_{53}F_2N_{10}O_4S^+$ 855.4, found 855.3.

28

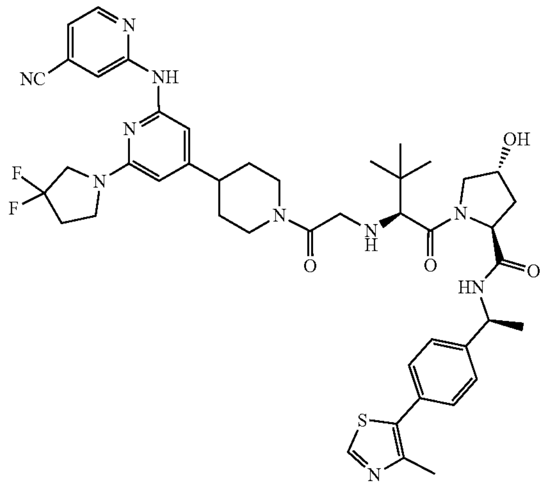

Compound 28. To a solution of chloroacetic acid (14 mg, 0.15 mmol, 1.7 eq) and N-methylmorpholine (0.02 mL, 0.18 mmol, 2 eq.) in DMF (1 mL) was added HATU (38 mg, 0.1 mmol, 1.1 eq). After 5 minutes this solution was added to a solution of 2-((6-(3,3-difluoropyrrolidin-1-yl)-4-(piperidin-4-yl)pyridin-2-yl)amino)isonicotinonitrile dioxalate salt (50 mg, 0.09 mmol, 1 eq.) and N-methylmorpholine (0.05 mL, 0.45 mmol, 5 eq.) in anhydrous DMF (1 mL). The reaction was stirred for 1 hour after which water was added. The reaction mixture was partitioned between water and dichloromethane and the aqueous layer was extracted with dichloromethane twice. The combined organic extracts were washed with saturated $NaHCO_3$ and brine. The organic layer was then dried over sodium sulfate, filtered, and concentrated in vacuo. The crude solid was dissolved in dichloromethane and loaded onto a silica cartridge and purified by flash chromatography 0 to 10% methanol in dichloromethane to afford the 2-chloroacetyl intermediate as a yellow solid. This intermediate (21 mg, 0.05 mmol, 1 eq.) was dissolved in acetonitrile (3 mL). To this solution was added (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (22 mg, 0.05 mmol, 1 eq.), potassium carbonate (31 mg, 0.22 mmol, 5 eq.), and potassium iodide (4 mg, 0.02 mmol, 0.5 eq.). The reaction was then stirred at 80° C. for 7 hours. The reaction mixture was cooled to room temperature, filtered, and concentrated. The crude was partitioned between water and dichloromethane. The organic layer was washed with brine, dried over sodium sulfate, filtered, and concentrated in vacuo. The crude solid was dissolved in dichloromethane and loaded onto a silica cartridge and purified by flash chromatography 0 to 10% methanol in dichloromethane to afford the product as a yellow solid. The product was further purified by reverse phase HPLC using a Waters XBridge Prep C18 5 μm 19 mm×150 mm column in water (0.05% TFA with an increasing gradient of acetonitrile (0.05% TFA). The combined fractions were lyophilized to afford the product as a fluffy yellow solid. LCMS: 94.0% pure (254 nm). Calcd for $C_{45}H_{55}F_2N_{10}O_4S^+$ 869.4, found 869.4.

29

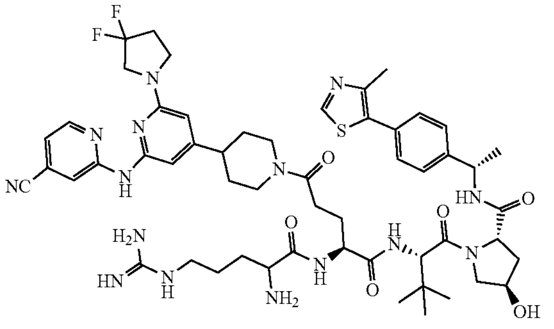

yl)amino)-6-(3,3-difluoropyrrolidin-1-yl)pyridin-4-yl)piperidin-1-yl)-5-oxopentanamido)-3,3-dimethylbutanoyl)-4-hydroxy-N—((S)-1-(4-(4-methylthiazol-5-yl)phenyl)ethyl)pyrrolidine-2-carboxamide (15 mg, 0.02 mmol) in DMF (1 mL) and the reaction was stirred for 1 hour. Water was added to the reaction mixture and extracted with ethyl acetate (3×20 mL). The combined organic extracts were washed with brine, dried over sodium sulfate, and concentrated. The crude solid was dissolved in dichloromethane and loaded onto a silica cartridge and purified by flash chromatography 0 to 20% methanol in dichloromethane to afford the product as a yellow solid. The product was further purified by reverse phase HPLC using a Waters XBridge Prep C18 5 μm 19 mm×150 mm column in water (0.05% TFA with an increasing gradient of acetonitrile (0.05% TFA). The combined fractions were lyophilized to afford the product as a fluffy yellow solid. LCMS: 97.4% pure (254 nm). Calcd for $C_{54}H_{72}F_2N_{15}O_6S^+$ 1096.6 found 1096.4.

Compound 29. HATU (86 mg, 0.23 mmol) was added to a solution of Fmoc-L-glutamic acid 5-tert-butyl ester (96 mg, 0.23 mmol) and N-methylmorpholine (52 μL, 0.46 mmol) in DMF and the mixture was stirred for 5 mins. The activated acid was then added to a solution of (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (100 mg, 0.21 mmol)N-methylmorpholine (76 μL, 0.68 mmol) in DMF and the reaction was stirred for 1 hour at room temperature. After 1 hour water and ethyl acetate was added and the ethyl acetate layer was washed with water, sodium bicarbonate, and brine. The organic layer was then dried over sodium sulfate, filtered, and concentrated. The crude solid was then treated with 5 mL TFA/DCM (1:1) and the reaction was stirred for 1 hour and then concentrated. The crude solid was dissolved in DMF (2 mL) and N-methylmorpholine was added (67 μL, 0.60 mmol), followed by HATU (76 mg, 0.23 mmol). To this solution was added a solution of 2-((6-(3,3-Difluoropyrrolidin-1-yl)-4-(piperidin-4-yl)pyridin-2-yl)amino)isonicotinonitrile oxalic acid salt (98 mg, 0.23 mmol), N-methylmorpholine (112 μL, 1.0 mmol) in DMF (1 mL). After 1 hour water was added to the reaction mixture and extracted with ethyl acetate (3×20 mL). The combined organic extracts were washed with brine, dried over sodium sulfate, and concentrated. The crude solid was dissolved in dichloromethane and loaded onto a silica cartridge and purified by flash chromatography 0 to 10% methanol in dichloromethane to afford 69 mg of a yellow solid. This solid (0.06 mmol) was dissolved in acetonitrile (5 mL) and THF (1 mL) and diethylamine was added (183 μL, 1.77 mmol) and stirred overnight. The reaction was then concentrated, re-dissolved in acetonitrile/water (9:1) and washed with hexane three times to afford the deprotected amine (52 mg, 0.06 mmol). To a solution of Fmoc-Arg(Boc)$_2$-OH (14 mg (0.02 mmol) and N-methylmorpholine (10 μL, 0.09 mmol) in DMF (1 mL) was added HATU (8 mg, 0.02 mmol) and the mixture was stirred for 5 minutes. This mixture was then added to a solution of (2S,4R)-1-((S)-2-((S)-2-amino-5-(4-(2-((4-cyanopyridin-2-

32

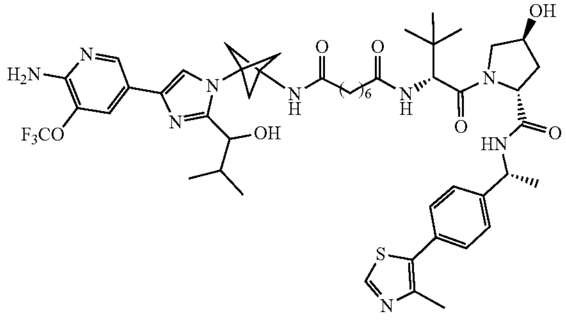

Compound 32. $^1$H NMR (400 MHz, dmso) δ 8.97 (s, 1H), 8.63 (s, 1H), 8.43 (d, J=2.0 Hz, 1H), 8.35 (d, J=7.8 Hz, 1H), 8.07 (s, 1H), 8.00 (t, J=1.8 Hz, 1H), 7.76 (d, J=9.3 Hz, 1H), 7.51-7.23 (m, 4H), 4.90 (t, J=7.2 Hz, 1H), 4.68 (d, J=7.1 Hz, 1H), 4.50 (d, J=9.3 Hz, 1H), 4.40 (t, J=8.0 Hz, 1H), 4.26 (s, 1H), 3.59 (d, J=4.5 Hz, 2H), 2.75-2.56 (m, 6H), 2.43 (s, 3H), 2.23 (dt, J=14.7, 7.7 Hz, 1H), 2.15-1.95 (m, 4H), 1.78 (ddd, J=12.9, 8.5, 4.7 Hz, 1H), 1.46 (s, 6H), 1.36 (d, J=7.0 Hz, 3H), 1.23 (d, J=7.3 Hz, 5H), 1.00 (d, J=6.6 Hz, 3H), 0.92 (s, 9H), 0.82 (d, J=6.7 Hz, 3H). $^{13}$C NMR (101 MHz, dmso) δ 173.54, 172.47, 171.06, 170.06, 153.44, 151.95, 151.92, 150.20, 148.18, 145.10, 131.56, 130.24, 130.13, 129.27, 126.83, 126.71, 122.22, 119.65, 118.11, 116.97, 115.18, 110.00, 69.20, 59.00, 56.79, 56.70, 56.39, 49.02, 48.14, 44.02, 38.19, 35.83, 35.64, 35.34, 33.93, 28.92, 28.90, 26.90, 25.78, 25.31, 22.86, 19.14, 18.00, 16.41. $^{19}$F NMR (376 MHz, dmso) δ−57.10. LC-MS: 980.200.

31

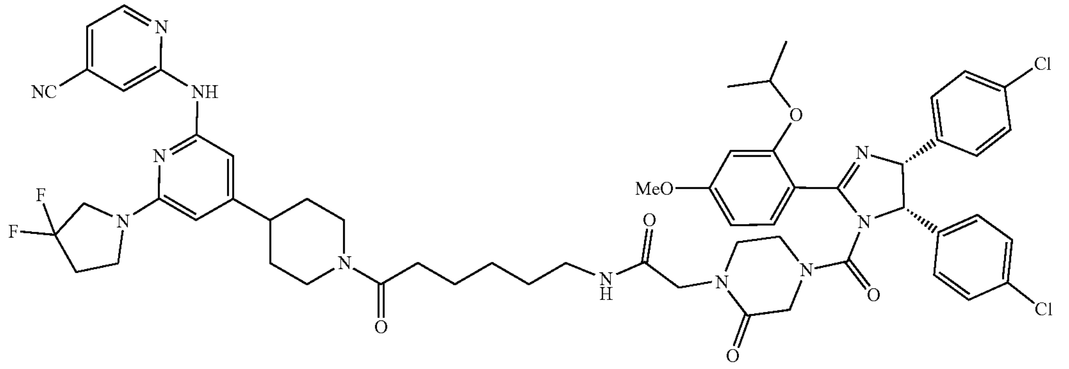

Compound 31. LCMS: 99.2% pure (254 nm). Calcd for $C_{58}H_{64}Cl_2F_2N_{11}O_6^+$ 1118.4, found 1118.

33

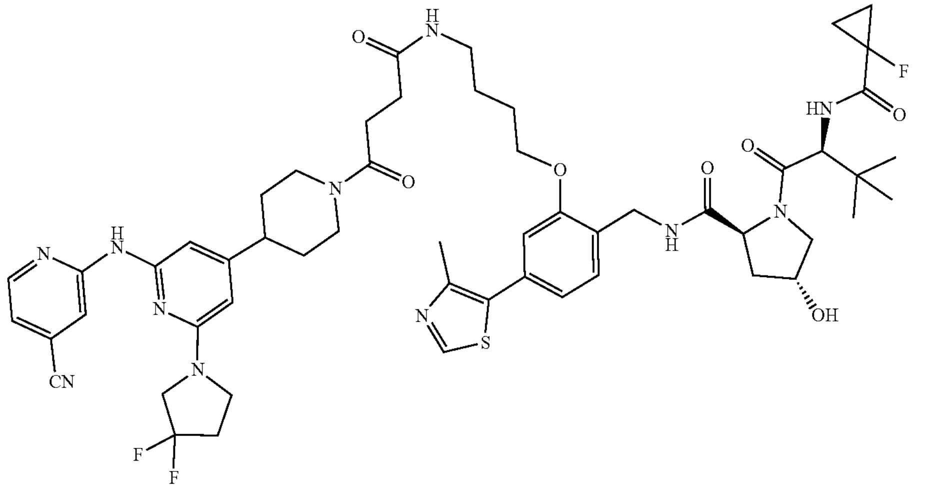

Compound 33. To a solution of 4-(4-(2-((4-cyanopyridin-2-yl)amino)-6-(3,3-difluoropyrrolidin-1-yl)pyridin-4-yl)piperidin-1-yl)-4-oxobutanoic acid (13 mg, 0.027 mmol) and N-methylmorpholine (12 μL, 0.11 mmol) in DMF (1.5 mL) was added HATU (10 mg, 0.026 mmol) and the reaction was stirred for 5 minutes. To this reaction mixture was added (2S,4R)—N-(2-(4-Aminobutoxy)-4-(4-methltihiazol-5-yl)benzyl)-1-((S)-2-(1-fluorocyclopropane-1-carboxamido)-3,3-dimethylbutanoyl)-4-hydroxypyrrolidine-2-carboxamide dihydrochloride (12 mg, 0.017 mmol) and the reaction was stirred for 1 hour. Dichloromethane and water was then added and the dichloromethane layer was washed with saturated sodium bicarbonate, brine, dried over sodium sulfate, filtered, and, concentrated. The crude solid was dissolved in dichloromethane and loaded onto a silica cartridge and purified by flash chromatography 0 to 25% methanol in dichloromethane to afford the product as a yellow solid. The product was further purified by reverse phase HPLC using a Waters XBridge Prep C18 5 μm 19 mm×150 mm column in water (0.05% TFA with an increasing gradient of acetonitrile (0.05% TFA). The combined fractions were lyophilized to afford the product as a fluffy yellow. LCMS: 97.4% pure (254 nm). Calcd for $C_{54}H_{72}F_2N_{15}O_6S^+$ 1096.6 found 1096.4.

34

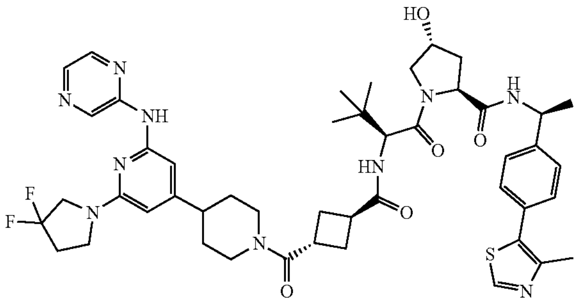

Compound 34. LCMS: 100% pure (254 nm). Calcd for $C_{47}H_{59}F_2N_{10}O_5S^+$ 913.4, found 913.2.

35
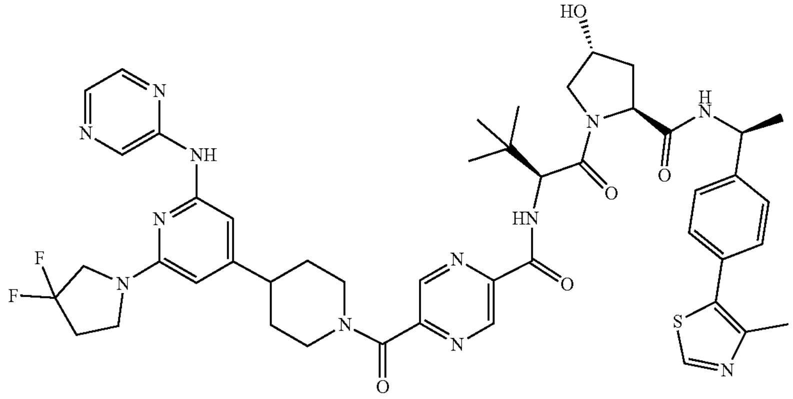
Compound 35. LCMS: 100% pure (254 nm). Calcd for $C_{47}H_{55}F_2N_{12}O_5S^+$ 937.4, found 937.2.
36
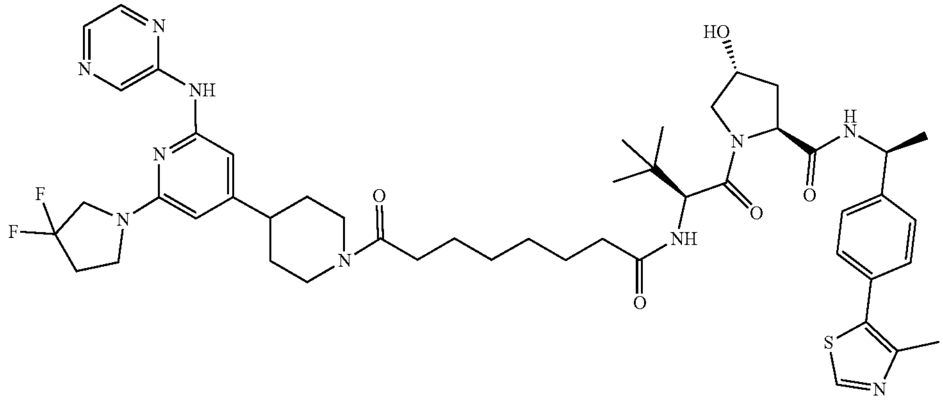
Compound 36. LCMS: 99.7% pure (254 nm). Calcd for $C_{49}H_{65}F_2N_{10}O_5S^+$ 943.5, found 943.2.
37
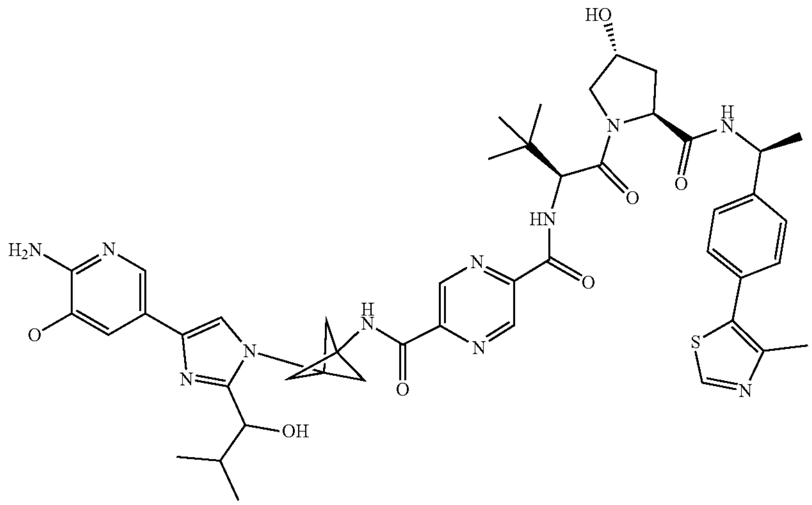

Compound 37 LCMS 100% pure (254 m) Calcd for $C_{47}H_{65}F_2N_{10}O_5S^+$ 943.5, found 943.2.
38
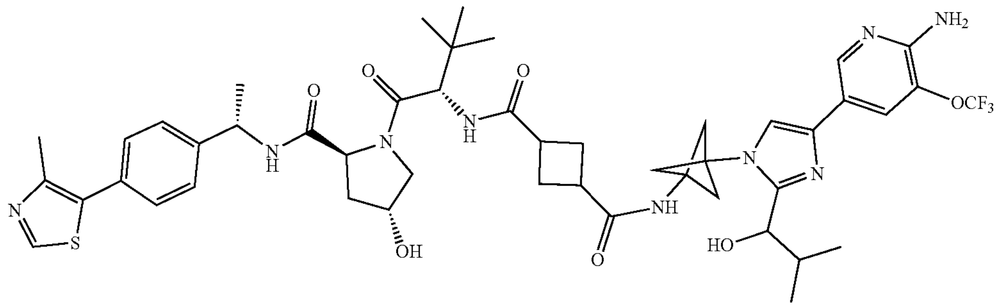
Compound 38. $^1$H NMR (400 MHz, dmso) δ 8.97 (s, 1H), 8.57 (s, 1H), 8.42 (d, J=2.0 Hz, 1H), 8.35 (d, J=7.8 Hz, 1H), 7.98 (d, J=12.8 Hz, 2H), 7.72 (d, J=9.2 Hz, 1H), 7.56-7.31 (m, 4H), 4.90 (q, J=7.1 Hz, 1H), 4.62 (s, 1H), 4.50 (d, J=9.2 Hz, 1H), 4.40 (t, J=8.1 Hz, 1H), 4.27 (s, 1H), 3.16 (t, J=7.4 Hz, 1H), 2.99 (q, J=8.1 Hz, 1H), 2.77-2.54 (m, 6H), 2.44 (s, 3H), 2.34-1.92 (m, 6H), 1.77 (ddd, J=16.8, 8.5, 4.2 Hz, 1H), 1.35 (d, J=7.0 Hz, 3H), 1.22 (s, 2H), 1.00 (d, J=6.6 Hz, 3H), 0.92 (s, 9H), 0.82 (d, J=6.8 Hz, 3H). $^{19}$F NMR (376 MHz, dmso) 6-57.06. LC-MS: 950.200.
39
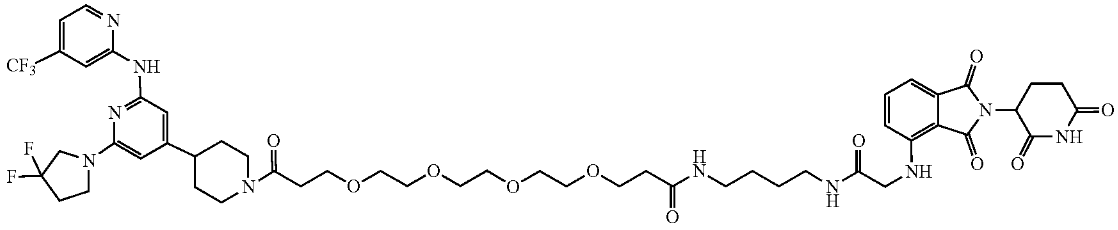
Compound 39. LCMS: 95.5% pure (280 nm). Calcd for $C_{51}H_{64}F_5N_{10}O_{11}^+$ 1087.5, found 1087.5.
40
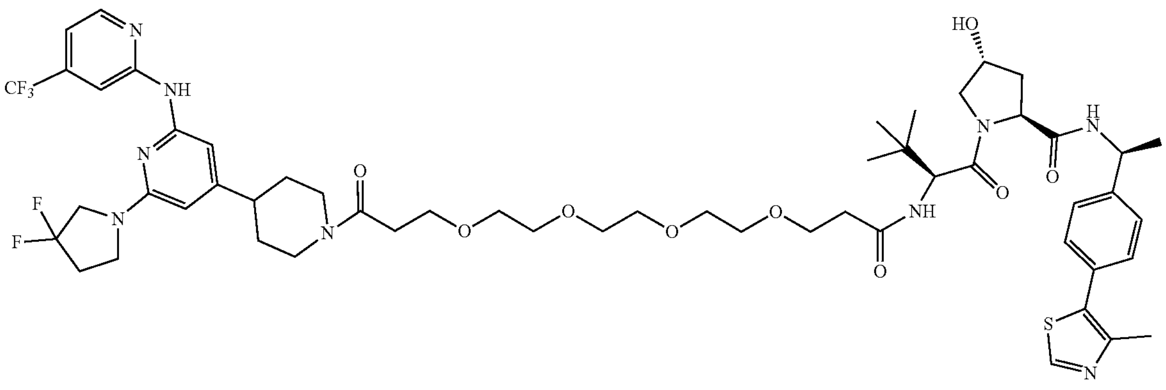
Compound 40. LCMS: 95.2% pure (280 nm). Calcd for $C_{55}H_{73}F_5N_9O_9S^+$ 1130.5, found 1130.5.

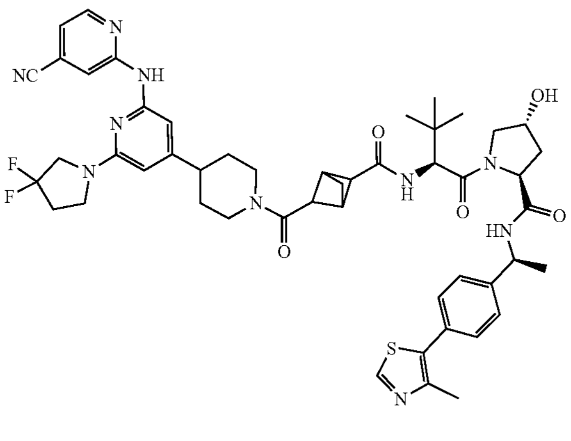

Compound 45. LCMS: >99% pure (254 nm). Calcd for $C_{50}H_{59}F_2N_{10}O_5S^+$ 949.4, found 949.2.

Compound 47. LCMS: >99% pure (254 nm). Calcd for $C_{48}H_{57}F_2N_{10}O_5S^+$ 923.4, found 923.2.

Example 2

LZK Inhibition in Squamous Cell Carcinomas with the 3q Amplicon

Figure 5:
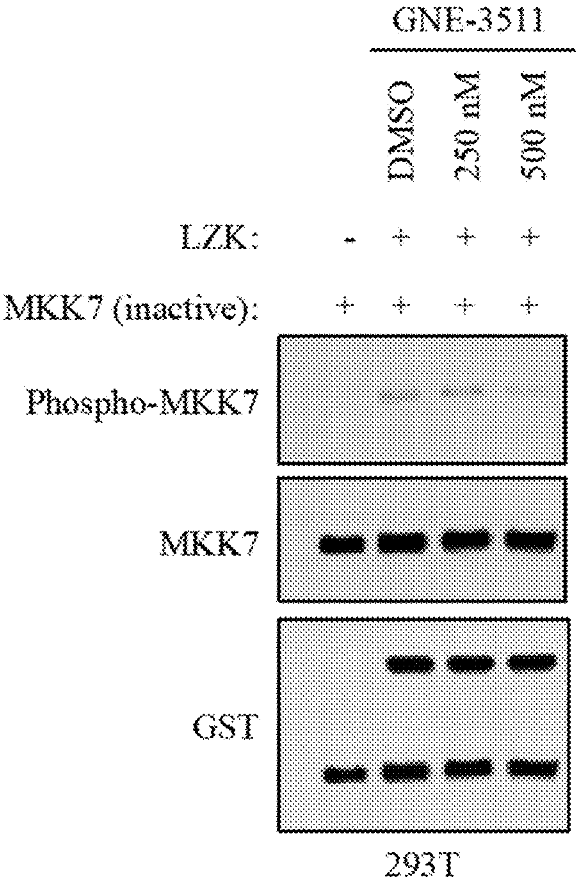
FIG. 5 shows that GNE-3511 decreased in vitro phosphorylation of MKK7, a direct downstream target of LZK.

A dual leucine zipper kinase (DLK) inhibitor, GNE-3511, was evaluated for inhibition of LZK catalytic activity. LZK and DLK have greater than 90% homology within their kinase domains, and GNE-3511 was also reported to inhibit the catalytic activity of LZK (Patel et al., *J Med Chem* 2015, 58:401-418). To verify that GNE-3511 (FIG. 1), would inhibit LZK catalytic activity in cells, expression of doxycycline (dox)-inducible LZK was induced in the 3q amplicon-positive CAL33 HNSCC cell line. GNE-3511 is a potent LZK inhibitor in cells, as measured by inhibition of downstream JNK pathway activation (FIGS. 2A-B, 3, 4). Similar results were observed in vitro (FIG. 5).

Treatment of HNSCC cells harboring amplified MAP3K13 (CAL33 and BICR56) with 200 nM of GNE-3511 resulted in an 80% or greater reduction in colony formation, phenocopying results observed when LZK was

46

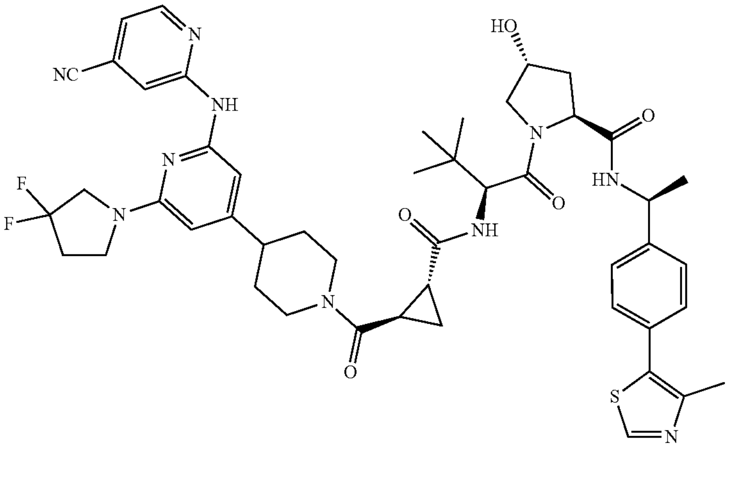

Compound 46. LCMS: >99% pure (254 nm). Calcd Chemical Formula: $C_{48}H_{57}F_2N_{10}O_5S^+$ 923.4, found 923.2.

47

Figure 6B:
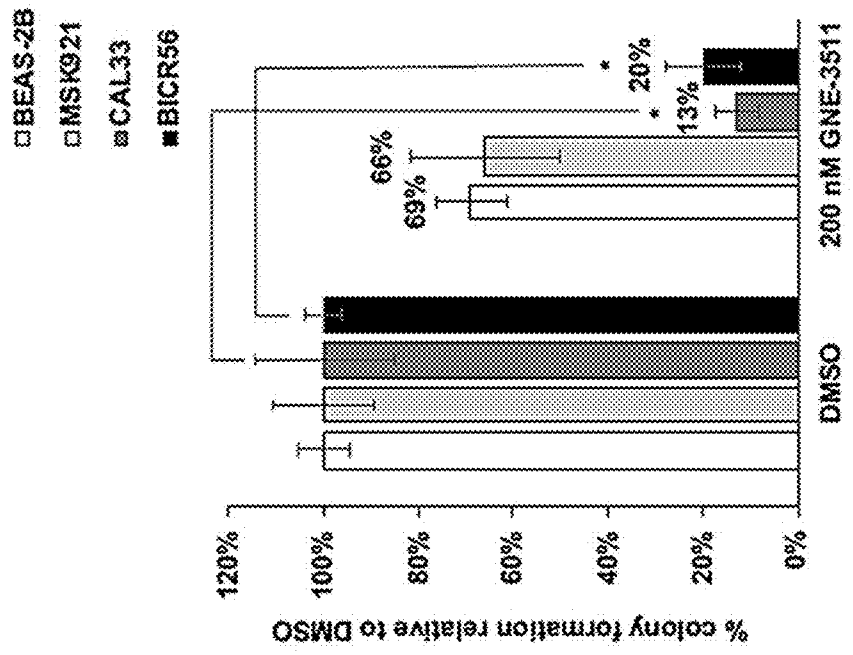
FIGS. 6A and 6B are a series of images (6A) and a bar graph (6B) showing that GNE-3511 suppressed clonogenic growth after 14 days in head and neck squamous cell carcinoma (HNSCC) cell lines with amplified MAP3K13 (CAL33 and BICR56) with only mild effects on clonogenic growth in the control HNSCC cell line (MSK921) or the immortalized normal human bronchial epithelial cell line (BEAS-2B).
Figure 6A:
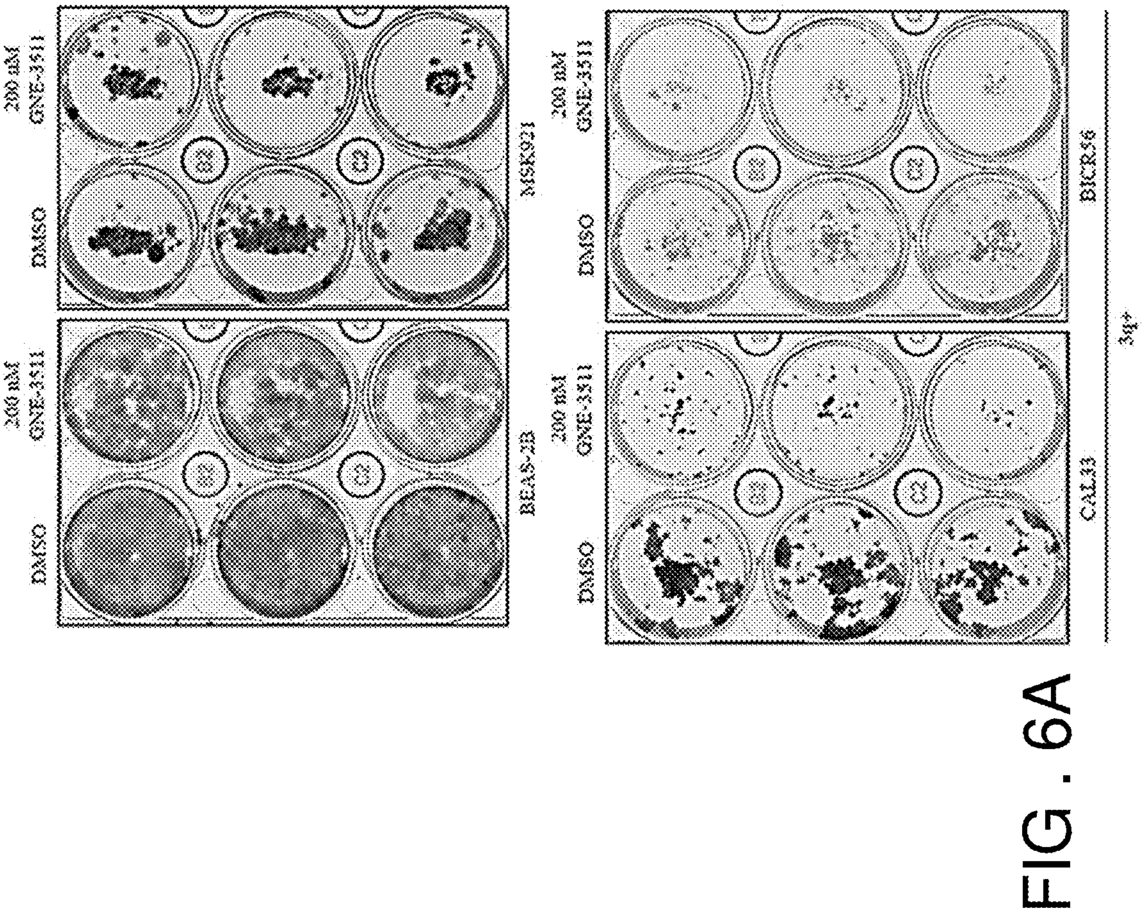

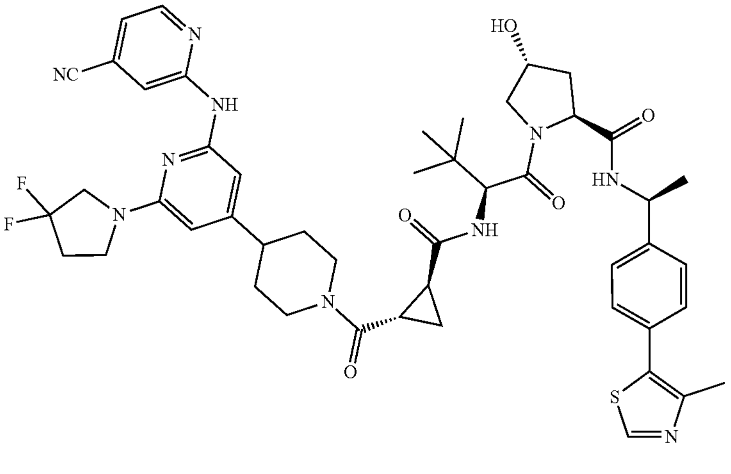

depleted from these cells (Edwards et al., *Cancer Res* 2017, 77:4961-4972), while there was only a minor reduction in colony formation in cells lacking amplified MAP3K13 (BEAS-2B and MSK921) (FIGS. 6A and 6B). Quantification reveals a significant decrease in growth in the CAL33 and BICR56 cell lines. *p<0.05, Student's t-test.

Figure 7B:
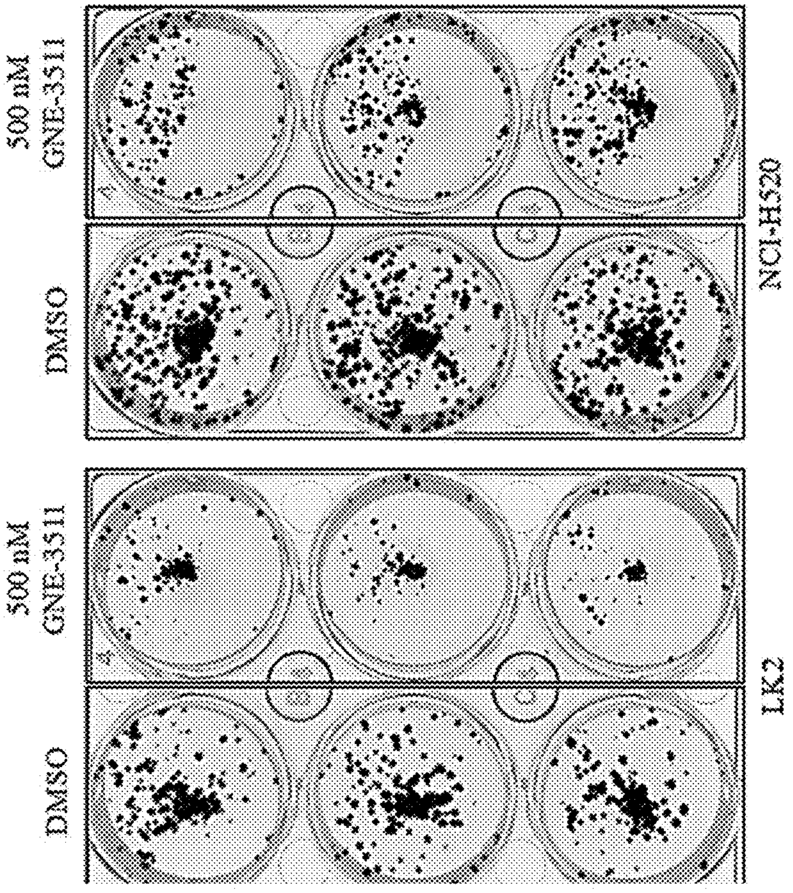
FIGS. 7A and 7B are a bar graph (7A) and images (7B) showing that LZK inhibition with GNE-3511 at 500 nM reduced clonogenic growth of lung squamous cell carcinoma (LSCC) cell lines with 3q amplification (LK2 and NCI-H520).
Figure 7A:
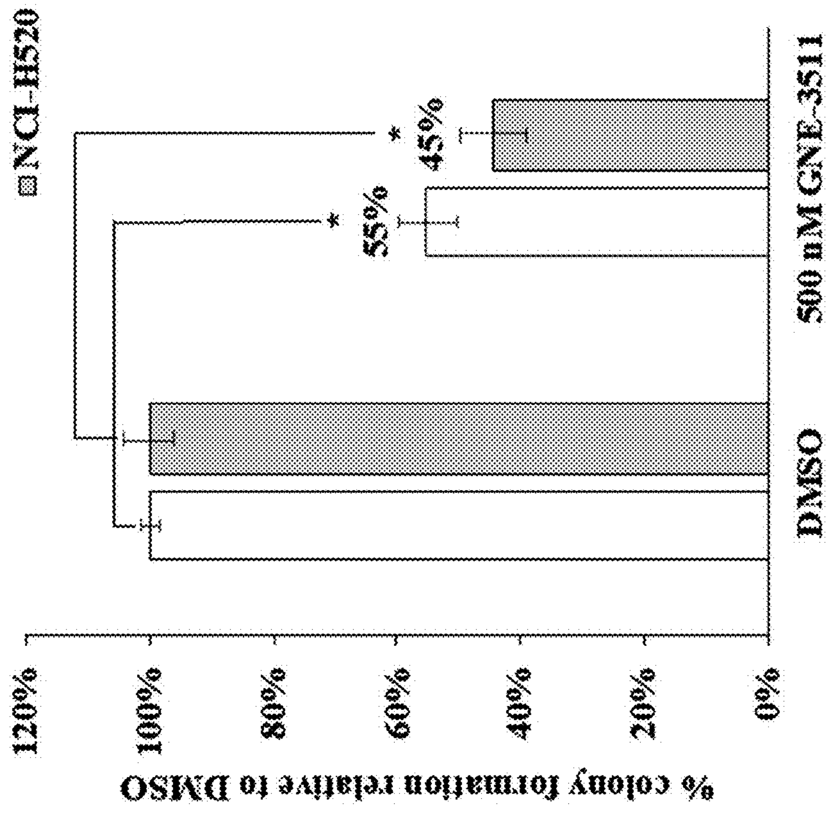
Figure 8:
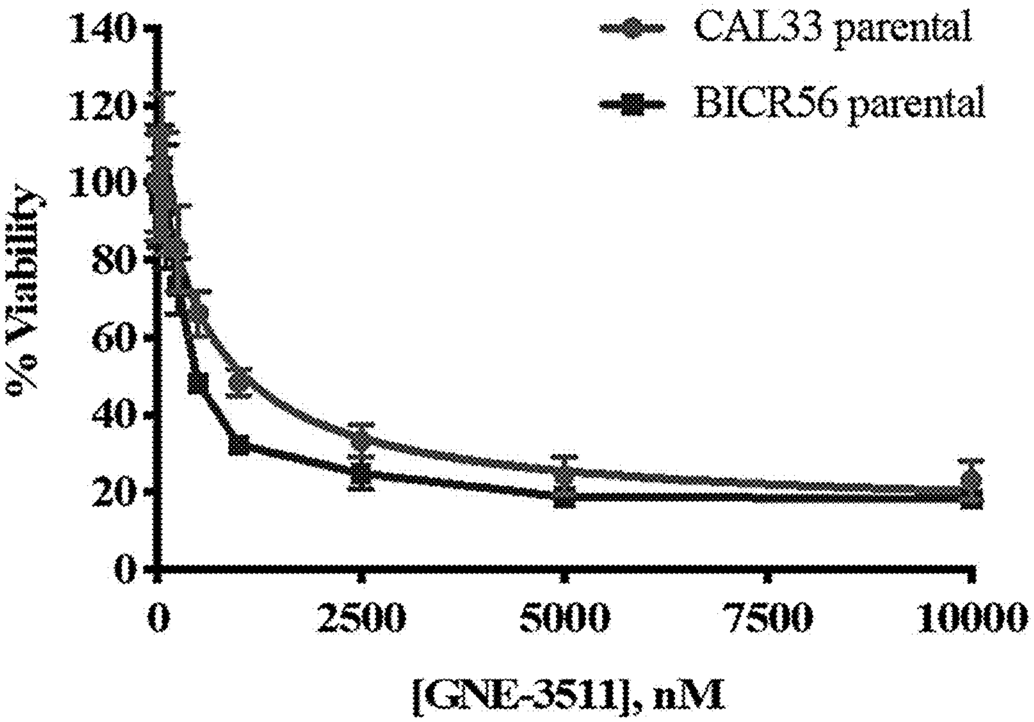
FIG. 8 is a graph showing that GNE-3511 treatment significantly reduced cell viability in CAL33 and BICR56 cells for 72 hours.

To determine whether other squamous cell carcinomas harboring the 3q amplicon are sensitive to LZK inhibition, LK2 and NCI-H520 lung squamous cell carcinoma (LSCC) cells were treated with 500 nM GNE-3511. A 45% and 55% reduction in colony formation was observed, respectively, which indicates that additional squamous cell carcinomas rely upon LZK to maintain viability (FIG. 7). A significant decrease in viability in the CAL33 and BICR56 cells in short-term MTS assays was also observed, with an $IC_{50}$ of 687.7±114.1 nM and 410.5±59.6 nM, respectively (FIG. 8). $IC_{50}$ values were calculated with GraphPad Prism 8.

Figure 9:
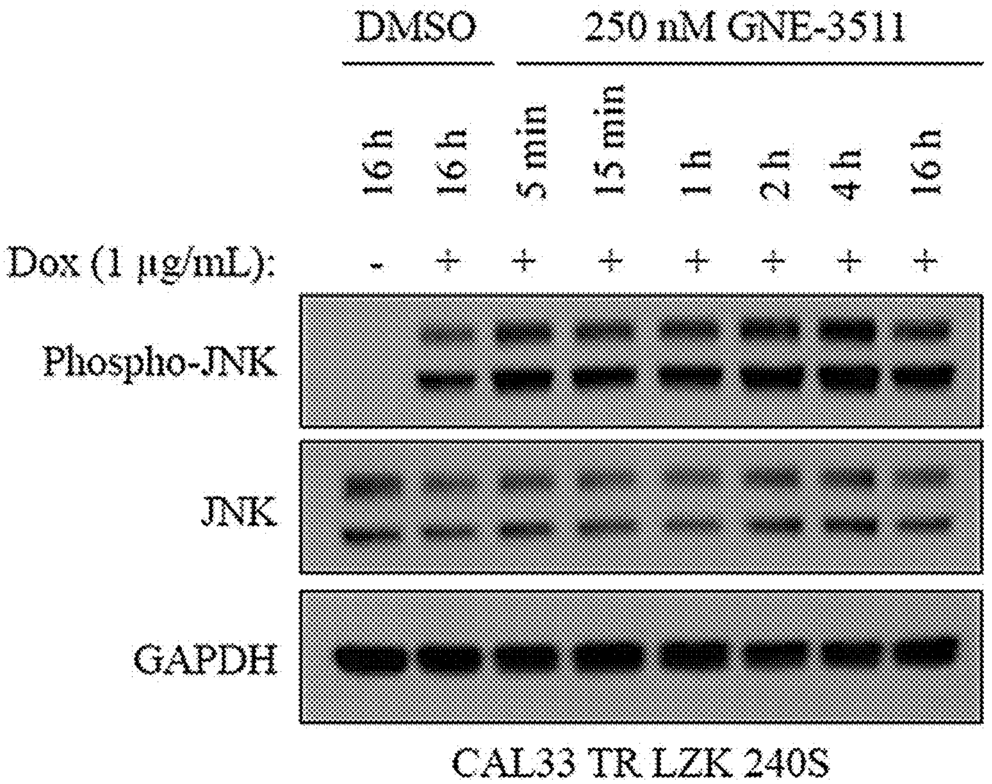
FIG. 9 shows that a drug-resistant mutant form of LZK, Q240S, maintained catalytic activity in the presence of GNE-3511, as assessed by downstream JNK phosphorylation.
Figure 10:
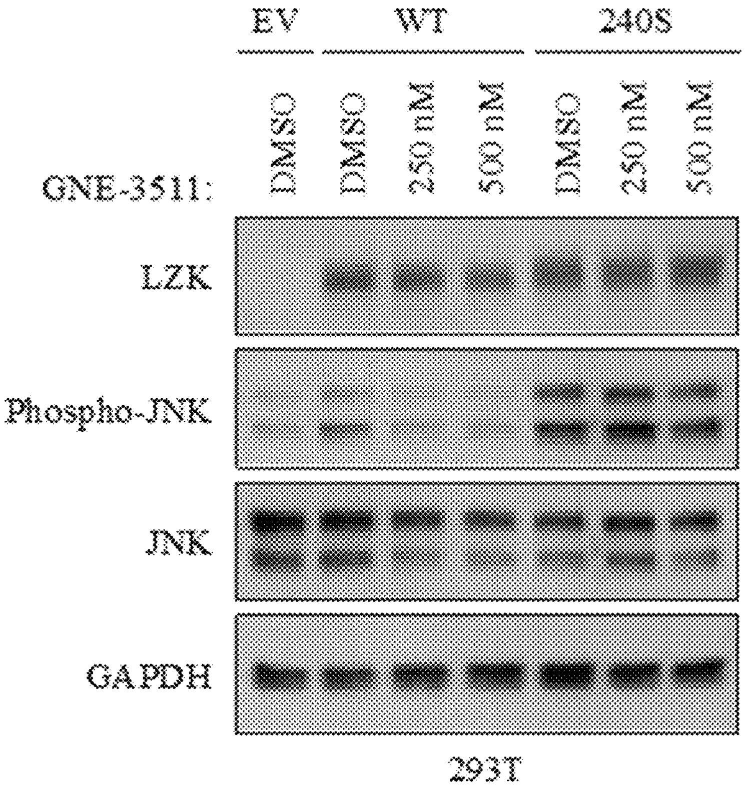
FIG. 10 shows that one-hour GNE-3511 treatment specifically inhibited LZK activity, as observed with the rescue of JNK signaling by the overexpression of the $LZK^{Q240S}$ drug-resistant mutant in 293T cells.
Figure 11:
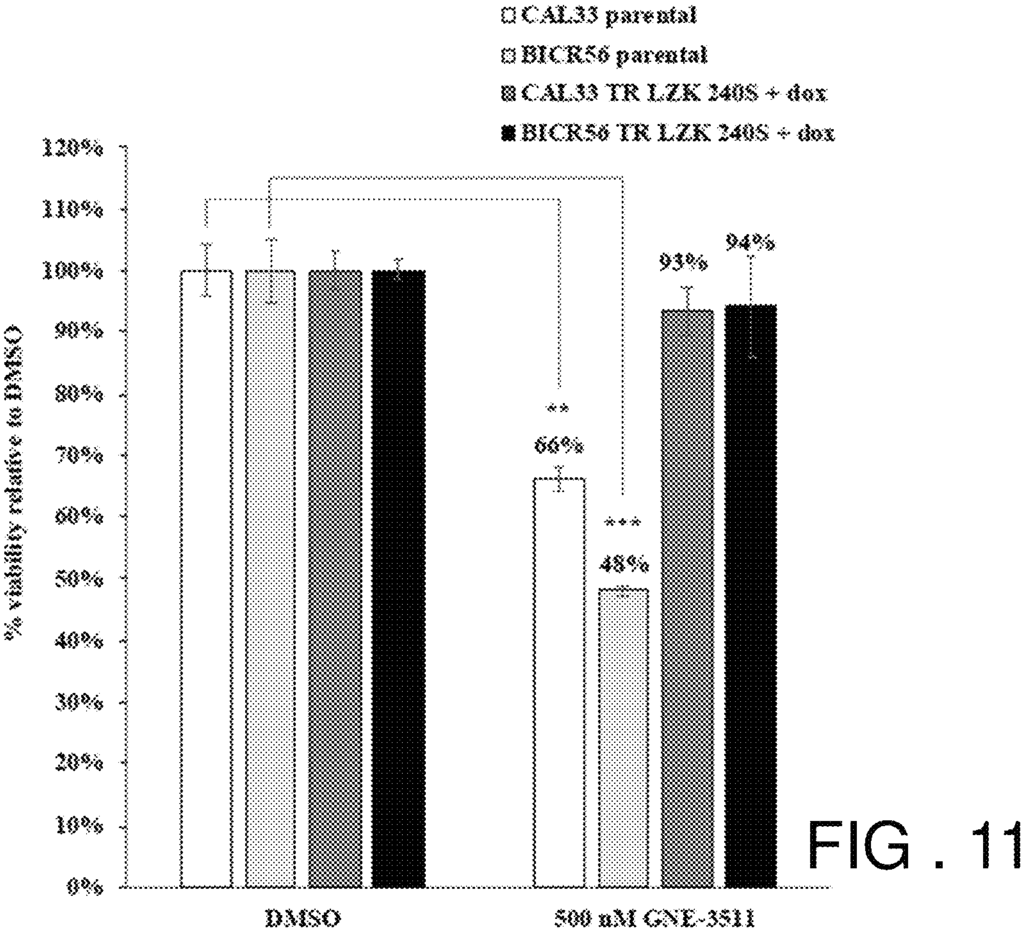
FIG. 11 shows that GNE-3511 suppressed HNSCC viability in a 72-hour MTS assay in CAL33 and BICR56 cell lines that harbor amplified MAP3K13 and viability was rescued by expression of $LZK^{Q240S}$.

Kinase inhibitors are promiscuous compounds that will often target additional kinases, and GNE-3511 was initially developed as a DLK inhibitor. To validate that the drug-induced toxicity was specifically due to LZK inhibition, a drug-resistant mutant form of LZK (Q240S) was generated that maintains catalytic activity in the presence of the drug, as assessed by JNK pathway activation (FIGS. 9, 10). As shown in FIG. 9, Q240S maintains catalytic activity in the presence of GNE-3511, as assessed by downstream JNK phosphorylation. FIG. 10 shows that one-hour GNE-3511 treatment specifically inhibits LZK, as observed with the rescue of JNK signaling by the overexpression of the $LZK^{Q240S}$ drug-resistant mutant in 293T cells. Expression of $LZK^{Q240S}$ in CAL33 and BICR56 cells resulted in an almost complete rescue of GNE-3511-induced toxicity, indicating that GNE-3511 suppresses HNSCC cell viability specifically through LZK inhibition, and confirming LZK as a drug target in HNSCC (FIG. 11; *p<0.001, p<0.01, Student's t-test).

Figure 12A:
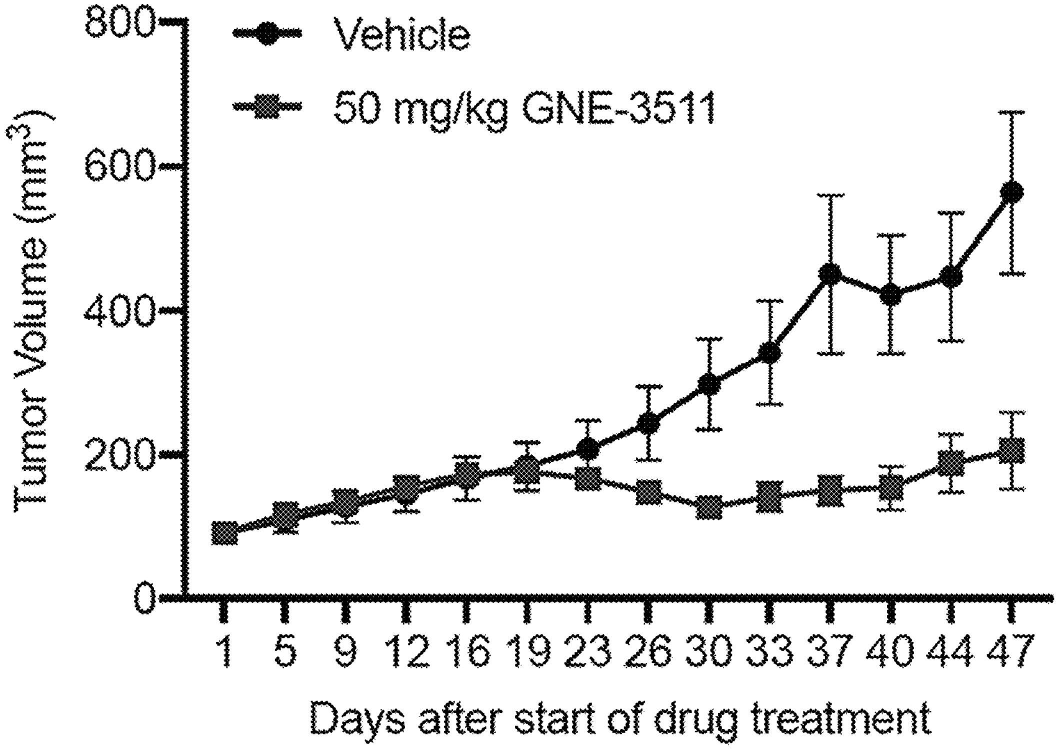
FIGS. 12A-12C show suppression of tumor growth in mice (n=10) treated with GNE-3511 (50 mg/kg, q.d., five days on/two days off) compared to the vehicle control group in an in vivo HNSCC PDX mouse model with amplified LZK.
Figure 12B:
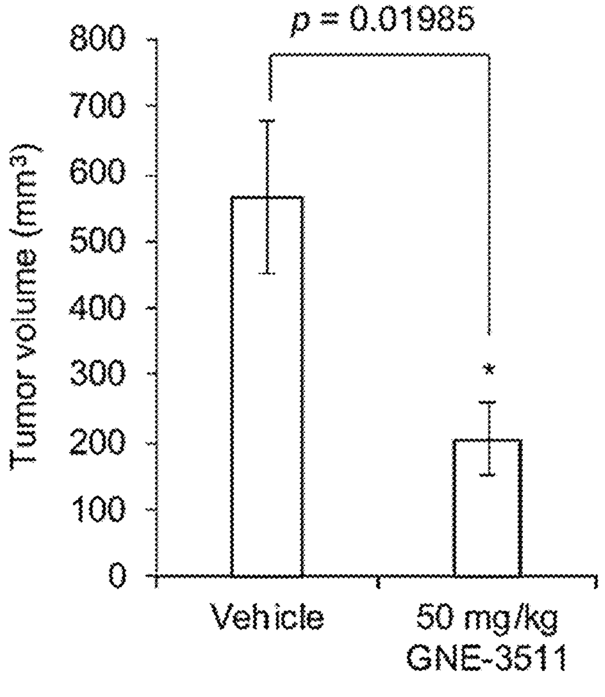
Figure 12C:
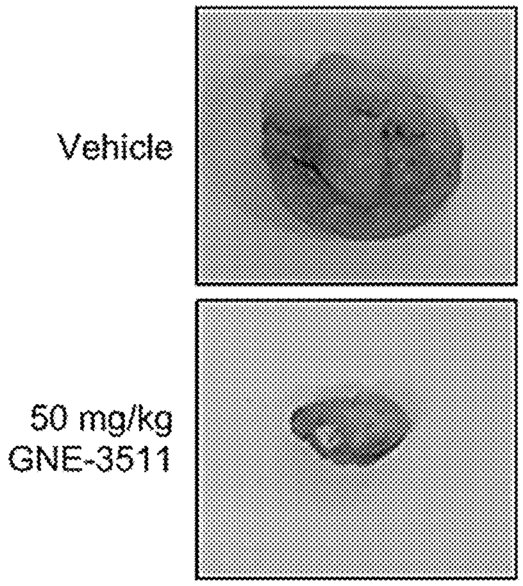
Figure 13:
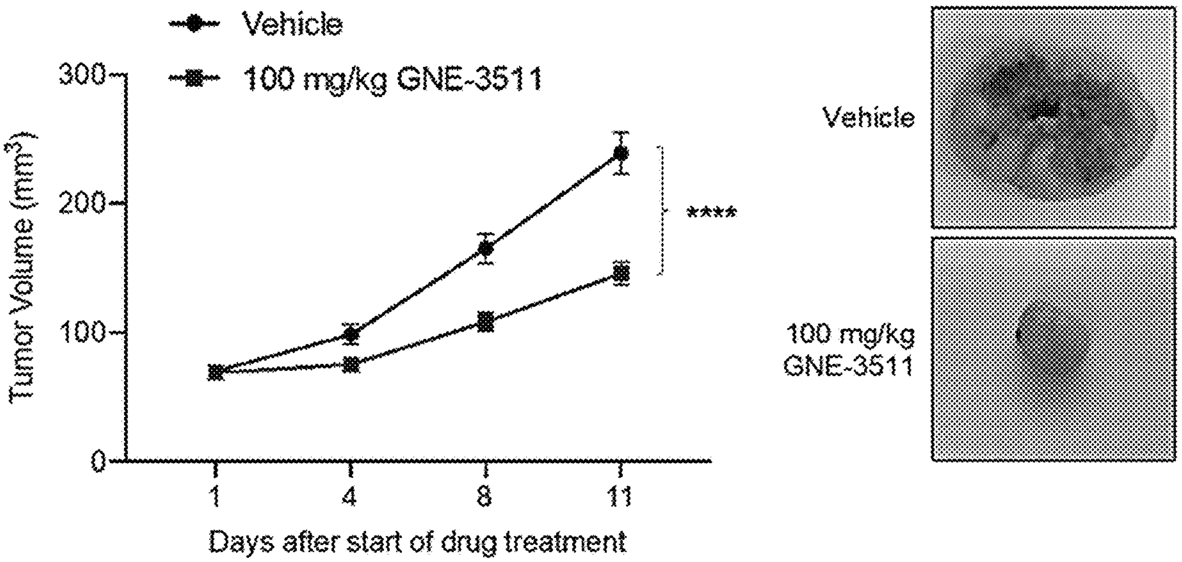
FIG. 13 shows that tumor growth was suppressed in mice (n=10) treated with 100 mg/kg GNE-3511 (100 mg/kg, b.i.d., five days on/two days off) compared to the vehicle control group in an in vivo HNSCC CAL33 xenograft mouse model; the graph represents the mean tumor volumes SEM; the pictures are tumor images at the end of the study.

Evaluation of GNE-3511 in a patient-derived xenograft mouse model of 3q-amplified HNSCC demonstrated that 50 mg/kg GNE-3511 can significantly suppress HNSCC tumor growth in vivo with almost complete tumor regression and no detectable tumors in 3 mice (FIGS. 12A-12C; **p<0.0001, two-way ANOVA.). Similar results were observed with 100 mg/kg GNE-3511 treatment in a CAL33-based xenograft mouse model of HNSCC (FIG. 13; mean±SEM, **p<0.0001, two-way ANOVA).

Figure 14A:
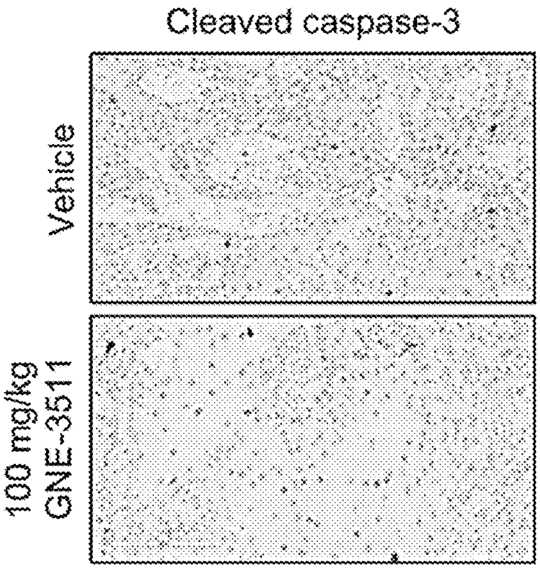
FIGS. 14A and 14B are images of immunohistochemistry (IHC) staining of an apoptotic marker, cleaved caspase 3, in CAL33 xenografts for teach treatment group (14A), and quantification of the cleaved caspase-3 staining revealing an increase in the apoptotic marker with GNE-3511 treatment compared to the control in tumors (14B).
Figure 14B:
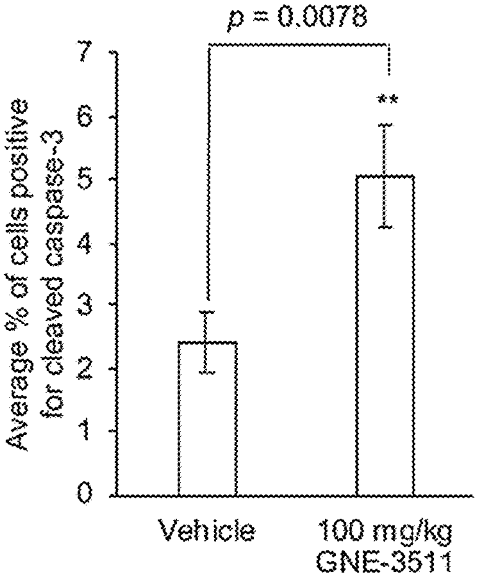

Immunohistochemistry (IHC)staining revealed an increase in cleaved caspase-3 expression in the GNE-3511 treated tumors compared to control (FIGS. 14A and 14B; mean±SEM, Student's t-test, *p<0.001). The study was terminated early due to toxicity at this concentration and dosing regimen (100 mg/kg, b.i.d., five days on/two days off) and decreases in body weight of the inhibitor treated mice were observed. GNE-3511 was further evaluated in vivo utilizing a daily administration of a lower dose (50 mg/kg, q.b.) in a patient-derived xenograft mouse model of 3q-amplified HNSCC (PDX model: 391396-364-R. GNE-3511 significantly suppressed HNSCC PDX tumor growth in vivo with almost complete tumor regression and no detectable tumors in three mice (FIGS. 12A-12C), with no effect on body weights of the mice.

Figure 15:
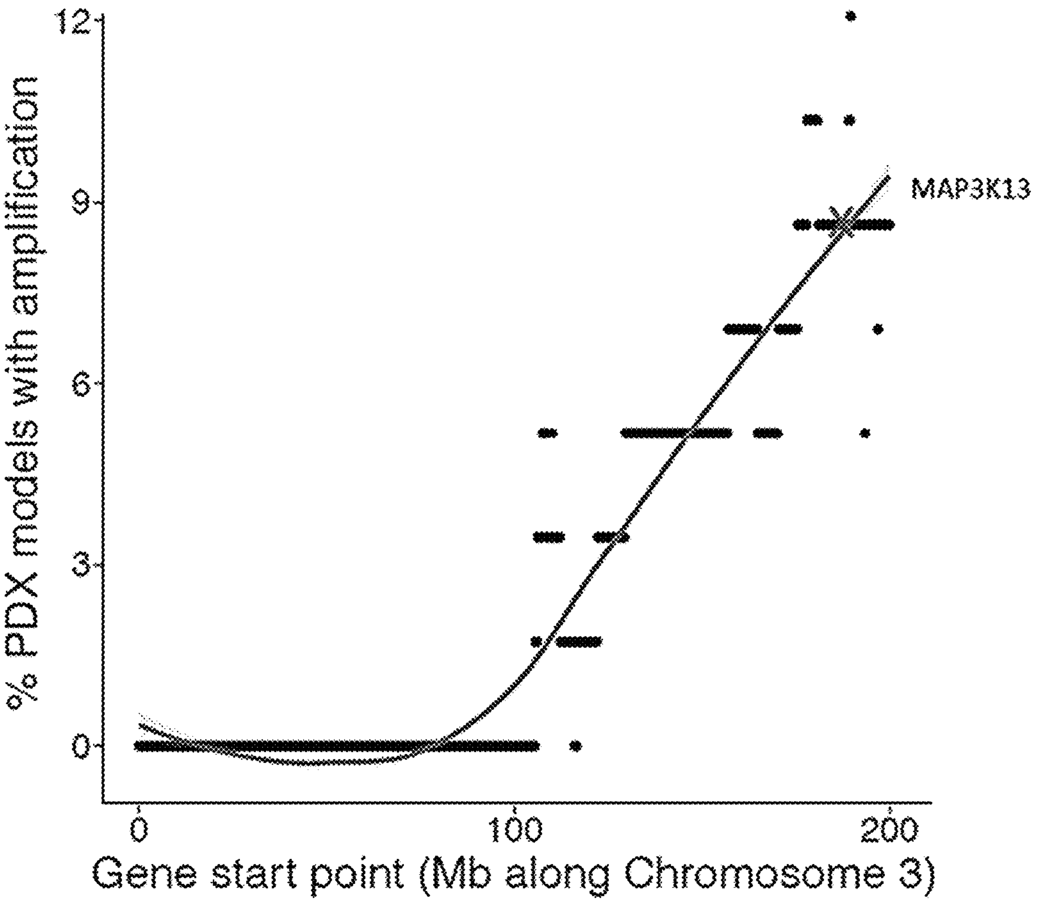
FIG. 15 is a graph representing percentage of the HNSCC PDX models with amplification of each gene on chromosome 3; the genes were ordered by gene start point along chromosome 3; MAP3K13 is marked with a cross; the line is the regression line by loss method.

The expression and amplification of LZK in additional HNSCC PDX models from the NCI Patient-Derived Models Repository (PDMR) was further examined. Utilizing Next-Generation Sequencing (NGS) and RNA-sequencing data from fifty-eight HNSCC PDX mouse models, amplification of MAP3K13 in five samples was revealed, including PDX 391396-364-R, with an additional 31 containing gains of LZK. MAP3K13 was identified as one of the top genes amplified within chromosome 3 in these patient samples. Finally, increased copy number of MAP3K13 was highly associated with an increase in mRNA expression levels (FIG. 15).

Figure 16:
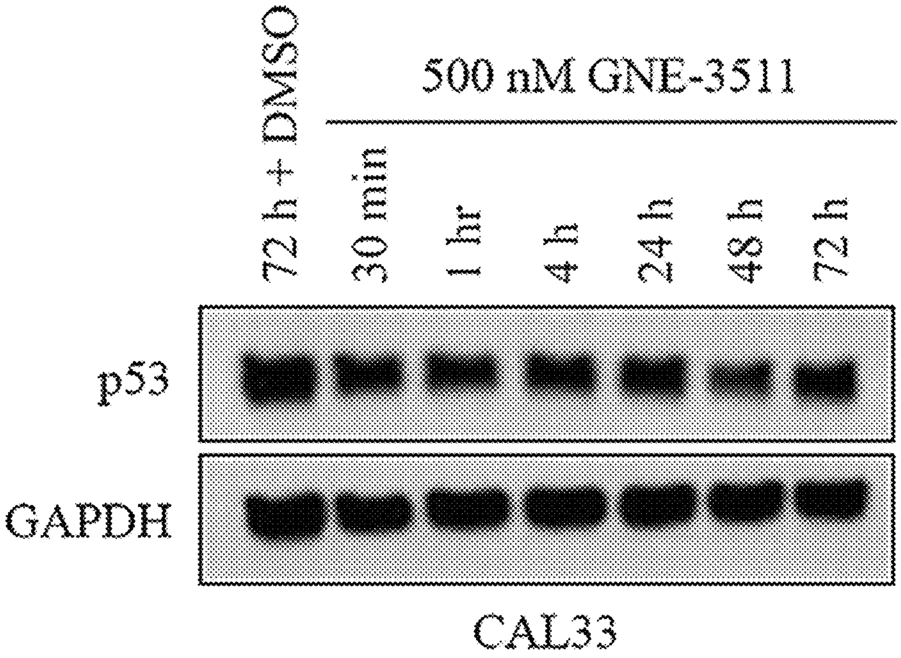
FIG. 16 shows that treatment of CAL33 HNSCC cell line with GNE-3511 did not decrease gain-of-function (GOF) mutant p53 (R175H) abundance.
Figure 17:
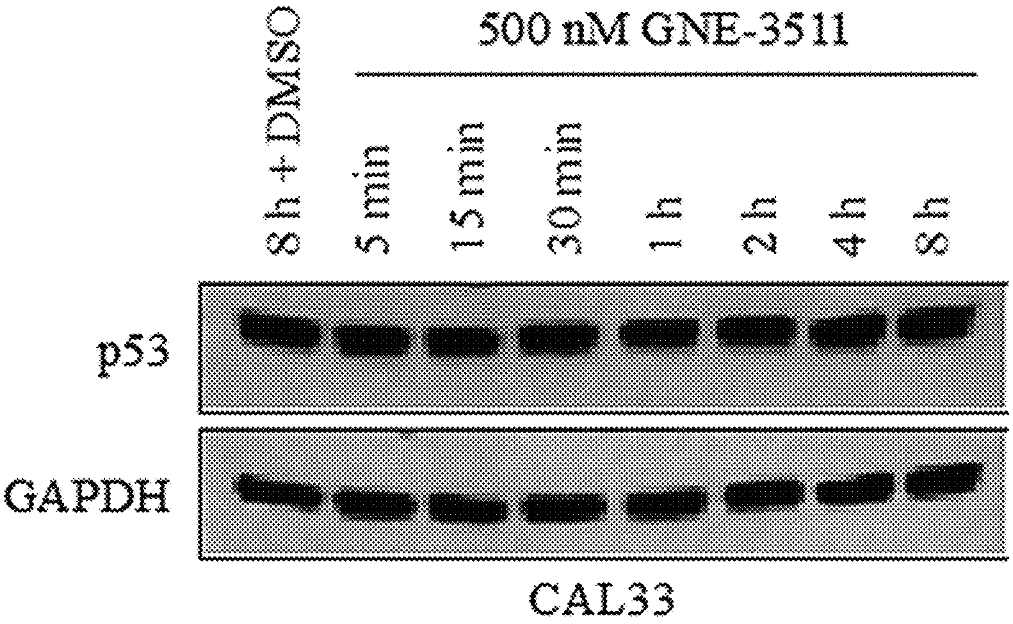
FIG. 17 shows that protein expression of GOF-p53 was unaltered after the CAL33 HNSCC cell line was treated with GNE-3511 for five minutes to eight hours.
Figure 18:
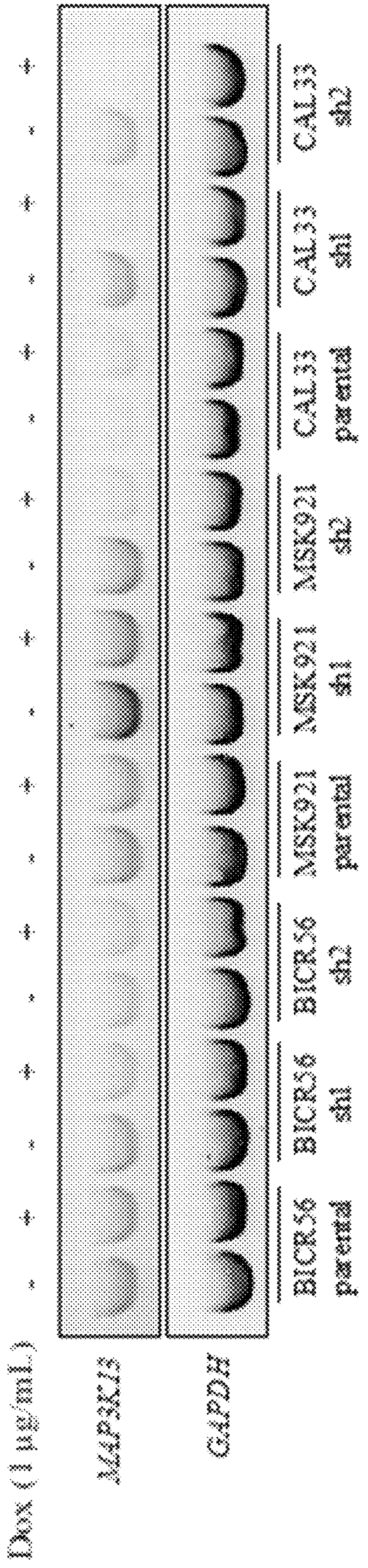
FIG. 18 shows RT-PCR analysis of the CAL33, BICR56, and MSK921 cell lines with dox-inducible knockdown of LZK.
Figure 19:
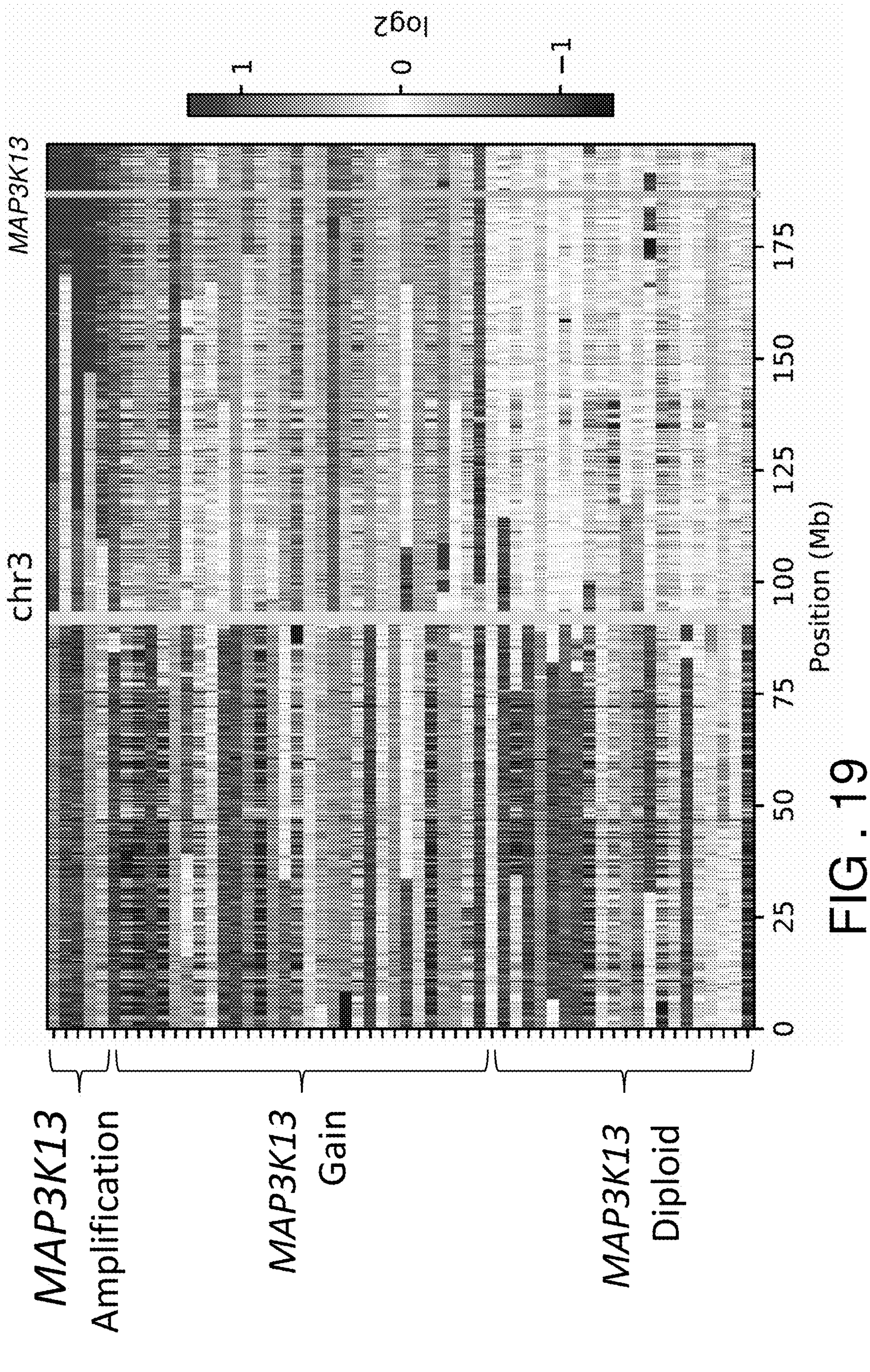
FIG. 19 shows copy number (CN) profiles of fifty-eight HNSCC PDX mouse models on chromosome 3 obtained from the NCI PDMR; the heatmap color indicates the log 2 ratio of copy numbers.
Figure 20:
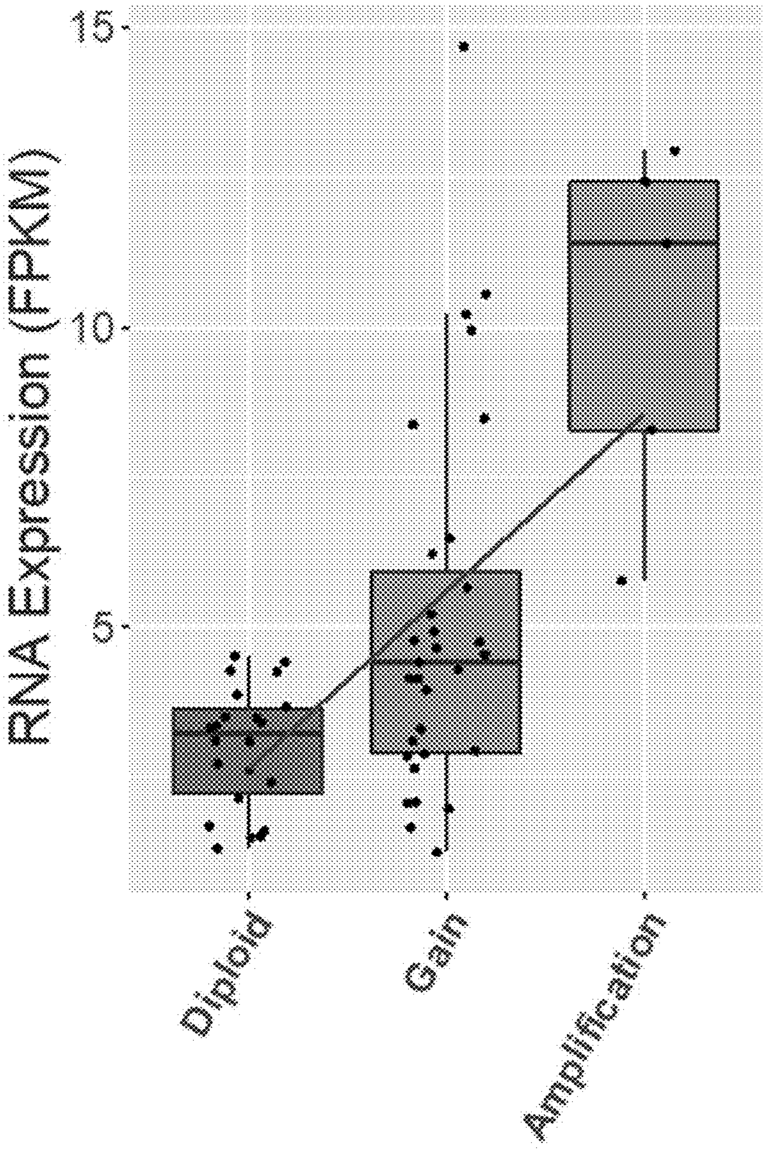
FIG. 20 shows a boxplot of MAP3K13 gene expression in fifty-eight PDX models with different MAP3K13 copy numbers.

To define the mechanism by which catalytic activity of LZK maintains HNSCC cell survival, expression levels of GOF mutant p53, a downstream target of LZK, were assessed. In contrast to knockdown of LZK (Edwards et al., *Cancer Res* 2017, 77:4961-4972), GNE-3511 did not alter GOF-p53 expression levels in CAL33 HNSCC cells, indicating that LZK regulates GOF-p53 in a kinase-independent manner (FIGS. 16, 17). A reverse phase protein array (RPPA) was then performed to identify targets downstream of amplified MAP3K13. Dox-inducible depletion of LZK in CAL33, BICR56, and MSK921 cell lines with two unique LZK shRNAs (as described in Edwards et al. and FIG. 18) reduced c-MYC abundance in 3q amplicon-positive HNSCC cells (CAL33 and BICR56), but not control cells (MSK921); this was confirmed by Western blot analysis. FIG. 19 shows copy number (CN) profiles of fifty-eight HNSCC PDX mouse models on chromosome 3 obtained from the NCI PDMR. Each row indicates the copy number profile of one PDX model. Models were ordered by MAP3K13 copy number data (highlighted as yellow line). The heatmap color indicates the log 2 ratio of copy numbers. FIG. 20 shows a boxplot of MAP3K13 gene expression in fifty-eight PDX models with different MAP3K13 copy numbers. X-axis indicates the copy number status of MAP3K13 where 2=diploid, >2 and <5=gain, and ≥5=amplification. Y-axis indicates the MAP3K13 gene expression in average fragments per kilobase million (FPKM). Each black dot indicates one PDX model. Copy number of MAP3K13 is highly correlated with gene expression (ANOVA, p=1.34e-6).

Figure 21:
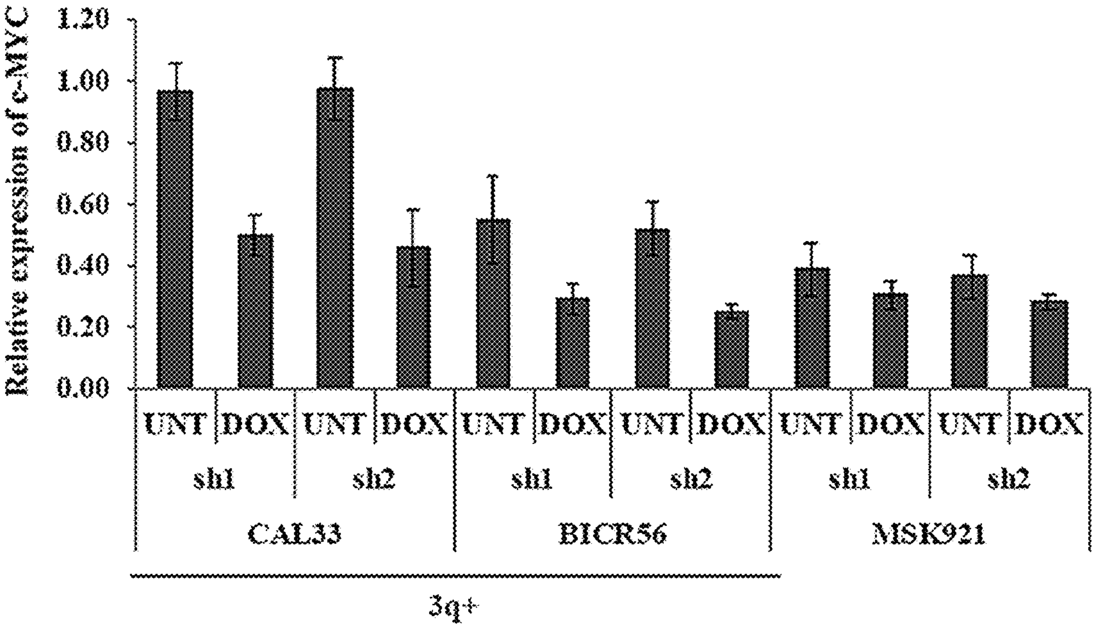
FIG. 21 is RPPA assay results identifying decreased c-MYC levels in CAL33 and BICR56 cells depleted of LZK for 48 hours.
Figure 22:
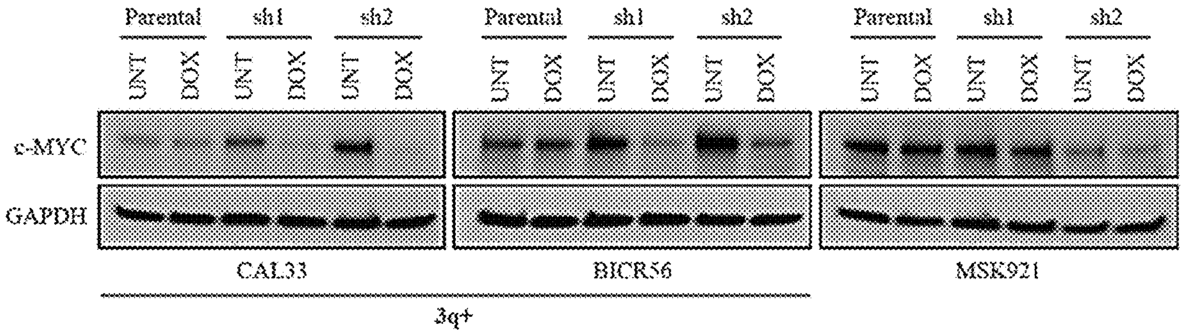
FIG. 22 is a series of Western blots of c-MYC abundance in CAL33 and BICR56 cells depleted of LZK for 48 hours.
Figure 23:
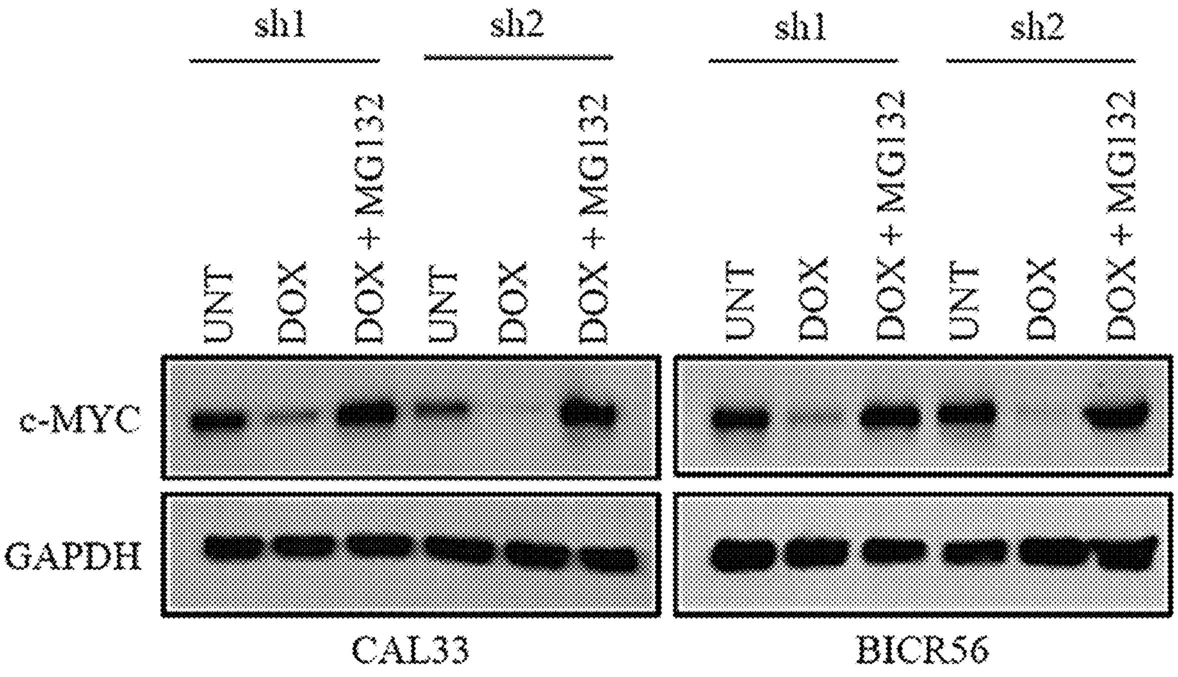
FIG. 23 shows that treatment with MG132 (10 μM) for six hours rescued decreases in c-MYC levels in CAL33 and BICR56 cells depleted of LZK for 48 hours.

FIG. 21 is RPAA assay results identifying decreased c-MYC levels in CAL33 and BICR56 cells depleted of LZK for 48 hours. FIG. 22 is Western blots of c-MYC abundance in cells depleted of LZK for 48 hours. These results corroborate a recent high-throughput siRNA screen identifying M4P3K13 as a required gene for cell survival specifically with c-MYC overexpression (Toyoshima et al., *PNAS USA* 2012, 109:9545-9550). Loss of c-MYC expression was dependent on proteasome-mediated degradation, as addition of the proteasome inhibitor MG132 (10 μM for six hours) suppressed this loss and rescued decreases in the c-MYC levels (FIG. 23). This observation is consistent with a previous report that LZK phosphorylates and stabilizes expression of the E3 ubiquitin ligase TRIM25, which ubiquitinates FBXW7, a subunit of the SKP1-Cullin-F-Box (SCF) complex that directly regulates c-MYC stability (Zhang et al., *Cell Death Differ* 2020, 27:420-433). Loss of TRIM25 phosphorylation through depletion or catalytic inhibition of LZK leads to the degradation of the ligase, increased stability of FBXW7, and degradation of c-MYC (Ibid.).

Figure 24:
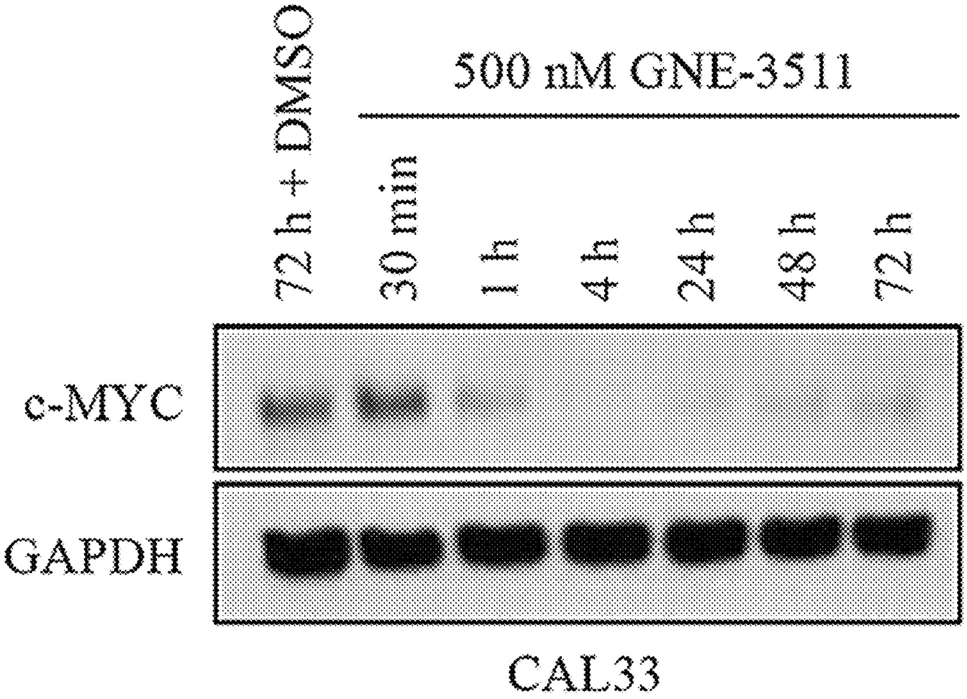
FIG. 24 shows that treatment of CAL33 cells with GNE-3511 decreased c-MYC abundance for up to 72 hours.
Figure 25:
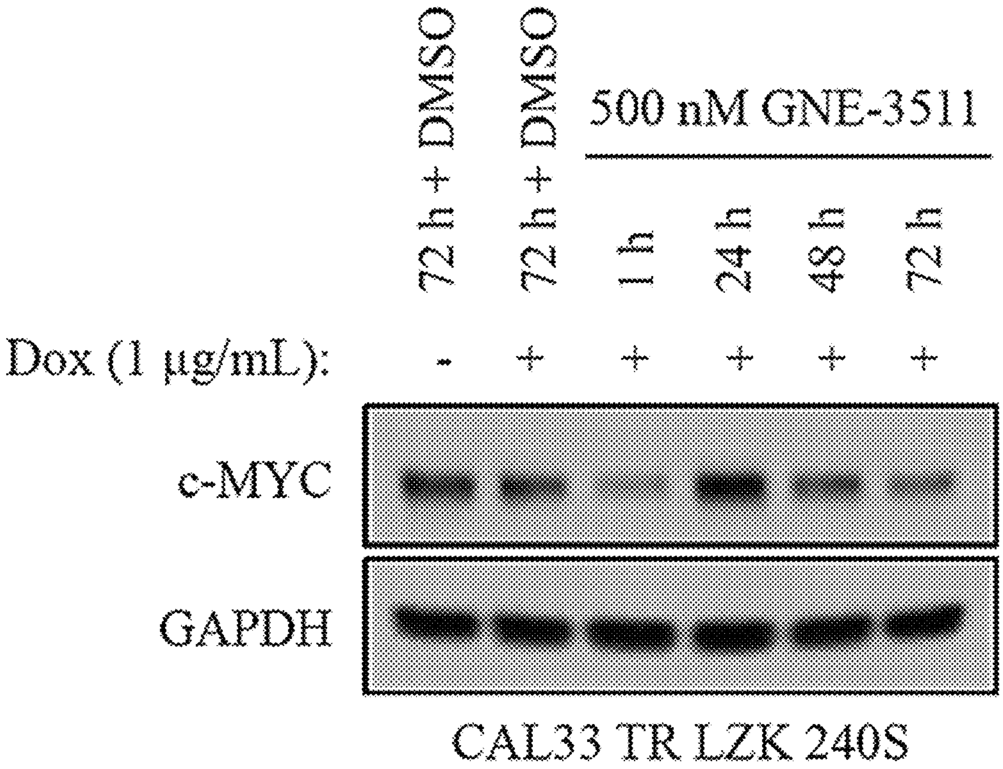
FIG. 25 shows that $LZK^{Q240S}$ expression rescued loss in c-MYC levels in CAL33 cells treated with GNE-3511.

To determine if LZK catalytic inhibition would suppress c-MYC expression, CAL33 cells were treated with 500 nM GNE-3511 and c-MYC expression was monitored over time. Within the first hour, the LZK inhibitor resulted in a reduction in c-MYC levels that was subsequently maintained for 72 hours (FIG. 24). Importantly, expression of the $LZK^{Q240S}$ drug-resistant mutant rescued the loss of c-MYC expression, indicating that LZK catalytic activity is essential to maintain c-MYC stability in HNSCC cells with amplified MAP3K13 (FIG. 25). Thus, LZK has both kinase-dependent and kinase-independent functions that promote cancer.

Example 3

LZK Degradation by LZK-Targeted Degraders

Figure 26:
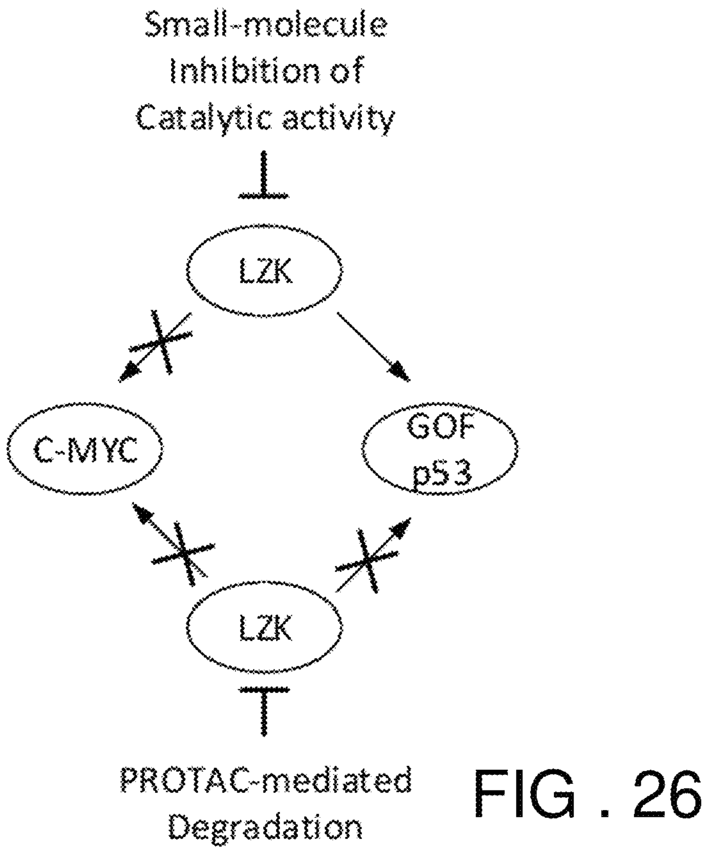
FIG. 26 is a schematic diagram showing that an LZK targeted degrader will target both GOF-p53 and c-MYC for degradation.

One way to effectively block all of these pro-cancer LZK-mediated pathways is to eliminate LZK from the cell at the protein level. LZK-targeted degraders (Churcher et al., *J Med Chem* 2018, 61:444-452; Lai et al., *Nat Rev Drug Discov* 2017, 16:101-114; Tour et al., *Angew Chem Int Ed Engl* 2016, 55:1966-1973) capable of degrading LZK within the cell should produce effects similar to those observed with LZK knockdown: reduction in c-MYC and GOF mutant p53 expression. As illustrated in FIG. 26, inhibiting LZK catalytic activity reduces c-MYC expression. However, targeted degrader-mediated LZK degradation inhibits both c-MYC and GOF mutant p53 expression.

To develop LZK targeted degraders, various E3-ligase-binding moieties were tethered to LZK inhibitors disclosed by Patel et al. (*J Med Chem* 2015, 58:401-418). The structures of LZK inhibitors 1 (compound 49 of Patel) and 2 (compound 21 of Patel) are shown below; the structures targeted degraders 3-8 are shown in Table 3 supra.

(1)

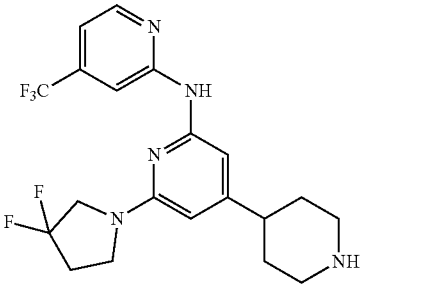

(2)

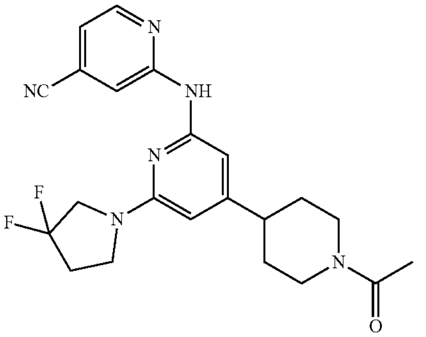

Figure 27:
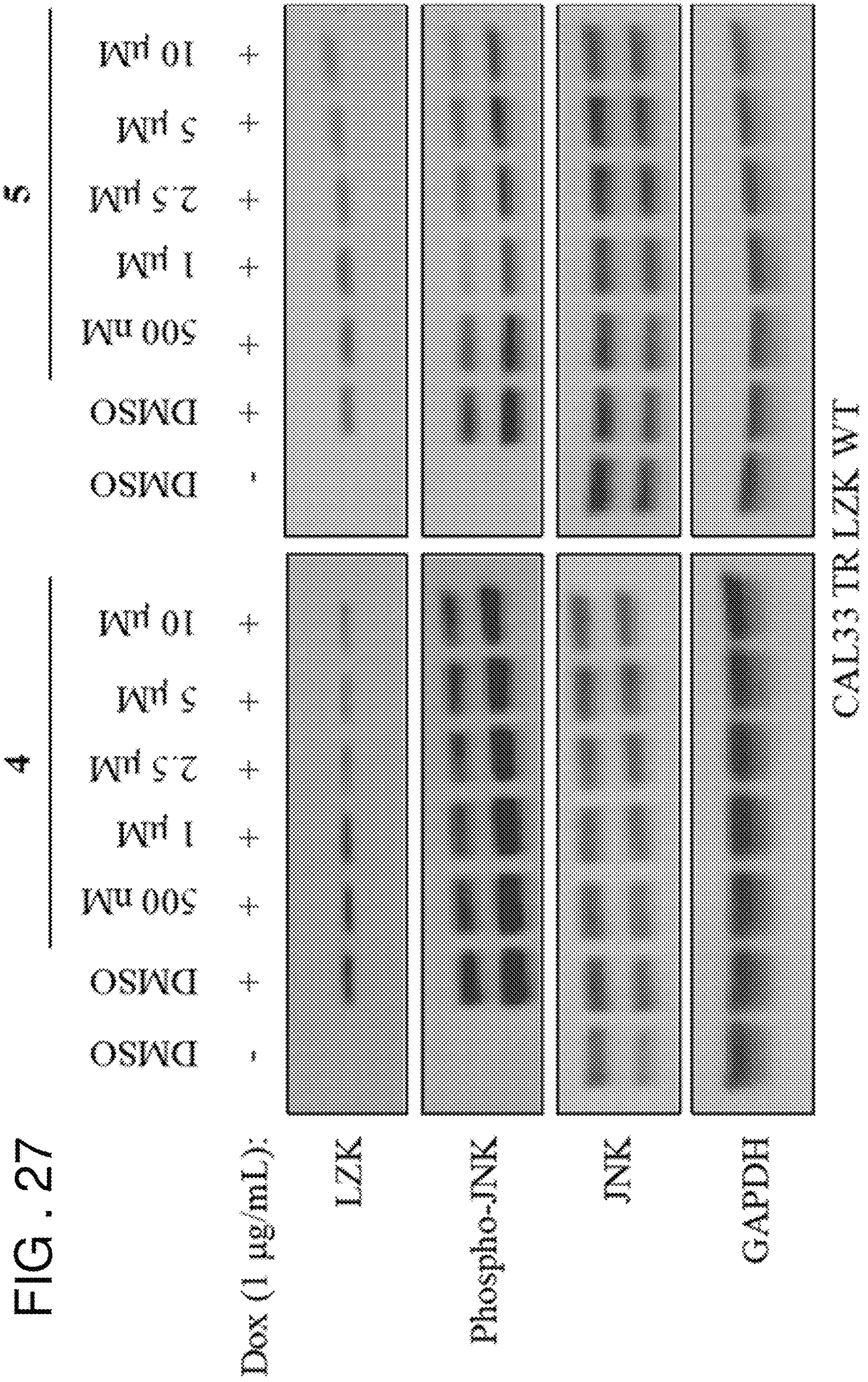
FIG. 27 shows that high concentrations of two targeted degraders (4 and 5) utilizing LZK inhibitor 1 as a ligand slightly decreased dox-induced LZK expression for 24 hours; compound 5 inhibited LZK as observed through JNK signaling.

Compounds 4 and 5, targeted degraders tethered to 1, were ineffective at degrading LZK (FIG. 27). High concentrations of 4 and 5 slightly decreased dox-induced LZK expression for 24 hours. Compound 5 inhibited LZK as observed through JNK signaling.

Figure 28:
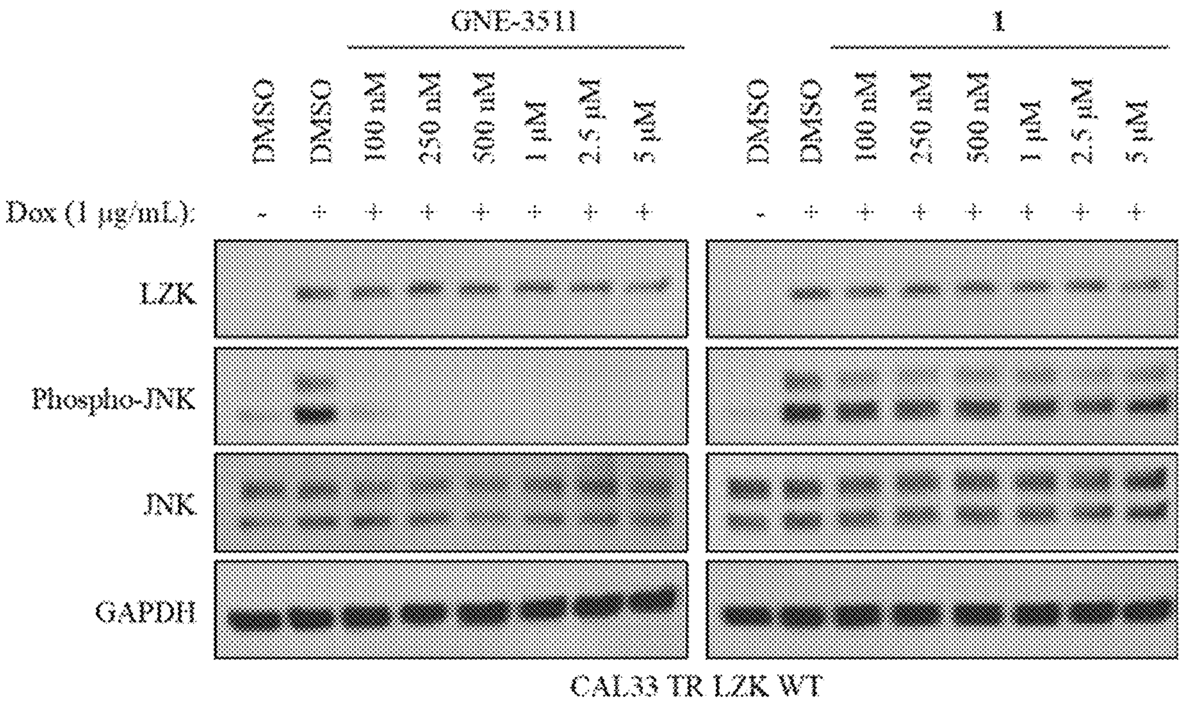
FIG. 28 is a comparison of GNE-3511 and LZK inhibitor 1 efficacy revealing that LZK inhibitor 1 poorly inhibited LZK signaling through JNK pathway activation.
Figure 29:
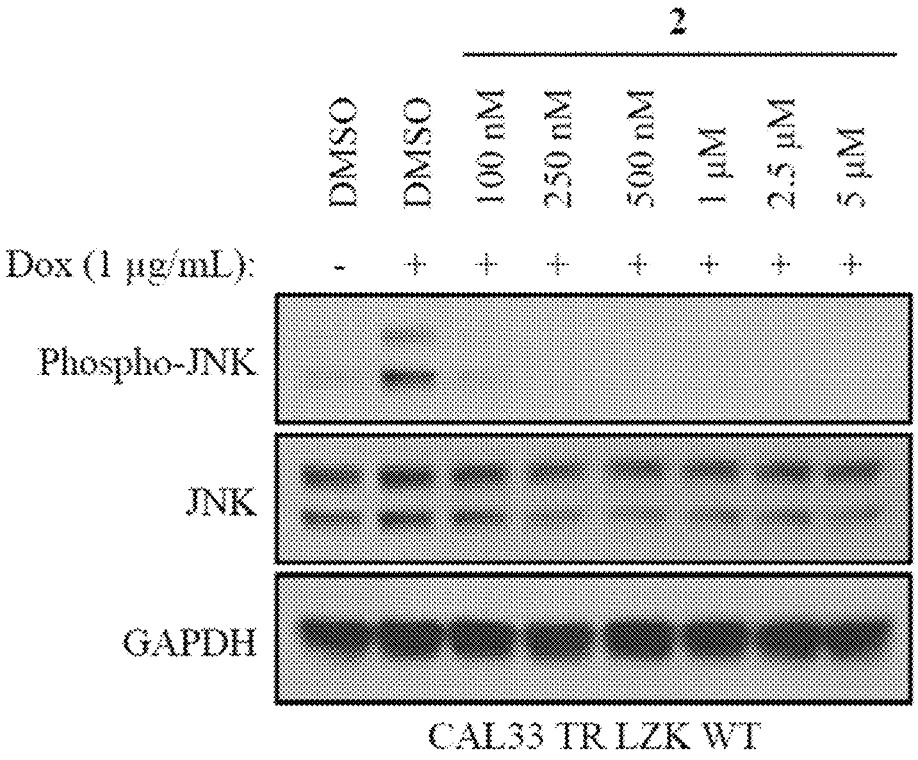
FIG. 29 shows that LZK inhibitor 2 is a potent LZK inhibitor at 100 nM for 1 hour.
Figure 30:
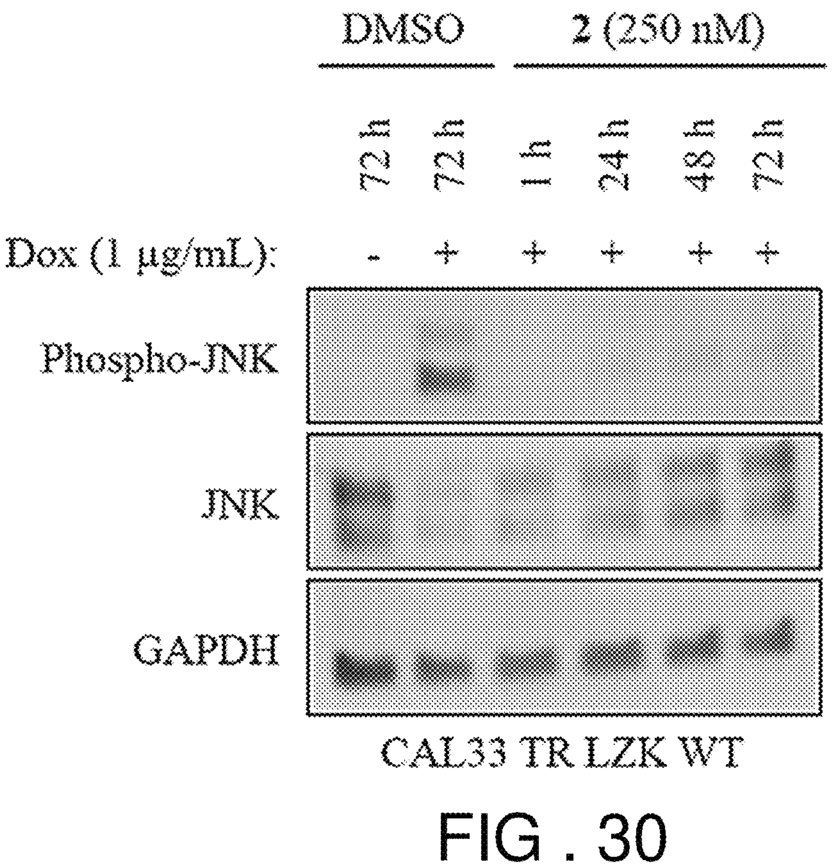
FIG. 30 shows that LZK inhibitor 2 maintained JNK pathway inactivation for 72 hours at 250 nM.
Figure 31:
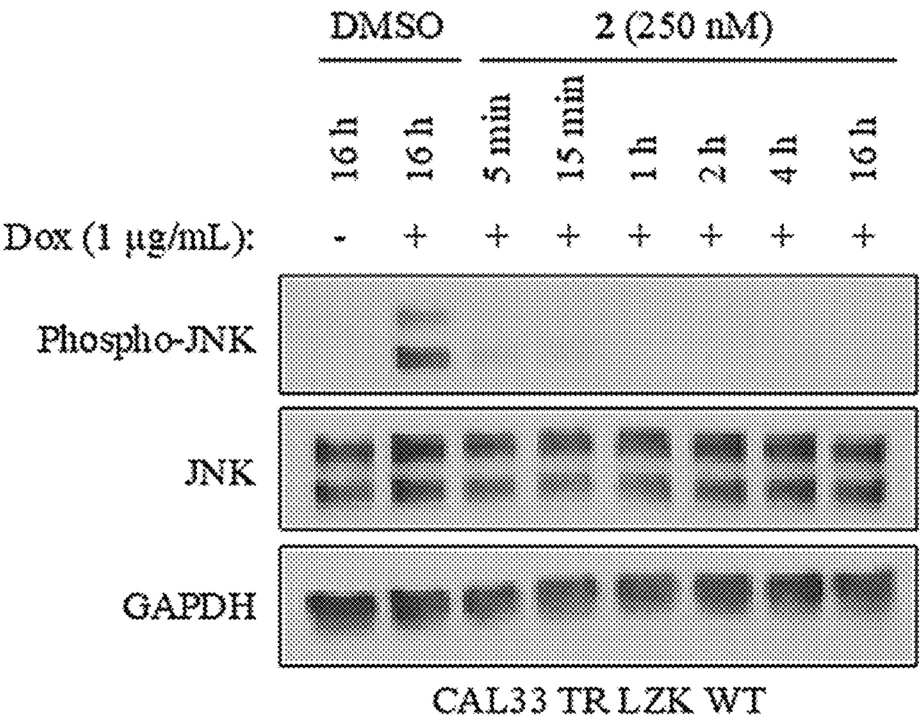
FIG. 31 shows that LZK signaling activity was suppressed with LZK inhibitor 2 (250 nM) at five minutes.
Figure 32:
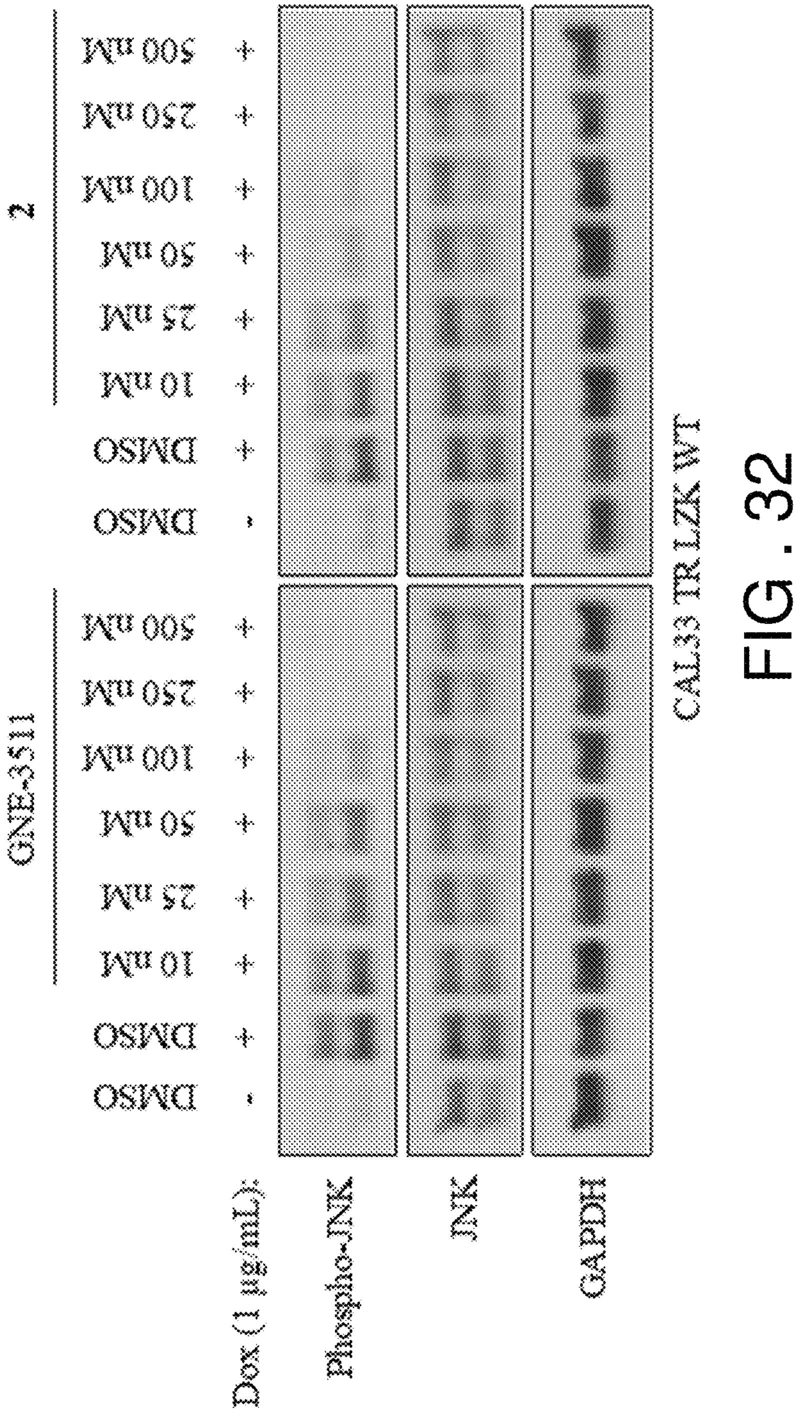
FIG. 32 shows that LZK inhibitor 2 inhibited JNK signaling at lower concentrations than GNE-3511 for one hour.
Figure 33A:
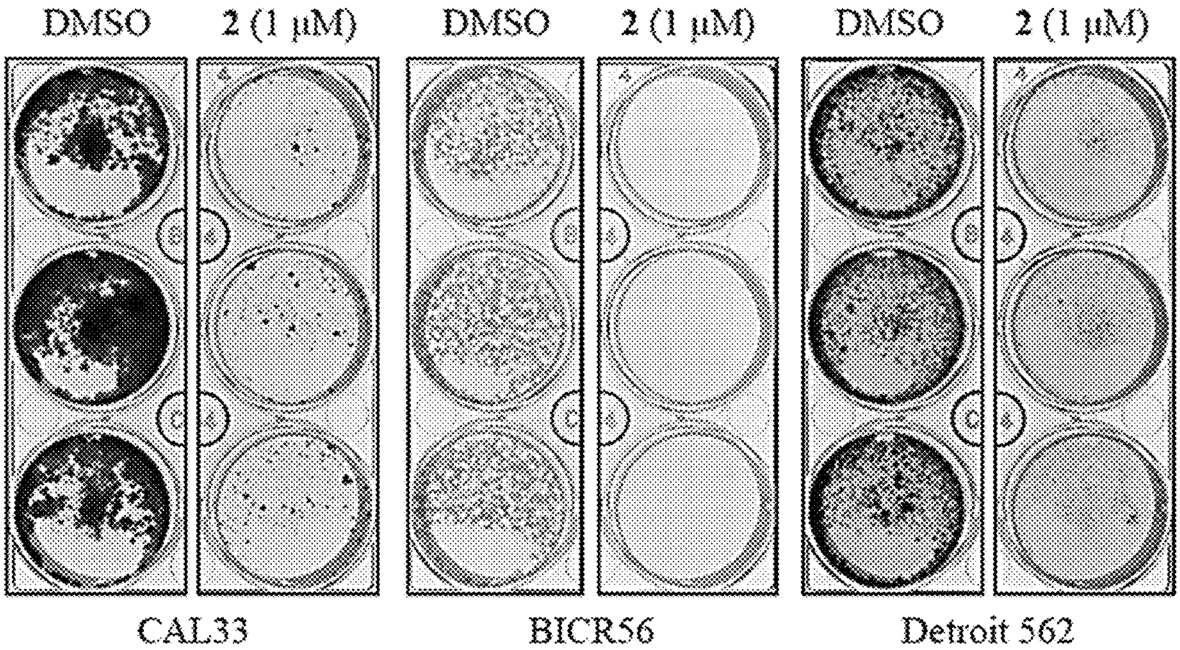
FIGS. 33A and 33B are images of colonies treated with compound 2 or vehicle, showing that LZK inhibitor 2 suppressed clonogenic growth of HNSCC cells harboring amplified MAP3K13 (CAL33, BICR56, and Detroit 562) (33A) and quantification revealing a significant decrease in growth in all three cell lines. Mean±SEM; Student's t-test; **p<0.01, *p<0.05 (33B).
Figure 33B:
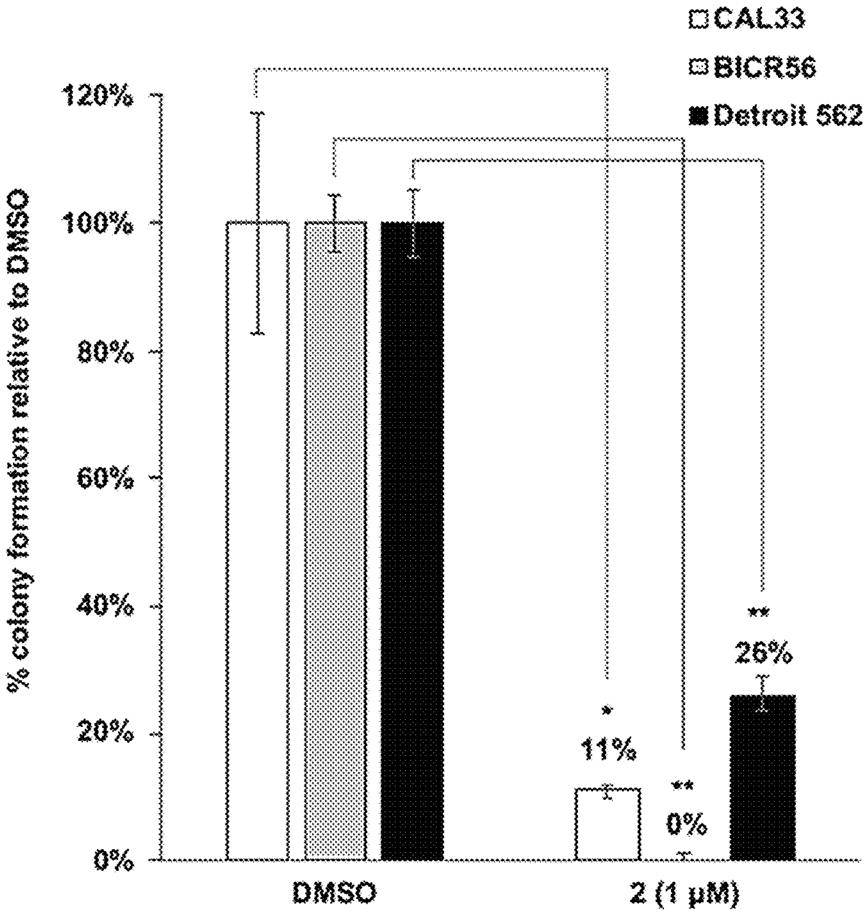
Figure 34:
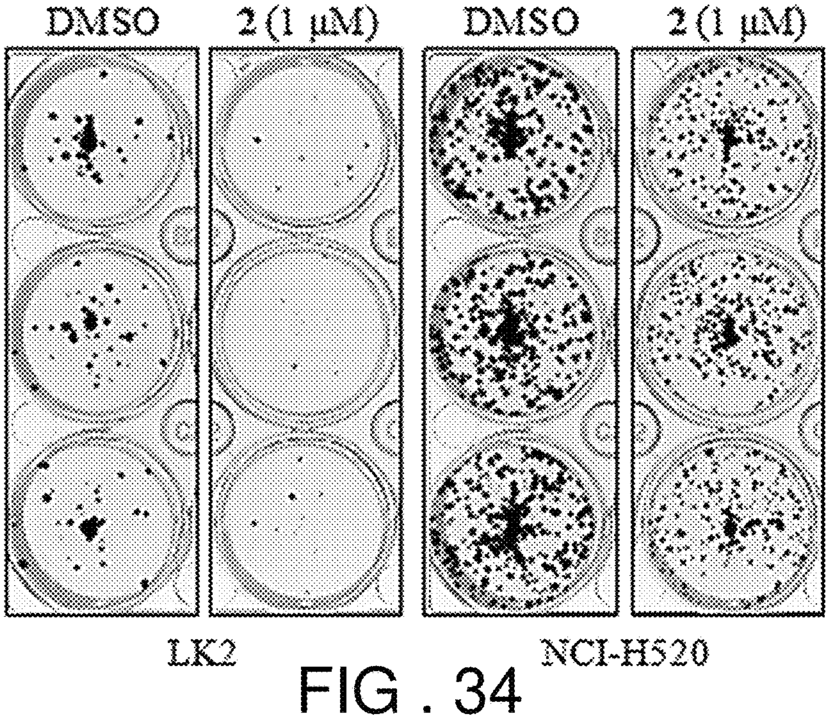
FIG. 34 shows that LZK inhibitor 2 (1 μM) significantly decreased LSCC cell growth in LK2 and NCI-H520 cell lines.
Figure 35:
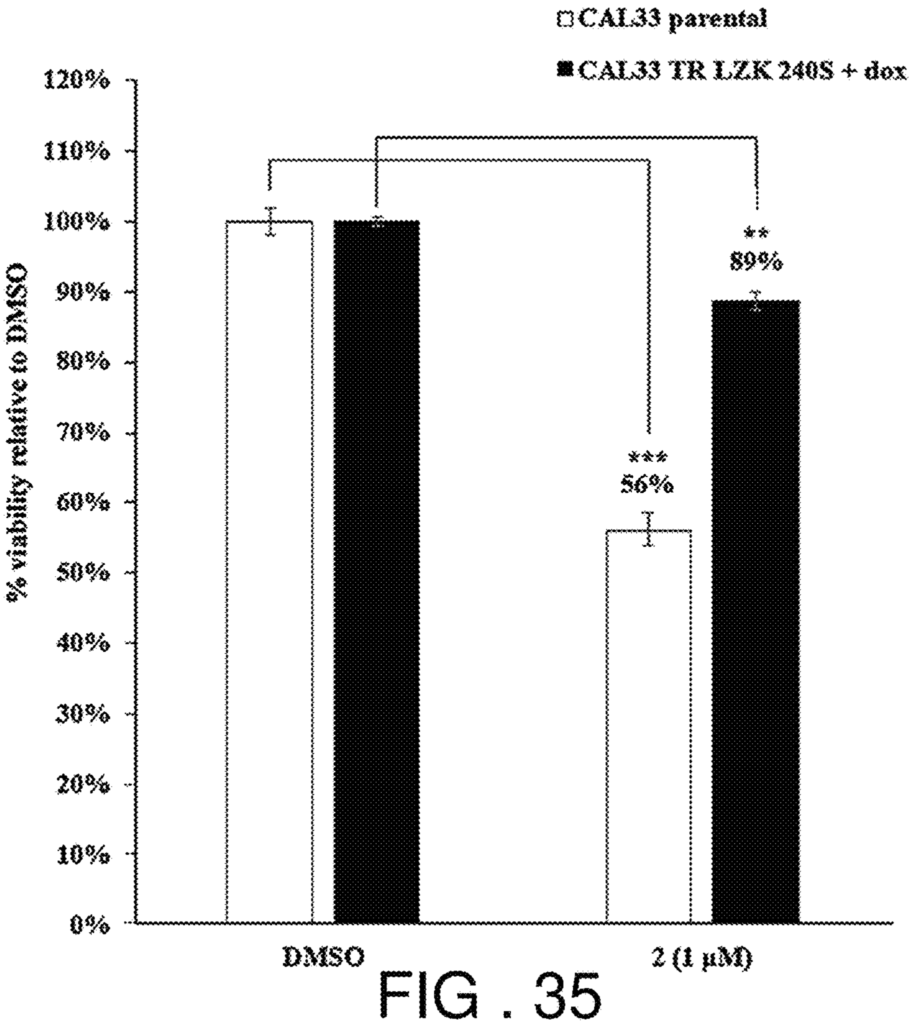
FIG. 35 is a graph showing that $LZK^{Q240S}$ drug-resistant mutant expression rescued decreases in viability in CAL33 cells treated with LZK inhibitor 2.
Figure 36:
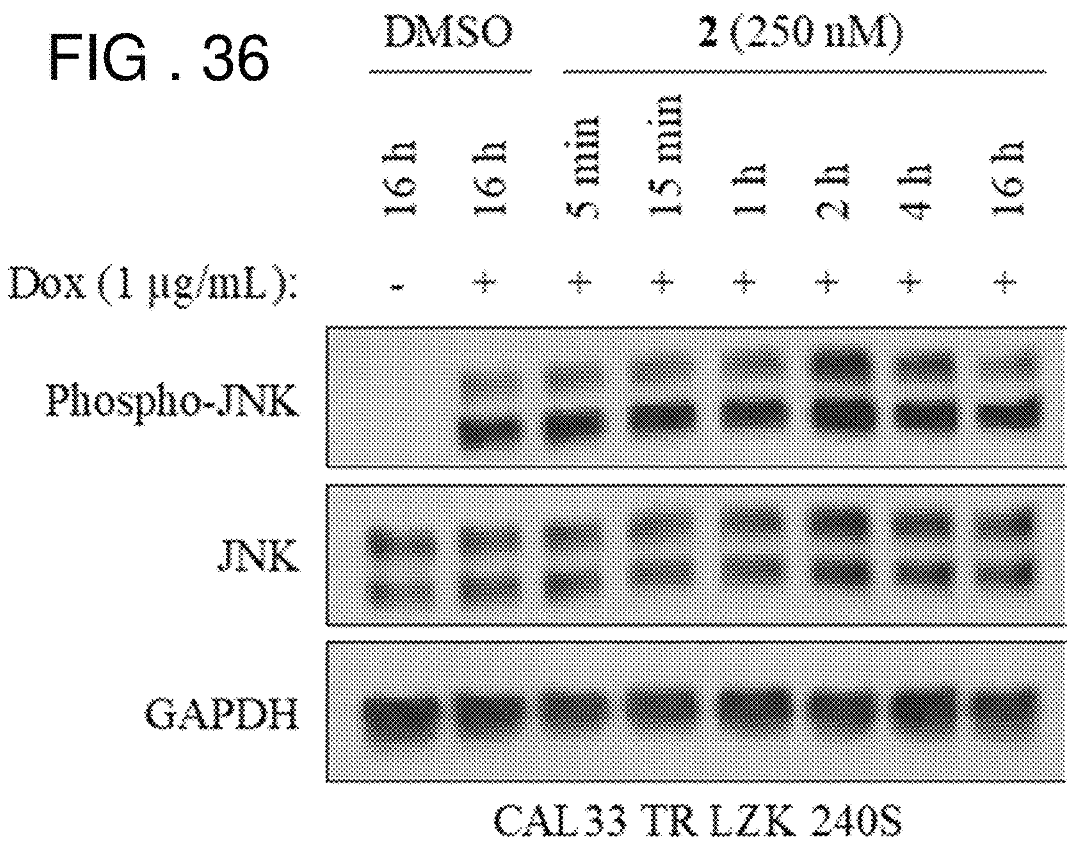
FIG. 36 shows that $LZK^{Q240S}$ drug-resistant mutant expression during treatment with LZK inhibitor 2 (250 nM) rescued JNK signaling.

A comparison of GNE-3511 and LZK inhibitor 1 shows that LZK inhibitor 1 is a poor LZK inhibitor in cells (FIG. 28). However, LZK inhibitor 2 was a potent LZK inhibitor that suppressed LZK activity at 100 nM, similar to treatment with GNE-3511, out to 72 hours (FIGS. 29-32). In addition, LZK inhibitor 2 suppressed colony formation in 3q amplicon-positive HNSCC cells —CAL33, BICR56, and Detroit 562 cells (FIGS. 33A. 33B), and LSCC cells—LK2 and NCI-H520 cells (FIG. 34). Drug-induced reductions in CAL33 cell viability were rescued by $LZK^{Q240S}$ drug-resistant mutant expression (FIG. 35; *p<0.001, p<0.01, Student's t-test). FIG. 36 shows that $LZK^{Q240S}$ drug-resistant mutant expression during treatment with LZK inhibitor 2 (250 nM) also rescued JNK signaling.

Figure 37:
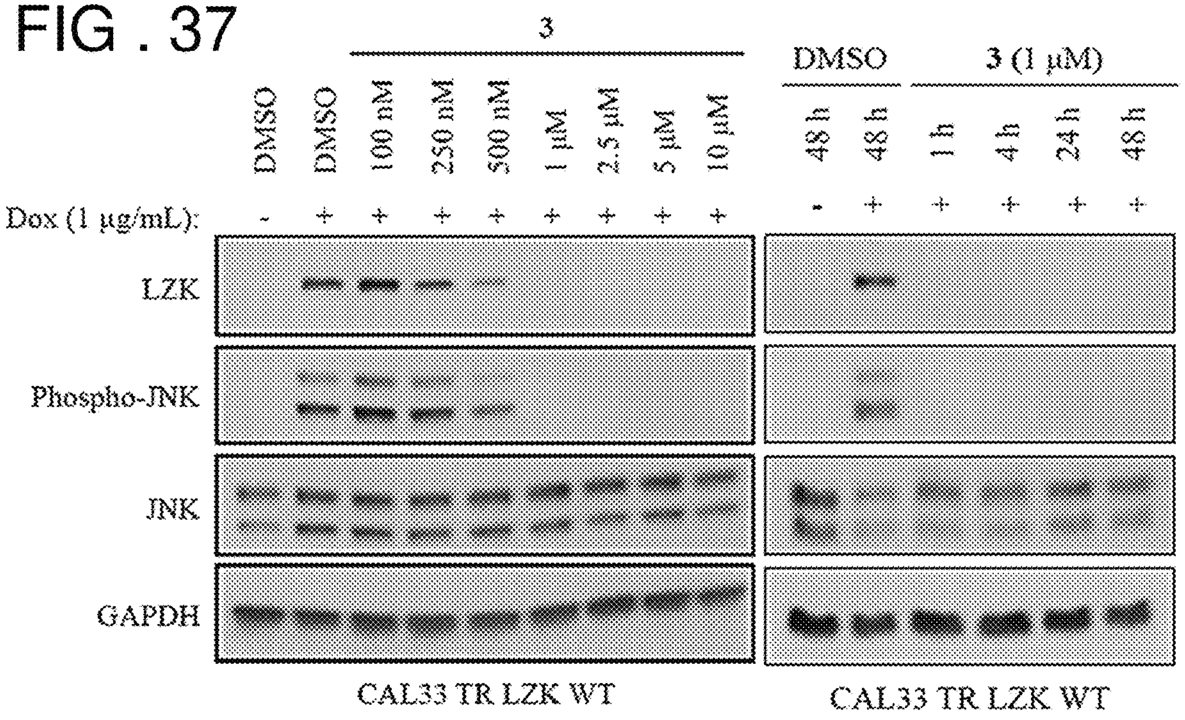
FIG. 37 shows that a targeted degrader comprising LZK inhibitor 2, compound 3, suppressed doxycycline-induced LZK expression at 1 μM for 48 hours.
Figure 38:
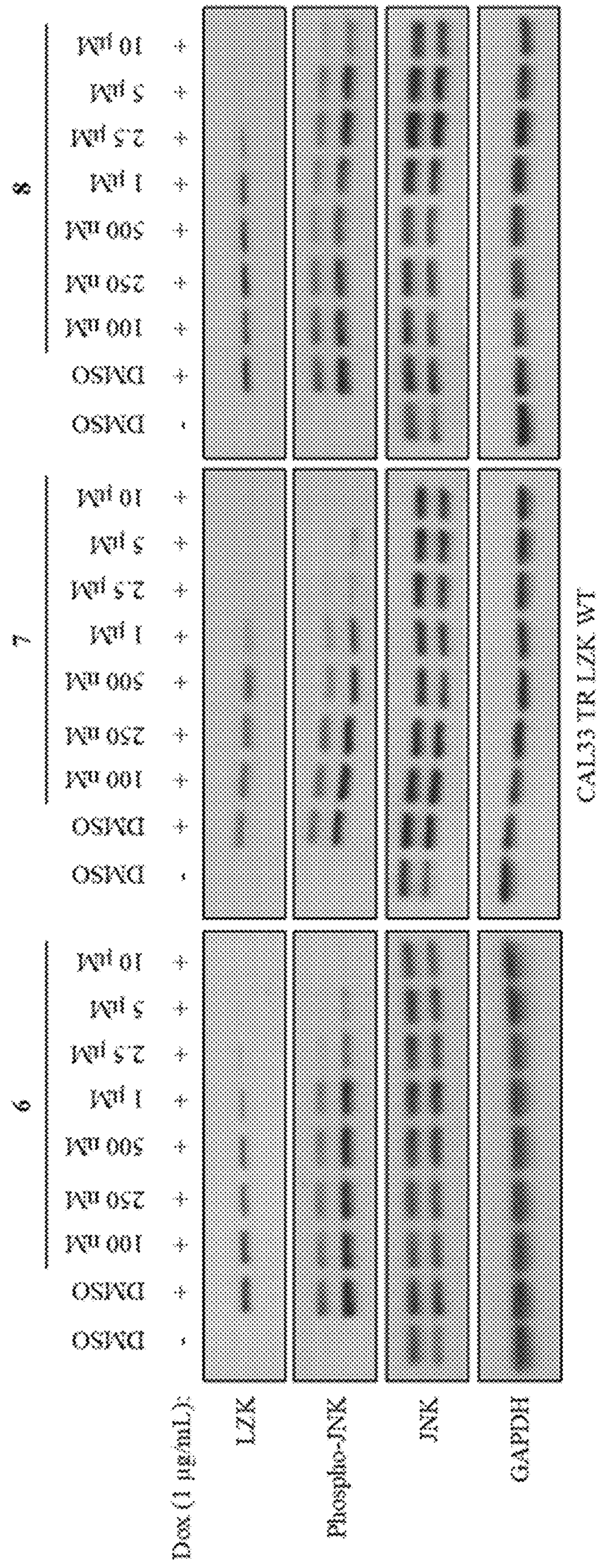
FIG. 38 shows that additional targeted degraders comprising LZK inhibitor 2, compounds 6-8, decreased LZK expression and inhibited JNK signaling.
Figure 39:
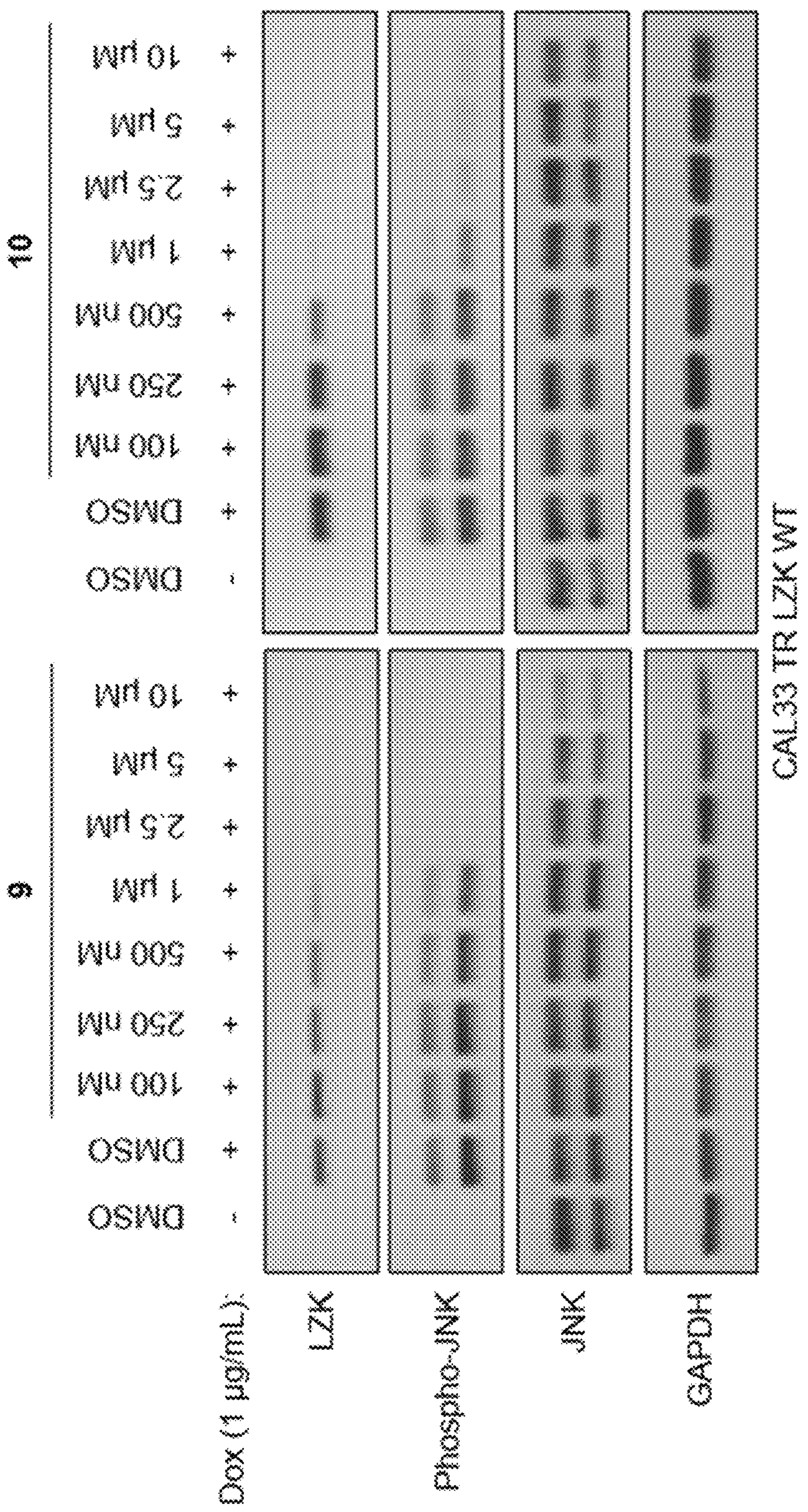
FIGS. 39-49 show that targeted degraders 9-26 and 31-32 also decreased LZK expression and inhibited JNK signaling in CAL33 cells induced with doxycycline; targeted degrader 30 did not decrease LZK expression (FIG. 48).
Figure 40:
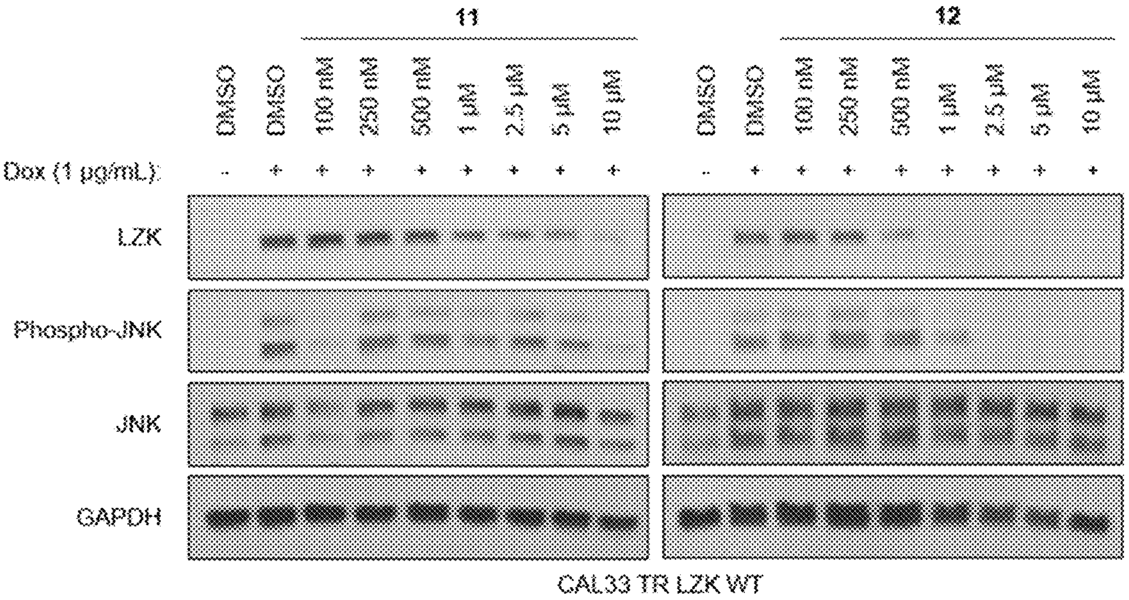
Figure 41:
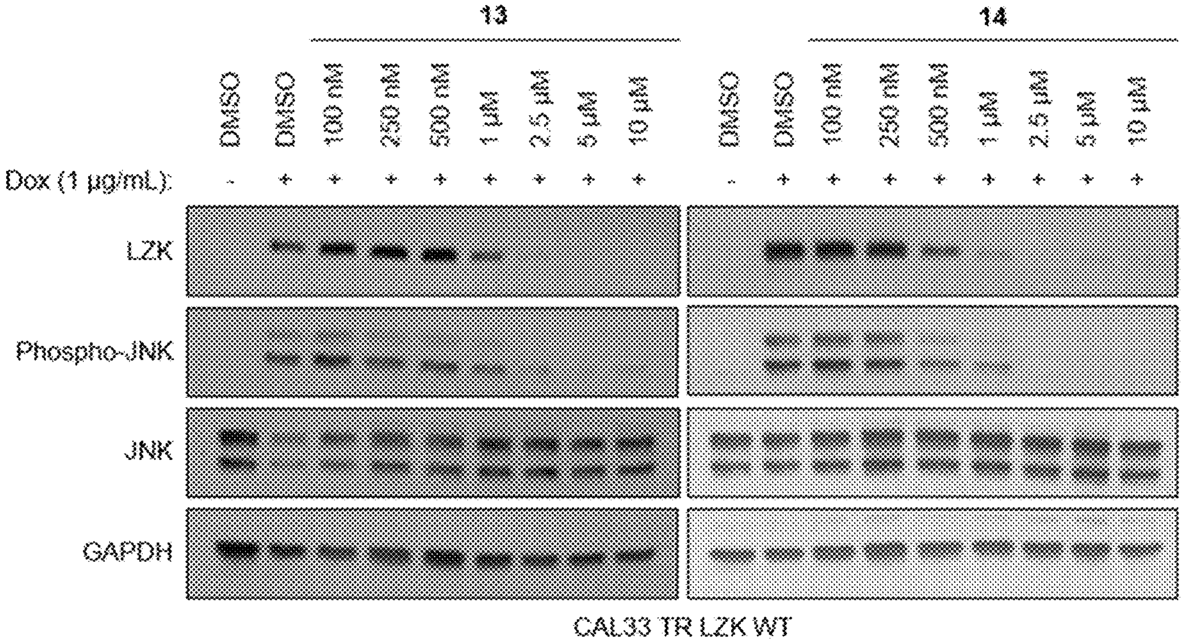
Figure 42:
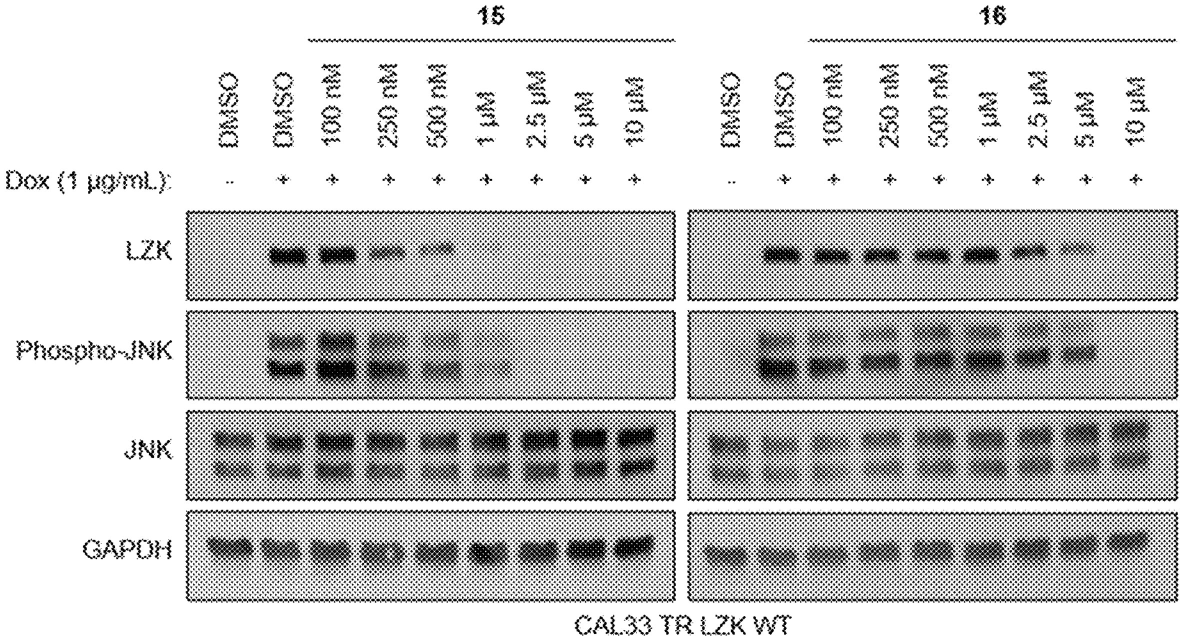
Figure 43:
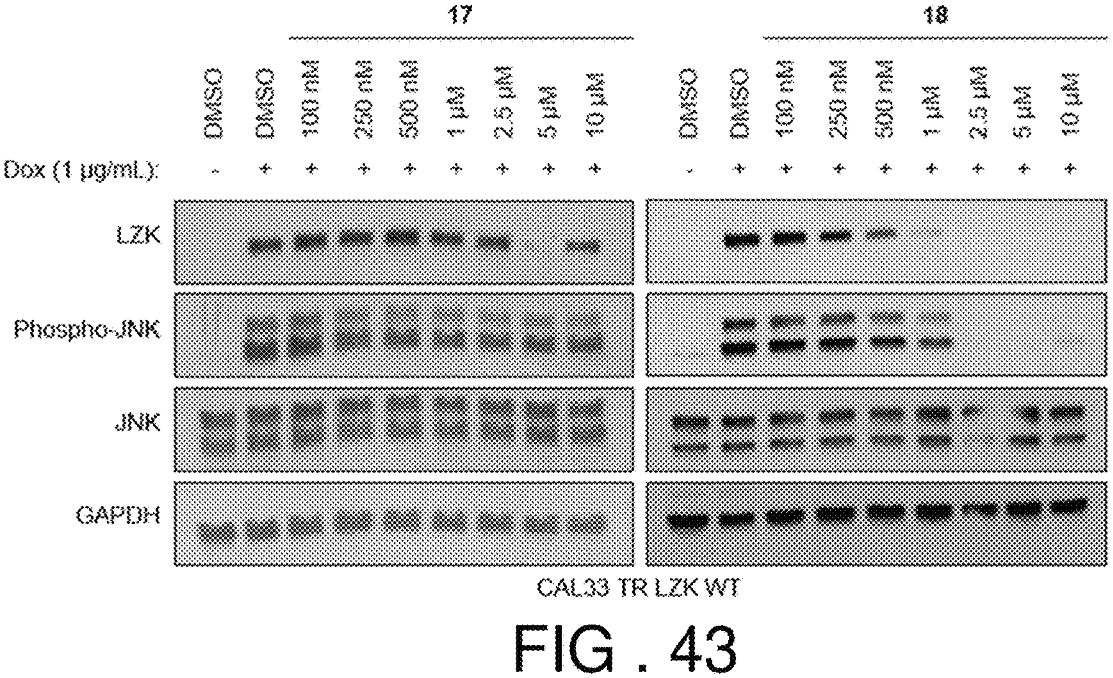
Figure 44:
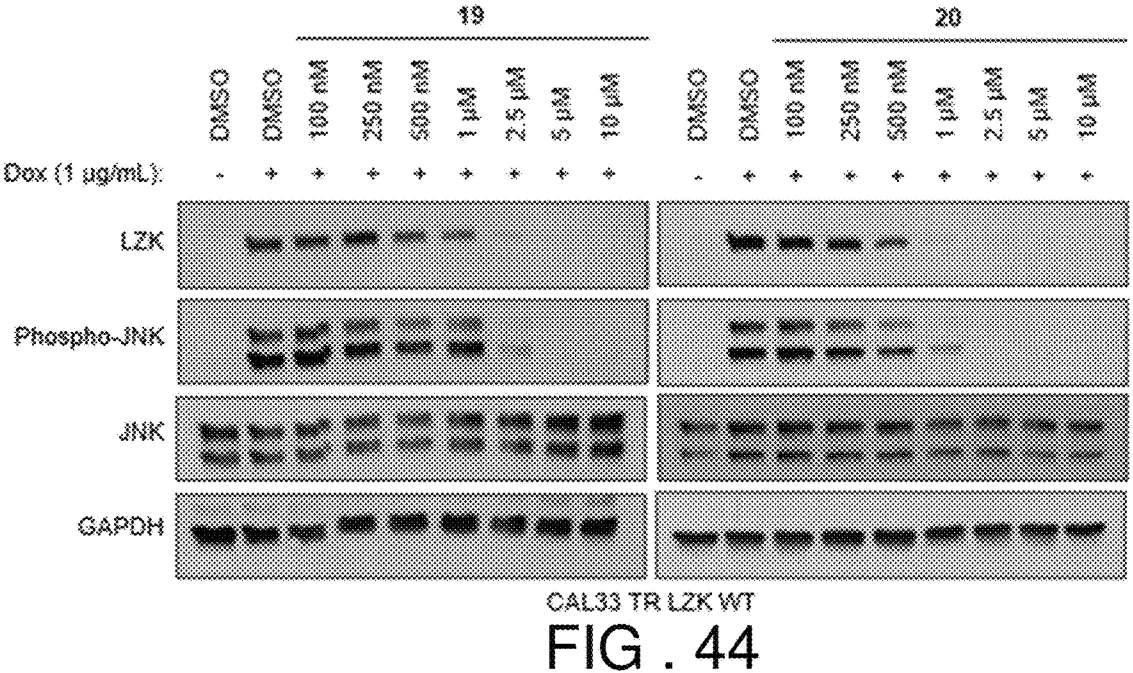
Figure 45:
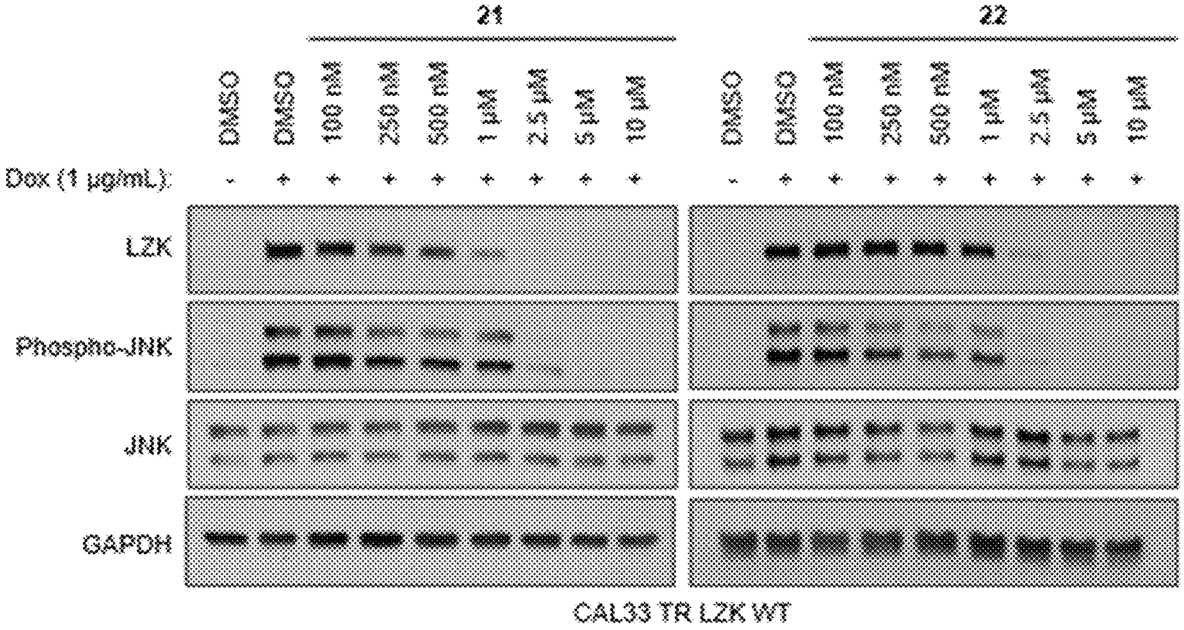
Figure 46:
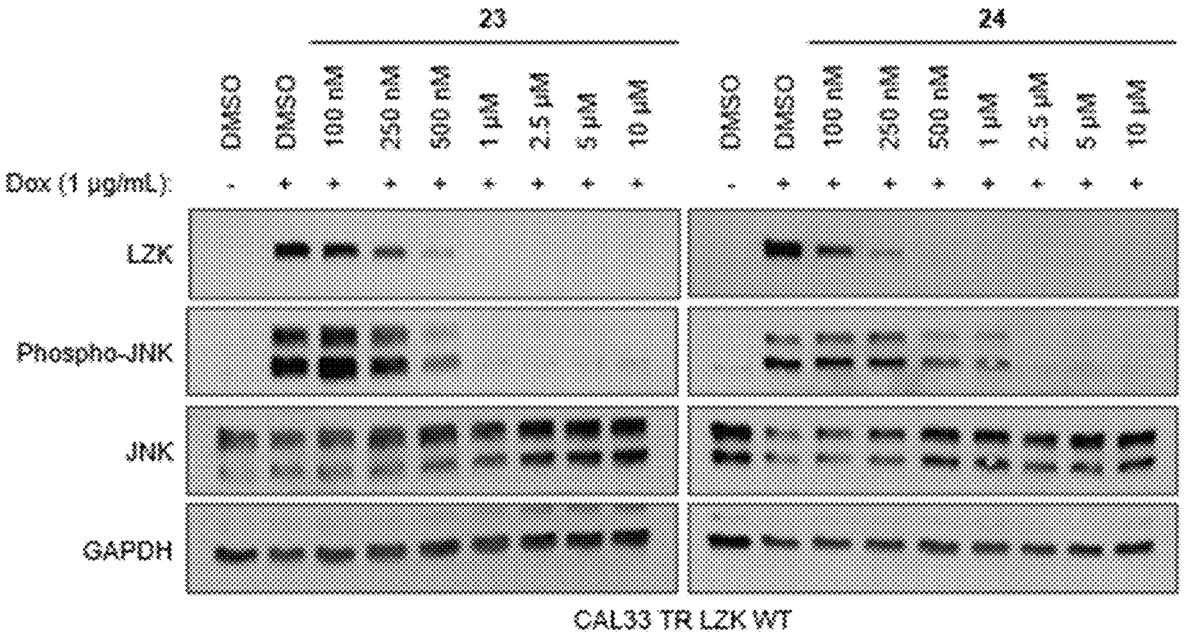
Figure 47:
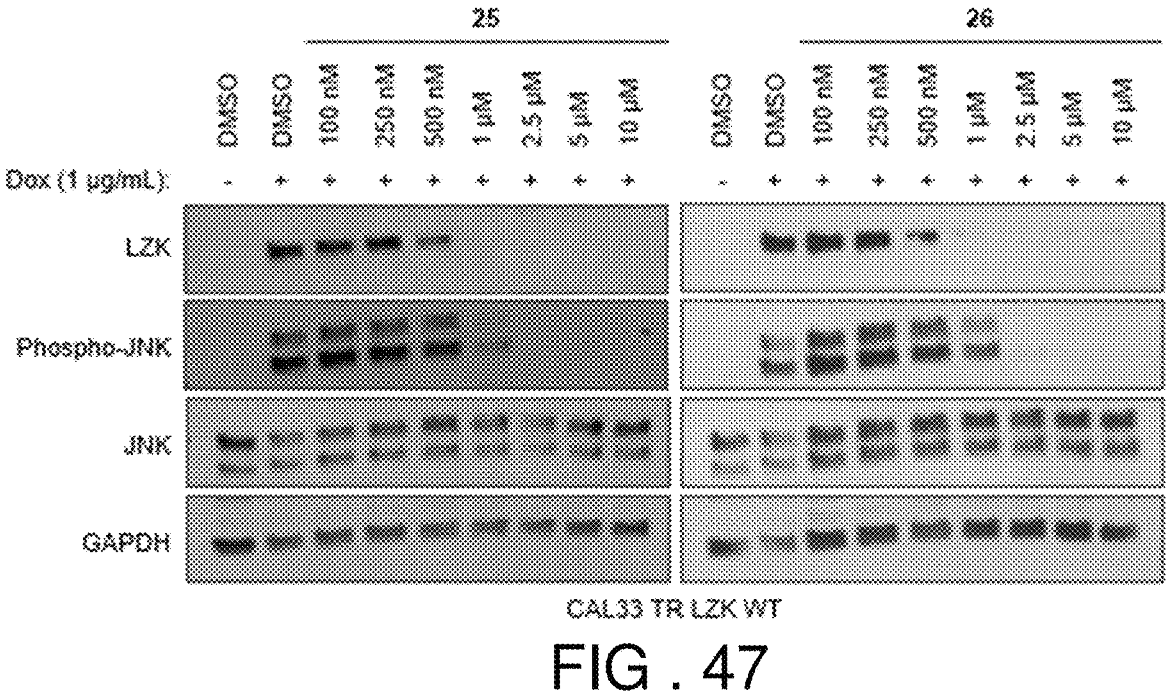

An LZK PROTAC comprising LZK inhibitor 2 (compound 3) was synthesized. Compound 3 degraded LZK at 1 μM for 48 hours and inhibited JNK signaling (FIG. 37). Additional targeted degraders comprising LZK inhibitor 2 (compounds 6-8) also promoted LZK degradation and inhibited JNK signaling at higher concentrations (FIG. 38), although to a lesser degree than compound 3.

Figure 48:
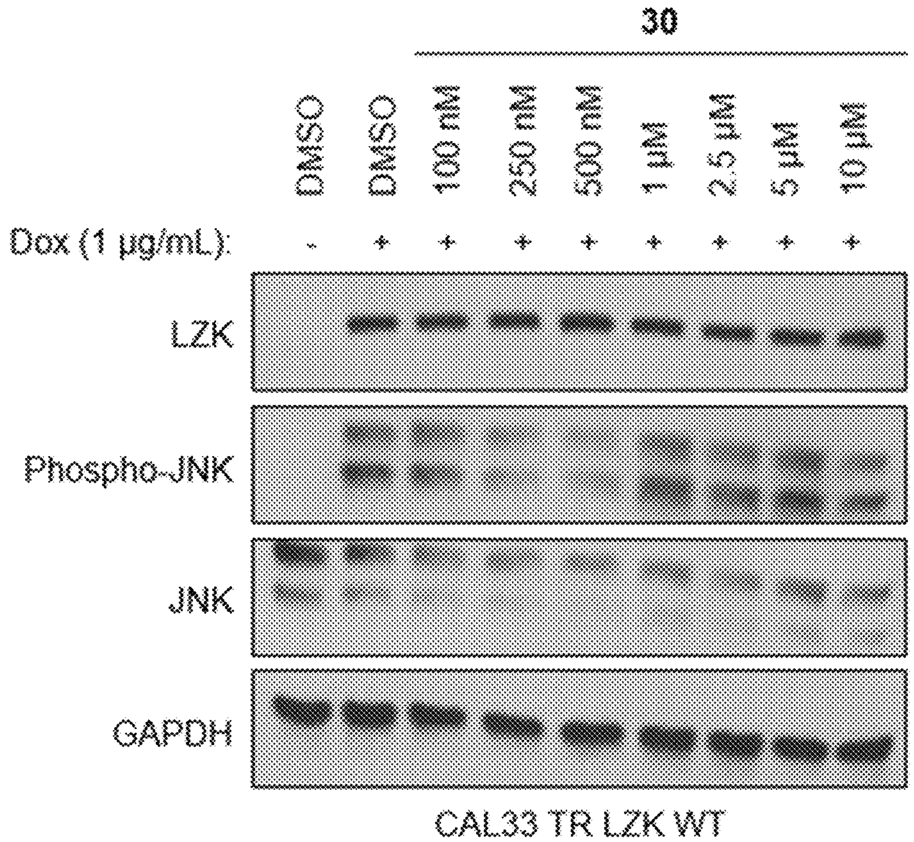
Figure 49:
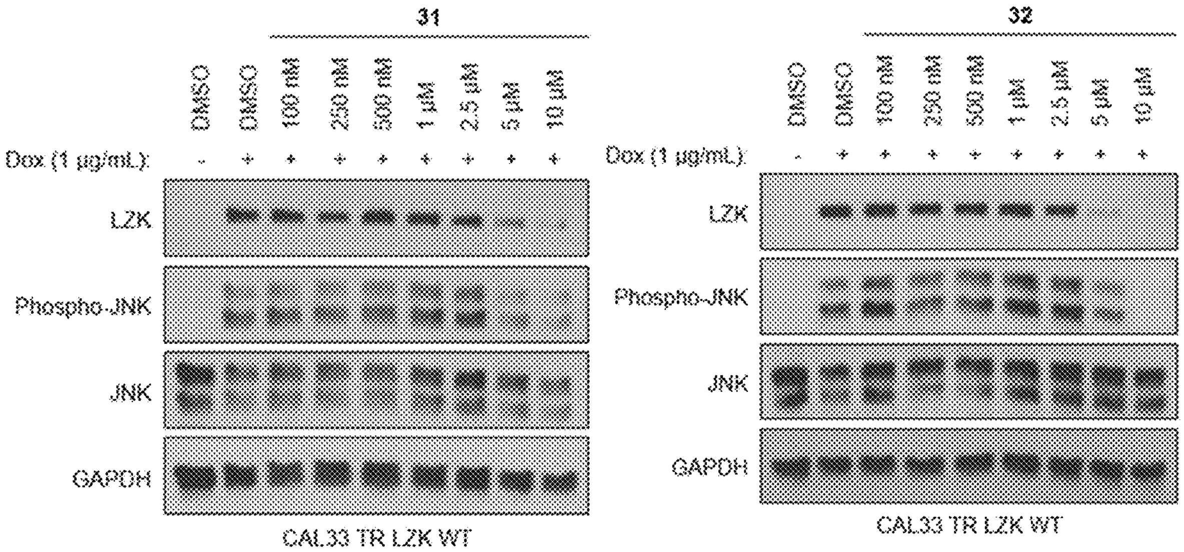

FIGS. 27 and 39-49 show LZK degradation and JNK signaling inhibition by compounds 4-5, 9-26, and 30-32 at concentrations from 0-10 μM in CAL33 cells treated with doxycycline for 48 hours and the LZK PROTAC for 24 hours. FIG. 48 shows that compound 30 did not degrade LZK.

Figure 50:
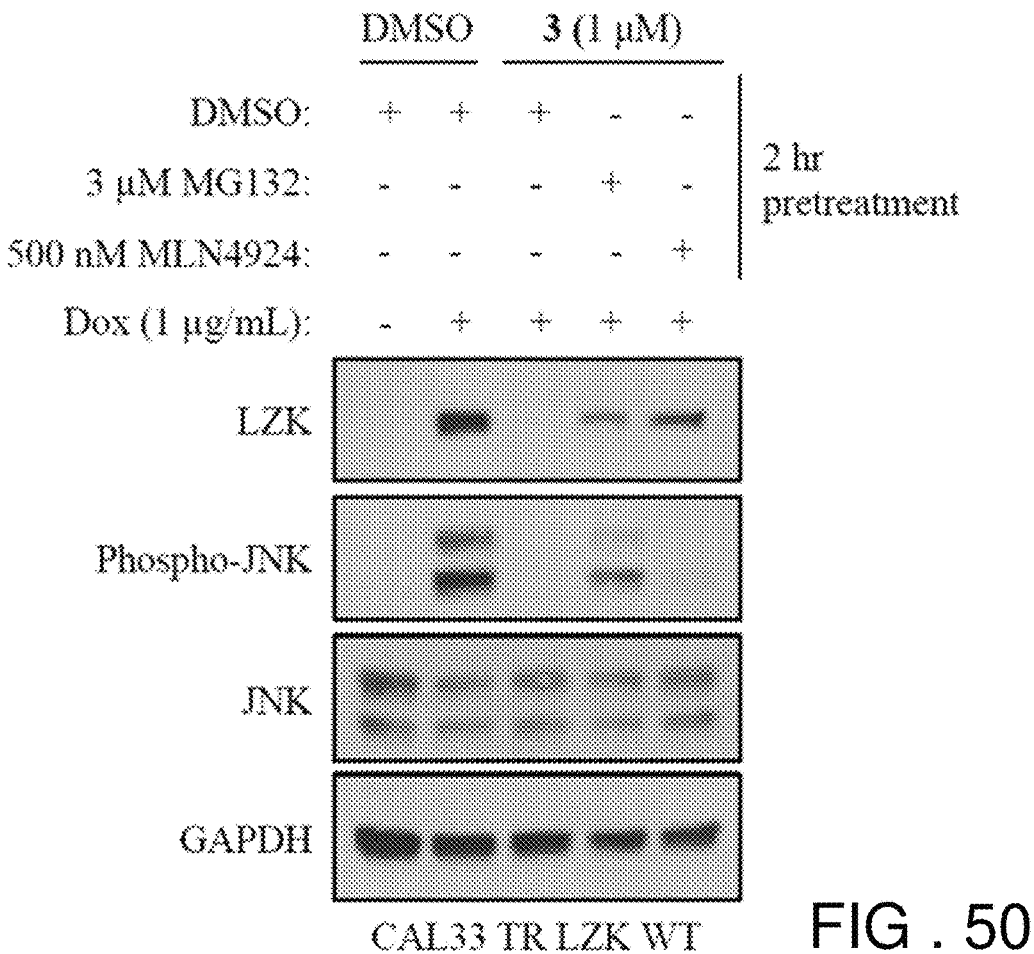
FIG. 50 shows that two-hour pretreatment with MG132 (3 μM) or MLN4924 (500 nM) restores doxycycline-induced LZK expression in CAL33 cells treated with compound 3 at 1 μM for 24 hours.
Figure 51:
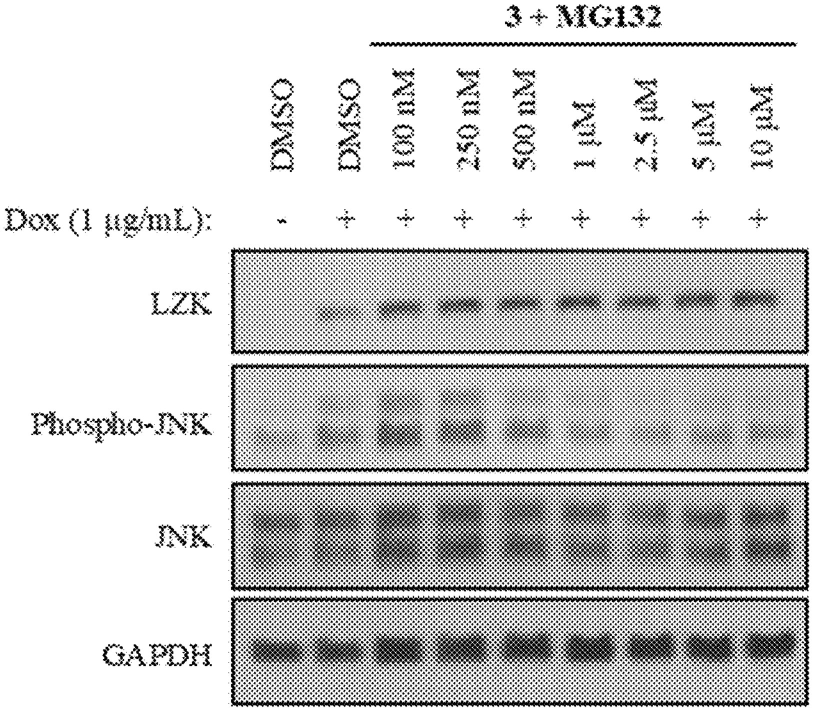
FIG. 51 shows that compound 3 in combination with MG132, a proteasome inhibitor, rescued LZK expression in CAL33 cells.

Compound 3-mediated loss of LZK expression in CAL33 was rescued by adding a proteasome inhibitor (MG132), confirming that ubiquitination mediated the degradation (FIGS. 50-51). Furthermore, loss of LZK expression was rescued with MLN4924 (a NEDD8 inhibitor), validating that ubiquitination mediates LZK degradation (FIG. 50).

Figure 52:
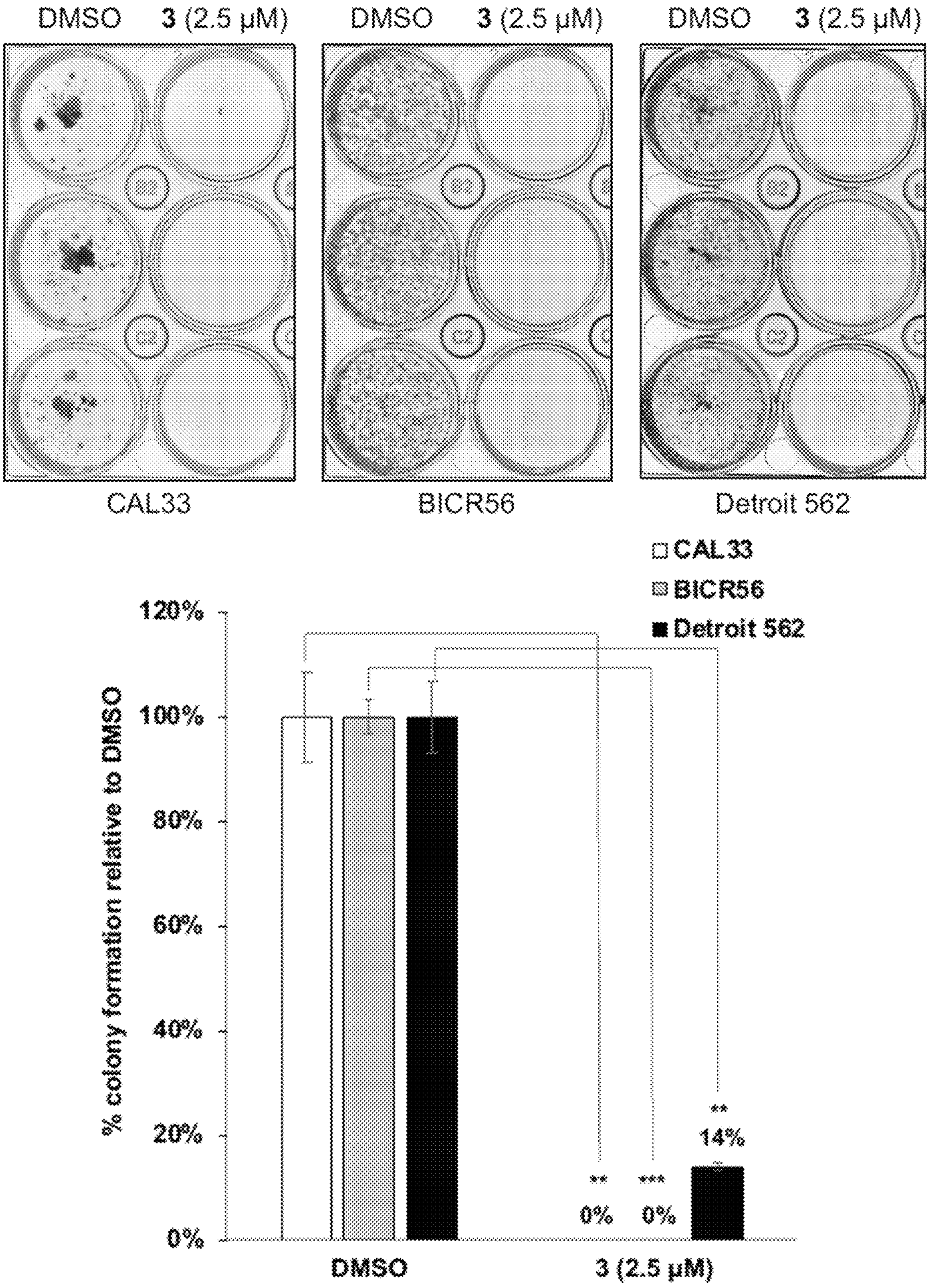
FIG. 52 is a series of images and a bar graph showing that compound 3 suppressed clonogenic growth of HNSCC cell lines with amplified MAP3K13 (CAL33, BICR56, and Detroit 562).
Figure 53:
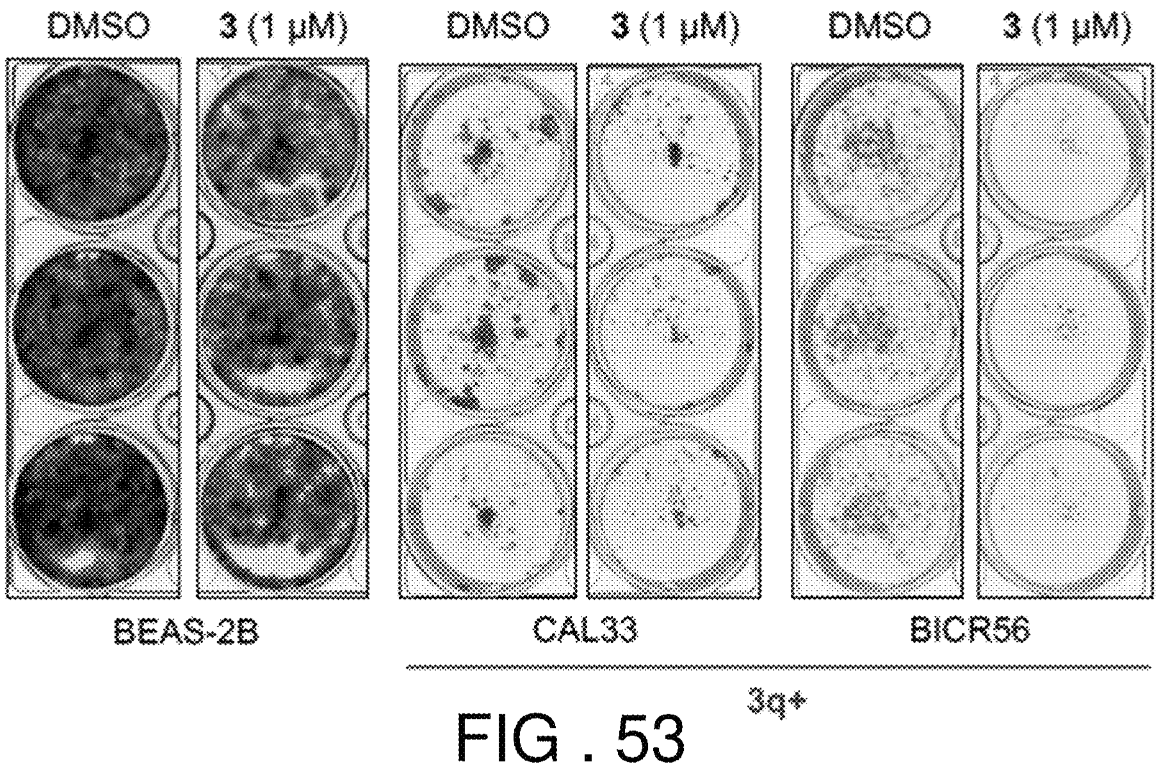
FIG. 53 shows that compound 3 at a concentration of 1 μM for 14 days resulted in significant decreases in clonogenic growth of CAL33 and BICR56 cells compared to little effect on control cells (BEAS-2B).
Figure 54:
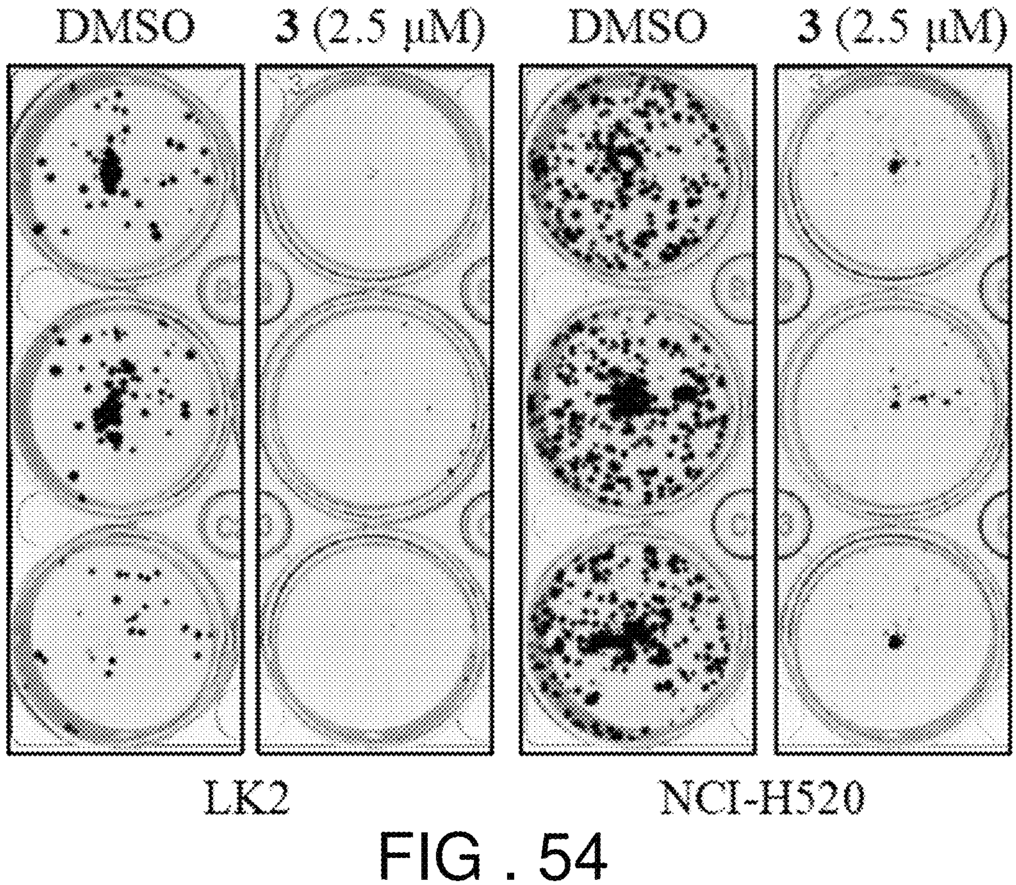
FIG. 54 shows that compound 3 (2.5 μM) significantly decreased LSCC cell growth (LK2 and NCI-H520 cell lines).
Figure 55A:
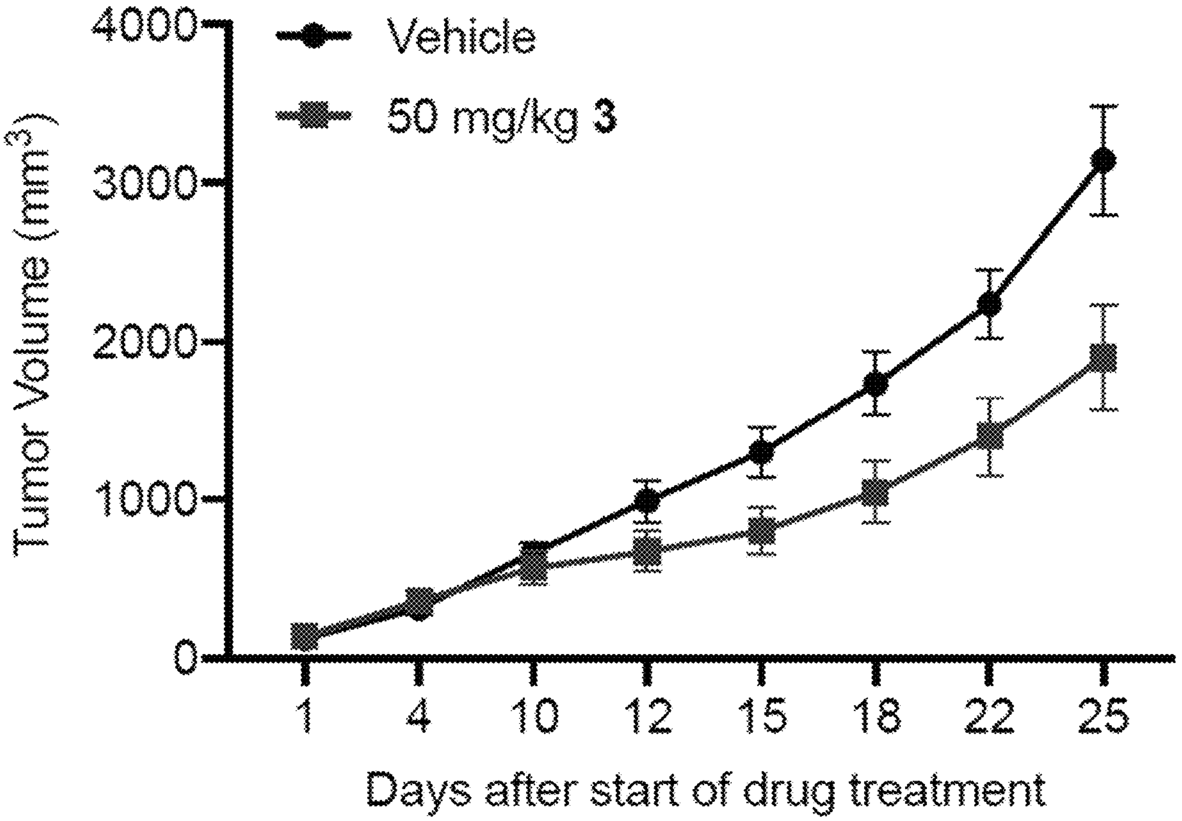
FIGS. 55A-55C show suppression of tumor growth in mice (n=10) treated with compound 3 (50 mg/kg, q.d., five days on/two days off) compared to the vehicle control group in an in vivo HNSCC PDX mouse model with amplified LZK.
Figure 55B:
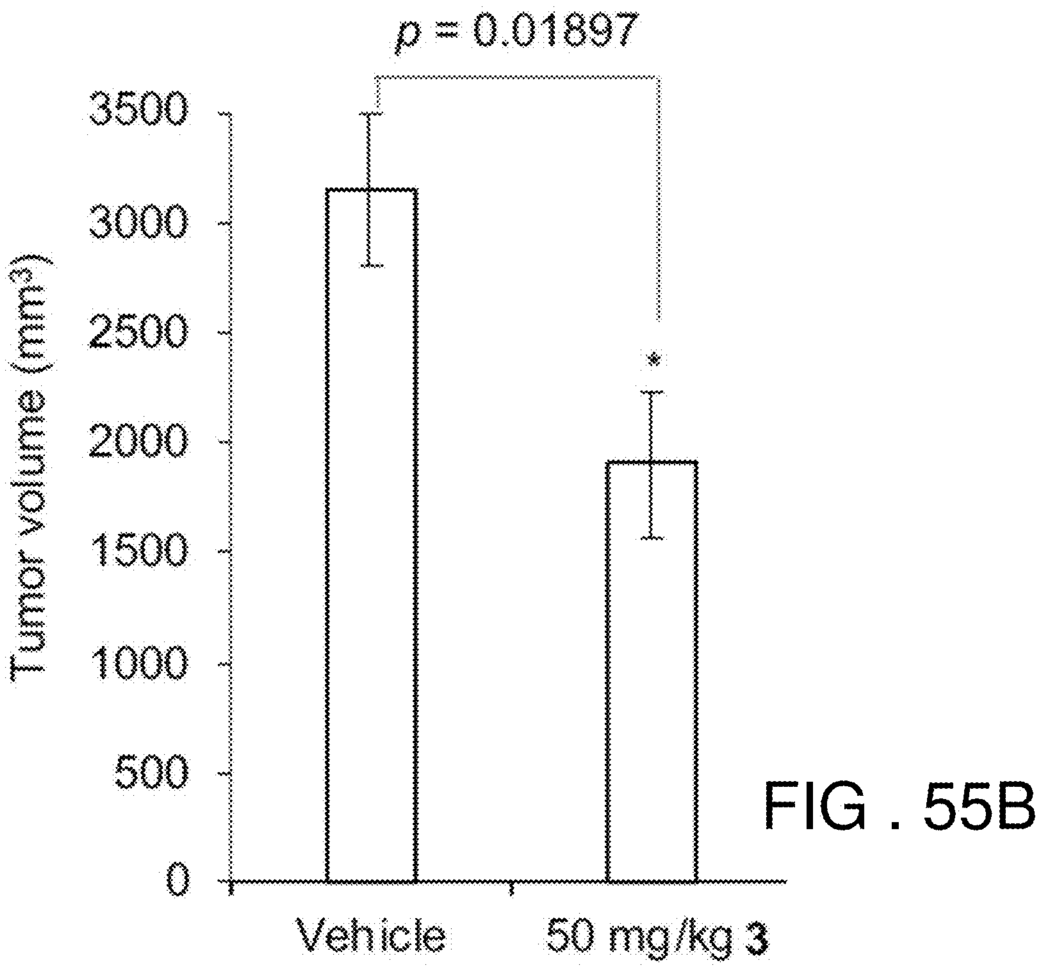
Figure 55C:
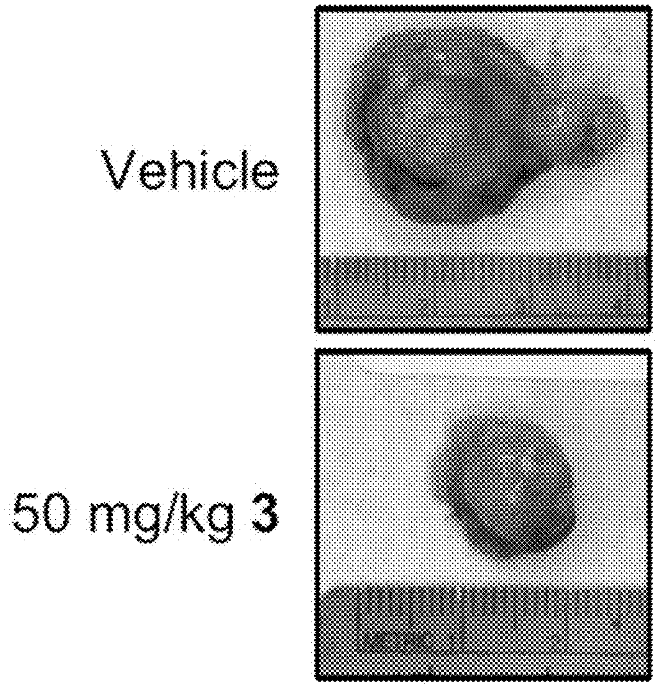
Figure 56A:
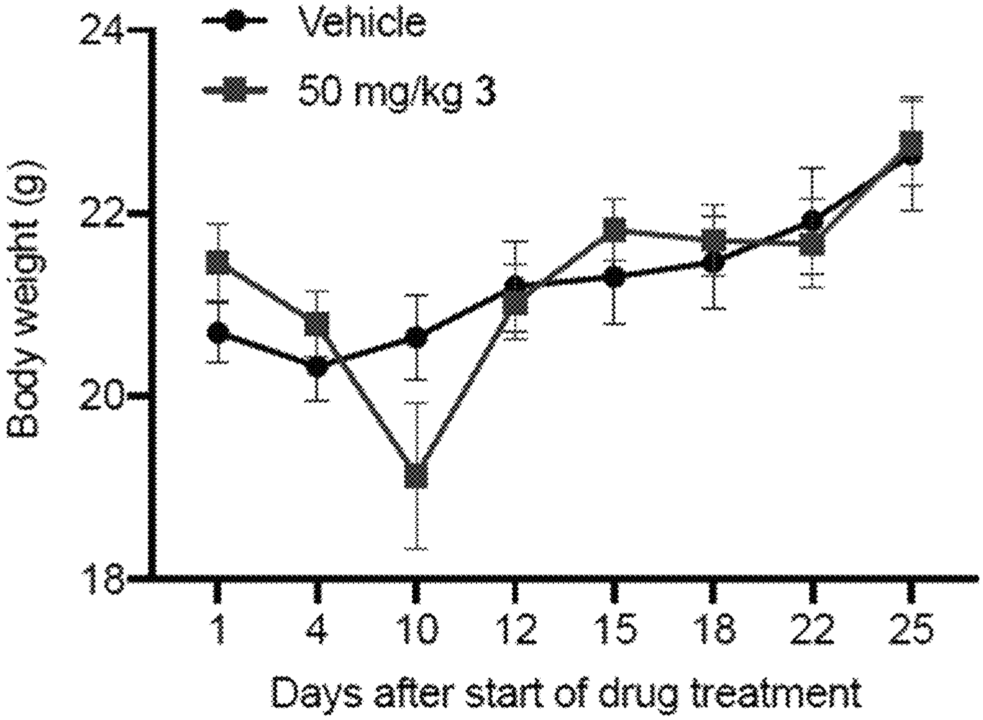
FIGS. 56A and 56B are graphs showing mouse body weights of HNSCC PDX mice treated with compound 3 (50 mg/kg, q.d., five days on/two days off); mean mouse body weight±SEM; Student's t-test; N.S.=not significant.
Figure 56B:
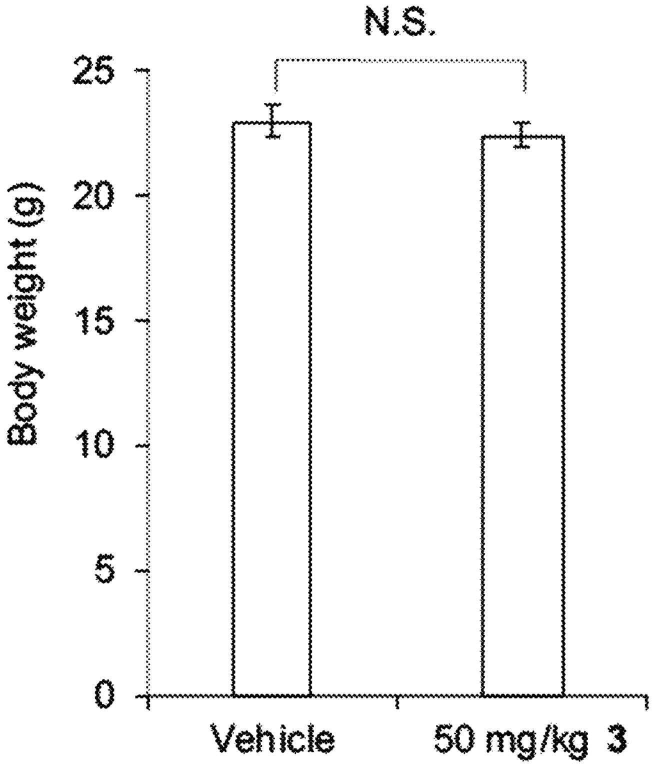

To determine if compound 3 suppressed colony formation in HNSCC cells, CAL33, BICR56, and Detroit 562 (3q amplicon-positive HNSCC cells) were treated with 2.5 μM of compound 3. An almost complete loss of colony formation was observed (FIG. 52) with slight decreases in growth in control cells. Similar results were obtained at 1 μM of compound 3 (FIG. 53). Quantification of growth is indicated in the bar chart. *p<0.001, p<0.01, Student's t-test. Similar results also were obtained in LSCC cells—LK2 and NCI-H520 (FIG. 54). Similar results were obtained with 1 μM of compound 3. Short-term cell viabilitywas reduced in the CAL33 and BICR56 cells after treatment with compound 3. PROTAC-mediated loss of LZK expression was rescued by adding a proteasome inhibitor(MG132), confirming that ubiquitination mediated the degradation (FIGS. 51, 52). Furthermore, loss of LZK expression could be rescued with MLN4924 (a NEDD8 inhibitor), validating that ubiquitination mediates LZK degradation (FIG. 54).

Figure 57:
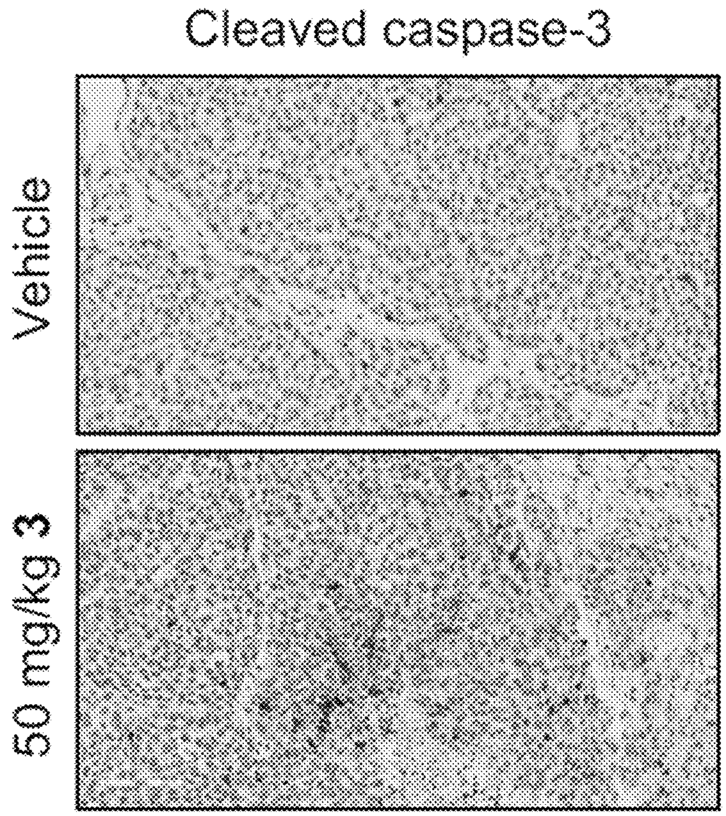
FIG. 57 shows representative IHC staining images of cleaved caspase-3 for each treatment group.
Figure 58:
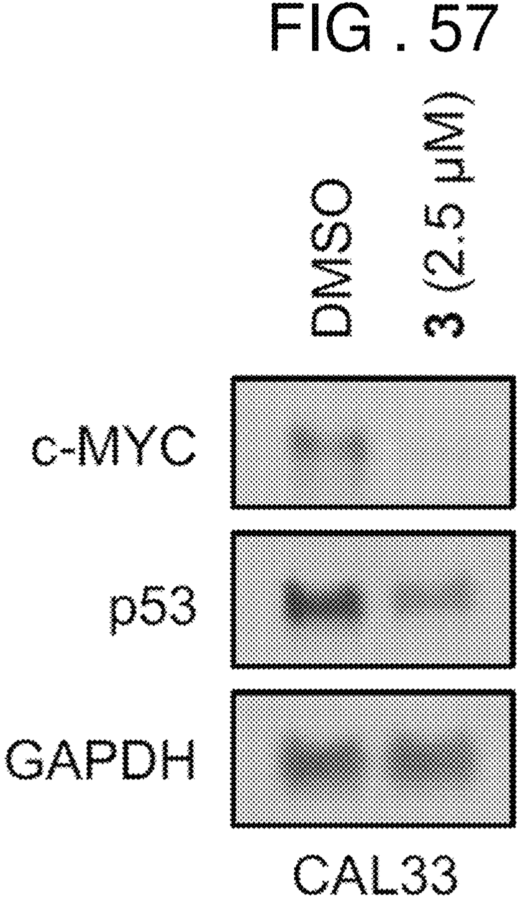
FIG. 58 shows that compound 3 (2.5 μM) treatment in the CAL33 cells suppresses both GOF-p53 and c-MYC levels at 48 hours.
Figure 59:
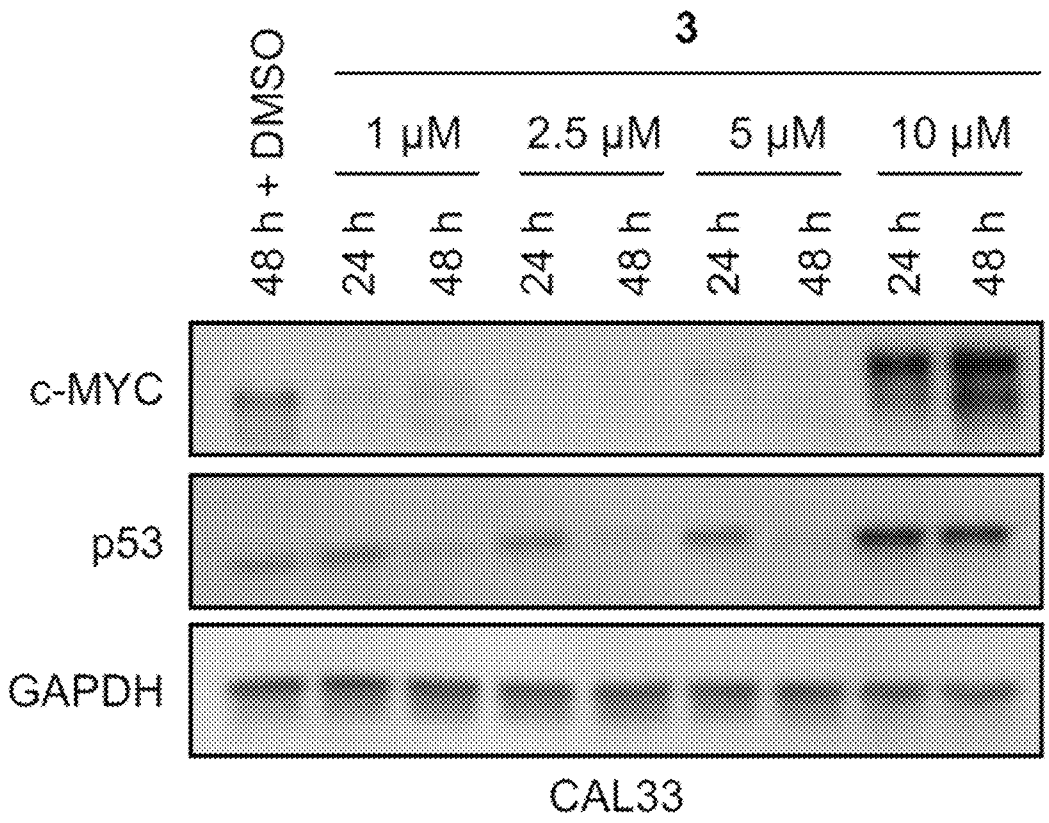
FIG. 59 shows that treatment with various concentrations of compound 3 for 24 hours and 48 hours causes decreases in c-MYC and GOF-p53 expression in CAL33 cells, with an observed hook effect at the highest concentration (10 μM).

To assess compound 3 in vivo, a patient-derived xenograft mouse model of HNSCC with amplified LZK (PDX model: HN5120) was used. Depletion of LZK expression with 3 (50 mg/kg, q.b.) suppressed tumor growth compared to vehicle control treated mice without effects on overall weight (FIGS. 55A-55C, 56A-56B). IHC staining revealed an increase in staining for cleaved caspase-3, an apoptotic marker, with PROTAC 3 treatment (FIG. 57). Furthermore, as shown in FIGS. 58 and 59, loss of both GOF mutant p53 (R175H) and c-MYC abundance in the CAL33 cells treated with compound 3 was observed, indicating that using a targeted degrader to degrade LZK potently suppresses two critical oncogenic pathways in HNSCC cells at 24 and 48 hours with the observed hook effect at the highest concentration.

Figure 60:
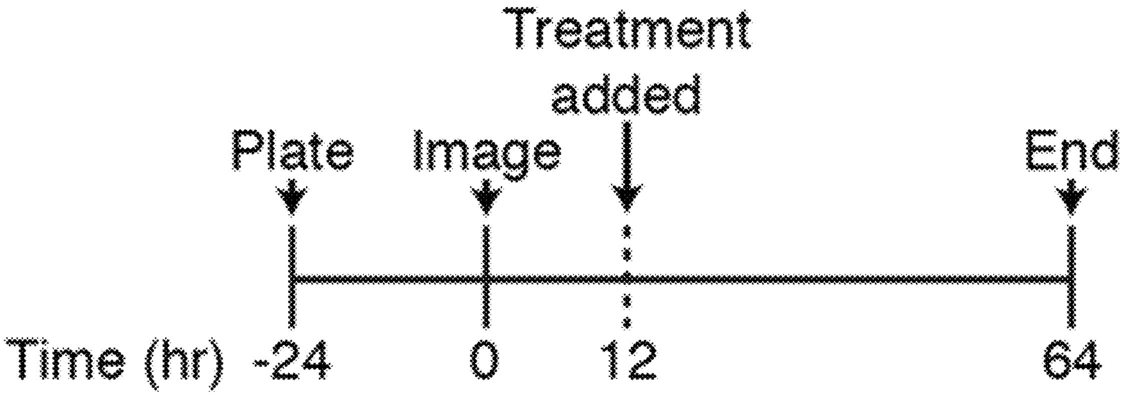
FIG. 60 is a schematic diagram of an experimental setup of live-cell imaging experiments.

Given the observation that LZK regulates c-MYC and GOF-p53, which both regulate the cell cycle, the impact of the LZK inhibitor GNE-3511 and targeted degrader 3 on cell cycle progression was assessed. To monitor the two compounds' effects, a single-cell assay was used to track asynchronously dividing cells and monitor CDK2 activity (Cappell et al., *Cell* 2016, 166:167-180), which gradually increases over the cell cycle (Spencer et al., *Cell* 2013, 155:369-383), in SCC-15 HNSCC cells that are 3q amplicon-positive and have high levels of LZK expression. Treatment with GNE-3511 or the LZK-targeting degrader 3 conferred a slower increase in CDK2 activity over the cell cycle compared to the control, which resulted in an elongated G1, S, and G2 phase. In fact, many cells failed to undergo a second mitosis within the 64 hour imaging period following drug treatment. FIG. 60 is a schematic diagram of the experimental setup of live-cell imaging experiments.

Figure 61A:
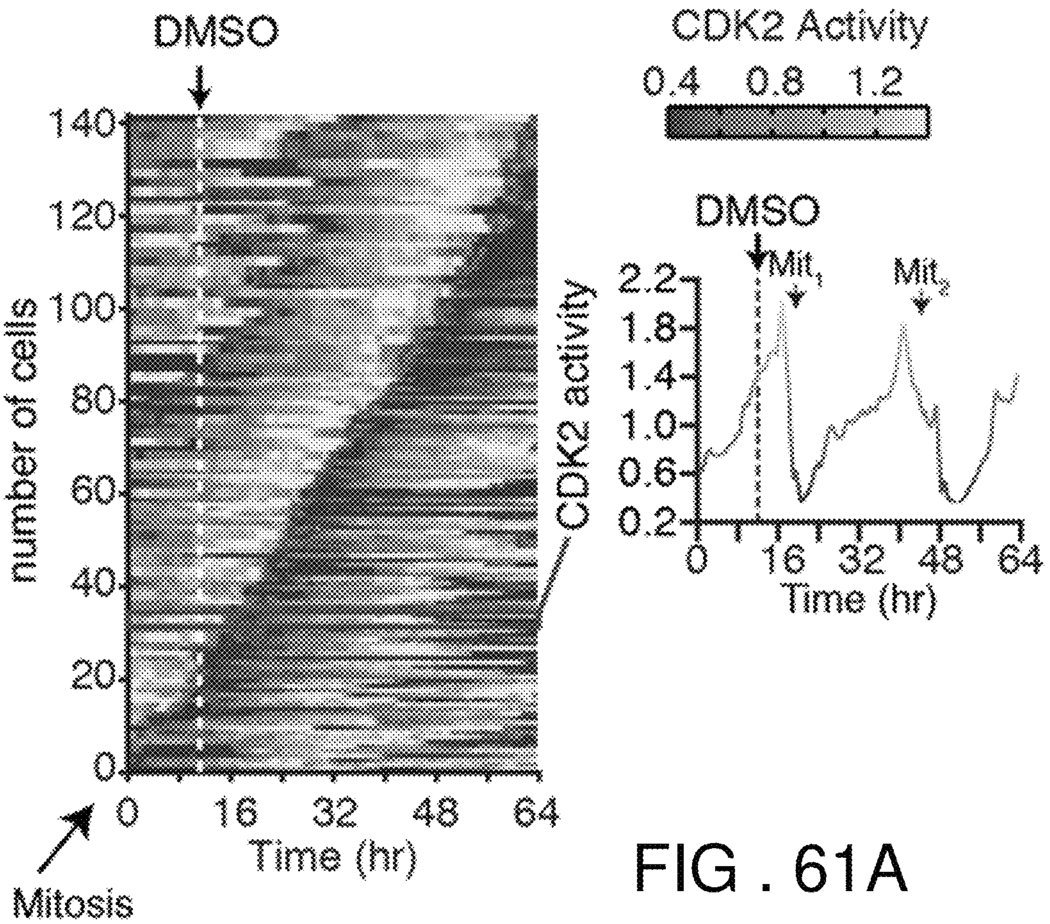
FIGS. 61A-61C are heat maps of CDK2 activity in asynchronously cycling cells treated with DMSO (61A), compound 3 (61B), or GNE-3511 (61C) at the indicated time.
Figure 61B:
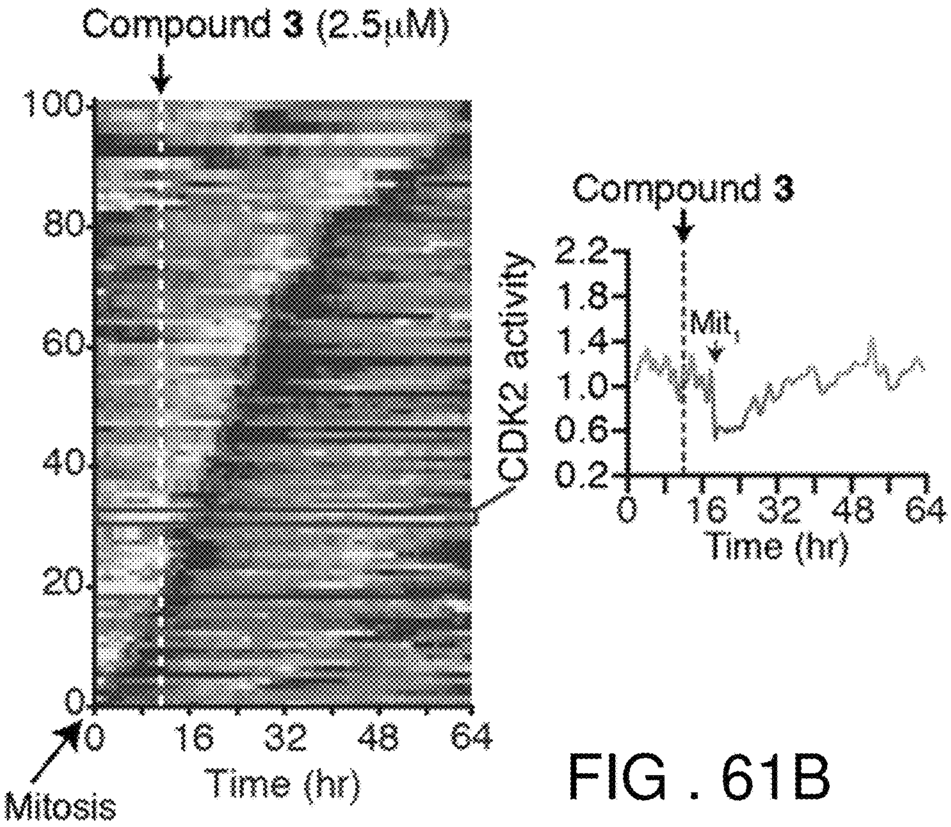
Figure 61C:
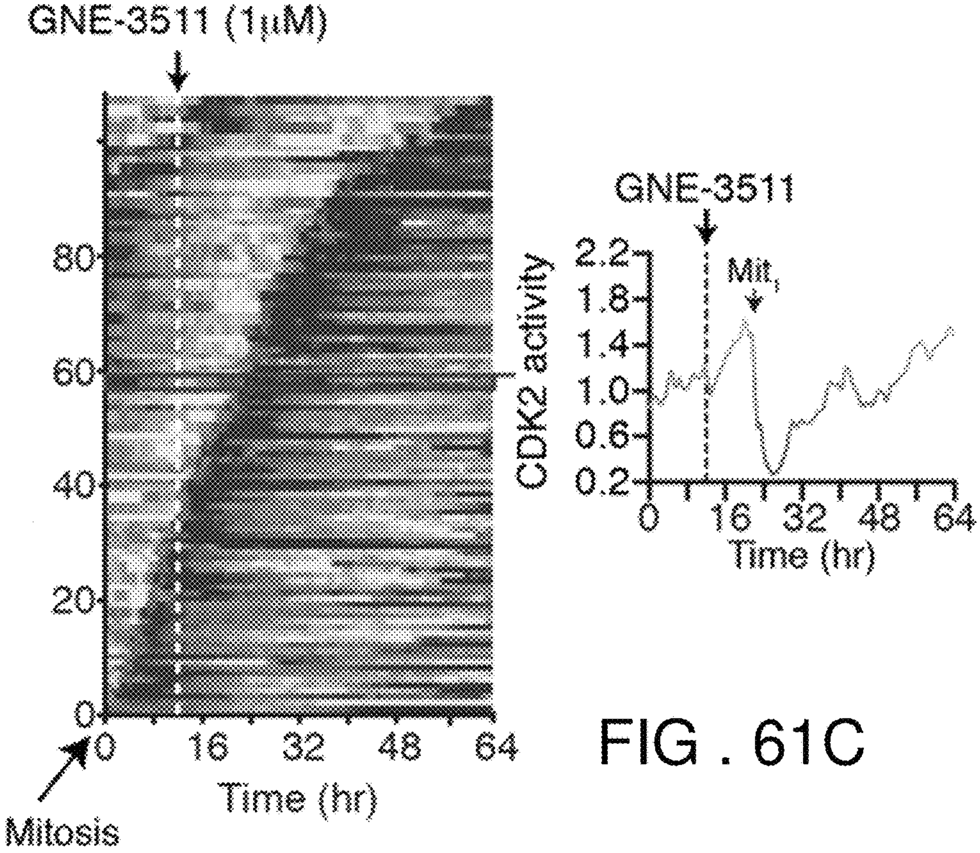
Figure 62:
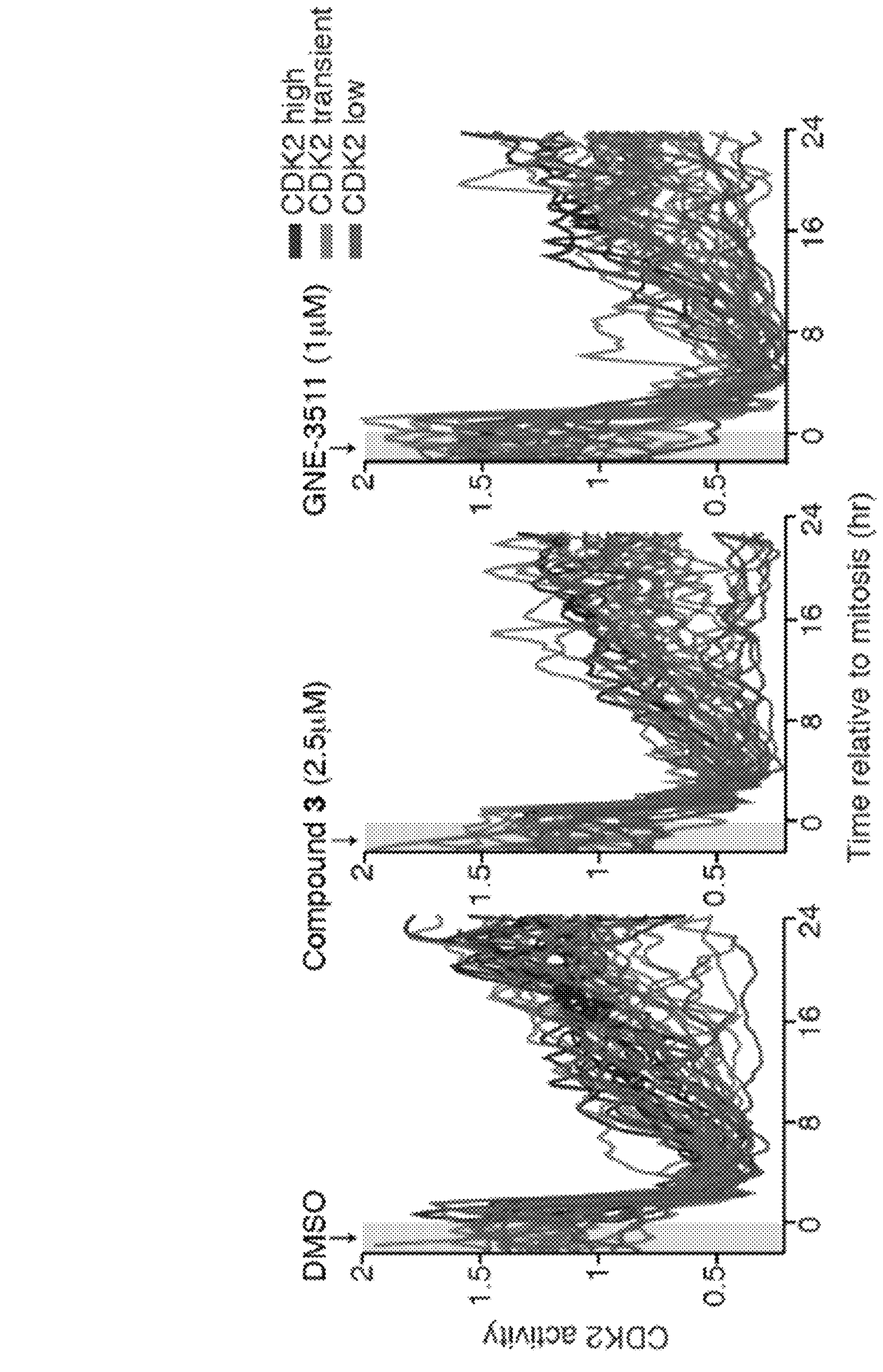
FIG. 62 is a series of graphs showing that GNE-3511 and compound 3 caused cells to have lower CDK2 activity throughout the cell cycle.
Figure 63:
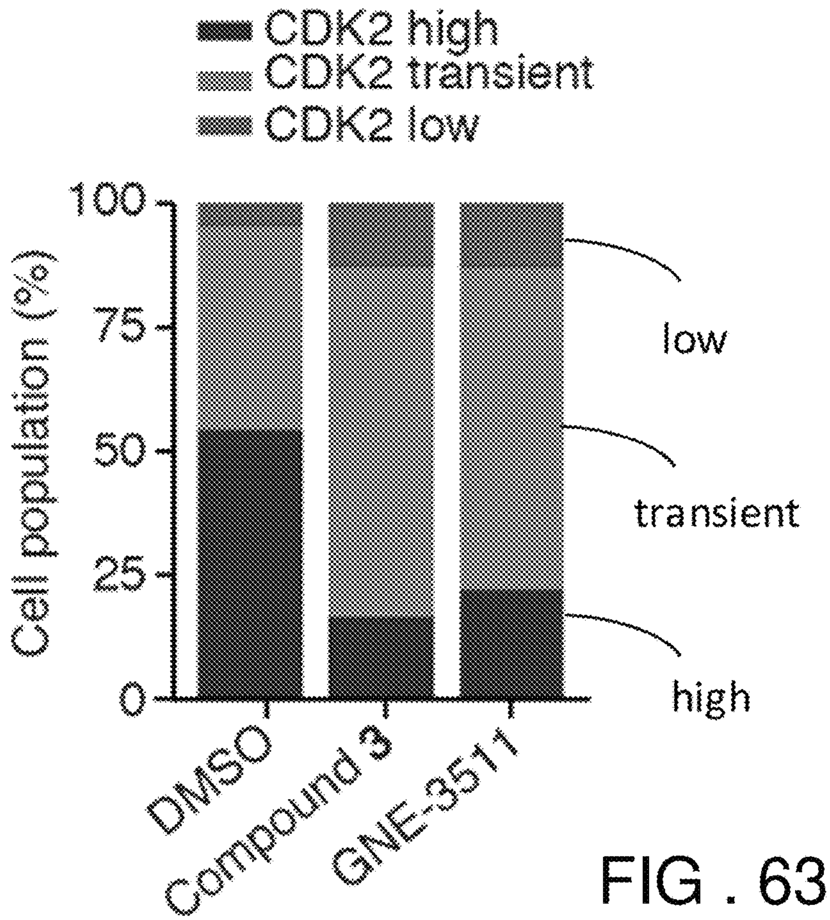
FIG. 63 is a bar graph showing that GNE-3511 and compound 3 caused an increased fraction of cells entering a quiescent state.
Figure 64:
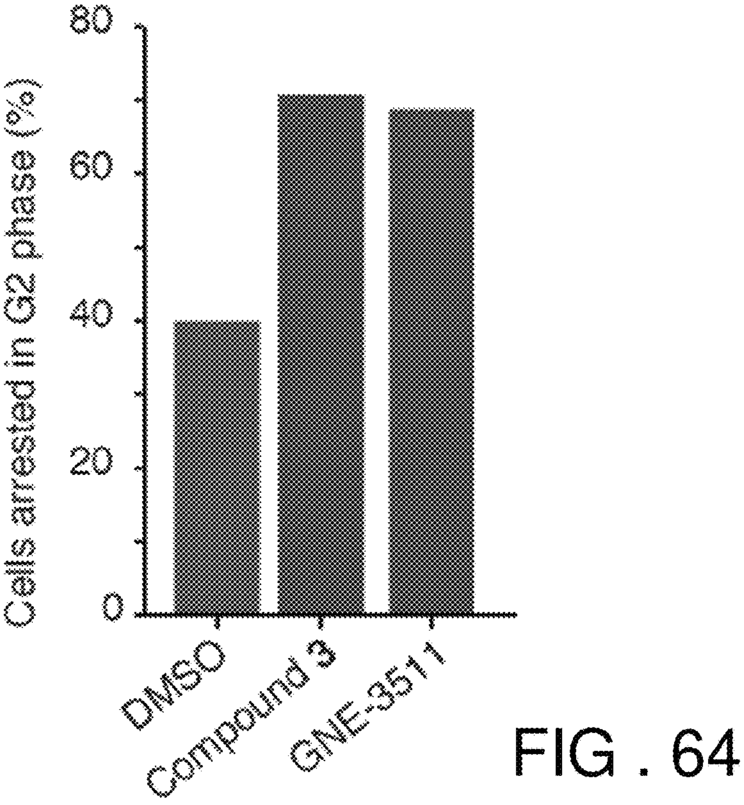
FIGS. 64 and 65 are graphs showing that GNE-3511 and compound 3 caused a G2-phase cell-cycle arrest.
Figure 65:
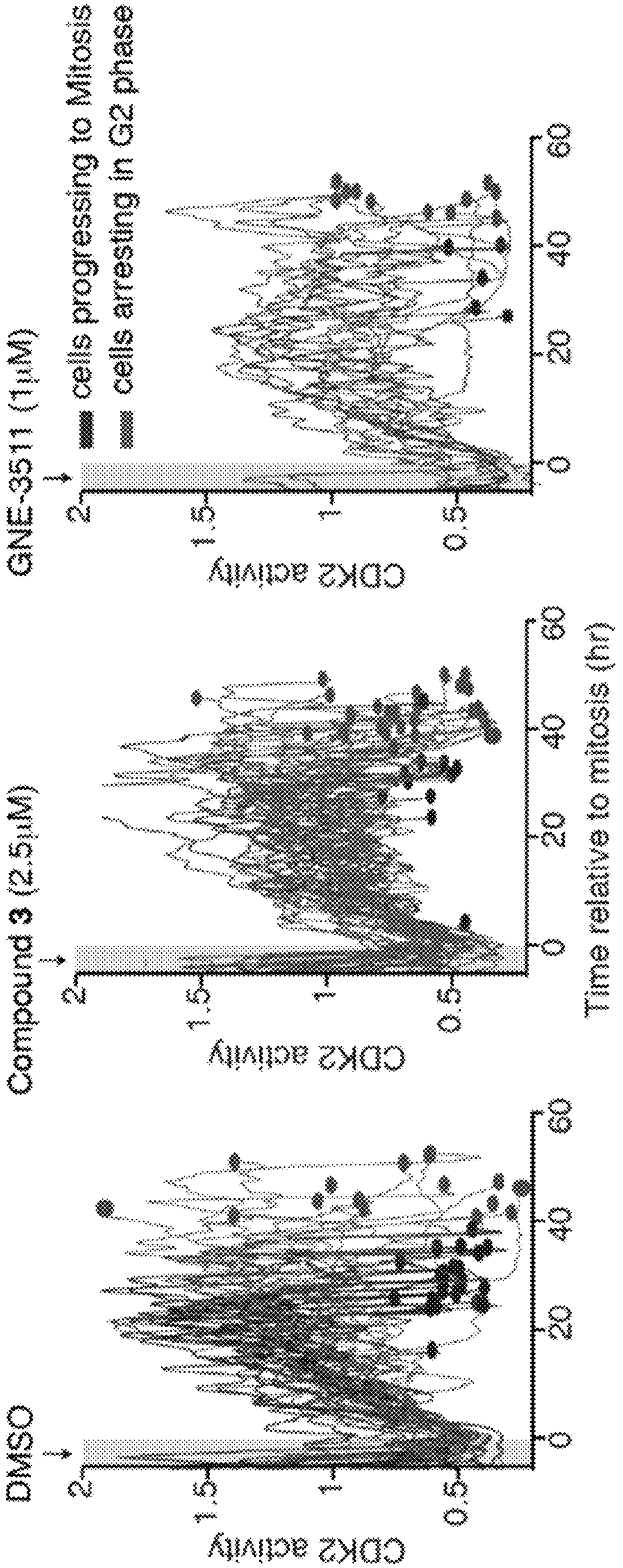
Figure 67:
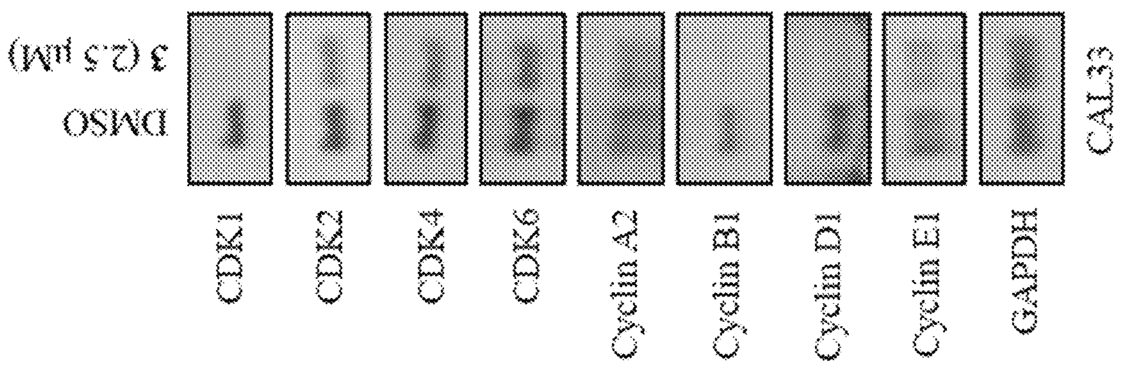
FIG. 67 shows abundance of a panel of CDKs and cyclins in CAL33 cells treated with compound 3 for 48 hours.
Figure 66:
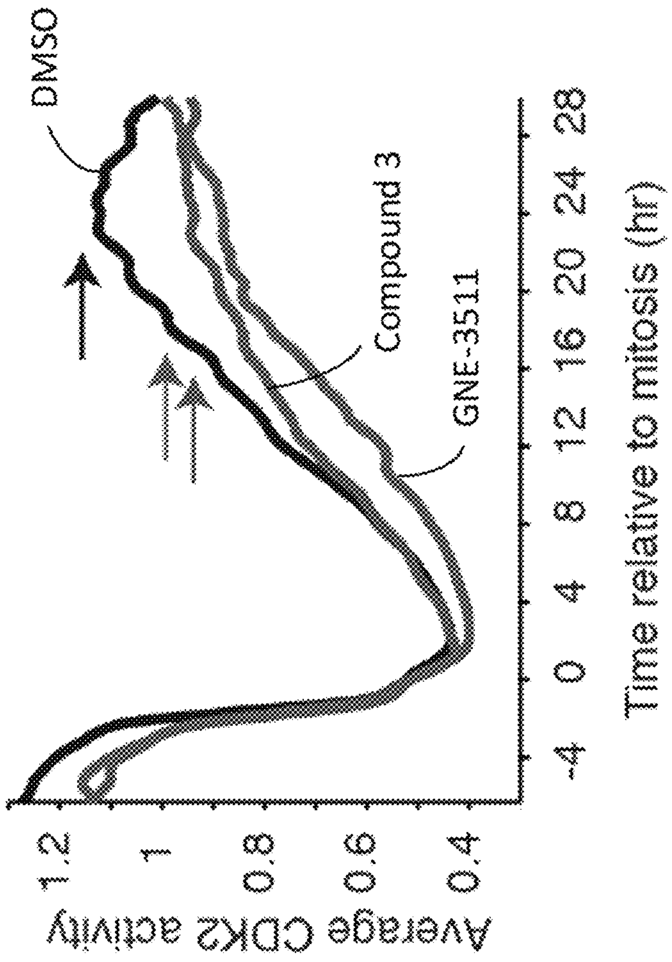
FIG. 66 is a graph showing that GNE-3511 and compound 3 caused slower increase in and lower overall CDK2 activity during progression through the cell cycle.
Figure 68:
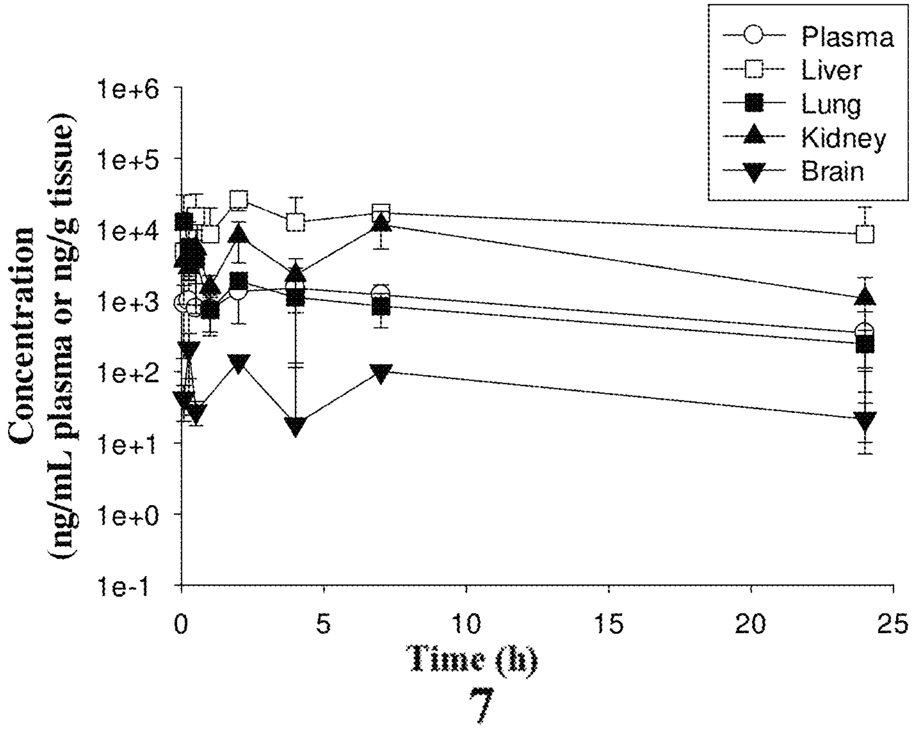
FIG. 68 shows pharmacokinetic profile of targeted degraders 3 and 7 in female NSG mice after single IP administration of 50 mg/kg (mean±SD; n=3 per time point).
Figure 68:
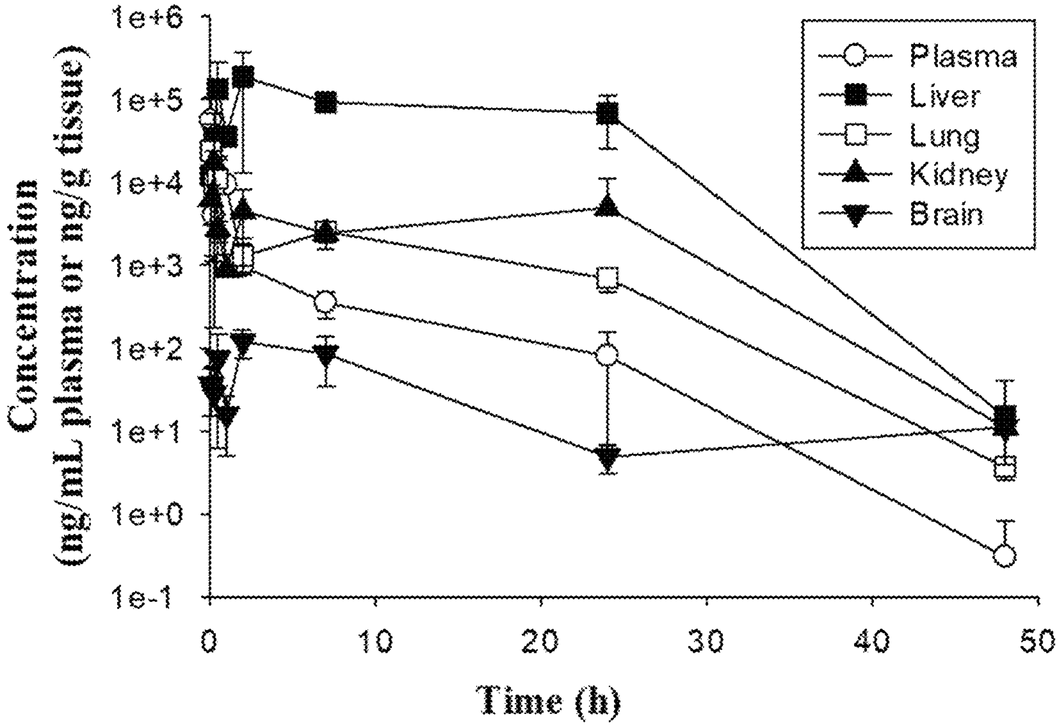

FIGS. 61A-61C are heat maps of CDK2 activity in asynchronously cycling cells treated with DMSO (61A), compound 3 (61B), or GNE-3511 (61C) at the indicated time. Cells were sorted by the time of the first mitosis relative to the start of the imaging. Although the time of mitosis was independently identified using the nuclear marker H2B-mTurquoise, it can also be visualized by a rapid drop in CDK2 activity, as indicated by the black arrow. Inset is a CDK2 activity trace for a single representative cell. The red line indicates the position of that cell within the heat map. Quantification of the single-cell data showed a significant increase in the percentage of cells halting in G2 phase. FIG. 62 is a series of graphs showing that GNE-3511 and compound 3 caused cells to have lower CDK2 activity throughout the cell cycle. FIG. 63 is a bar graph showing that GNE-3511 and compound 3 caused an increased fraction of cells entering a quiescent state. FIGS. 64 and 65 are graphs showing that GNE-3511 and compound 3 caused a G2-phase cell-cycle arrest. FIG. 66 is a graph showing that GNE-3511 and compound 3 caused slower increase in and lower overall CDK2 activity during progression through the cell cycle. Importantly, the fraction of cells exiting mitosis with low CDK2 activity, which indicates entry into a quiescent state (Spencer et al., *Cell* 2013, 155:369-383), was also elevated by treatment with either GNE-3511 or targeted degrader 3. Thus, LZK inhibition causes either a G2 arrest or a G0 arrest. Consistent with these results, targeted degrader treatment resulted in decreased expression of cyclins and cyclin-dependent kinases in the CAL33 HNSCC cell line (FIG. 67). Finally, in vivo studies demonstrated variable tissue distribution and overall promising drug characteristics for compound 3; results for compound 7 also are shown (FIG. 68). Female NSG mice received a single IP administration of 50 mg/kg of compound 3 or compound 7 (mean±SD; n=3 per time point). However, in vitro ADME (absorption, distribution, metabolism, and excretion) properties of compounds 3 and 7 show that membrane permeability may be a concern (Table 6, PAMPA=parallel artificial membrane permeability assay, RLM=rat liver microsome). PAMPA results of additional compounds are shown in Table 7.

TABLE 6

| Targeted Degrader | Solubility (μg/mL) | PAMPA pH 7.4 ($10^{-6}$ cm/sec) | RLM Stability ($t_{1/2}$, min) |
|---|---|---|---|
| 3/CCW-V-97 | <1 | <1 | >30 |
| 7/CCW-V-101 | 26 | <1 | >30 |

TABLE 7

| Targeted Degrader | Mean permeability ($10^{-6}$ cm/sec) | Ratio of mean permeability ($\times 10^4$ cm/s) related to low permeability control (atenolol) |
|---|---|---|
| 29/EL1-192 | 0.0100 | 6.74 |
| 24/EL1-124 | 0.0100 | 6.74 |
| 26/EL1-125 isomer 2 | 0.0022 | 1.47 |
| 13/EL1-37/40 | 0.0019 | 1.31 |
| 12/CCW-VI-052 | 0.0009 | 0.61 |
| 23/EL1-119 | 0.0006 | 0.44 |
| 25/EL1-125 isomer 1 | 0.0006 | 0.43 |
| 32/VS-01 | 0.0002 | 0.015 |
| 30/CCW-VII-069 | 0.0001 | 0.05 |
| 27/EL1-163 | 0.0000 | 0.01 |
| 20/EL1-114 | 0.0000 | −0.01 |
| 21/EL1-116 | −0.0002 | −0.11 |
| 15/EL1-44 | −0.0002 | −0.14 |
| 9/CCW-V-296 | −0.0007 | −0.46 |
| 14/EL1-42 | −0.0008 | −0.51 |
| 28/EL1-172 | −0.0028 | −1.86 |
| Atenolol | 0.00 | low permeability control |
| Verapamil | 16.49 | high permeability control |

Example 4

Therapeutic Uses

A subject identified as having a disease or condition characterized at least in part by overexpression of LZK is administered a therapeutically effective amount of a pharmaceutical composition comprising an LZK-targeting degrader as disclosed herein. In some examples, the subject is identified as having cancer, such as HNSCC, LSCC, hepatocellular carcinoma, ovarian cancer, small cell lung cancer, neuroendocrine prostate cancer, or esophageal cancer cell (e.g., esophageal adenocarcinoma). In one example, the subject has cancer and identified as having upregulated levels of LZK expression. In any of the foregoing examples, the subject may be administered the therapeutically effective amount of the pharmaceutical composition at periodic intervals for an effective period of time to mitigate at least one sign or symptom of the disease or condition. For example, the subject may be administered the therapeutically effective amount of the pharmaceutical composition once daily or in divided doses over the course of a day, such as 2-3 divided doses per day. The pharmaceutical composition is administered by any suitable route including, but not limited to, parenterally (e.g., intravenously, intramuscularly, subcutaneously), orally, or topically.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound, or a stereoisomer, tautomer, or pharmaceutically acceptable salt thereof, having a general formula:

Q-L-Z where

Z is an E3-ligase binding moiety having a structure

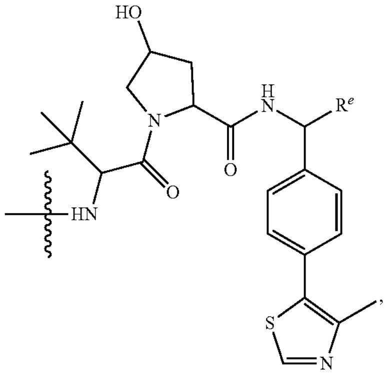

-continued

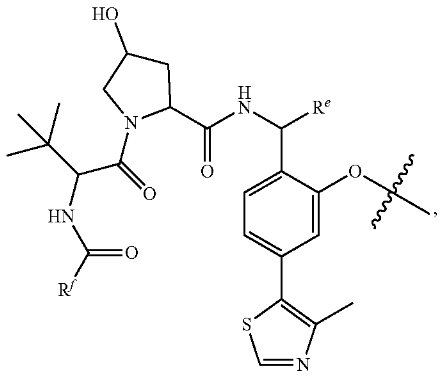

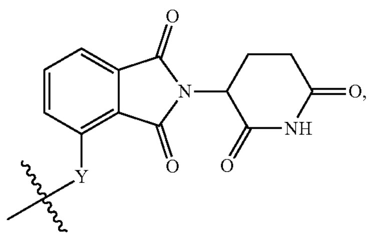

-continued

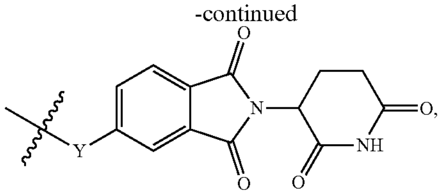

,

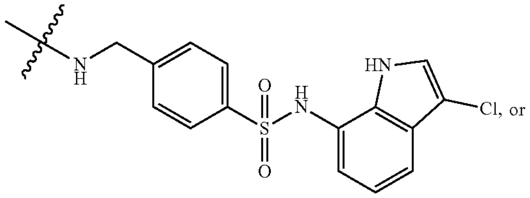

or

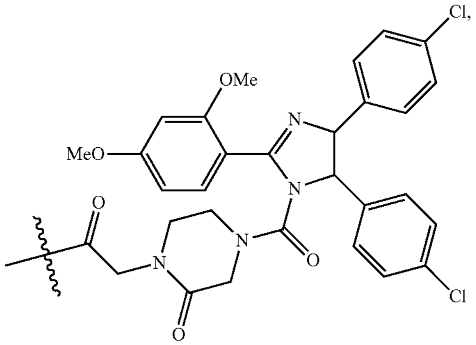

where each $R^e$ independently is substituted or unsubstituted $C_1$-$C_3$ alkyl or H;

$R^f$ is substituted or unsubstituted $C_1$-$C_3$ alkyl or $-N(R^e)_2$; and

Y is O or $N(R^e)$;

L is a linker having a general formula

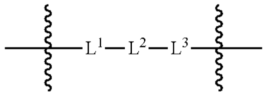

wherein $L^1$ is $-C(O)-$, $-S(O)_2-$, $-CH_2-$, $-C(R^b)(R^c)-$, $-(CH_2)_nC(O)-$, $-C(O)-(CH_2)_n-$, $-N(R^e)-$, $-N(R^e)-(C(H)(R^a))_s-C(O)-$, or $-C(O)-(C(H)(R^a))_s-N(R^e)-$, and $L^1$ binds to Q, or $L^1$ is absent and $L^2$ binds to Q;

$L^3$ is $-C(O)-$, $-S(O)_2-$, $-CH_2-$, $-C(R^b)(R^c)-$, $-C(O)-(CH_2)_n-$, $-(CH_2)_n-C(O)-$, $-N(R^e)-$, $-N(R^e)-(C(H)(R^a))_s-C(O)-$, or $-C(O)-(C(H)(R^a))_s-N(R^e)-$, and $-L^3$ binds to Z, or $L^3$ is absent and $L^2$ binds to Z;

$L^2$ is $-(R^d)_p-$, $-N(R^b)-(R^d)_p-$, $-(R^d)_p-N(R^b)-$, $-N(R^b)-(R^d)_p-N(R^b)-$, $-(N(R^b)-(C(H)(R^a))_s-C(O))_m-N(R^b)-C(H)(R^a)-$, or $-C(H)(R^a)-N(R^b)-(C(O)-(C(H)(R^a))_s-N(R^b))_m-$;

each $R^a$ independently is an amino acid side chain;

each $R^b$ independently is H or $R^c$;

each $R^c$ independently is substituted or unsubstituted aliphatic, substituted or unsubstituted heteroaliphatic, substituted or unsubstituted aryl, substituted or unsubstituted heteroaryl, substituted or unsubstituted arylalkyl, or substituted or unsubstituted alkylaryl;

each $R^d$ independently is substituted or unsubstituted aliphatic, substituted or unsubstituted heteroaliphatic, substituted or unsubstituted aryl, substituted or unsubstituted heteroaryl, $-(CH_2-CH_2-O)_r-$, $-(C(H)(R^a))_s-C(O)-$, $-C(O)N(R^b)-$, or $-N(R^b)C(O)-$;

each $R^e$ independently is substituted or unsubstituted $C_1$-$C_3$ alkyl or H;

m is an integer from 0-11;

n is an integer from 1-10;

p is an integer from 0-5;

r is an integer from 2-20; and s is an integer from 1-20, wherein (i) $L^2$ is not solely $-C(O)N(R^b)-$ or $-N(R^b)C(O)-$, (ii) if $L^2$ terminates in $-C(H)(R^a)-C(O)-$ or $-N(R^b)C(O)-$, then $L^3$ is not $-C(O)-$ or $-S(O)_2-$, and (iii) if $L^3$ is absent, $L^2$ is $-(R^d)_p-$ and p is 0, then $L^1$ binds directly to Z;

Q is a leucine zipper kinase (LZK) binding moiety having a structure (Q1)

(Q1)

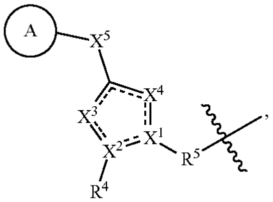

, where each bond represented by ------ is a single or double bond as needed to satisfy valence requirements;

$X^5$ is $-N(H)-$ or absent;

ring A

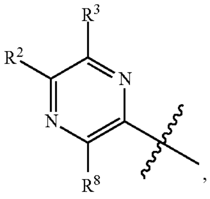

,

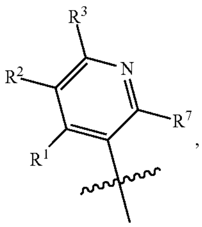

,

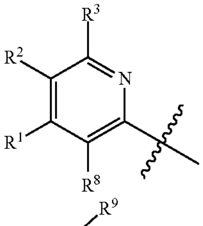

,

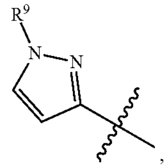

,

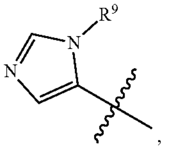

,

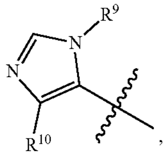

,

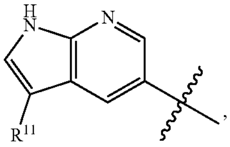

,

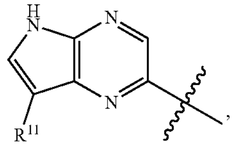

,

-continued

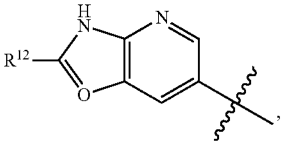

,

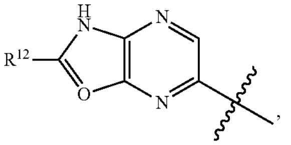

,

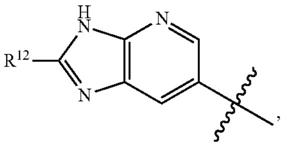

,

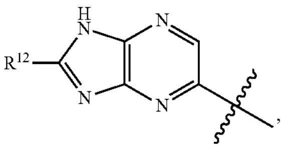

, or

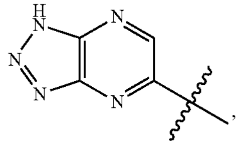

, $R^1$ is cyano, perhaloalkyl, H, alkyl, or perhaloalkoxy;

$R^2$ is H, alkoxy, perhaloalkyl, perhaloalkoxy, haloalkoxy, haloalkyl, cyano, alkyl, cyanoalkyl, amino, or heteroarylalkoxy, or $R^1$ and $R^2$ together with the atoms to which they are attached form a 5- or 6-membered substituted or unsubstituted aryl or substituted or unsubstituted heteroaryl ring;

$R^3$ is H, amino, alkylamino, aminoalkyl, alkoxy, or R'C(O)N(H)— where R' is alkyl, or $R^2$ and $R^3$ together with the atoms to which they are attached form a 5- or 6-membered substituted or unsubstituted aryl or substituted or unsubstituted heteroaryl ring:

$R^7$ and $R^8$ independently are H, alkyl, alkoxy, perhaloalkyl, perhaloalkoxy, or cyano;

each $R^9$ independently is H or alkyl;

each $R^{10}$ independently is H, alkyl, or cyano, $R^{11}$ and $R^{12}$ are H, alkyl, perhaloalkyl, alkoxy, perhaloalkoxy, cyano, or amino and

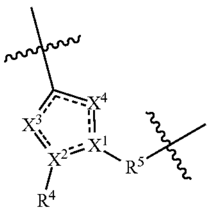

is:

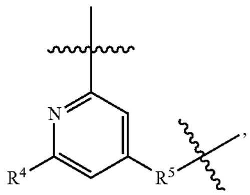

,

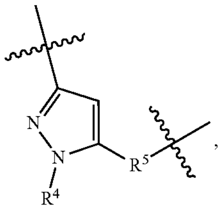

,

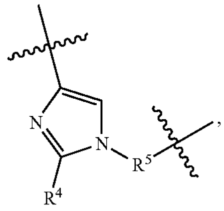

, or

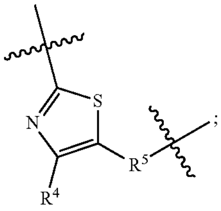

;

wherein $R^4$ is 3,3-difluoro-1-pyrrolidinyl, isopropyl, —C(H)(OH)—C($CH_3$)$_2$, cyclopropyl, or

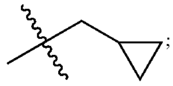 [SMILES: *CC1CC1]

;

$R^5$ is

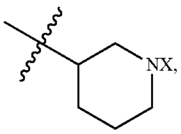

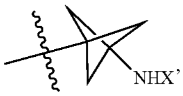

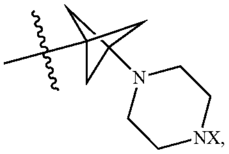

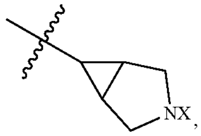

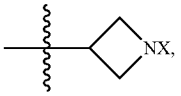

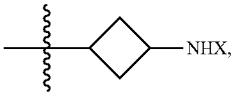

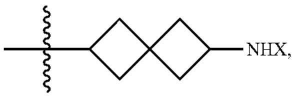

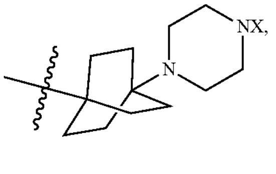

or

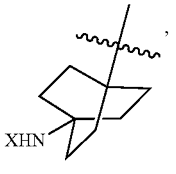

, or where X is a bond or alkyl group binding Q to L.

2. The compound of claim 1, wherein:

(i) N($R^b$) is NH; or (ii) $R^c$ is unsubstituted $C_1$-$C_5$ alkyl, unsubstituted heteroalkyl comprising 1-4 carbon atoms and 1-3 heteroatoms selected from O, N, and S, unsubstituted phenyl, unsubstituted heteroaryl comprising 1-3 heteroatoms selected from O, N, and S, unsubstituted arylalkyl comprising from 1-3 carbon atoms in the alkyl portion, or unsubstituted alkylaryl comprising from 1-3 carbon atoms in the alkyl portion; or (iii) each $R^d$ independently is alkyl, alkylamino, amino-alkyl, amino-alkyl-amino, piperazinyl, piperidinyl, phenyl, $—(CH_2—CH_2—O)_r—$, —C(O)N(H)—,

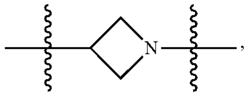,

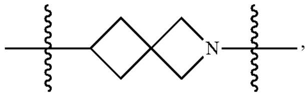, or

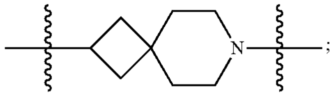;

or (iv) any combination of (i), (ii), and (iii).

3. The compound of claim 1, wherein $L^2$ is one or more of

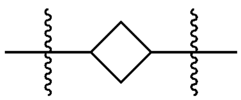, 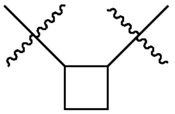,

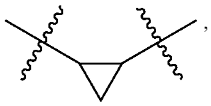, 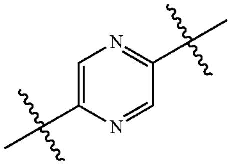,

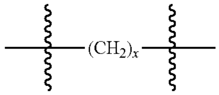,

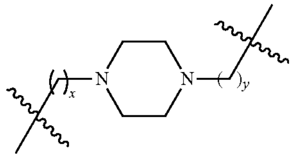,

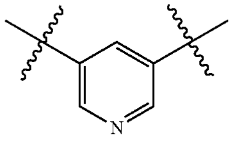, 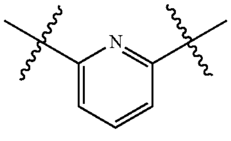,

-continued

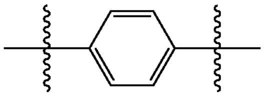,

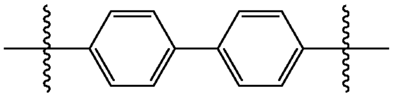,

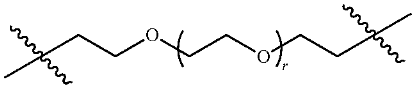,

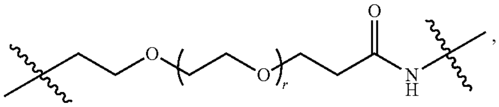,

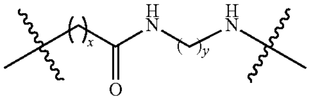,

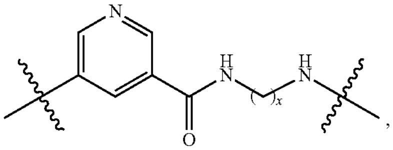,

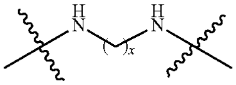, 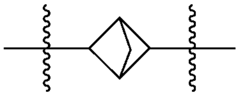,

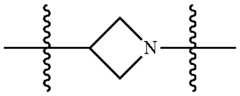,

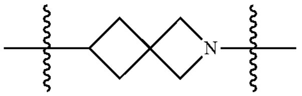,

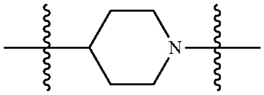, or

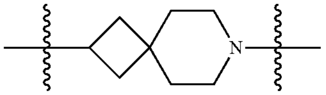, where x and y independently are integers from 1-20, optionally in combination with one or more of —C(O)N(H)— and —N(H)C(O)—.

4. The compound of claim 1, wherein L is:

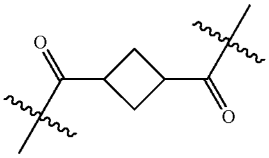, 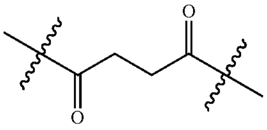, 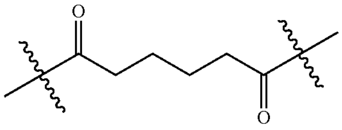,

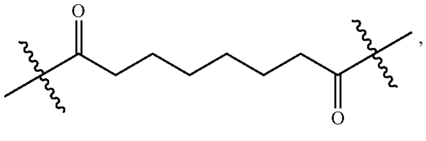, 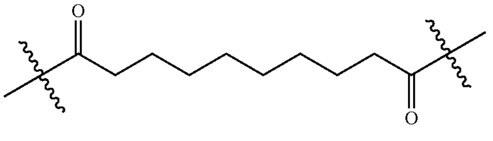,

-continued
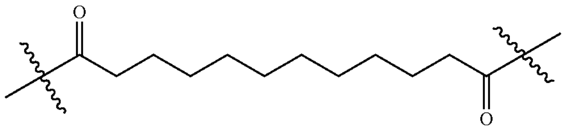,
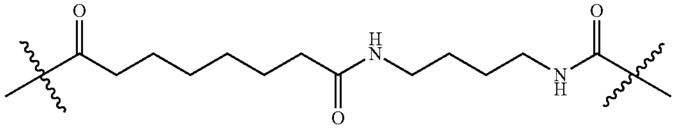, 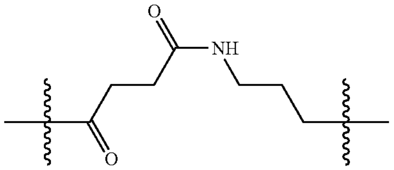,
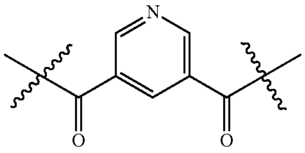, 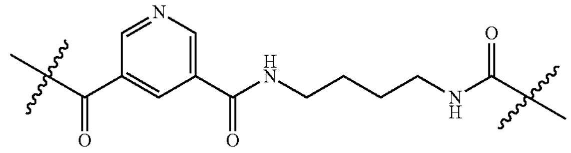,
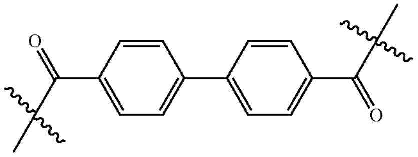,
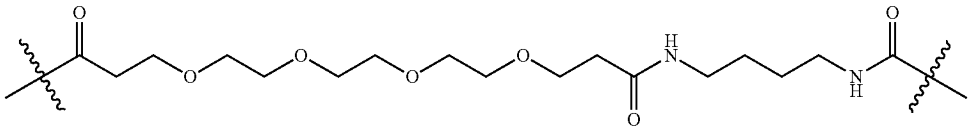,
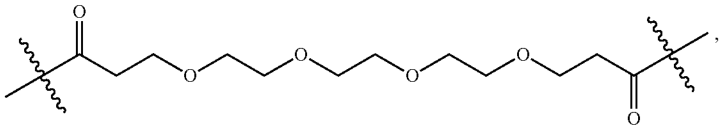,
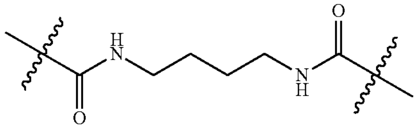, 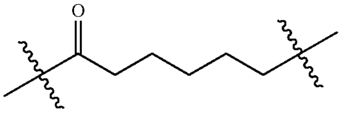,
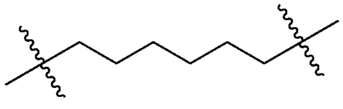, 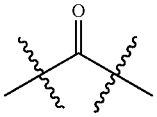, 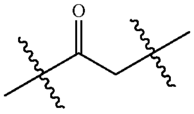, 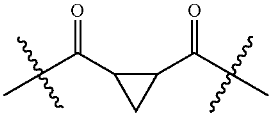,
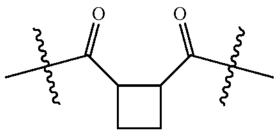, 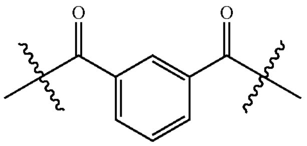, 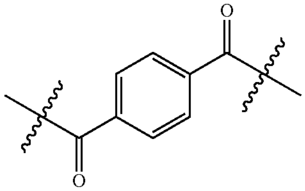,
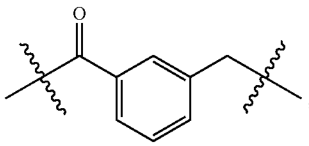, 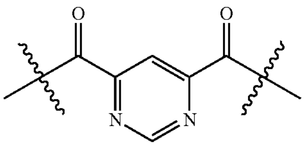, 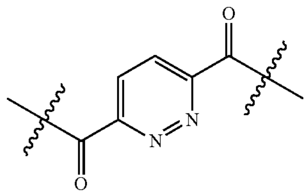,
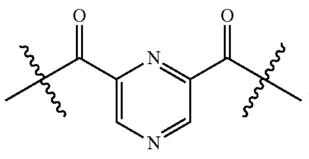, 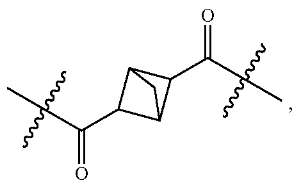, 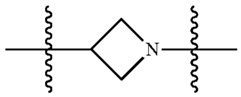, -continued
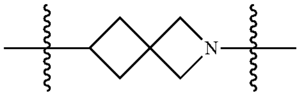, 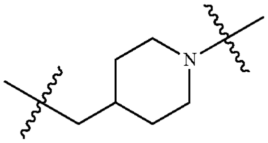, or 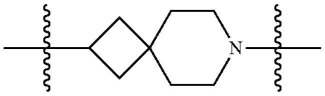.
5. The compound of claim 1, wherein ring A is:
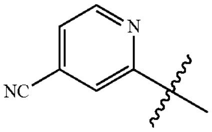, 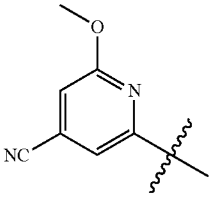,
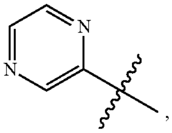, 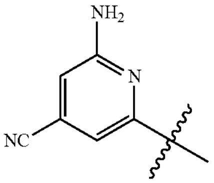,
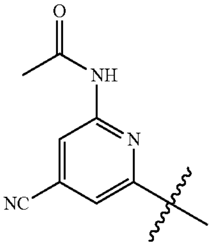, 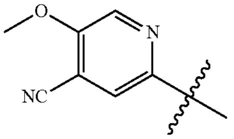,
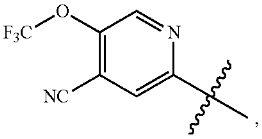,
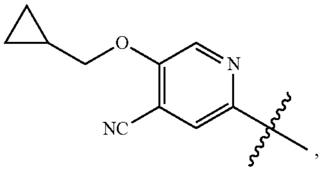,
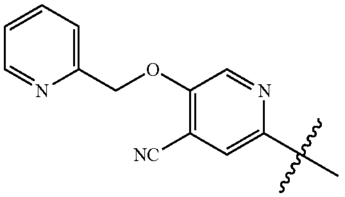,
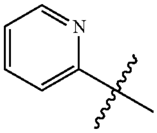, 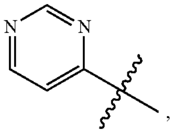,
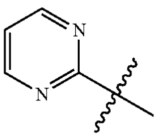, 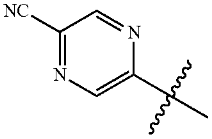,
-continued
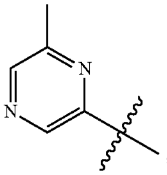, 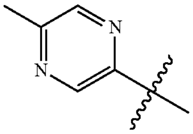,
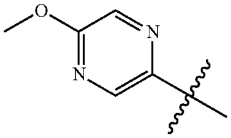, 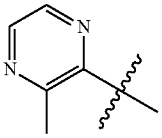,
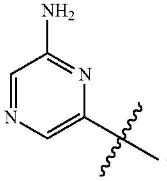, 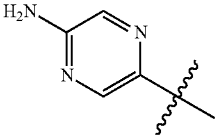,
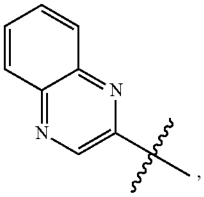, 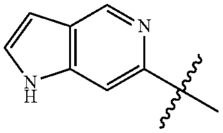,
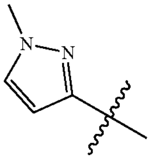, 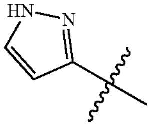,
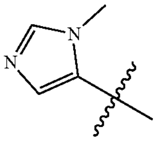, 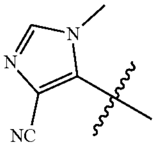,
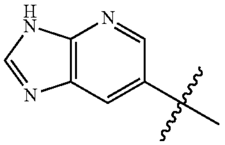, 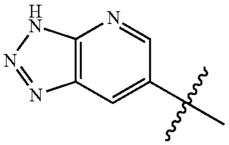,
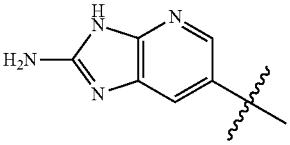,
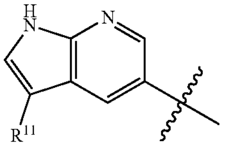, 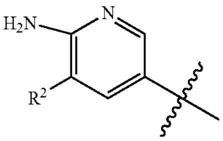, -continued
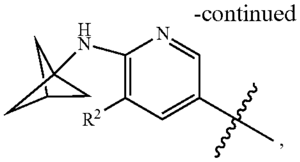
,
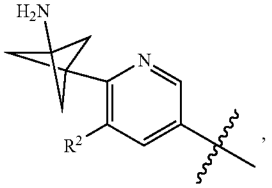
,
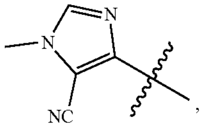
,
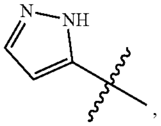
,
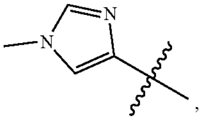
, or
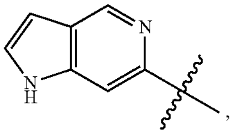
,
where $R^2$ is —$CF_3$, —$OCF_3$, —$OCHF_2$, —$OCH_3$, —CN, or —H, and
$R^{11}$ is —$CF_3$, —$OCF_3$, —CN, or -H.
6. The compound of claim 1, wherein Q is:
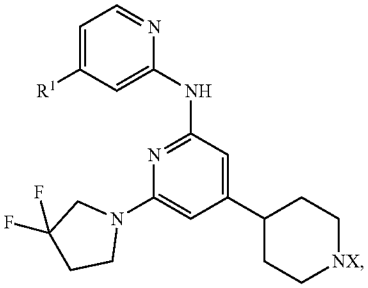
,
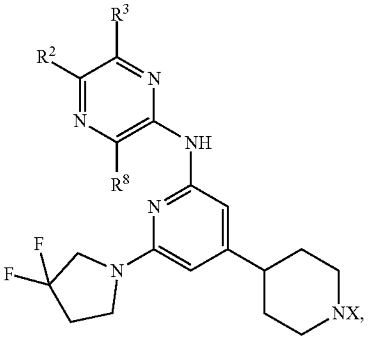
,
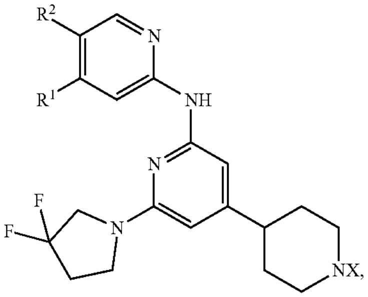
,
-continued
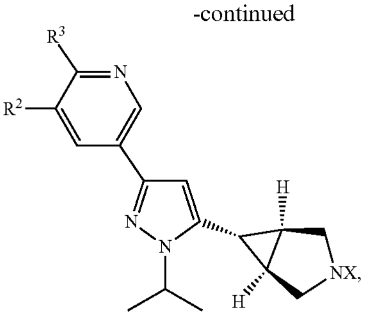
,
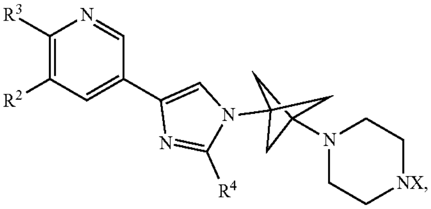
,
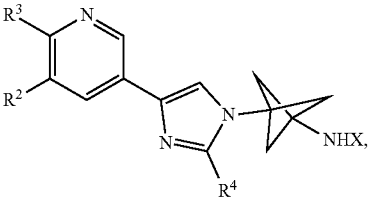
,
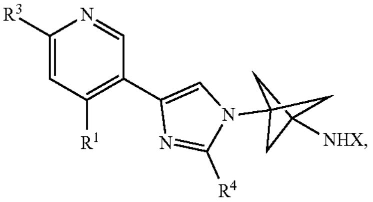
,
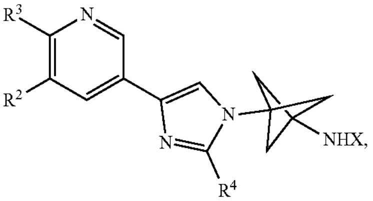
,
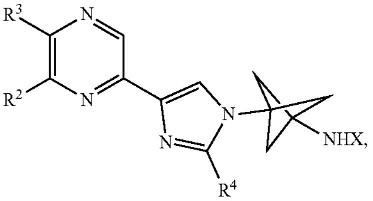
,
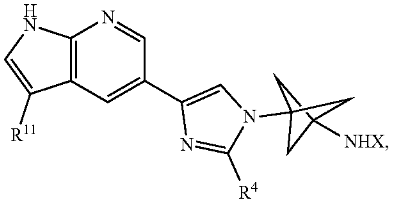
,
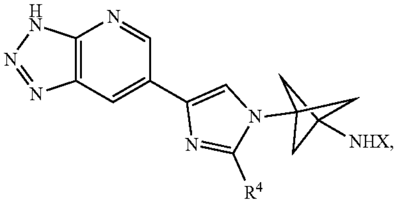
, -continued
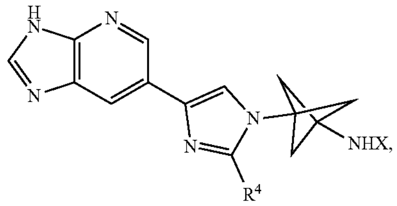
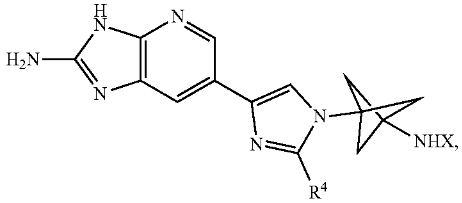
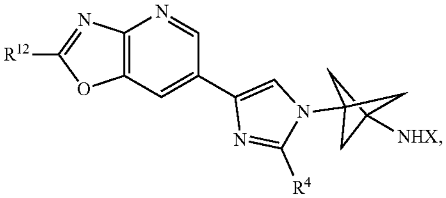
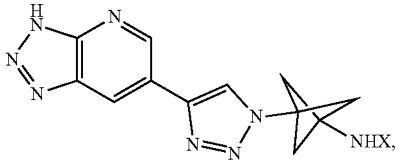
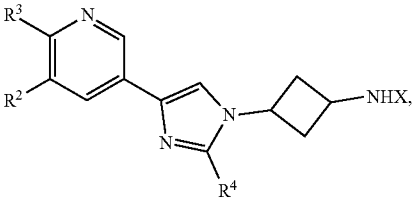
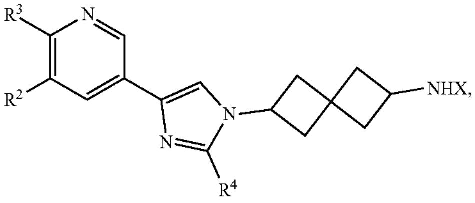
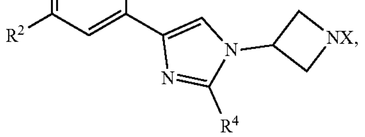
or
-continued
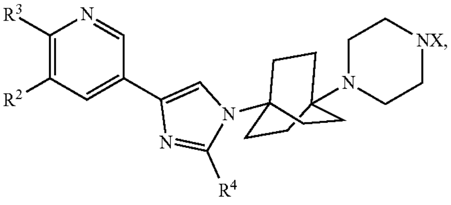
where $R^4$ is isopropyl, —C(H)(OH)—C($CH_3$)$_2$, cyclopropyl, or
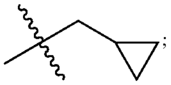 [SMILES: *CC1CC1]
and
$R^{11}$ and $R^{12}$ are H, alkyl, perhaloalkyl, alkoxy, perhaloalkoxy, cyano, or amino.
7. The compound of claim 6, wherein:
$R^1$ is —CN or —$CF_3$;
$R^2$ is —$OCH_3$, —$OCF_3$, —$CH_3$, —$CF_3$,—CN, —$OCHF_2$,
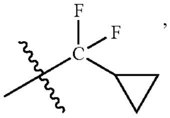
,
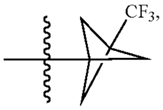
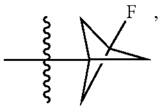
,
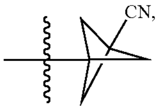
or H;
$R^3$ is —$NH_2$,
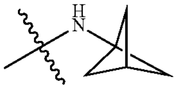
,
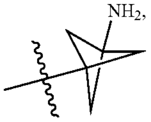
or H;
$R^8$ is —$OCF_3$, —CN, —$CH_3$, or H;
$R^{11}$ and $R^{12}$ independently are —$CF_3$, —CN, —H, —$OCH_3$, or —$OCF_3$; and
X is a bond.

8. A compound, wherein the compound is:
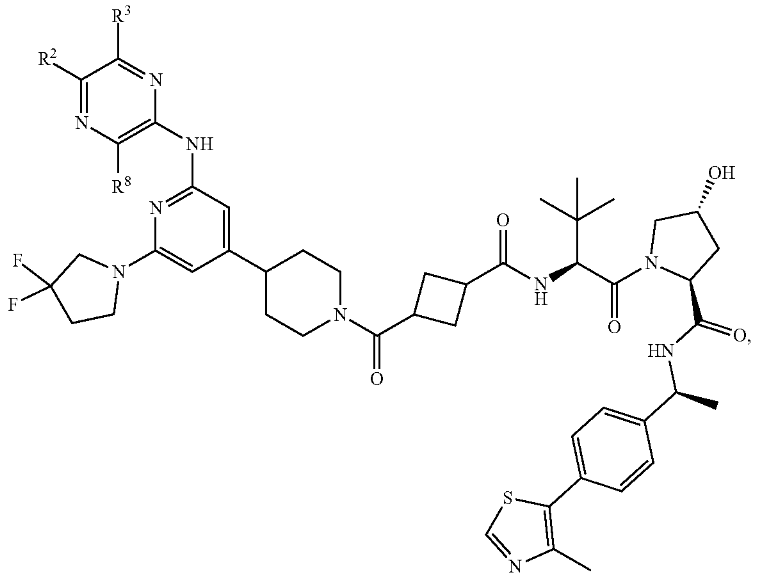
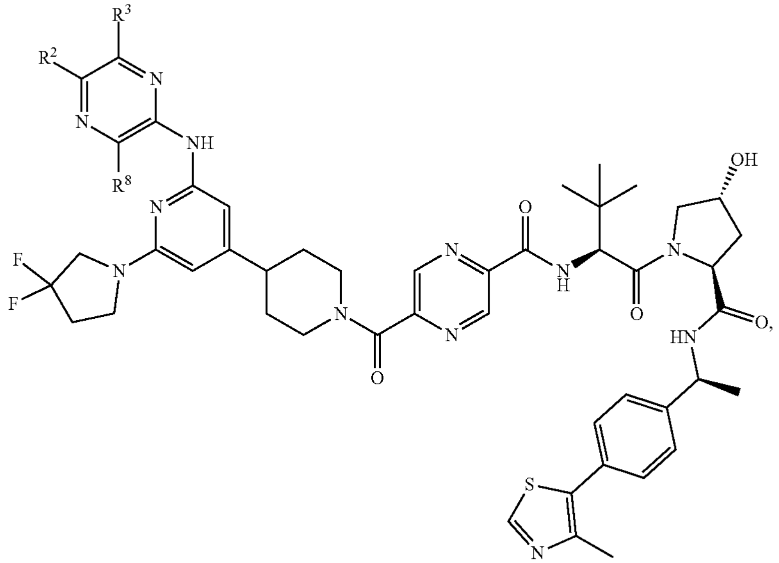
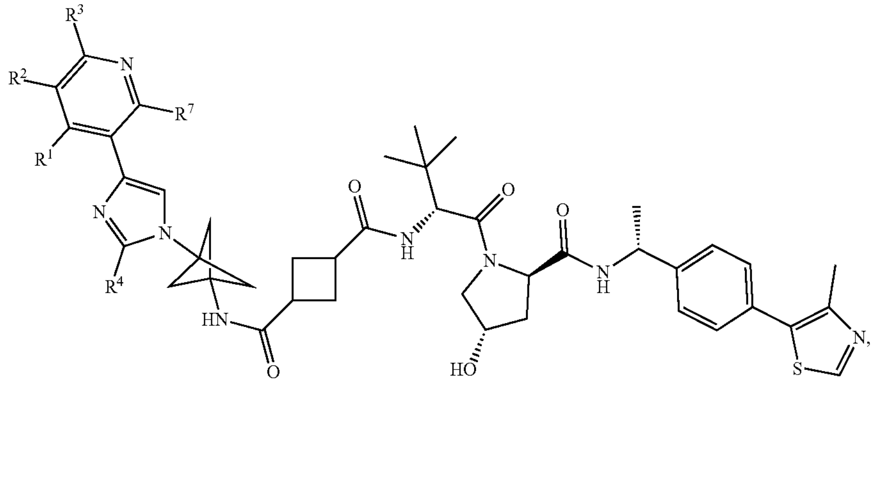
or

-continued
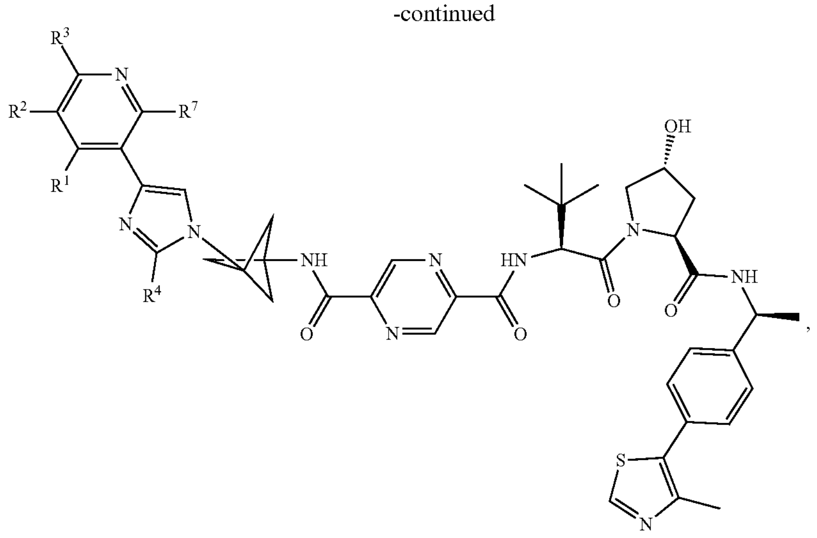
wherein $R^1$, $R^2$, $R^3$, $R^4$, $R^7$ and $R^8$ are as defined in claim 1.
9. A compound wherein the compound is:
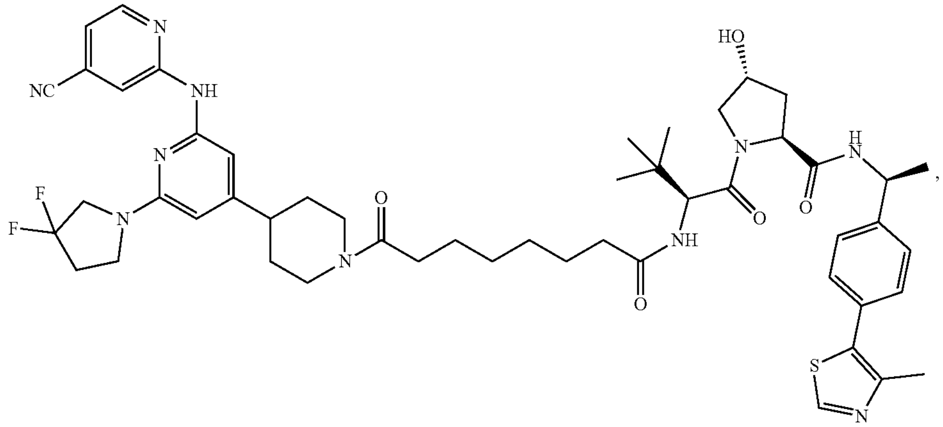
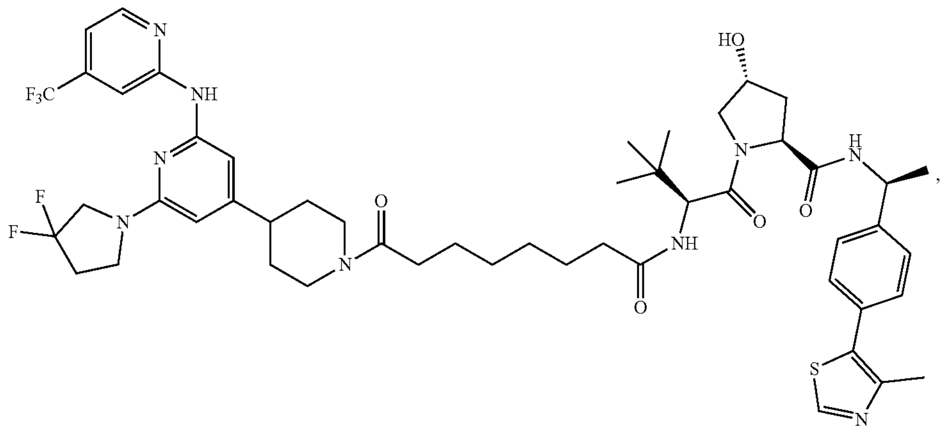

-continued
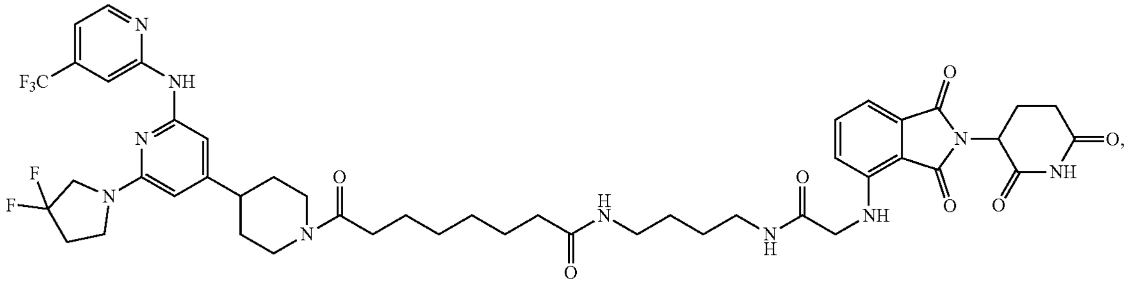
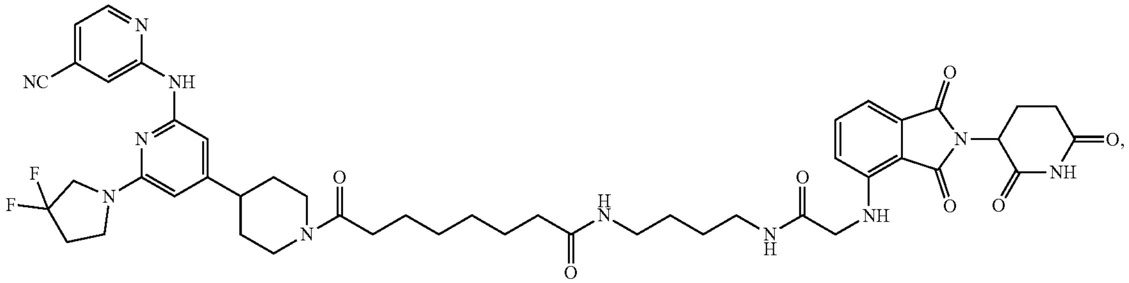
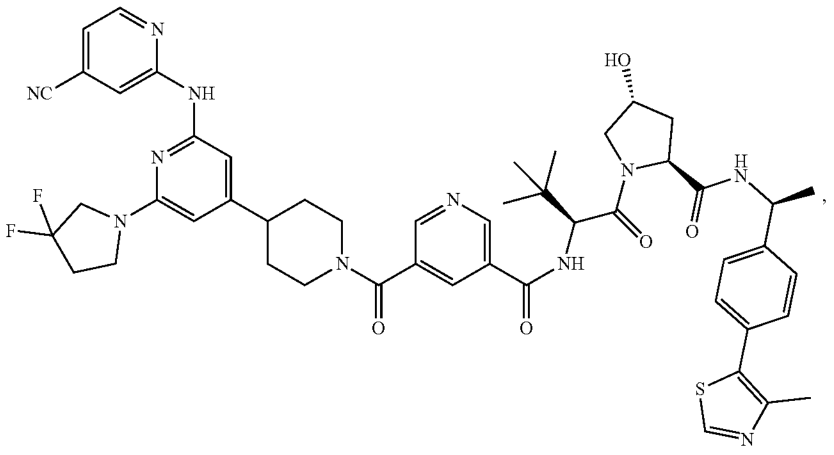
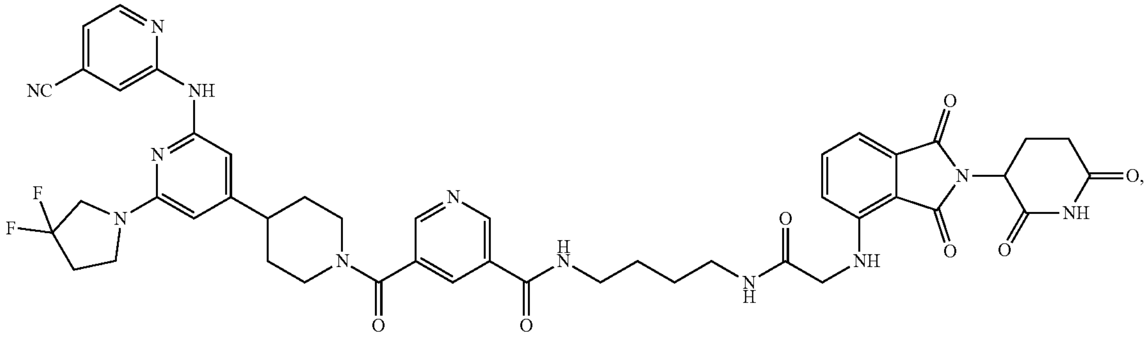

-continued
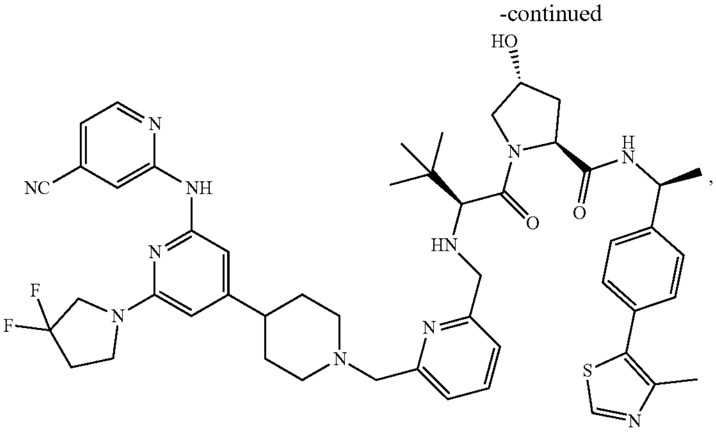,
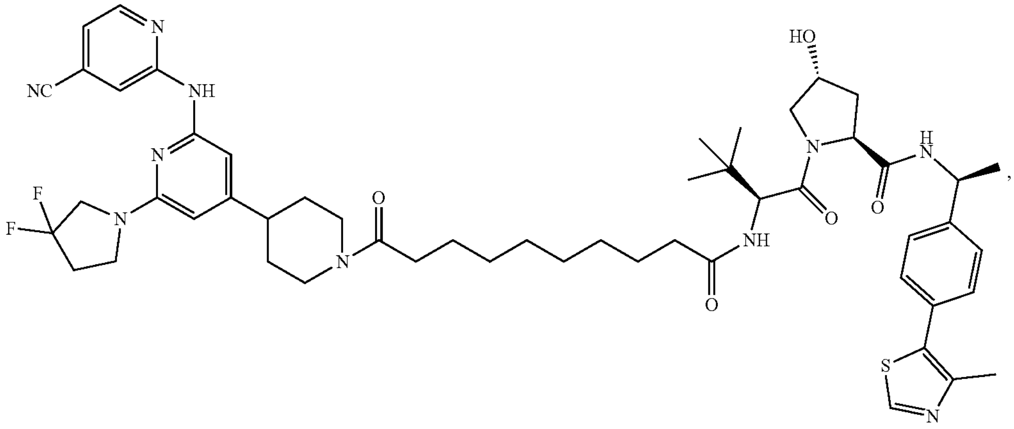,
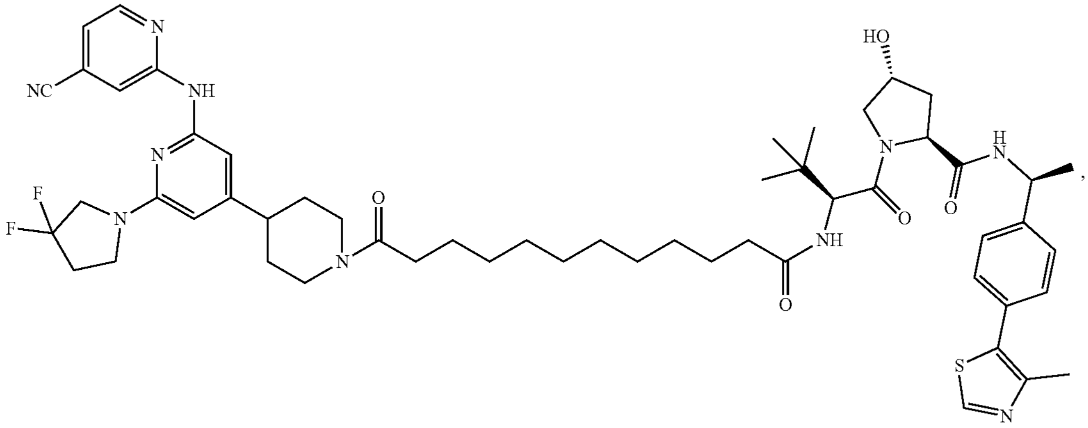,
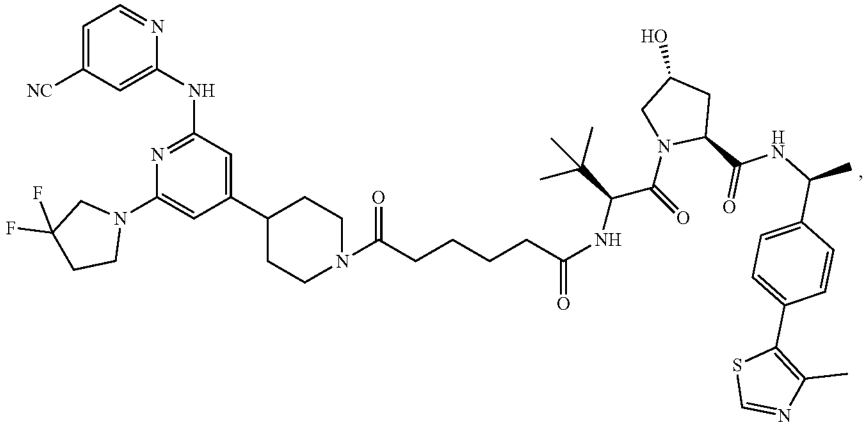,

-continued
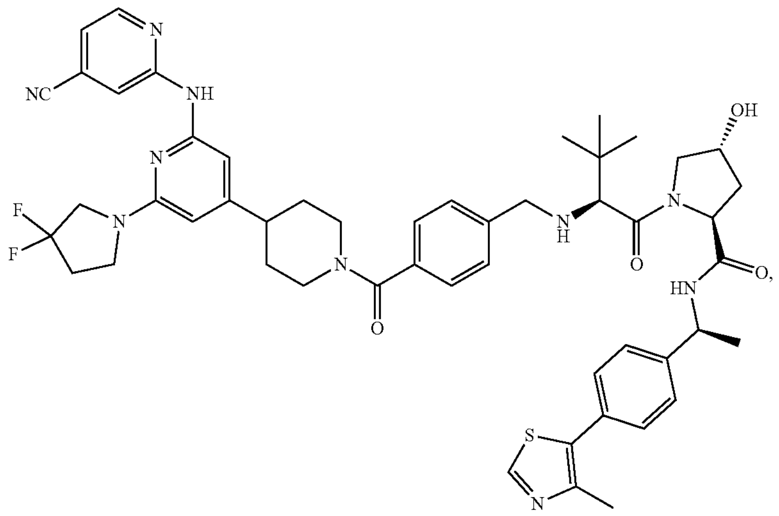
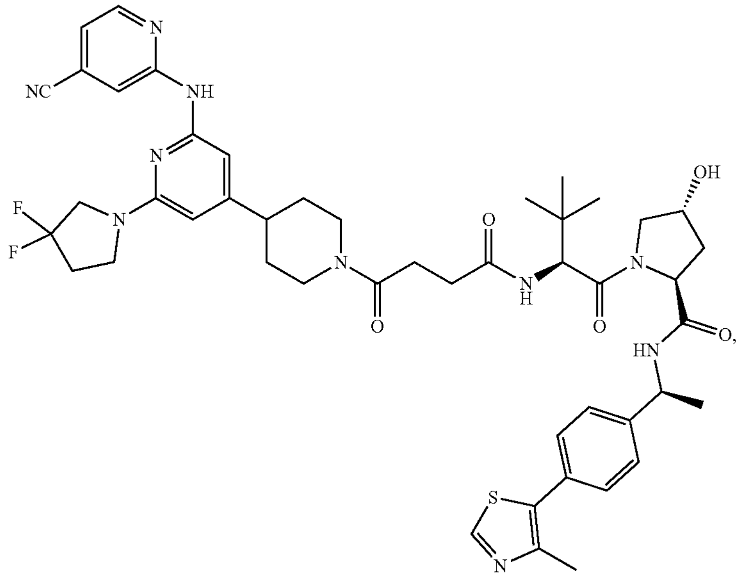
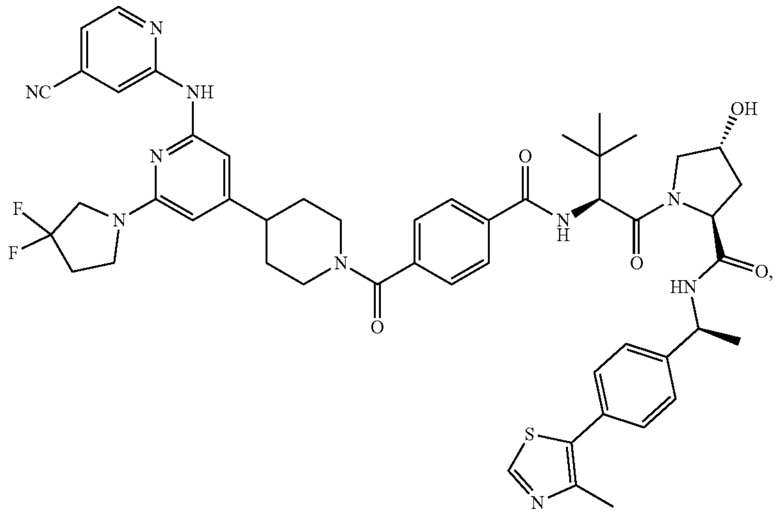

-continued
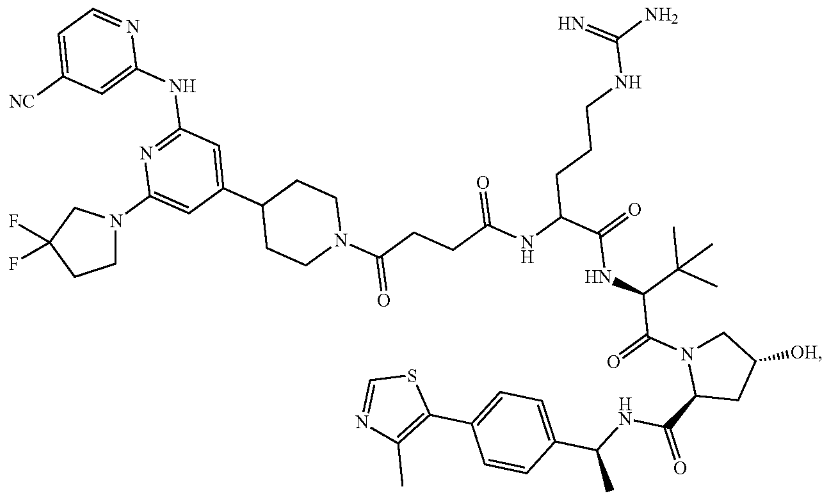
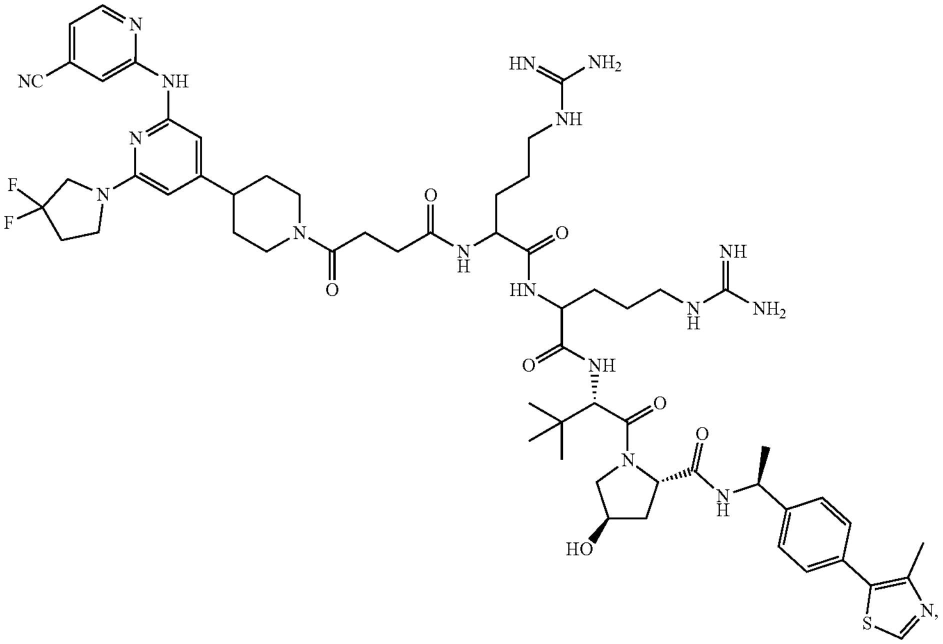
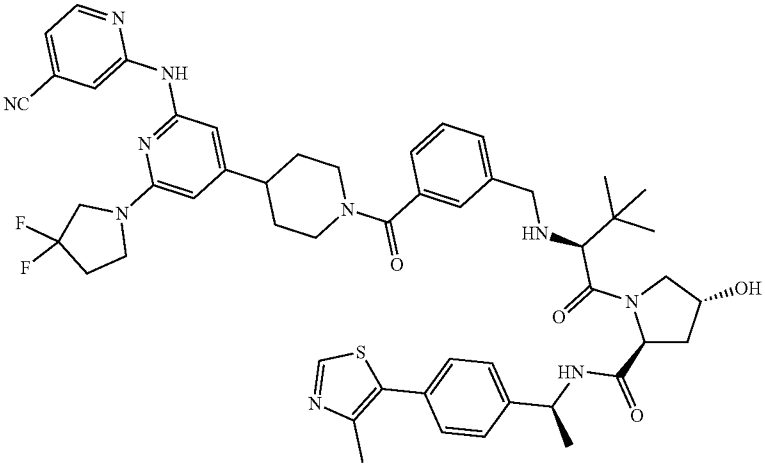

-continued
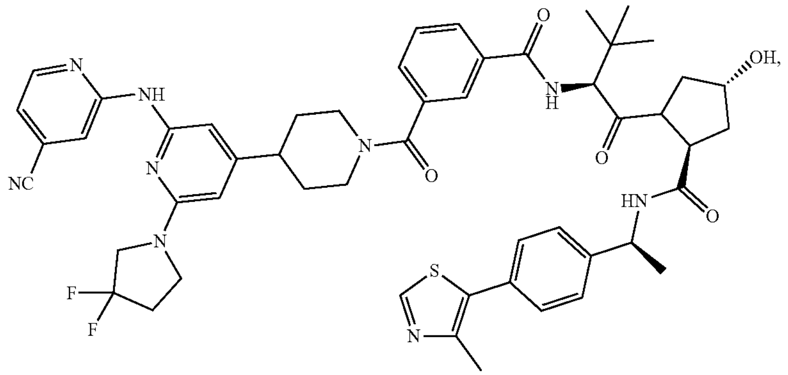
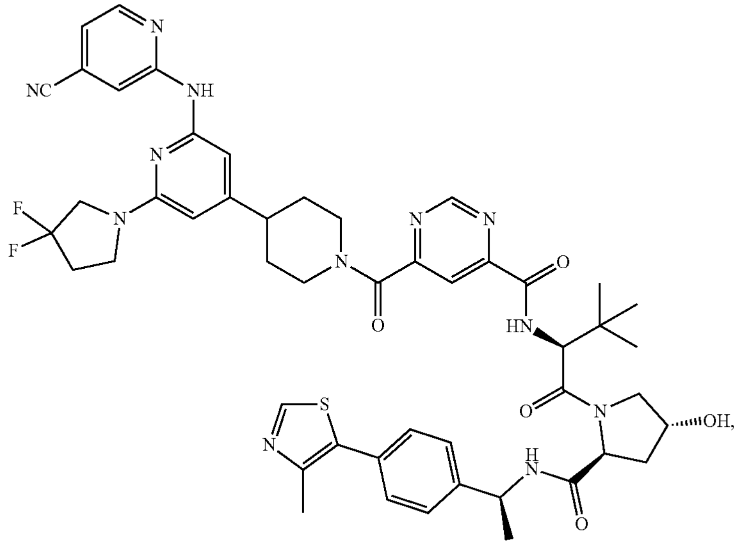
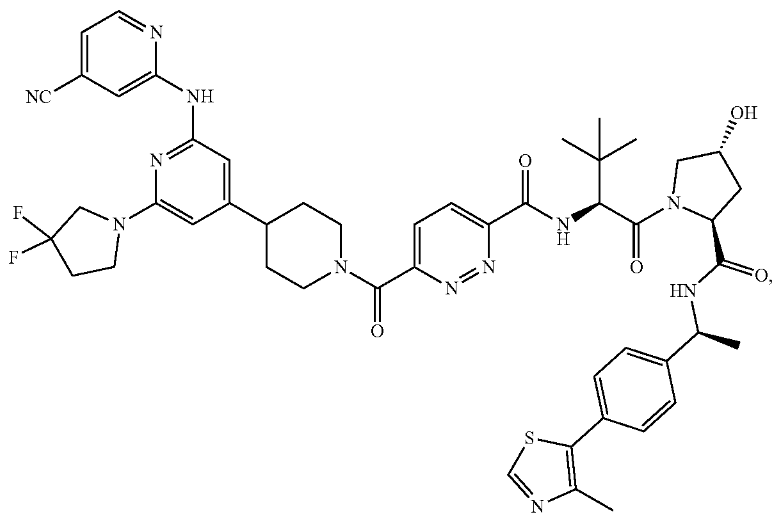

-continued
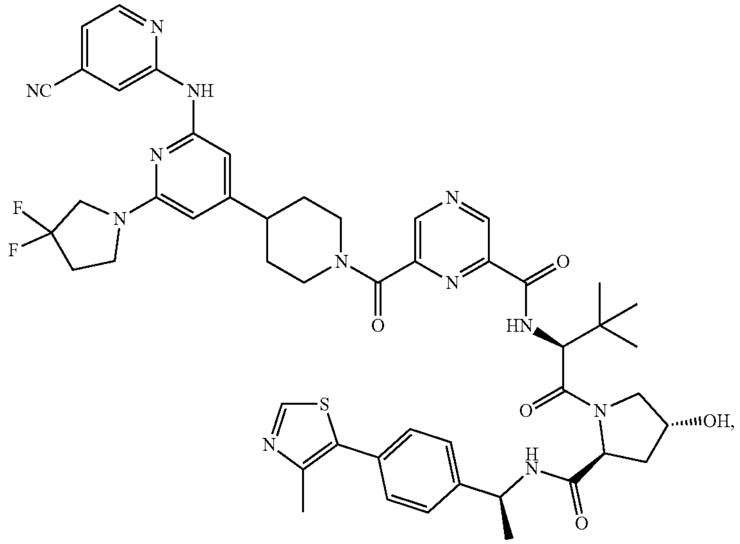
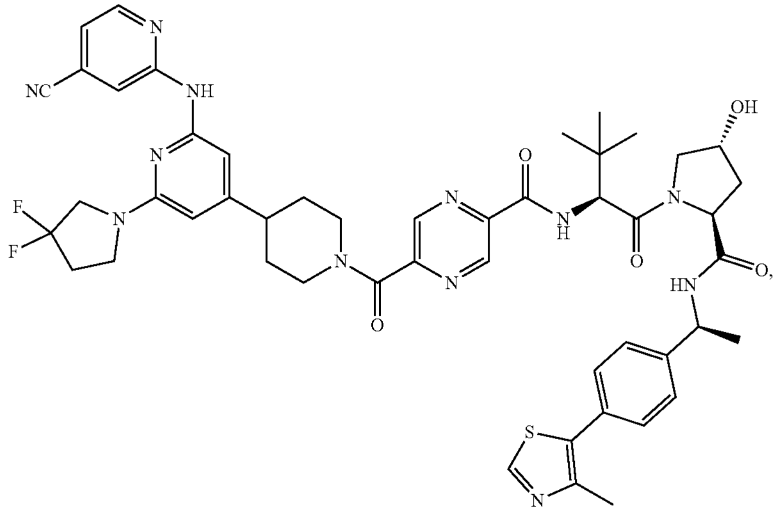
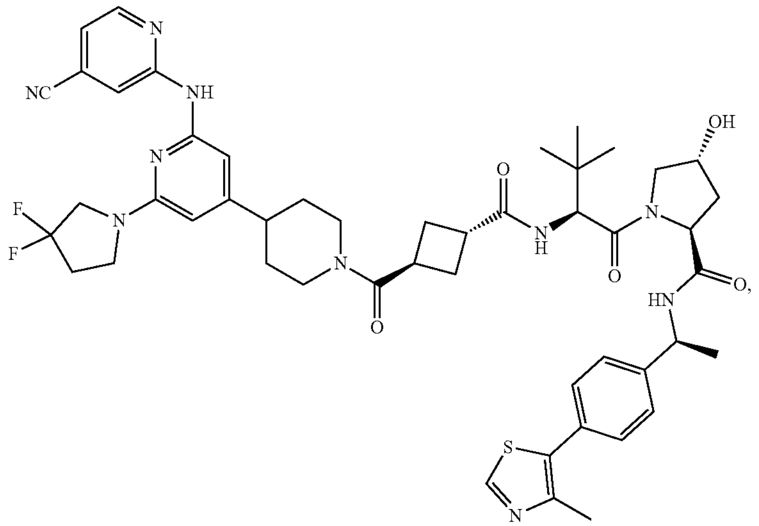

-continued
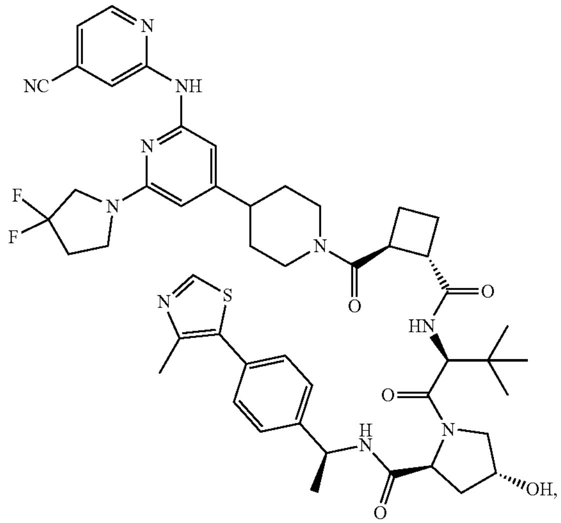
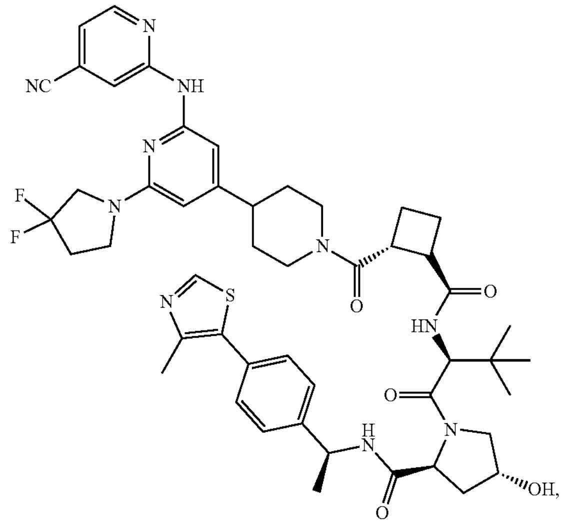
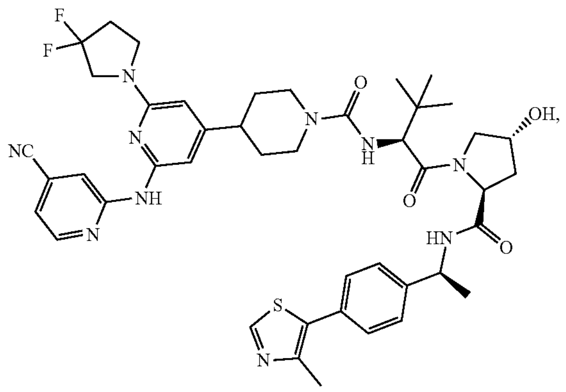
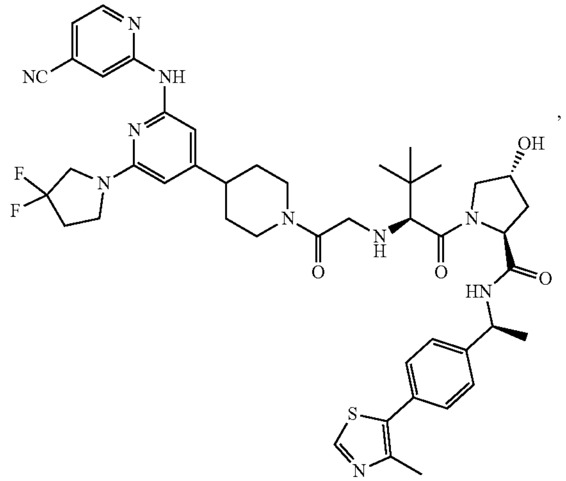
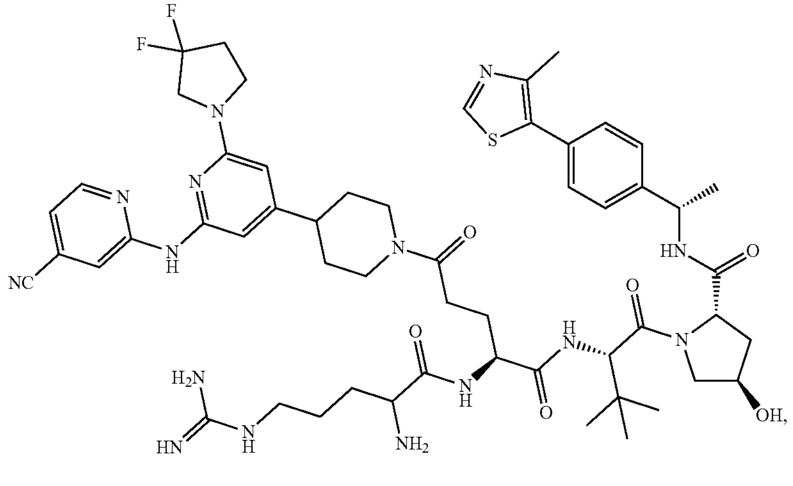

-continued
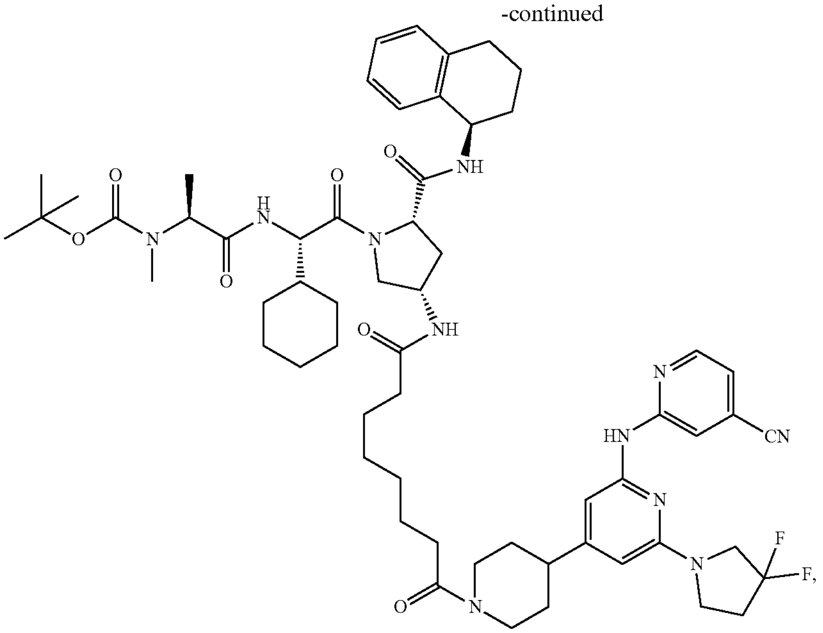
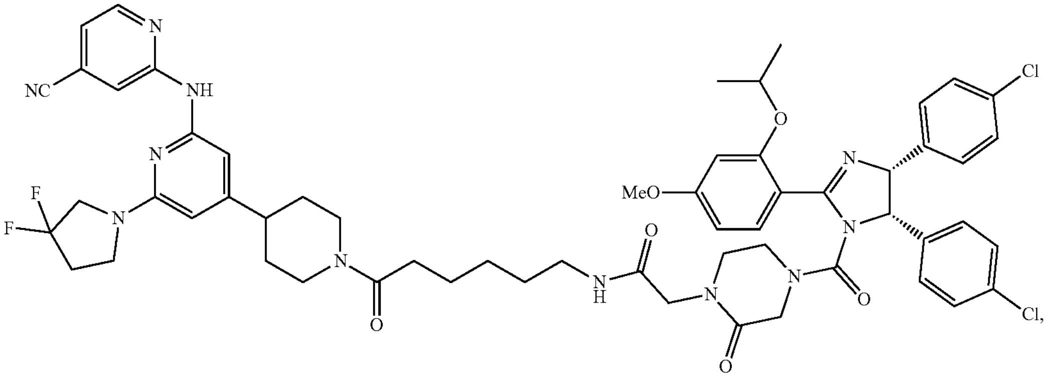
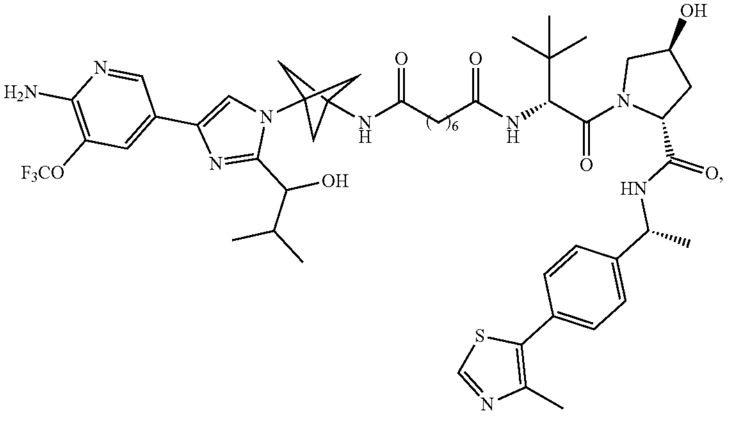

-continued
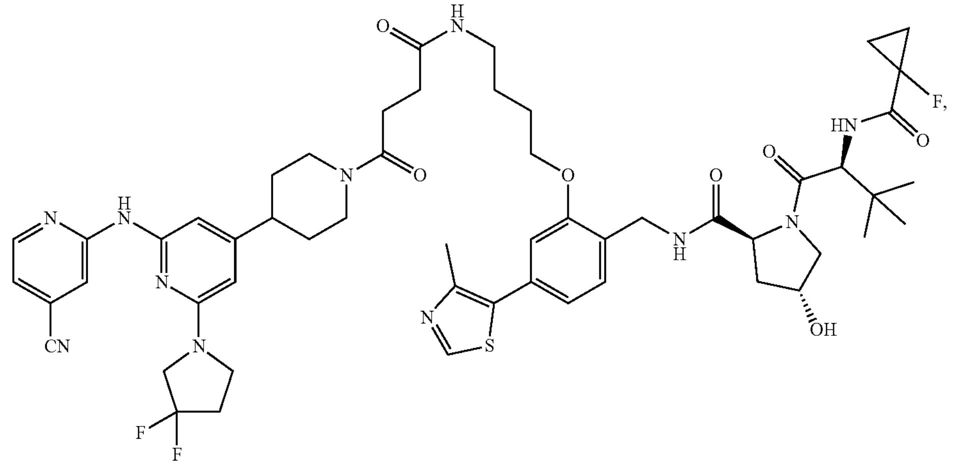
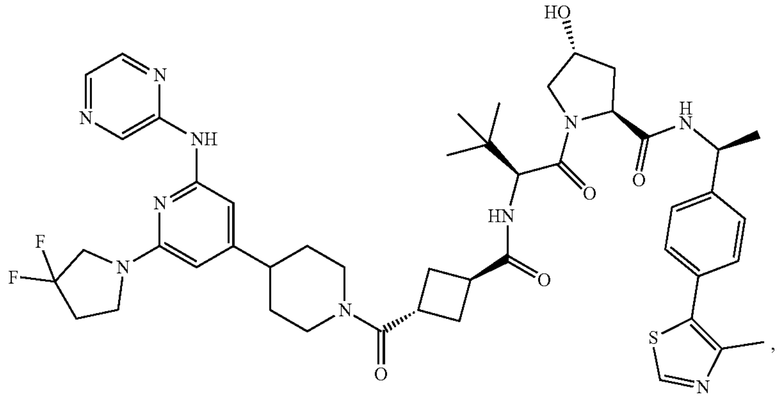
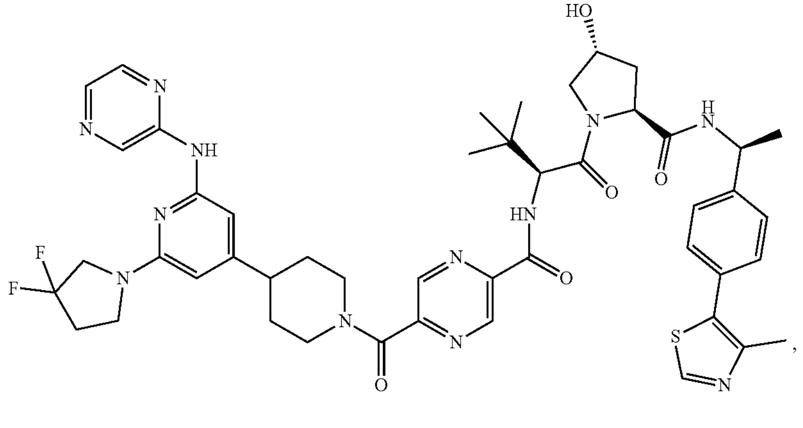

-continued
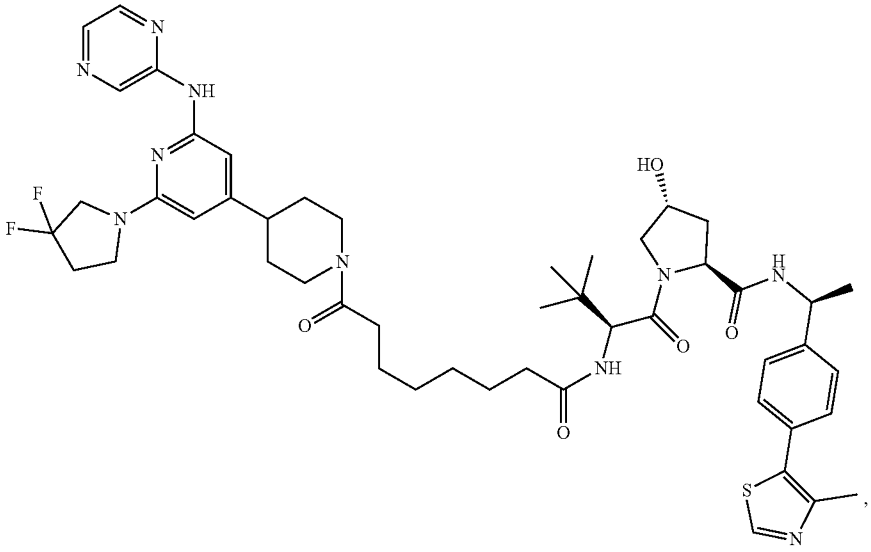
,
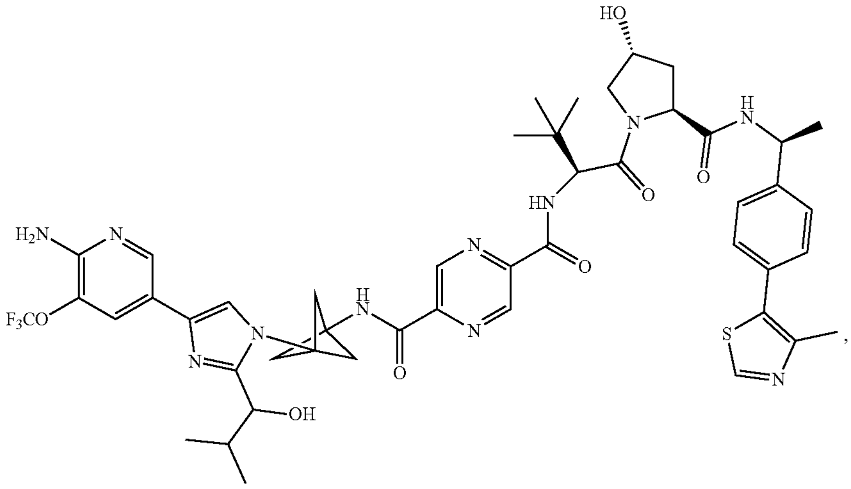
,
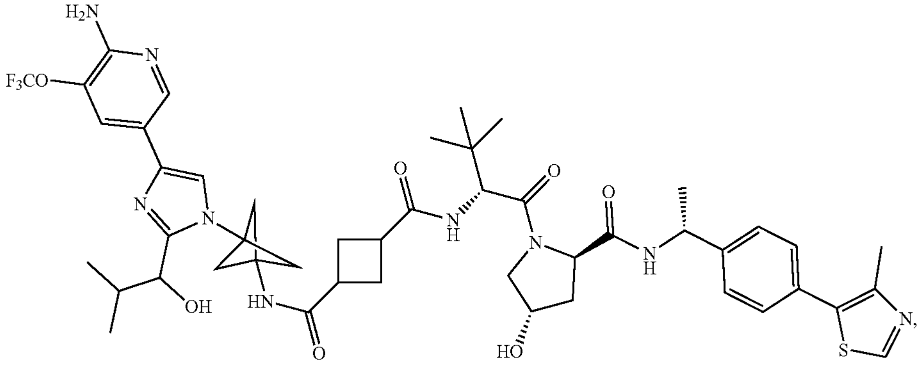
,

-continued
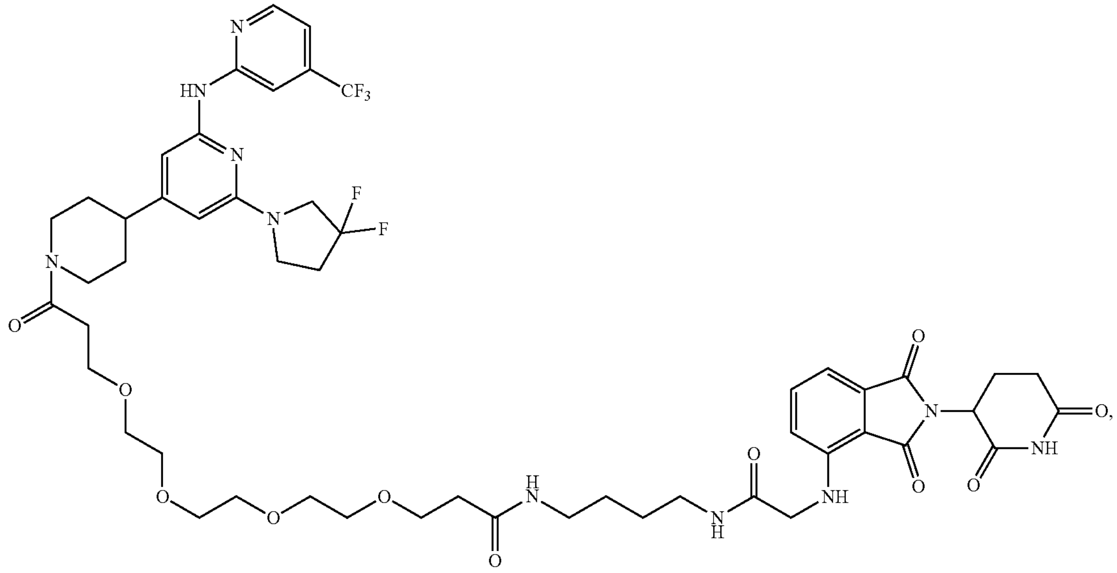
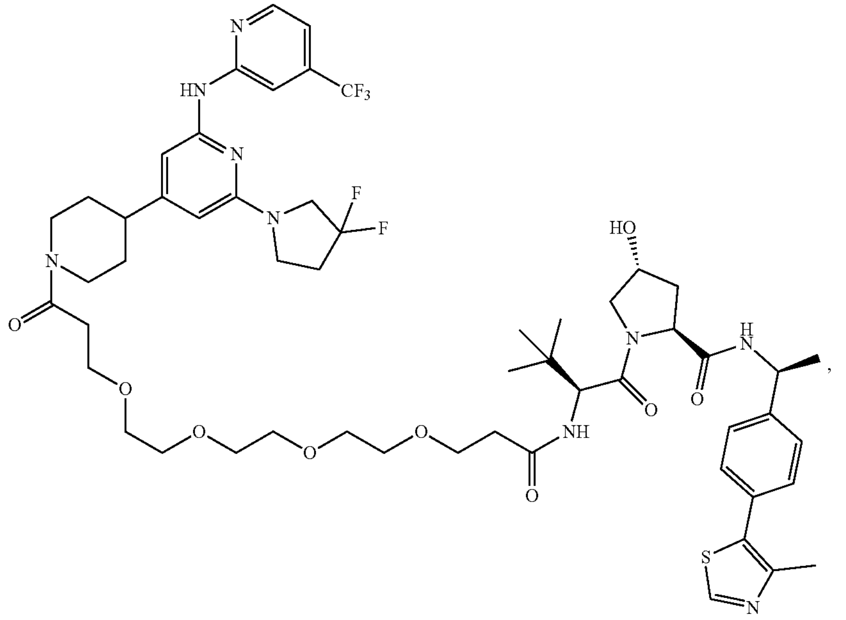
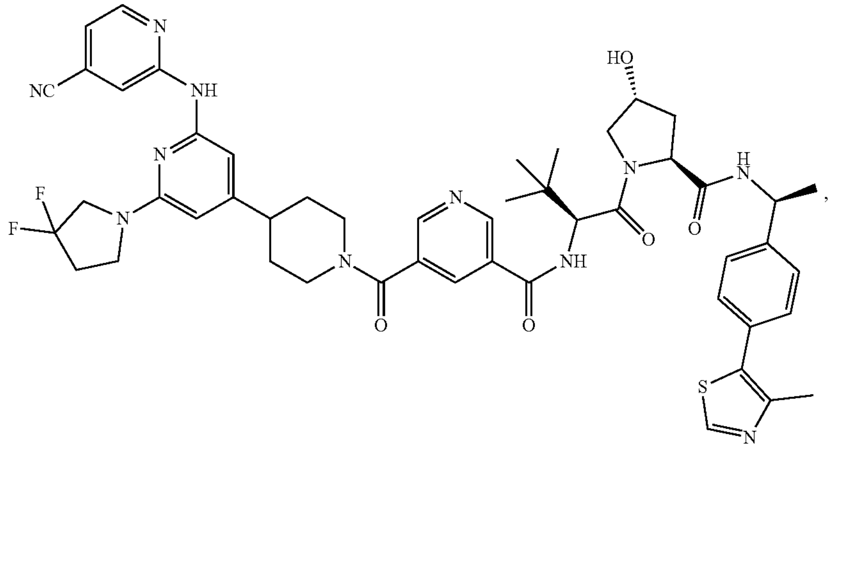

-continued
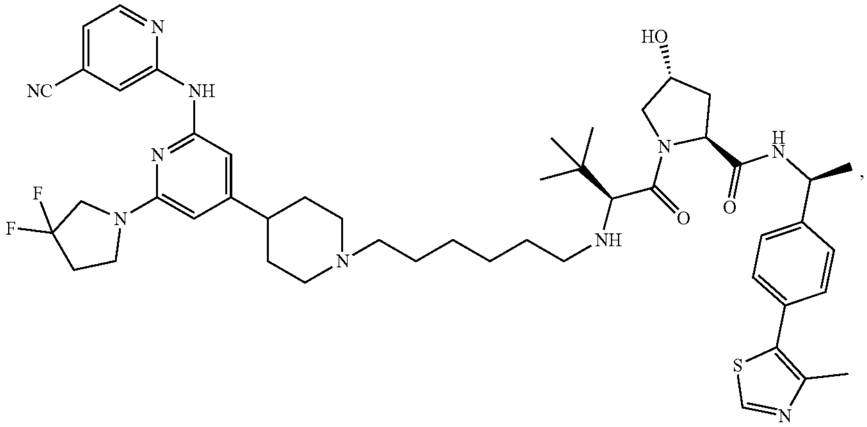
,
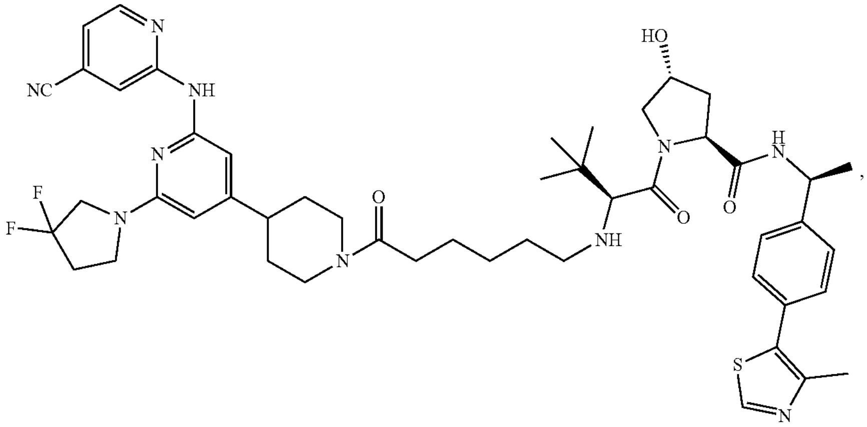
,
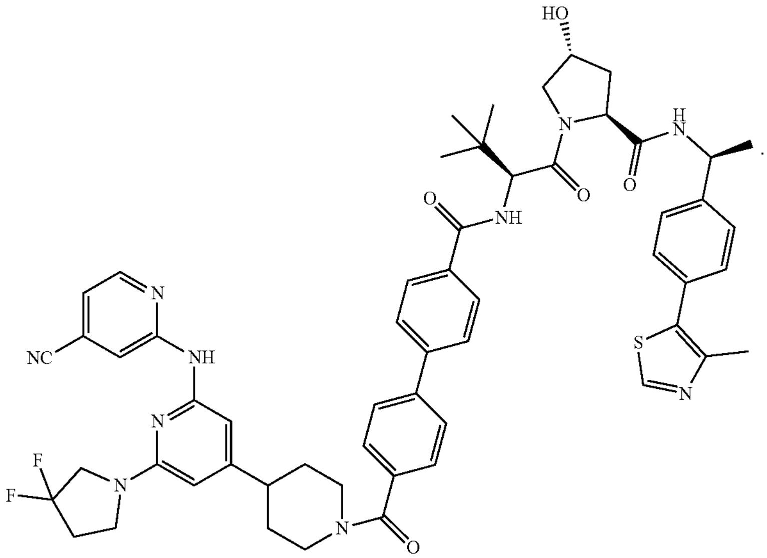
.

-continued
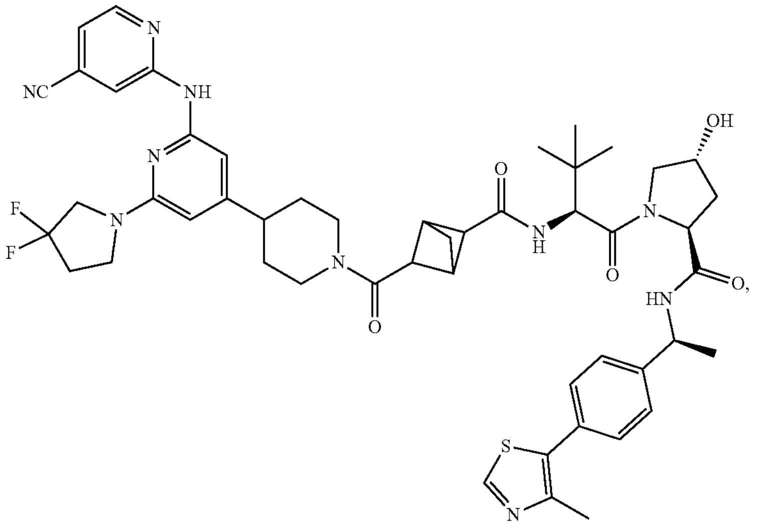
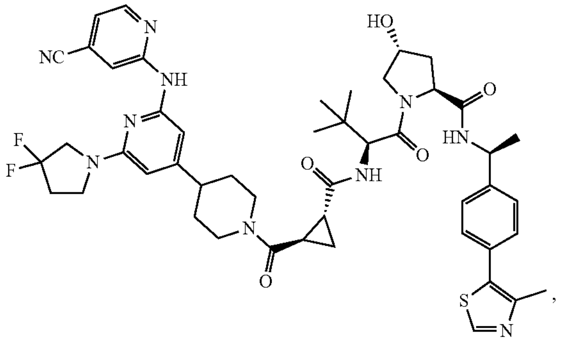
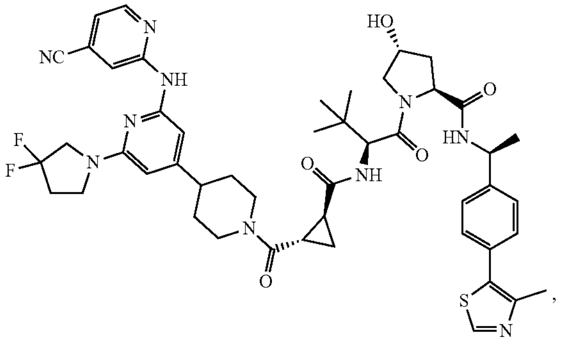
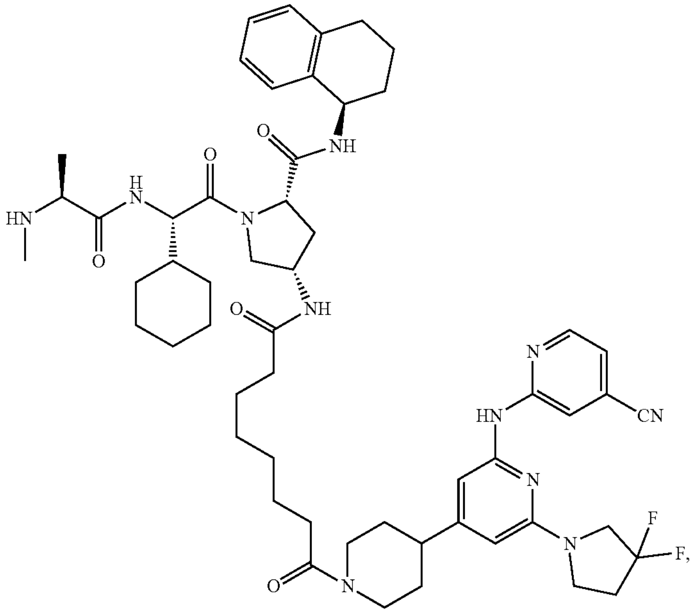

-continued
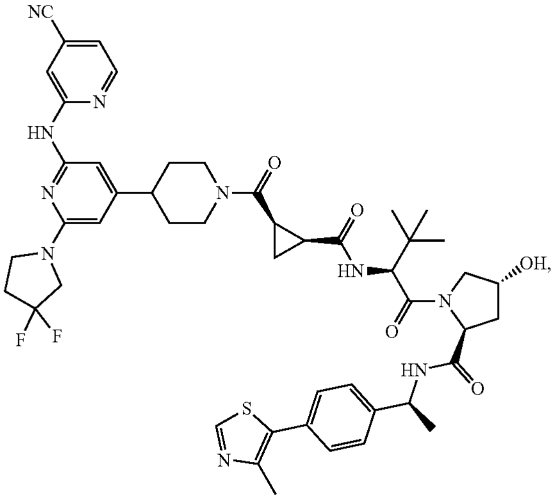
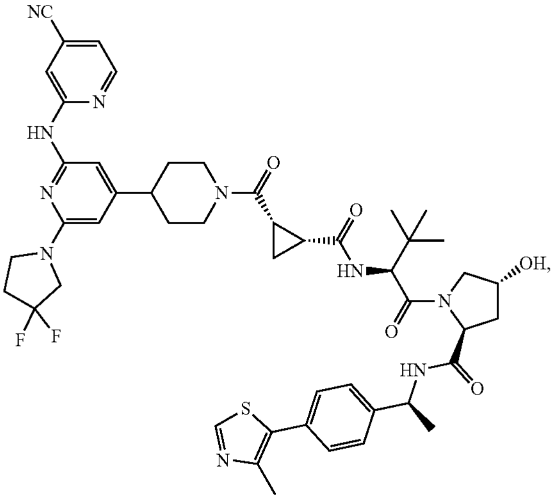
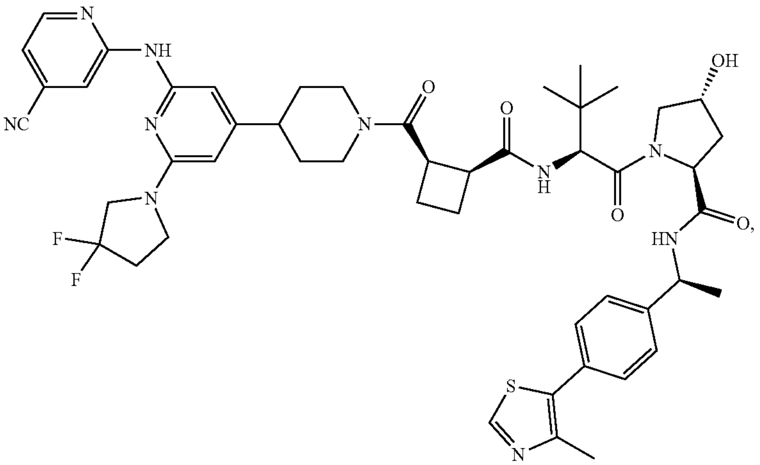
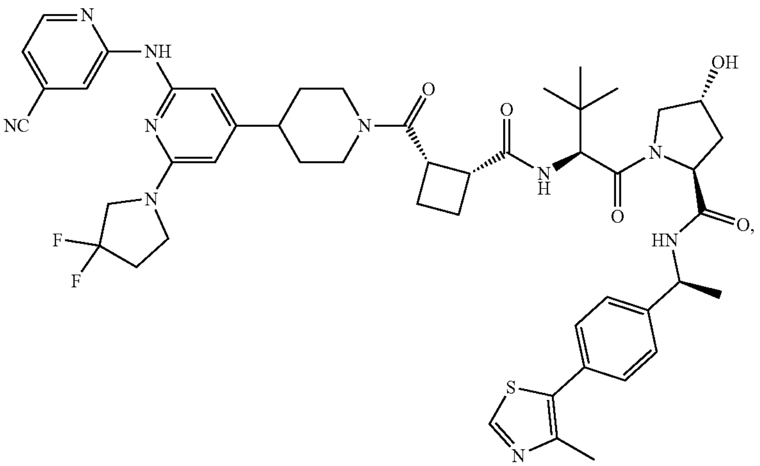

-continued
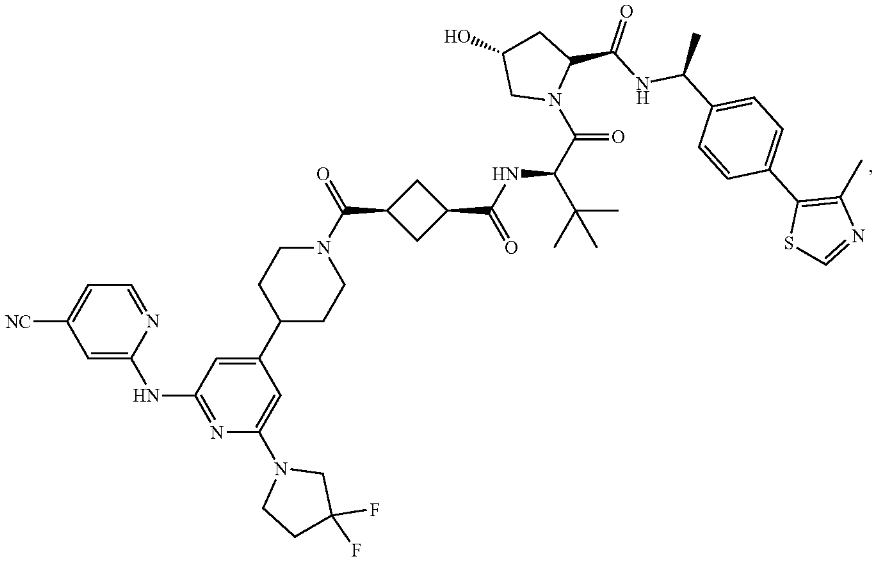
,
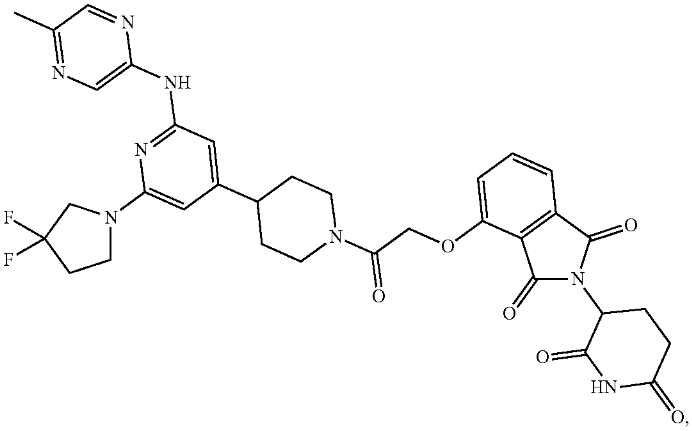
,
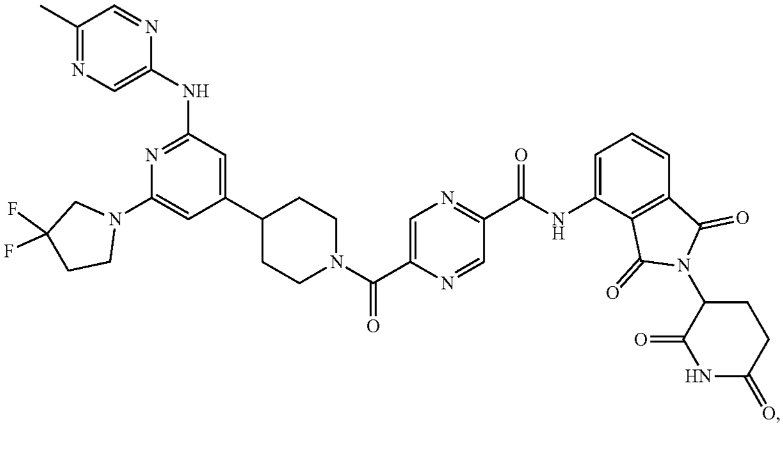
,

-continued
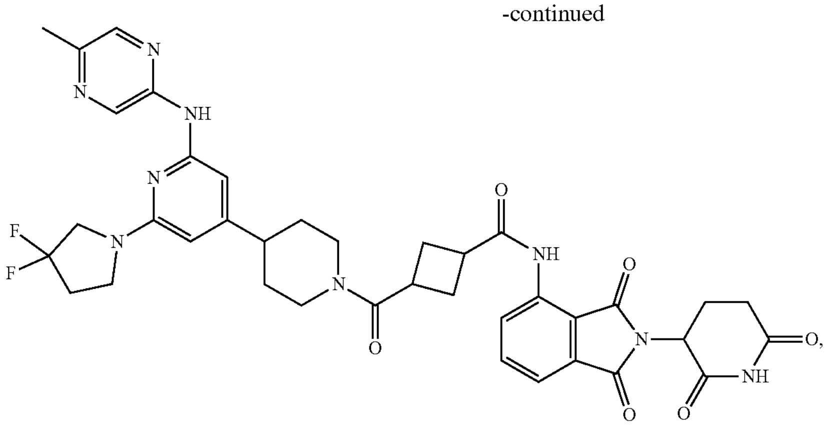
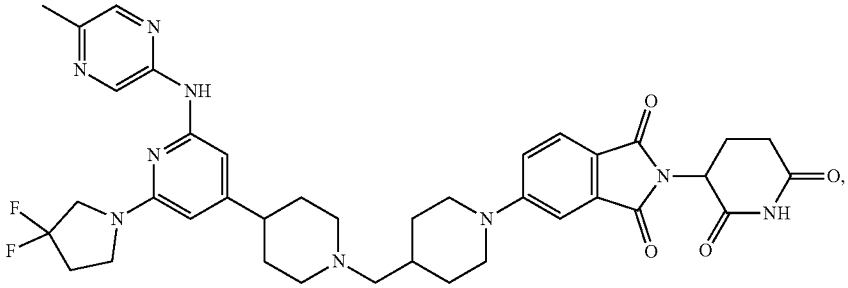
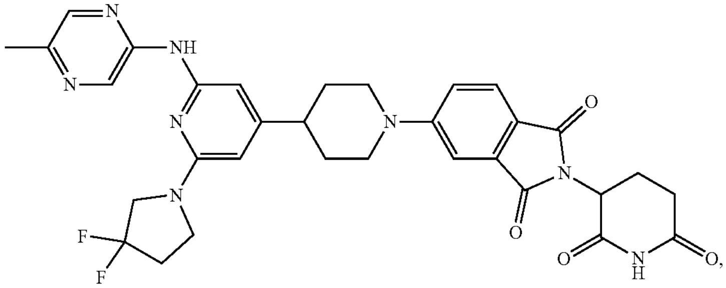
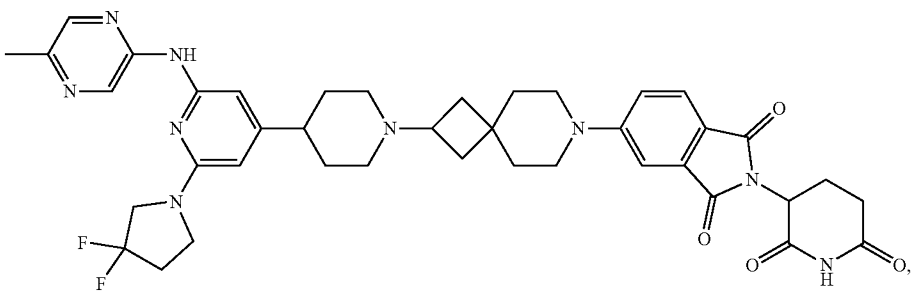
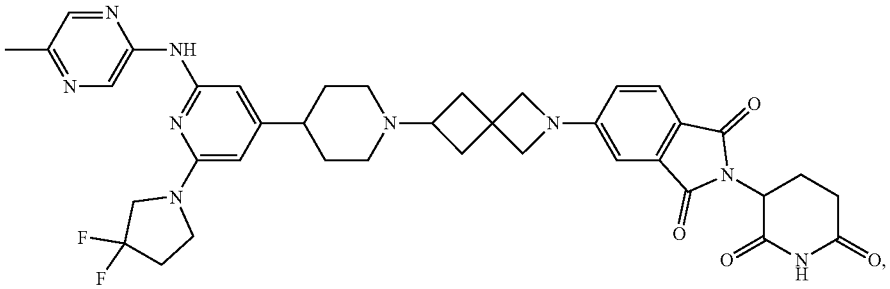
or

-continued

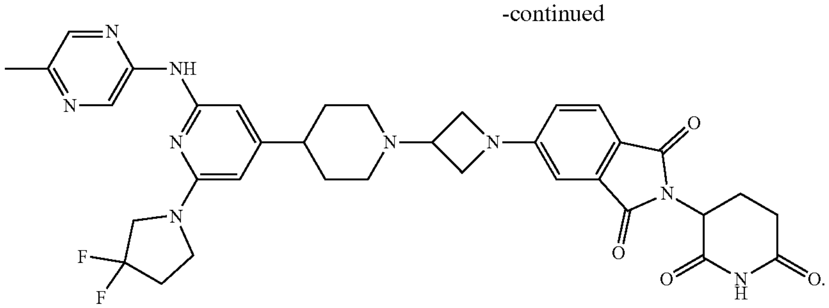

10. A pharmaceutical composition comprising a compound according to claim 1 and at least one pharmaceutically acceptable carrier.

11. A method of inhibiting leucine zipper-bearing kinase (LZK) activity, comprising:
contacting a cell expressing LZK with an effective amount of a compound according to claim 1, thereby inhibiting LZK activity.

12. The method of claim 11, wherein:
(i) inhibiting LZK activity comprises degrading LZK; or
(ii) inhibiting LZK activity inhibits cell cycle progression, reduces c-MYC expression, reduces gain-of-function (GOF) mutant p53 expression, inhibits c-Jun N-terminal kinase (JNK) pathway signaling, inhibits PI3K/AKT pathway signaling, inhibits cyclin dependent kinase 2 (CDK2) activity, or any combination thereof; or
(iii) both (i) and (ii).

13. The method of claim 11, wherein the cell is characterized by amplification of chromosome 3q, overexpression of mitogen-activated protein kinase kinase kinase 13 (MAP3K13), or both.

14. The method of claim 11, wherein contacting the cell with the compound comprises administering a therapeutically effective amount of the compound, or an amount of a pharmaceutical composition comprising the therapeutically effective amount of the compound, to a subject.

15. The method of claim 14, wherein the subject has a disease or condition characterized at least in part by LZK overexpression.

16. The method of claim 15, wherein the disease or condition is cancer, and the cancer is head and neck squamous cell carcinoma, lung squamous cell carcinoma, hepatocellular carcinoma, ovarian cancer, small cell lung cancer, neuroendocrine prostate cancer, or esophageal cancer.

17. The method of claim 16, wherein administering the therapeutically effective amount of the compound, or the amount of the pharmaceutical composition, decreases viability of cancer cells, inhibits tumor growth, or a combination thereof.

* * * * *